(12) United States Patent
Lancellotti et al.

(10) Patent No.: US 11,434,241 B2
(45) Date of Patent: *Sep. 6, 2022

(54) PYRIMIDINE DERIVATIVES FOR PREVENTION AND TREATMENT OF BACTERIAL INFECTIONS

(71) Applicant: UNIVERSITE DE LIEGE, Liege (BE)

(72) Inventors: Patrizio Lancellotti, Liege (BE); Cécile Oury, Liege (BE); Bernard Pirotte, Liege (BE)

(73) Assignee: UNIVERSITÉ DE LIÈGE, Liège (BE)

( * ) Notice: Subject to any disclaimer, the term of this patent is extended or adjusted under 35 U.S.C. 154(b) by 106 days.

This patent is subject to a terminal disclaimer.

(21) Appl. No.: 16/958,023

(22) PCT Filed: Feb. 14, 2019

(86) PCT No.: PCT/EP2019/053711
§ 371 (c)(1),
(2) Date: Jun. 25, 2020

(87) PCT Pub. No.: WO2019/158655
PCT Pub. Date: Aug. 22, 2019

(65) Prior Publication Data
US 2021/0061804 A1    Mar. 4, 2021

(30) Foreign Application Priority Data
Feb. 14, 2018 (EP) .................................... 18156797

(51) Int. Cl.
*C07D 473/40* (2006.01)
*A61K 9/00* (2006.01)
*C07D 473/28* (2006.01)

(52) U.S. Cl.
CPC .......... *C07D 473/40* (2013.01); *A61K 9/0024* (2013.01); *C07D 473/28* (2013.01)

(58) Field of Classification Search
CPC combination set(s) only.
See application file for complete search history.

(56) References Cited

U.S. PATENT DOCUMENTS

| | | | |
|---|---|---|---|
| 10,905,691 B2 * | 2/2021 | Oury ..................... | A61L 2/0082 |
| 2009/0048203 A1 * | 2/2009 | Cavero-Tomas ........ | A61P 43/00 514/46 |
| 2019/0194213 A1 * | 6/2019 | Oury ..................... | C07D 487/04 |
| 2020/0093826 A1 * | 3/2020 | Oury ..................... | A61L 2/0082 |
| 2021/0290625 A1 * | 9/2021 | Lancellotti .............. | A61P 31/02 |

FOREIGN PATENT DOCUMENTS

| | | | |
|---|---|---|---|
| EP | 3 292 867 81 | | 3/2018 |
| GB | 1143150 | * | 4/1968 |
| WO | WO 2009/034386 A1 | | 3/2009 |
| WO | WO-2020212553 A1 | * | 10/2020 ........... C07D 473/24 |

OTHER PUBLICATIONS

National Center for Biotechnology Information. PubChem Compound Summary for CID 24737634. https://pubchem.ncbi.nlm.nih.gov/compound/24737634. Create Date Mar. 3, 2008. (Year: 2008).*
Geng; Bioorganic & Medicinal Chemistry Letters 2008, 18, 4368-4372. DOI:10.1016/j.bmcl.2008.06.068 (Year: 2008).*
Goffin; European Journal of Medicinal Chemistry 2020, 208, 112767. DOI:10.1016/j.ejmech.2020.112767 (Year: 2020).*
Sellmyer; Proceedings of the National Academy of Sciences 2017, 114, 8372-8377. DOI: 10.1073/pnas.1703109114 (Year: 2017).*
Serpi; J. Med. Chem. 2016, 59, 23, 10343-10382. DOI: 10.1021/acs.jmedchem.6b00325 (Year: 2016).*
Springthorpe; Bioorg. Med. Chem. Lett, 2007, 17, 6013-6018. doi:10.1016/j.bmcl.2007.07.057 (Year: 2007).*
International Search Report, PCT/EP2019/053711, dated Apr. 29, 2019.
Written Opinion of the International Searching Authority, PCT/EP2019/053711, dated Apr. 29, 2019.

* cited by examiner

*Primary Examiner* — Daniel R Carcanague
(74) *Attorney, Agent, or Firm* — Knobbe, Martens, Olson & Bear, LLP

(57) ABSTRACT

Pyrimidine derivatives of formula (I):

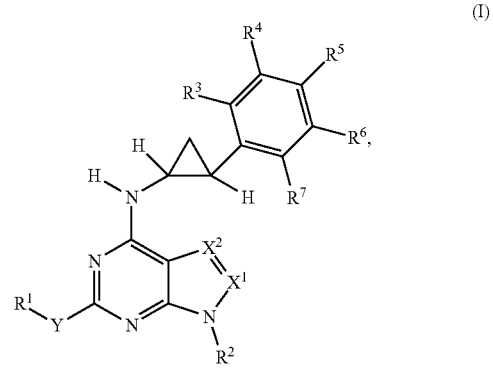

optionally with a detectable isotope, pharmaceutical composition and method of preparation thereof. Pyrimidine derivatives for use in treatment or prevention of bacterial infection in a host mammal in need of such treatment or prevention and use as inhibitors of biofilm formation on a surface of biomaterial or medical device, particularly of cardiovascular device such as prosthetic heart valve or pacemakers. Pyrimidine derivatives for use as radiotracer in diagnosing or prognosing bacterial infection in a host mammal.

30 Claims, 2 Drawing Sheets

PYRIMIDINE DERIVATIVES FOR PREVENTION AND TREATMENT OF BACTERIAL INFECTIONS

FIELD OF THE INVENTION

The present invention relates to new pyrimidine derivatives, optionally with a detectable isotope, their pharmaceutical composition and a method of preparation thereof. The present invention also relates to new pyrimidine derivative for use in prevention and treatment of bacterial infection and their use in inhibition of biofilm formation.

Finally the present invention provides pyrimidines derivative optionally with a detectable isotope for use as radiotracer in diagnosis or prognosis of bacterial infection.

INTRODUCTION

Bacteria are often incriminated in healthcare-associated infections (including medical device-related infections), causing increased patient morbidity and mortality, and posing huge financial burden on healthcare services. The situation has become critical since more and more bacteria are becoming resistant to antibiotics belonging to various classes such as Penicillins, Carbapenems, Cephalosporins, Quinolones, Amino-glycosides, and Glycopeptides, and an increasing number of infections are becoming difficult to cure.

The increasing resistance to antibiotics is a growing public health concern because of the limited treatment options available for these serious infections. According to the World Health Organization, «antibiotic resistance is one of the biggest threats to global health, food security, and development today. Antibiotic resistance can affect anyone, of any age, in any country. Antibiotic resistance occurs naturally, but misuse of antibiotics in humans and animals is accelerating the process. Antibiotic resistance leads to longer hospital stays, higher medical costs and increased mortality.»

In Europe, antibiotic resistance causes approximately 25,000 deaths per year and 2.5 millions extra hospital days (Source: Center for Disease Control and prevention, Global Health). The clinical burden associated with antimicrobial resistance is estimated to cost approximately €1.5 billion per year.

For instance, in 15 European countries more than 10% of bloodstream *Staphylococcus aureus* (*S. aureus*) infections are caused by methicillin-resistant strains (MRSA), with several of these countries presenting resistance rates closer to 50% (European Centre for Disease Prevention and Control Antimicrobial Resistance Interactive Database (EARS-NET)).

According to the Center for Disease Control and Prevention, there were more than 80,000 invasive MRSA infections and 11,285 related deaths in 2011. A study by researchers at UC Davis found that the number of children hospitalized due to community-acquired MRSA doubled between 2000 and 2007 (Agency for Healthcare Research and Quality statistics).

MRSA is epidemic in some regions of the world.

There is therefore an urgent need in the art for a new antibacterial therapy.

SUMMARY OF THE INVENTION

We have surprisingly found new pyrimidine derivatives, optionally with a detectable isotope that possess antibacterial activity and can be used in the treatment or prevention of bacterial infection in a host mammal and the treatment and/or prevention of bacterial contamination and fouling.

The pyrimidines derivatives, optionally with a detectable isotope, can also be used as radiotracer in diagnosis or prognosis of bacterial infection.

We have also found that such pyrimidine derivatives can be used in a method for controlling bacterial growth in biofilm formation at early stage such as step 1 or 2 or for killing bacteria at all steps of biofilm formation including the latest step 3 wherein the biofilm has reached its maturation stage of matrix formation and start detachment from the surface with a consequent spreading of bacteria into other locations.

DETAILED DESCRIPTION

Figure 1:
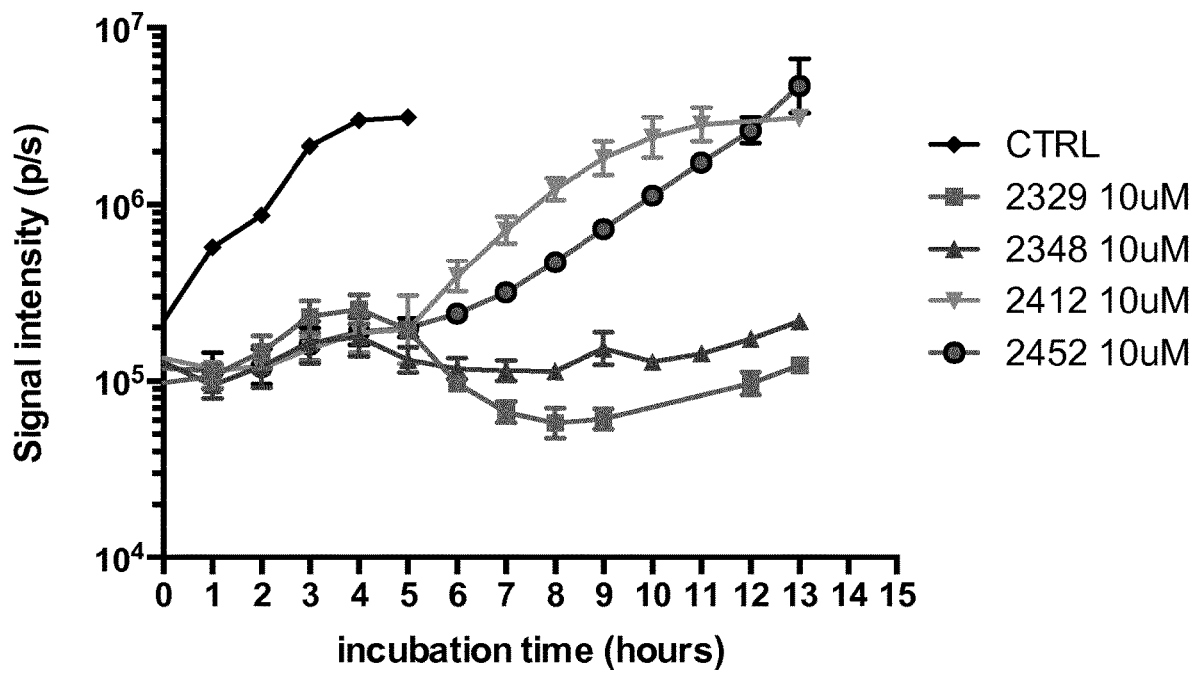
FIG. 1 illustrates the inhibition of *Staphylococcus aureus* (Xen29-ATCC 12600) biofilm formation (step 2) in medium containing the tested molecules 2329 (1c), 2348 (3c), 2412 (15c), 2452 (17c) at a concentration of 10 µM compared to medium containing the vehicle alone as control (CTRL).

In a first aspect, the invention provides new pyrimidine derivatives represented by formula (I)

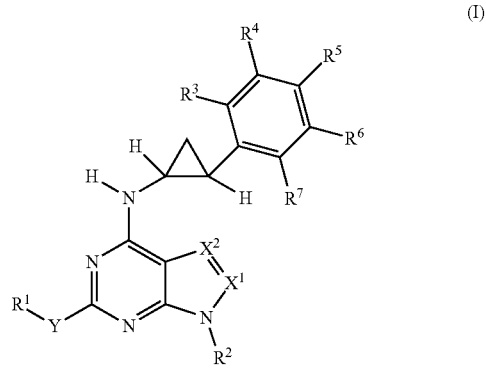

or isomers, racemic mixtures thereof, pharmaceutically acceptable acid addition salts, pharmaceutically acceptable metal salts, or alkylated ammonium salts or prodrug thereof; wherein:

$X^1$ and $X^2$ are independently N, CH, $CR^8$ wherein $R^8$ is $C_{1-6}$ alkyl, $C_{2-6}$ alkenyl or $C_{2-6}$ alkynyl; with the exception that if one of $X^1$ or $X^2$ is equal to N, then the remaining $X^1$ or $X^2$ are selected from CH, $CR^8$;

—Y— is —O— or —S—;

$R^1$ and $R^2$ are independently $C_{1-6}$-alkyl, $C_{2-6}$-alkenyl, $C_{2-6}$-alkynyl, $C_{3-6}$-cycloalkyl, aryl, aryl-$C_{1-6}$-alkyl wherein the alkyl or cycloalkyl moiety is optionally mono or polysubstituted with OH or an halogen and the aryl moiety is optionally mono or polysubstituted with an halogen, —$C_{1-6}$ alkyl, —$C_{1-6}$ alkoxy, —OH, —$NO_2$, —CN, —$NH_2$, —$NHR^8$, —$N(R^8)_2$ —COOH, —$COOR^8$, —$CONH_2$, —$CONHR^8$, —$CON(R^8)_2$, —$SO_2NH_2$, —$SO_2NHR^8$, or —$SO_2N(R^8)_2$;

$R^3$, $R^4$, $R^5$, $R^6$ and $R^7$ are independently H, an halogen, a $C_{1-6}$ alkyl, $C_{1-6}$ alkoxy, —OH, —$NO_2$, —CN, —$NH_2$, —$NHR^8$, —$N(R^8)_2$ —COOH, —$COOR^8$, —$CONH_2$, —$CONHR^8$, —$CON(R^8)_2$, —$SO_2NH_2$, —$SO_2NHR^8$, or —$SO_2N(R^8)_2$.

Within its scope, the invention includes all optical isomers of pyrimidine derivatives of formula (I), some of which are optically active, and also their mixtures including racemic mixtures thereof, but also their polymorphic forms.

The term "$C_{1-6}$-alkyl" as used herein, alone or in combination, refers to a straight or branched, saturated hydrocarbon chain having 1 to 6 carbon atoms such as for example methyl, ethyl, n-propyl, isopropyl, n-butyl, sec-butyl, isobutyl, tert-butyl, n-pentyl, 2-methylbutyl, 3-methylbutyl, n-hexyl, 4-methylpentyl, neopentyl, n-hexyl, 1,2-dimethylpropyl, 2,2-dimethylpropyl, 1,2,2-trimethylpropyl, and the like.

The term "$C_{2-6}$-alkenyl" as used herein, alone or in combination, refers to a straight or branched, unsaturated hydrocarbon chain having 2 to 6 carbon atoms with at least one carbon-carbon double bond such as for example vinyl, allyl, 1-butenyl, 2-butenyl, isobutenyl, 1-pentenyl, 2-pentenyl, 3-methyl-1-butenyl, 1-methyl-2-butenyl, 2,3-dimethyl-2-butenyl, 1-hexenyl, 2-hexenyl, 3-hexenyl and the like.

The term "$C_{2-6}$-alkynyl" as used herein, alone or in combination, refers to a straight or branched, unsaturated hydrocarbon chain having 2 to 6 carbon atoms with at least one carbon-carbon triple bond such as for example acetylenyl, propynyl, 1-butynyl, 2-butynyl, 1-pentynyl, 2-pentynyl, 3-methyl-1-butynyl, 1-hexynyl, 2-hexynyl, 3-hexenyl and the like.

The term "$C_{3-6}$-cycloalkyl" as used herein, alone or in combination refers to a radical of a saturated cyclic hydrocarbon with 3 to 6 carbon atoms such as cyclopropyl, cyclobutyl, cyclopentyl or cyclohexyl.

The term "aryl" as used herein, alone or in combination refers to a monocyclic or polycyclic aromatic ring having 6 to 20 carbon atoms, such as phenyl, anthracenyl, naphthyl and the like.

The term "$C_{1-6}$-alkoxy" as used herein, refers to a straight or branched monovalent substituent comprising a $C_{1-6}$-alkyl group linked through an ether oxygen having its free valence bond from the ether oxygen and having 1 to 6 carbon atoms e.g. methoxy, ethoxy, propoxy, isopropoxy, butoxy, pentoxy.

The term "—CN" as used herein refers to a carbon-nitrogen triple bond.

The term halogen as used herein refers to fluorine, chlorine, bromine or iodine.

The acceptable salts include pharmaceutically acceptable acid addition salts, pharmaceutically acceptable metal salts, or optionally alkylated ammonium salts, such as hydrochloric, hydrobromic, hydroiodic, phosphoric, sulfuric, trifluoroacetic, trichloroacetic, oxalic, maleic, pyruvic, malonic, succinic, citric, tartaric, fumaric, mandelic, benzoic, cinnamic, methanesulfonic, ethanesulfonic, picric acid and the like, and include acids related to the pharmaceutically acceptable salts listed in Journal of Pharmaceutical Science, 66, 2 (1977) and incorporated herein by reference, or lithium, sodium, potassium, magnesium and the like.

The term prodrug has been defined in Burger's Medicinal Chemistry and Drug discovery (5$^{th}$ edition 1995) as compounds, which undergo biotransformation prior to exhibiting their pharmacological effects. The term prodrug as used herein refers therefore to an analogue or a derivative of a compound of general formula (I) that comprises biohydrolysable moieties such as biohydrolysable ester functions, biohydrolysable carbamate functions, biohydrolysable ureides and the like obtained under biological conditions. Prodrugs can be prepared using well-known methods such as those described in Burgers medicinal chemistry and drug discovery (1995)172-178, 949-982 (Manfred E. Wolff).

In one embodiment, the invention relates to pyrimidine derivatives comprising an imidazolo group and are represented by formula (I) wherein $X^1$ is CH or $CR^8$ and $X^2$ is N; or an acceptable salt or prodrug thereof; said pyrimidine derivatives comprising an imidazolo group may also be called purine derivatives.

Preferred pyrimidine derivatives comprising an imidazolo group comprise a phenylcyclopropyl group as illustrated in formula (IV)

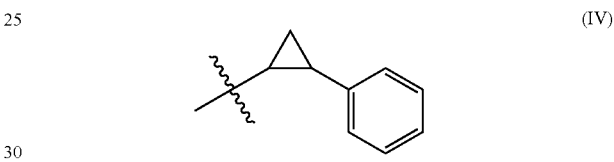

(IV)

such as for example 9-methyl-N-((1R,2S)-2-phenylcyclopropyl)-2-(propylthio)-9H-purin-6-amine (2c); or isomers, racemic mixtures thereof, pharmaceutically acceptable acid addition salts, pharmaceutically acceptable metal salts, or alkylated ammonium salts or prodrug thereof.

More preferred pyrimidine derivatives with an imidazolo group comprises a 3,4-difluorophenylcyclopropyl group as illustrated in formula II

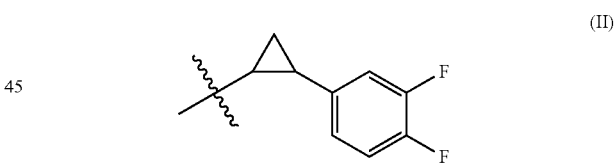

(II)

Most preferred pyrimidine derivatives with an imidazolo group are substituted by a 3,4-difluorophenylcyclopropylamino group as illustrated for example in formula (III)

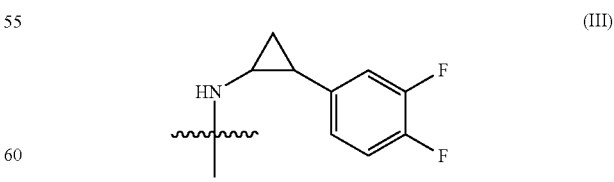

(III)

and are for example:
N-((1R,2S)-2-(3,4-difluorophenyl)cyclopropyl)-9-methyl-2-(propylthio)-9H-purin-6-amine (1c);
9-methyl-N-((1R,2S)-2-phenylcyclopropyl)-2-(propylthio)-9H-purin-6-amine (2c);

N-((1R,2S)-2-(3,4-difluorophenyl)cyclopropyl)-9-ethyl-2-(propylthio)-9H-purin-6-amine (3c);
N-((1R,2S)-2-(3,4-difluorophenyl)cyclopropyl)-9-propyl-2-(propylthio)-9H-purin-6-amine (4c);
N-((1R,2S)-2-(3,4-difluorophenyl)cyclopropyl)-9-isopropyl-2-(propylthio)-9H-purin-6-amine (5c);
9-cyclopropyl-N-((1R,2S)-2-(3,4-difluorophenyl)cyclopropyl)-2-(propylthio)-9H-purin-6-amine (6c);
9-butyl-N-((1R,2S)-2-(3,4-difluorophenyl)cyclopropyl)-2-(propylthio)-9H-purin-6-amine (7c);
9-(sec-butyl)-N-((1R,2S)-2-(3,4-difluorophenyl)cyclopropyl)-2-(propylthio)-9H-purin-6-amine (8c);
9-(tert-butyl)-N-((1R,2S)-2-(3,4-difluorophenyl)cyclopropyl)-2-(propylthio)-9H-purin-6-amine (9c);
9-cyclobutyl-N-((1R,2S)-2-(3,4-difluorophenyl)cyclopropyl)-2-(propylthio)-9H-purin-6-amine (10c);
N-((1R,2S)-2-(3,4-difluorophenyl)cyclopropyl)-9-pentyl-2-(propylthio)-9H-purin-6-amine (11c);
9-cyclopentyl-N-((1R,2S)-2-(3,4-difluorophenyl)cyclopropyl)-2-(propylthio)-9H-purin-6-amine (12c);
N-((1R,2S)-2-(3,4-difluorophenyl)cyclopropyl)-9-hexyl-2-(propylthio)-9H-purin-6-amine (13c);
9-cyclohexyl-N-((1R,2S)-2-(3,4-difluorophenyl)cyclopropyl)-2-(propylthio)-9H-purin-6-amine (14c);
9-allyl-N-((1R,2S)-2-(3,4-difluorophenyl)cyclopropyl)-2-(propylthio)-9H-purin-6-amine (15c);
2-(6-(((1R,2S)-2-(3,4-difluorophenyl)cyclopropyl)amino)-2-(propylthio)-9H-purin-9-yl)ethanol (16c);
N-((1R,2S)-2-(3,4-difluorophenyl)cyclopropyl)-9-(prop-2-yn-1-yl)-2-(propylthio)-9H-purin-6-amine (17c.);
N-((1R,2S)-2-(3,4-difluorophenyl)cyclopropyl)-2-(propylthio)-9-(2,2,2-trifluoroethyl)-9H-purin-6-amine (18c);
(1S,2R,3S,4R)-4-(6-(((1R,2S)-2-(3,4-difluorophenyl)cyclopropyl)amino)-2-(propylthio)-9H-purin-9-yl)cyclopentane-1,2,3-triol (19d);
N-((1R,2S)-2-(3,4-difluorophenyl)cyclopropyl)-2-(ethylthio)-9-methyl-9H-purin-6-amine (20c);
N-((1R,2S)-2-(3,4-difluorophenyl)cyclopropyl)-9-ethyl-2-(ethylthio)-9H-purin-6-amine (21c);
N-((1R,2S)-2-(3,4-difluorophenyl)cyclopropyl)-9-methyl-2-(methylthio)-9H-purin-6-amine (22c);
N-((1R,2S)-2-(3,4-difluorophenyl)cyclopropyl)-9-methyl-2-propoxy-9H-purin-6-amine hydrochloride (23t.HCl);
N-((1R,2S)-2-(3,4-difluorophenyl)cyclopropyl)-9-ethyl-2-(methylthio)-9H-purin-6-amine (24c);
2-(butylthio)-N-((1R,2S)-2-(3,4-difluorophenyl)cyclopropyl)-9-methyl-9H-purin-6-amine (25c);
2-(butylthio)-N-((1R,2S)-2-(3,4-difluorophenyl)cyclopropyl)-9-ethyl-9H-purin-6-amine (26c);
or isomers, racemic mixtures thereof, pharmaceutically acceptable acid addition salts, pharmaceutically acceptable metal salts, or alkylated ammonium salts or prodrug thereof.

The most preferred pyrimidine derivatives comprising an imidazolo group are:
N-((1R,2S)-2-(3,4-difluorophenyl)cyclopropyl)-9-methyl-2-(propylthio)-9H-purin-6-amine (1c);
N-((1R,2S)-2-(3,4-difluorophenyl)cyclopropyl)-9-ethyl-2-(propylthio)-9H-purin-6-amine (3c);
9-allyl-N-((1R,2S)-2-(3,4-difluorophenyl)cyclopropyl)-2-(propylthio)-9H-purin-6-amine (15c);
N-((1R,2S)-2-(3,4-difluorophenyl)cyclopropyl)-9-(prop-2-yn-1-yl)-2-(propylthio)-9H-purin-6-amine (17c);
(1S,2R,3S,4R)-4-(6-(((1R,2S)-2-(3,4-difluorophenyl)cyclopropyl)amino)-2-(propylthio)-9H-purin-9-yl)cyclopentane-1,2,3-triol (19d);
N-((1R,2S)-2-(3,4-difluorophenyl)cyclopropyl)-9-methyl-2-(methylthio)-9H-purin-6-amine (22c);
N-((1R,2S)-2-(3,4-difluorophenyl)cyclopropyl)-9-ethyl-2-(methylthio)-9H-purin-6-amine (24c);
N-((1R,2S)-2-(3,4-difluorophenyl)cyclopropyl)-2-(ethylthio)-9-methyl-9H-purin-6-amine (20c);
N-((1R,2S)-2-(3,4-difluorophenyl)cyclopropyl)-9-ethyl-2-(ethylthio)-9H-purin-6-amine (21c);
2-(butylthio)-N-((1R,2S)-2-(3,4-difluorophenyl)cyclopropyl)-9-methyl-9H-purin-6-amine (25c);
or isomers, racemic mixtures thereof, pharmaceutically acceptable acid addition salts, pharmaceutically acceptable metal salts, or alkylated ammonium salts or prodrug thereof.

In another embodiment, the invention relates to pyrimidine derivatives comprising a pyrazolo group and are represented by formula (I) wherein $X^1$ is N and $X^2$ is CH or $CR^8$; or isomers, racemic mixtures thereof, pharmaceutically acceptable acid addition salts, pharmaceutically acceptable metal salts, or alkylated ammonium salts or prodrug thereof.

Preferred pyrimidine derivatives comprising a pyrazolo group are substituted by a 3,4-difluorophenylcyclopropyl group, most preferred pyrimidine derivatives comprising a pyrazolo group are substituted by a 3,4-difluorophenylcyclopropylamino group as for example:
N-((1R,2S)-2-(3,4-difluorophenyl)cyclopropyl)-1-methyl-6-(methylthio)-1H-pyrazolo[3,4-d]pyrimidin-4-amine (27k);
N-((1R,2S)-2-(3,4-difluorophenyl)cyclopropyl)-6-(ethylthio)-1-methyl-1H-pyrazolo[3,4-d]pyrimidin-4-amine hydrochloride (28x.HCl);
N-((1R,2S)-2-(3,4-difluorophenyl)cyclopropyl)-6-(propylthio)-1-methyl-1H-pyrazolo[3,4-d]pyrimidin-4-amine hydrochloride (29x.HCl);
N-((1R,2S)-2-(3,4-difluorophenyl)cyclopropyl)-1-ethyl-6-(methylthio)-1H-pyrazolo[3,4-d]pyrimidin-4-amine (30k);
N-((1R,2S)-2-(3,4-difluorophenyl)cyclopropyl)-1-ethyl-6-(ethylthio)-1H-pyrazolo[3,4-d]pyrimidin-4-amine hydrochloride (31x.HCl);
N-((1R,2S)-2-(3,4-difluorophenyl)cyclopropyl)-1-ethyl-6-(propylthio)-1H-pyrazolo[3,4-d]pyrimidin-4-amine hydrochloride (32x.HCl);
N-((1R,2S)-2-(3,4-difluorophenyl)cyclopropyl)-1-isopropyl-6-(methylthio)-1H-pyrazolo[3,4-d]pyrimidin-4-amine hydrochloride (33k.HCl);
N-((1R,2S)-2-(3,4-difluorophenyl)cyclopropyl)-6-(methylthio)-1-propyl-1H-pyrazolo[3,4-d]pyrimidin-4-amine hydrochloride (34k.HCl);
or isomers, racemic mixtures thereof, pharmaceutically acceptable acid addition salts, pharmaceutically acceptable metal salts, or alkylated ammonium salts or prodrug thereof.

The most preferred pyrimidine derivatives comprising a pyrazolo group are:
N-((1R,2S)-2-(3,4-difluorophenyl)cyclopropyl)-1-methyl-6-(methylthio)-1H-pyrazolo[3,4-d]pyrimidin-4-amine (27k);
N-((1R,2S)-2-(3,4-difluorophenyl)cyclopropyl)-1-ethyl-6-(methylthio)-1H-pyrazolo[3,4-d]pyrimidin-4-amine (30k);
N-((1R,2S)-2-(3,4-difluorophenyl)cyclopropyl)-6-(ethylthio)-1-methyl-1H-pyrazolo[3,4-d]pyrimidin-4-amine hydrochloride (28xHCl);
N-((1R,2S)-2-(3,4-difluorophenyl)cyclopropyl)-1-isopropyl-6-(methylthio)-1H-pyrazolo[3,4-d]pyrimidin-4-amine hydrochloride (33kHCl);
or isomers, racemic mixtures thereof, pharmaceutically acceptable acid addition salts, pharmaceutically acceptable metal salts, or alkylated ammonium salts or prodrug thereof.

In another embodiment, the invention relates to pyrimidine derivatives comprising a pyrrolo group and are represented by formula (I) wherein $X^1$ and $X^2$ are CH or $CR^8$ or isomers, racemic mixtures thereof, pharmaceutically acceptable acid addition salts, pharmaceutically acceptable metal salts, or alkylated ammonium salts or prodrug thereof.

Preferred pyrimidine derivatives comprising a pyrrolo group, comprise a 3,4-difluorophenylcyclopropyl group. Most preferred pyrimidine derivatives comprising a pyrrolo group, comprise a 3,4-difluorophenylcyclopropylamino group.

The most preferred pyrimidine derivatives comprising a pyrrolo group is

N-((1R,2S)-2-(3,4-difluorophenyl)cyclopropyl)-7-ethyl-2-(methylthio)-7H-pyrrolo[2,3-d]pyrimidin-4-amine hydrochloride (35p.HCl);

or isomers, racemic mixtures thereof, pharmaceutically acceptable acid addition salts, pharmaceutically acceptable metal salts, or alkylated ammonium salts or prodrug thereof.

In a further aspect, the invention also relates to pyrimidine derivatives according to formula(I) or acceptable salt thereof comprising at least one detectable isotope.

A preferred pyrimidine derivative according to formula (I) comprises at least one detectable isotope selected from $^{3}H$, $^{18}F$, $^{19}F$, $^{11}C$, $^{13}C$, $^{14}C$, $^{75}Br$, $^{120}I$, $^{123}I$, $^{125}I$, $^{131}I$, $^{15}O$, and $^{13}N$.

Another preferred pyrimidine derivative according to formula (I) comprises a detectable isotope selected from $^{3}H$, $^{18}F$, $^{19}F$, $^{11}C$, $^{14}C$ and $^{123}I$.

A still other preferred pyrimidine derivative according to formula (I) comprises a detectable isotope selected from $^{18}F$ and $^{11}C$.

A most preferred pyrimidine derivative according to formula (I) or a salt thereof comprises the detectable isotope $^{18}F$.

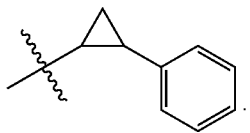

(IV)

The most preferred pyrimidine derivative comprising at least one detectable isotope also comprises a 3,4-difluorophenylcyclopropyl group.

In another aspect, the invention also relates to a new method of preparation of pyrimidine derivative represented by formula (I).

The pyrimidine derivative and acceptable salt thereof are prepared according to the following chemical pathways:

In the first embodiment, the pyrimidine derivative according to formula (I) or acceptable salts thereof, and comprising an imidazolo group or corresponding to purine derivatives are made according to a general common chemical pathway that comprises first: a preparation of a starting product, a 2-substituted-4,6-dihalogenopyrimidin-5-amine (Xh) such as for example a 2-substituted-4,6-dichloropyrimidin-5-amine according to scheme 1, and further reacting the starting product with reagents according to the following steps ib to iiib in scheme 2. The general chemical pathway is common for pyrimidine derivative with imidazolo group having —Y— equal to —S— or —O—. Formation of 3 intermediates Xa, Xb, Xc wherein $R^1$, $R^2$, $R^3$, $R^4$, $R^5$, $R^6$ and $R^7$ as defined in formula (I), are successively provided along the 3 steps ib to iiib.

Finally, pyrimidine derivative with an imidazolo group and having —Y═O— is differentiated by an additional chemical pathway that allows conversion of the thioether (wherein Y is S) pyrimidine derivative into a corresponding ether (Y═O) pyrimidine derivative (scheme 3).

1 Preparation of the Starting Product: 2-Substituted 4,6-Dihalogenopyrimidin-5-Amines Such as for Example 2-Substituted 4,6-Dichloropyrimidin-5-Amines According to the Following Chemical Pathway:

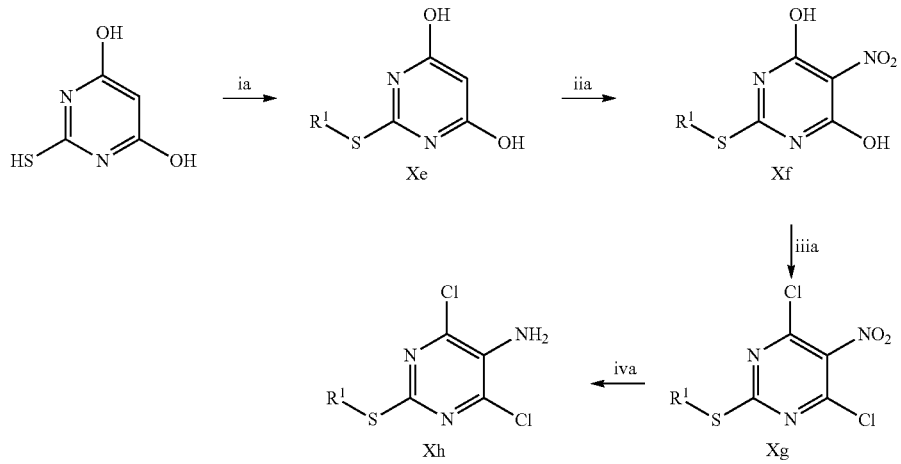

Preferred pyrimidine derivative or isomers, racemic mixtures thereof, pharmaceutically acceptable acid addition salts, pharmaceutically acceptable metal salts, or alkylated ammonium salts; comprising at least one detectable isotope also comprise a phenylcyclopropyl group (IV), wherein $R^1$ is defined as above in formula (I).

A 2-substituted 4,6-dihalogeno-5-nitropyrimidine Xg such as for example 2-substituted 4,6-dichloro-5-nitropyrimidine was obtained by reacting thiobarbituric acid with the halide $R^1$hal in aqueous alkaline medium such as KOH (step ia) at a temperature between 20° C. to 100° C., followed by a nitration reaction using nitric acid in the presence of another acid such as acetic acid at low temperature varying from −20° C. to room temperature (step iia) and an aromatic nucleophilic substitution at a varying temperature from −20° C. to 100° C. using an organic base such as for example diethylamine, 2,6 lutidine or the like, with a phosphoryl halide such as phosphoryl chloride (step iiia).

The 2-substituted 4,6-dihalogeno-5-nitropyrimidine Xg was then reduced at room temperature by iron in acidic medium such as for example acetic acid to obtain the corresponding 2-substituted 4,6-dihalogenopyrimidin-5-amine Xh such as for example 2-substituted 4,6-dichloropyrimidin-5-amine (step iva).

2° Reaction of Starting Product with Reagents According to the Following Steps ib to ivb dihalogenopyrimidin-5-amine (Xh) such as for example 2-substituted 4,6-dichloropyrimidin-5-amine and is carried out in an alcohol such as methanol at a temperature of for example 100° C.

The first step is followed by a ring closure reaction of the intermediate Xa by means of a trialkyl orthoformate such as triethyl orthoformate carried out at a temperature of for example 130° C., in the presence of an acid such as for example acetic acid (step iib) to obtain the corresponding intermediates 2,9-disubstituted 6-halogeno-9H-purines (Xb) such as for example 2,9-disubstituted 6-chloro-9H-purines.

In step iiib, 2,9-disubstituted N—(($R^3$-$R^7$)-substituted phenyl)cyclopropyl-9H-purin-6-amines (Xc) are obtained by nucleophilic substitution of the halogen atom preferably a chlorine atom of intermediate Xb by a ($R^3$-$R^7$)-substituted phenylcyclopropylamine at a temperature of for example 90° C.

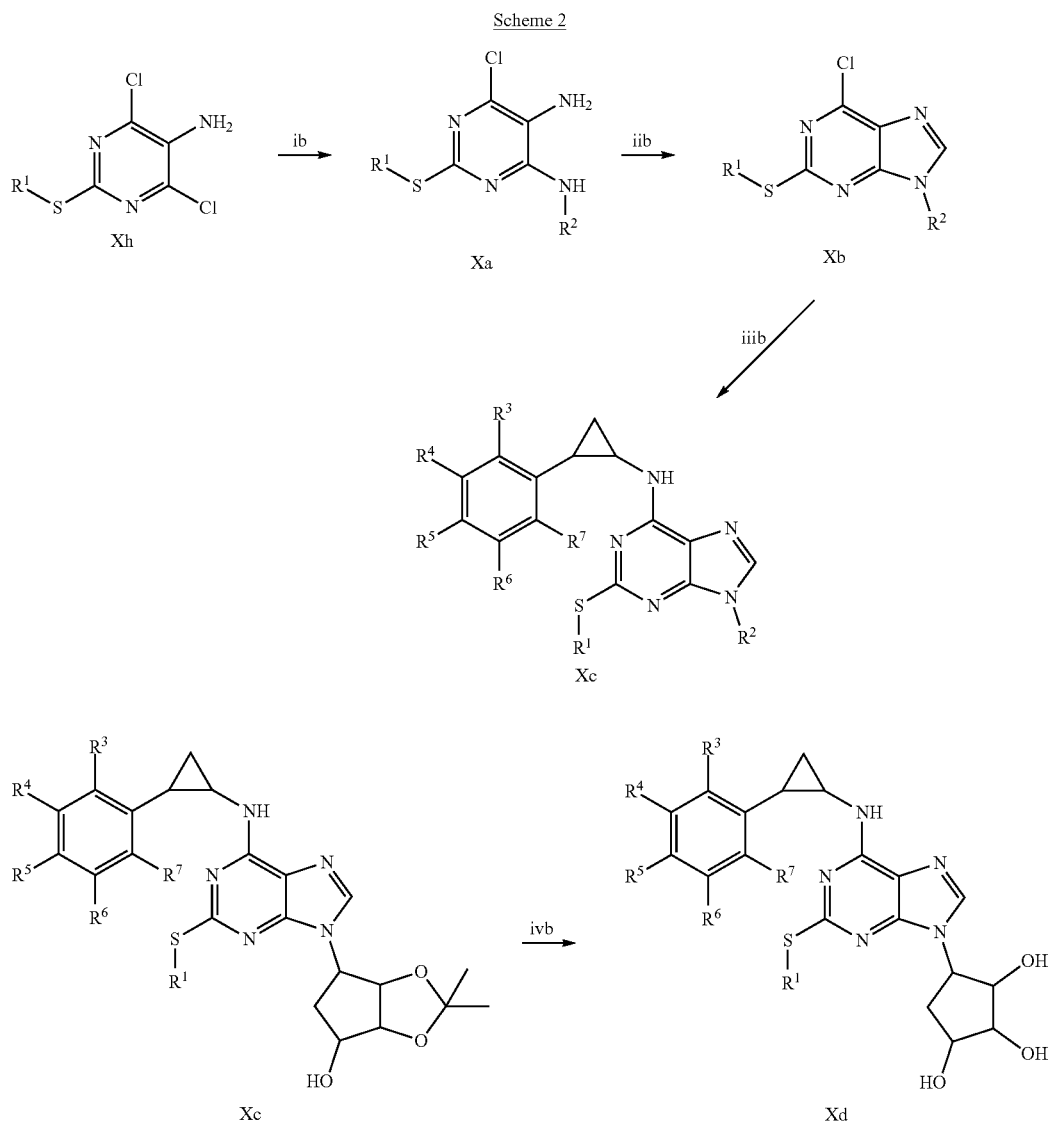

In a first step (ib), $N^4$,2-disubstituted 6-halogenopyrimidine-4,5-diamines (Xa) such as for example $N^4$,2-disubstituted 6-chloropyrimidine-4,5-diamines is obtained by reaction of $R^2NH_2$ with the 2-substituted 4,6-

In case of an acetonide of a pentane-1,2,3-triol intermediate, deprotection occurred in acidic hydroalcoholic conditions to provide a pentane-1,2,3-triol Xd (step ivb). The reaction is carried out at a room temperature.

3° Conversion of the Thioether (Y=S) Pyrimidine Derivative into a Corresponding Ether (Y=O) Pyrimidine Derivative:

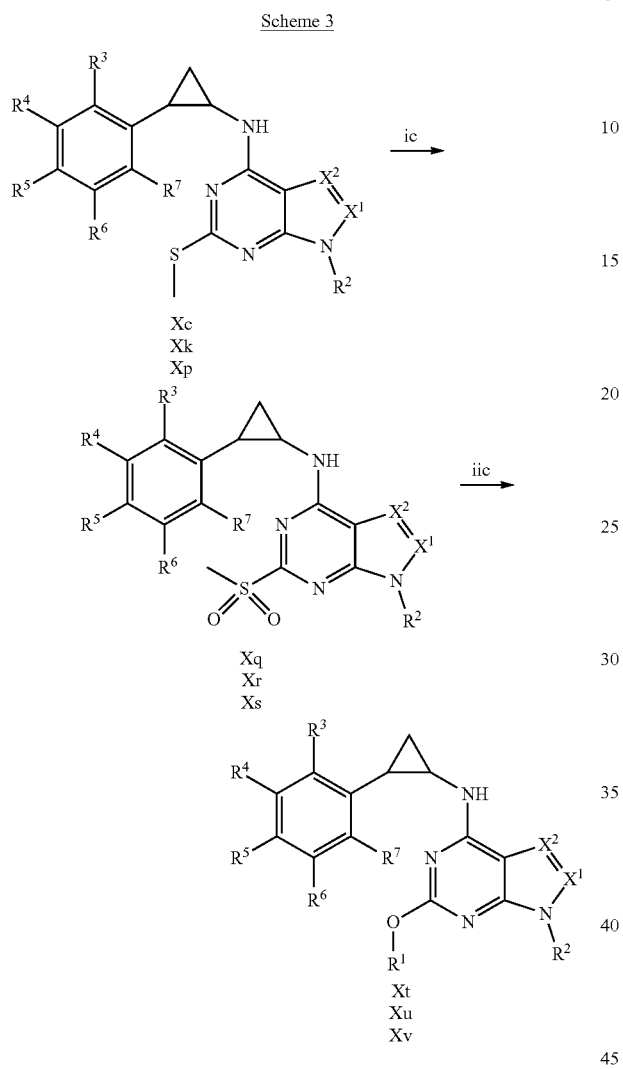

Scheme 3

Compounds Xt, Xu and Xv that correspond to pyrimidine derivative comprising respectively an imidazolo group (Xt), a pyrazolo (Xu) and a pyrrolo group (Xv), may be obtained in two steps starting from the corresponding methylthio compound Xc, Xk and Xp (scheme 3).

The first reaction consists in the oxidation of the sulfur atom of this thioether function, resulting in a methylsulfonyl group (step ic) carried out at room temperature or under heating. The substitution of Xq, Xr and Xs with an alcoolate led to the ether derivatives Xt, Xu and Xv (step iic) carried out at a temperature between 10° C. and 80° C.

Alternatively compounds Xw, Xx, Xy that corresponds to pyrimidine derivatives of formula (I) comprising respectively an imidazolo, a pyrazolo or a pyrrolo group and wherein Y is equal to S and R¹ is different from —CH₃, may be obtained according to scheme 3bis. It corresponds to a conversion of methylsulfanyl-substituted pyrimidine derivative wherein Y is S and R¹ is a methyl group into other corresponding alkylsulfanyl-substituted pyrimidine derivatives wherein Y is S and R¹ is different from a methyl group. The conversion is carried out in two steps. A first step starting from a corresponding methylthio compound Xc, Xk, Xp is an oxidation reaction of the sulphur atom of the thioether function resulting in a methylsulfonyl group (step ic) carried out at room temperature or under heating as in scheme 3.

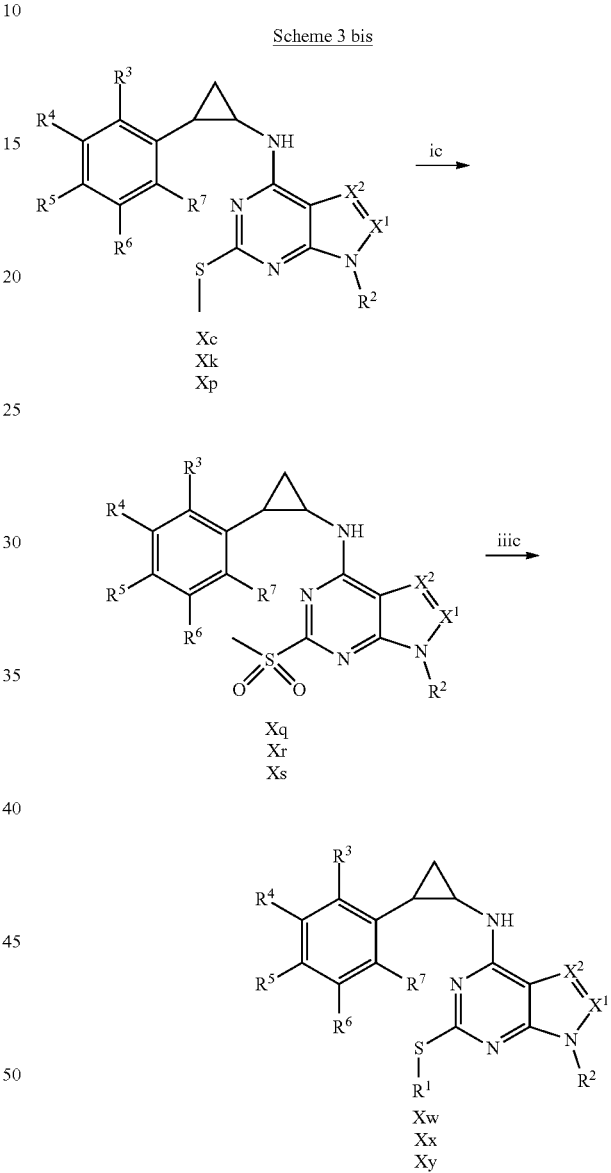

Scheme 3 bis

The second step (iiic in scheme 3bis) is a substitution reaction of the methylsulfonyl group in Xq, Xr, Xs with an alkylthiol leading to the alkylsulfanyl-substituted derivatives Xw, Xx, Xy wherein R¹ is different from —CH₃. The substitution reaction is carried out at a temperature between 10° C. and 100° C.

In the second embodiment, the preparation of the pyrimidine derivative comprising a pyrazolo group and represented by formula (I) wherein X¹ is N and X² is CH or CR⁸; or an acceptable salt thereof are generally made according to the following chemical pathway:

Scheme 4

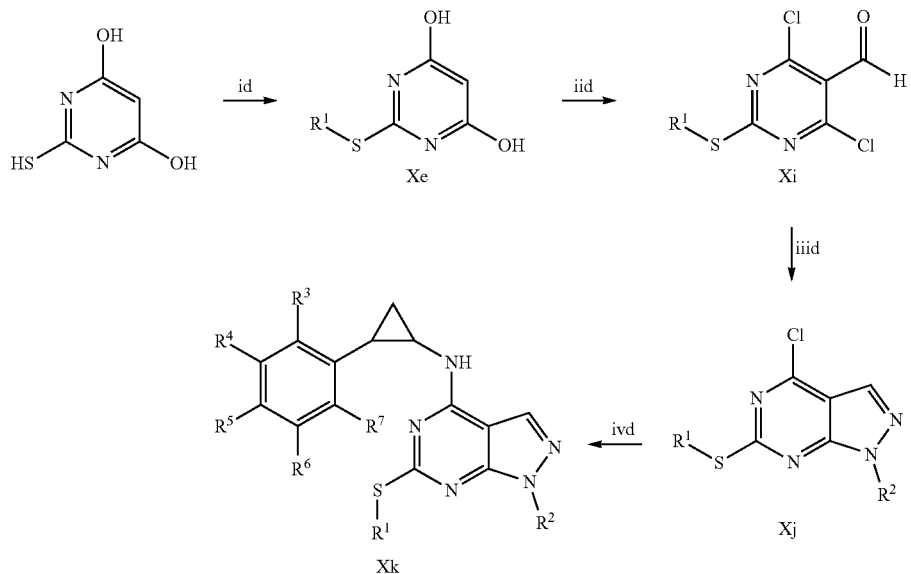

wherein R¹, R², R³, R⁴, R⁵, R⁶ and R⁷ are defined in the general formula (I).

After reaction between thiobarbituric acid and R¹-halide at a temperature of for example 80° C. (step id), the 2-substituted pyrimidine 4,6-diol Xe is reacted with phosphoryl halide such as for example phosphoryl chloride in presence of DMF at a temperature between 0° C. and 110° C. to obtain the corresponding 2-substituted 4,6-dichloro-pyrimidine-5-carbaldehyde Xi (step iid).

The ring closure reaction of Xi by means of a substituted hydrazine provided the corresponding 1H-pyrazolo[3,4-d]pyrimidine Xj at a temperature between –80° C. and 20° C. (step iiid).

Further conversion of the thioether (Y=S) pyrimidine derivative into a corresponding ether (Y=O) pyrimidine derivative (Xu) can be made according to scheme 3 as described above.

Alternatively the pyrimidine derivatives of formula (I) comprising a pyrazolo group may be prepared according to scheme 4bis wherein step (id) and (iid) are identical to scheme 4 but the ring closure of Xi is carried out in step (vd) by a non-substituted hydrazine to provide a non-alkylated 1H-pyrazolo[3,4-d]pyrimidine Xi' at a temperature between –80° C. and 20° C. (step vd), followed in step vid by a N-alkylation to provide Xj at a temperature between 0° C. and 80° C.

Scheme 4bis

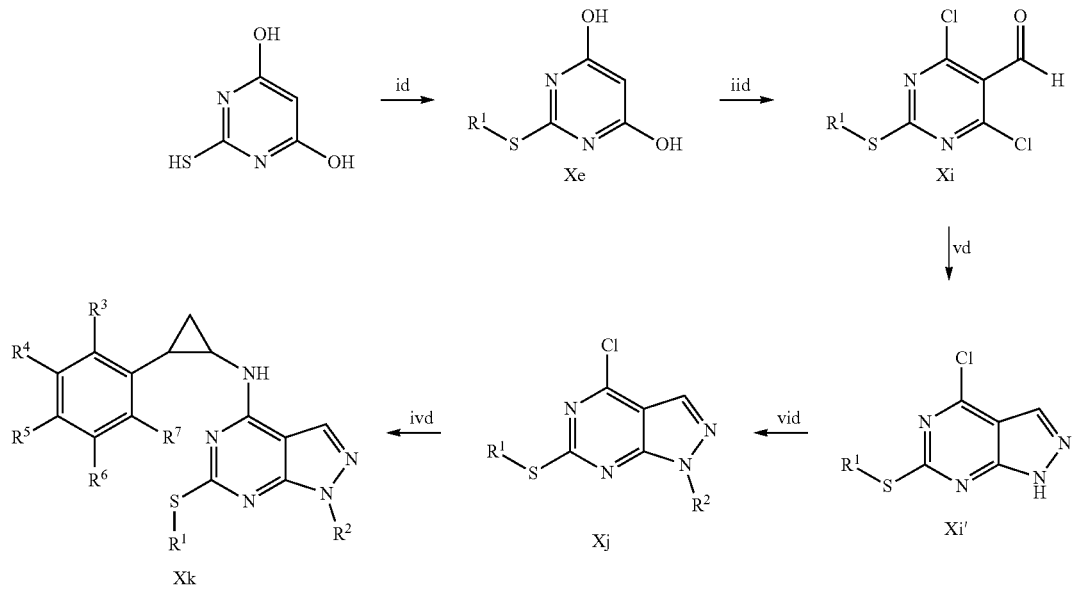

In the third embodiment, the preparation of the pyrimidine derivatives comprising a pyrrolo group and represented by formula (I) wherein $X^1$ and $X^2$ are CH or $CR^8$ or an acceptable salt thereof are generally made according to the following chemical pathway:

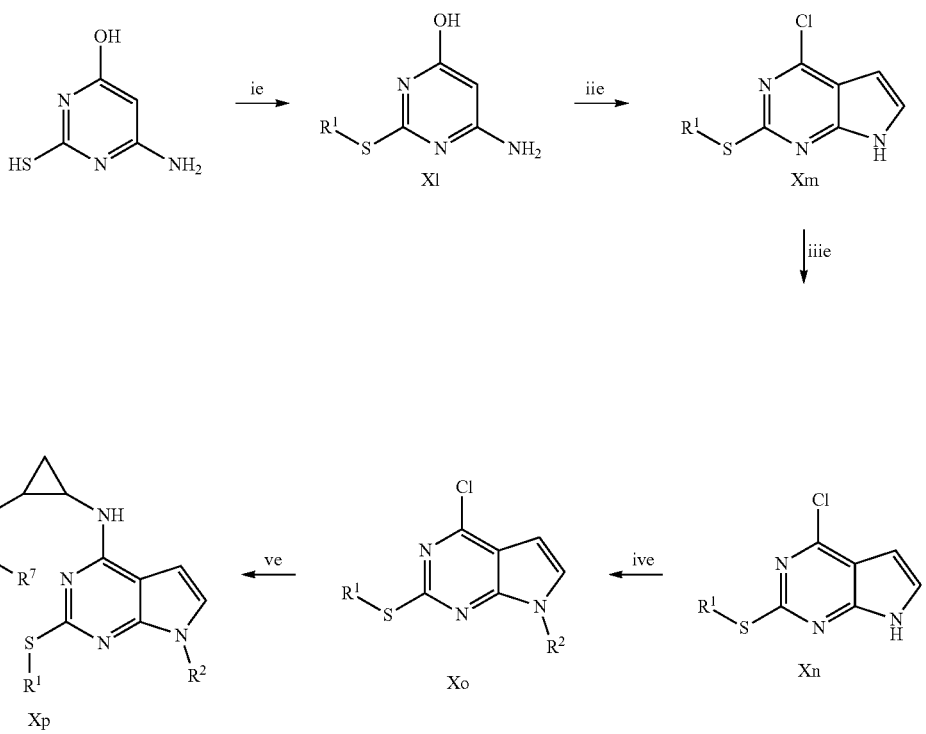

wherein $R^1$, $R^2$, $R^3$, $R^4$, $R^5$, $R^6$ and $R^7$ are defined as defined in formula (I).

The 2-substituted 6-amino-4-hydroxypyrimidine Xl was obtained by reacting 6-amino-2-mercaptopyrimidine-4-ol with the $R^1$-halide in alkaline medium a temperature between 70° C. and 110° C. (step ie).

Xl is converted into the corresponding 7H-pyrrolo[2,3-d] pyrimidine Xm by means of an halogenoacetaldehyde such as chloroacetaldehyde at a temperature between 60° C. and 100° C. (step iie).

An aromatic nucleophilic substitution using phosphoryl halide such as for example phosphoryl chloride at a temperature between 0° C. and 110° C. is then achieved to give Xn (step iiie), followed by a N-alkylation to give Xo (step ive) at a temperature between 0° C. and 100° C.

2,7-disubstituted N—(($R^3$-$R^7$)-substituted phenyl)cyclopropyl-7H-pyrrolo[2,3-d]pyrimidin-4-amines (Xp) were obtained by nucleophilic substitution of the chlorine atom of Xo by the appropriate phenylcyclopropylamine at a temperature between 40° C. and 90° C. (step ve).

Alternatively, the pyrimidine derivative comprising a pyrrolo group and represented by formula (I) wherein $X^1$ and $X^2$ are CH or $CR^8$ may be provided according to scheme 5bis, wherein step ie to iiie are identical to scheme 5 but the nucleophilic substitution of the halogen atom such as for example the chlorine atom in Xn is carried out with a ($R^3$-$R^7$)-substituted phenylcyclopropylamine at a temperature between 40° C. and 90° C. (step vie) to provide Xo', followed by the N-alkylation with a $R^2$-halide at a temperature between 0° C. and 100° C. (step viie) to provide Xp

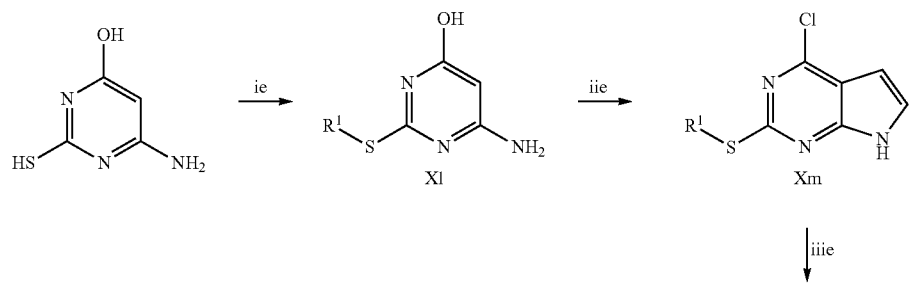

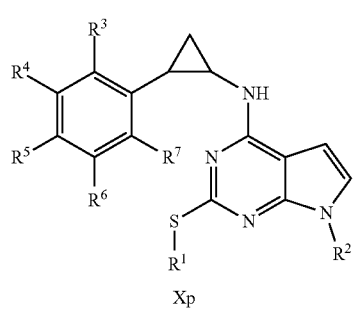
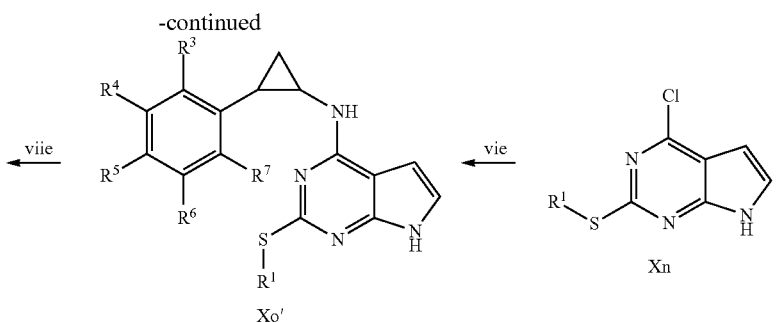

Further conversion of the thioether (Y=S) pyrimidine derivative into a corresponding ether(Y=O) pyrimidine derivative (Xv) can be made according to scheme 3 described above.

The same reactions are used for the preparation of pyrimidine derivatives represented by formula(I) or an acceptable salt thereof comprising at least one detectable isotope, with incorporation of the detectable isotope as the last step. Such incorporation of the detectable isotope or labelling step is well known to the one skilled in the art and is described in the art for example in Lanström et al Acta. Chem. Scand 1999, 53,651.

In a second aspect, the invention provides pyrimidine derivative of formula (I) or acceptable salt or prodrug thereof, for use in the treatment or prevention of bacterial infection in a host mammal in need of such treatment or prevention.

The term "bacterial infection" as used herein generally refers to the presence of undesirable bacteria and, while primarily relating to the an invasion of a body, body tissues or cells by bacteria, it is used interchangeably herein to also refer to bacterial fouling (which typically refers to unwanted contamination on surfaces, such as on bio-sensors, cardiovascular implants, catheters, contact lenses, and surgical tools) or other types of contamination (as in food, feed and other fluid products).

The source of bacterial contamination or infection may be diverse.

Infections caused by Gram-positive bacteria represent a major public health burden, not just in terms of morbidity and mortality, but also in terms of increased expenditure on patient management and implementation of infection control measures. *Staphylococcus aureus* and *enterococci* are established bacteria in the hospital environment, and their frequent multidrug resistance complicates therapy.

*Staphylococcus aureus* is an important bacterium responsible for a broad range of clinical manifestations ranging from relatively benign skin infections to life-threatening conditions such as endocarditis and osteomyelitis. It is also a commensal bacterium (colonizing approximately 30 percent of the human population).

Two major shifts in *S. aureus* epidemiology have occurred since the 1990s: an epidemic of community-associated skin and soft tissue infections (largely driven by specific methicillin-resistant *S. aureus* [MRSA] strains), and an increase in the number of healthcare-associated infections (especially infective endocarditis and prosthetic device infections).

The emergence of Glycopeptide antibiotic resistance found in the strain named glycopeptide intermediate *S. aureus* (GISA) is another source of great concern because, especially in hospitals, this class of antibiotics, particularly vancomycin, is one of the main resources for combating infections caused by methicillin-resistant *Staphylococcus aureus* strains (MRSA). Although the prevalence of GISA is relatively low (accounting for approximately 1.3% of all MRSA isolates tested), mortality due to GISA infections is very high (about 70%), especially among patients hospitalised in high-risk departments, such as intensive care units (ICU).

Coagulase-negative staphylococci (CoNS) are the most frequent bacteria of the normal flora of the skin. These bacteria are common contaminants in clinical specimens and are recognized as agents of clinically significant infection, including bacteremia and endocarditis. Patients at particular risk for CoNS infection include those with prosthetic devices, pacemakers, intravascular catheters, and immuno-compromised hosts.

Coagulase-negative staphylococci account for approximately one-third of bloodstream isolates in intensive care units, making these organisms the most common cause of nosocomial bloodstream infection.

Enterococcal species can cause a variety of infections, including urinary tract infections, bacteremia, endocarditis, and meningitis. Enterococci are relatively resistant to the killing effects of cell wall-active agents (penicillin, ampicillin, and vancomycin) and are impermeable to aminoglycosides.

Vancomycin-resistant enterococci (VRE) are an increasingly common and difficult-to-treat cause of hospital-acquired infection.

Multiple epidemics of VRE infection have been described in diverse hospital settings (e.g., medical and surgical intensive care units, and medical and pediatric wards) and, like methicillin-resistant *Staphylococcus aureus*, VRE is endemic in many large hospitals.

Beta-hemolytic *Streptococcus agalactiae* (Group B *Streptococcus*, GBS) is another Gram-positive bacteria. The bacteria can cause sepsis and/or meningitis in the newborn infants. It is also an important cause of morbidity and mortality in the elderly and in immuno-compromised adults. Complications of infection include sepsis, pneumonia, osteomyelitis, endocarditis, and urinary tract infections.

Besides human medicine, companion animals, such as cats, dogs, and horses, can also be colonized and infected by MRSA, without host adaptation, and therefore may act as reservoirs for human infections. Bacteria can also develop distinct resistance when hosted by animals.

In particular embodiments, the bacterial infection is an infection by Gram-positive bacteria. In further particular embodiments, the bacterial infection is an infection by *Staphylococcus aureus* and/or *enterococci* and/or *streptococci*.

In particular embodiments, the bacterial infection is caused by a bacteria that is resistant to traditional antibacterial agents. In further particular embodiments, the bacterial infection is caused by one or more of methicillin-resistant *S. aureus* (MRSA), methicillin-resistant *S. epidermidis* (MRSE), glycopeptide intermediate *S. aureus* (GISA), Coagulase-negative staphylococci (CoNS), Vancomycin-resistant enterococci (VRE), beta-hemolytic *Streptococcus agalactiae* (Group B *Streptococcus*, GBS).

By bacterial infection one means particularly Gram-positive bacterial infection such as for example pneumonia, septicemia, endocarditis, osteomyelitis, meningitis, urinary tract, skin, and soft tissue infections. The source of bacterial infection can be diverse, and can be caused for example by the use of biomaterial implants.

By biomaterials, or biomaterial implant, one means all implantable foreign material for clinical use in host mammals such as for prosthetic joints, pacemakers, implantable cardioverter-defibrillators, intravascular or urinary catheters, stent including coronary stent, prosthetic heart valves, bioprostheses, intraocular lens, dental implants, breast implants, endotracheal tubes, gastrostomy tubes and the like.

By host mammal, one means preferably a human, but also an animal in need of treatment or prevention of bacterial treatment.

By prevention of bacterial infection, one means a reduction in risk of acquiring infection, or reduction or inhibition of recurrence of infection. For example, the pyrimidine derivatives may be administered as prevention before a surgical treatment to prevent infection.

In the first embodiment pyrimidine derivatives for use in the treatment or prevention of bacterial infection are pyrimidine derivatives comprising an imidazolo group wherein $X^1$ is CH or $CR^8$ and $X^2$ is N in formula (I).

We have surprisingly found that said pyrimidine derivatives comprising an imidazolo group, preferably with the presence of a difluorophenylcyclopropyl group exhibit antibiotic activity.

Preferred and most preferred pyrimidine derivatives comprising an imidazolo group, or an acceptable salt or prodrug thereof, for use in the treatment or prevention of bacterial infection are the ones described in the first aspect of the invention.

In another embodiment the pyrimidine derivatives for use in the treatment or prevention of bacterial infection are pyrimidine derivatives comprising a pyrazolo group wherein $X^1$ is N and $X^{2\ is}$ CH or $CR^8$ in formula (I).

Again said pyrimidine derivatives comprising a pyrazolo group, preferably with the presence of a difluorophenylcyclopropyl group exhibits also surprisingly antibiotic activity.

Preferred and most preferred pyrimidine derivatives comprising a pyrazolo group,
or isomers, racemic mixtures thereof, pharmaceutically acceptable acid addition salts, pharmaceutically acceptable metal salts, or alkylated ammonium salts or prodrug thereof, for use in the treatment or prevention of bacterial infection are the ones described in the first aspect of the invention.

In another embodiment pyrimidine derivatives for use in the treatment or prevention of bacterial infection are pyrimidine derivatives comprising a pyrrolo group wherein $X^1$ and $X^2$ are CH or $CR^8$ in formula (I).

Again said pyrimidine derivatives comprising a pyrrolo group, preferably with the presence of a difluorophenylcyclopropyl group, also exhibit surprisingly antibiotic activity.

Preferred and most preferred pyrimidine derivatives comprising a pyrrolo group, or an acceptable salt or prodrug thereof, for use in the treatment or prevention of bacterial infection are the ones described in the first aspect of the invention.

In particular embodiments, the pyrimidine derivatives according to the invention are administered to the patient over several days (especially in case of prevention). The pyrimidine derivatives may be administered on their own or as a pharmaceutical composition, with non-toxic doses being inferior to 3 g per day.

A further preferred aspect of the invention is a pharmaceutical composition of pyrimidine derivative of formula (I) or isomers, racemic mixtures thereof, pharmaceutically acceptable acid addition salts, pharmaceutically acceptable metal salts, or alkylated ammonium salts or prodrug thereof; for use in the prevention or treatment of bacterial infection.

The pharmaceutical composition may be a dry powder or a liquid composition having physiological compatibility. The compositions include, in addition to pyrimidine derivative, auxiliary substances, preservatives, solvents and/or viscosity modulating agents. By solvent, one means for example water, saline or any other physiological solution, ethanol, glycerol, oil such as vegetable oil or a mixture thereof. By viscosity modulating agent on means for example carboxymethylcellulose.

The pyrimidine derivative of the present invention exhibits its effects through oral, intravenous, intravascular, intramuscular, parenteral, or topical administration, and can be additionally used into a composition for parenteral administration, particularly an injection composition or in a composition for topical administration. It may also be loaded in nanoparticles for nanomedicine applications or PEGylated to improve its bioavailability, particularly when used in an aerosol composition. An aerosol composition is for example a solution, a suspension, a micronised powder mixture and the like. The composition is administered by using a nebulizer, a metered dose inhaler or a dry powder inhaler or any device designed for such an administration.

Examples of galenic compositions include tablets, capsules, powders, pills, syrups, chewing, granules, and the like. These may be produced through well known technique and with use of typical additives such as excipients, lubricants, and binders.

Suitable auxiliary substances and pharmaceutical compositions are described in Remington's Pharmaceutical Sciences, 16th ed., 1980, Mack Publishing Co., edited by Oslo et al. Typically, an appropriate amount of a pharmaceutically-acceptable salt is used in the composition to render the composition isotonic. Examples of pharmaceutically acceptable substances include saline, Ringer's solution and dextrose solution. pH of the solution is preferably from about 5 to about 8, and more preferably from about 7 to about 7.5.

A still further aspect of the invention is a method of treatment or prevention of bacterial infection in a host mammal in need of such treatment or prevention. The method comprises administering to the host an effective amount of pyrimidine derivative as defined in formula (I) or isomers, racemic mixtures thereof, pharmaceutically acceptable acid addition salts, pharmaceutically acceptable metal salts, or alkylated ammonium salts or prodrug thereof; preferably a pyrimidine derivative that is substituted with a difluorophenylcyclopropyl group; such as for example the ones selected in the first aspect of the invention; and most preferably a pyrimidine derivative selected from the group:
N-((1R,2S)-2-(3,4-difluorophenyl)cyclopropyl)-9-methyl-2-(propylthio)-9H-purin-6-amine (1c);
9-allyl-N-((1R,2S)-2-(3,4-difluorophenyl)cyclopropyl)-2-(propylthio)-9H-purin-6-amine (15c);
N-((1R,2S)-2-(3,4-difluorophenyl)cyclopropyl)-9-(prop-2-yn-1-yl)-2-(propylthio)-9H-purin-6-amine (17c);

(1S,2R,3S,4R)-4-(6-(((1R,2S)-2-(3,4-difluorophenyl)cyclopropyl)amino)-2-(propylthio)-9H-purin-9-yl)cyclopentane-1,2,3-triol (19d);

N-((1R,2S)-2-(3,4-difluorophenyl)cyclopropyl)-9-methyl-2-(methylthio)-9H-purin-6-amine (22c);

N-((1R,2S)-2-(3,4-difluorophenyl)cyclopropyl)-9-ethyl-2-(methylthio)-9H-purin-6-amine (24c);

N-((1R,2S)-2-(3,4-difluorophenyl)cyclopropyl)-2-(ethylthio)-9-methyl-9H-purin-6-amine (20c);

N-((1R,2S)-2-(3,4-difluorophenyl)cyclopropyl)-9-ethyl-2-(ethylthio)-9H-purin-6-amine (21c);

2-(butylthio)-N-((1R,2S)-2-(3,4-difluorophenyl)cyclopropyl)-9-methyl-9H-purin-6-amine (25c);

N-((1R,2S)-2-(3,4-difluorophenyl)cyclopropyl)-1-methyl-6-(methylthio)-1H-pyrazolo[3,4-d]pyrimidin-4-amine (27k);

N-((1R,2S)-2-(3,4-difluorophenyl)cyclopropyl)-1-ethyl-6-(methylthio)-1H-pyrazolo[3,4-d]pyrimidin-4-amine (30k);

N-((1R,2S)-2-(3,4-difluorophenyl)cyclopropyl)-6-(ethylthio)-1-methyl-1H-pyrazolo[3,4-d]pyrimidin-4-amine hydrochloride (28x.HCl);

N-((1R,2S)-2-(3,4-difluorophenyl)cyclopropyl)-1-isopropyl-6-(methylthio)-1H-pyrazolo[3,4-d]pyrimidin-4-amine hydrochloride(33k.HCl);

N-((1R,2S)-2-(3,4-difluorophenyl)cyclopropyl)-7-ethyl-2-(methylthio)-7H-pyrrolo[2,3-d]pyrimidin-4-amine hydrochloride (35p.HCl);

or isomers, racemic mixtures thereof, pharmaceutically acceptable acid addition salts, pharmaceutically acceptable metal salts, or alkylated ammonium salts or prodrug thereof.

In still a further aspects, the invention provides the use of pyrimidine derivatives of formula (I) or isomers, racemic mixtures thereof, pharmaceutically acceptable acid addition salts, pharmaceutically acceptable metal salts, or alkylated ammonium salts or prodrug thereof as inhibitor of biofilm formation on a surface of a biomaterial implant in a host mammal.

More particularly, the invention provides derivatives of formula (I) or isomers, racemic mixtures thereof, pharmaceutically acceptable acid addition salts, pharmaceutically acceptable metal salts, or alkylated ammonium salts or prodrug thereof; for use in the prevention of a bacterial infection, wherein said pyrimidine derivative is applied to the surface of a biomaterial implant. In particular embodiments, the infection is an infection of implant-related infections (i.e. caused by the presence of the implant). Similarly, the invention provides for the use of the derivatives of the invention as described herein for the prevention and treatment of bacterial contamination or fouling, such as of an implant. It will be understood that throughout the description, the use of the derivatives is envisaged for these different in vivo, ex vivo and in vitro aspects.

Biomaterial implants such as for example pacemakers and implantable cardioverter-defibrillators [ICDs]) can become infected, with a rate of infections ranging from 0.8 to 5.7 percent.

The infection can involve subcutaneous pocket containing the biomaterial implant or subcutaneous segment of the leads. Deeper infection can also occur that involves the transvenous portion of the lead, usually with associated bacteremia and/or endovascular infection. This implies that patients that have such implants suffer from diseases related thereto.

The implant and/or pocket itself can be source of infection, usually due to contamination at the time of implantation, or can be secondary to bacteremia from a different source.

Perioperative contamination of the pacemaker pocket with skin flora appears to be the most common source of subcutaneous infection.

For instance, Cardiac implant-related infective endocarditis (CDRIE) is a life-threatening condition, with increasing incidence due to growing number of implantations (81,000 pacemaker implantation per year in Europe).

*Staphylococcus aureus* and coagulase-negative staphylococci (often *Staphylococcus epidermidis*) cause 65 to 75 percent of generator pocket infections and up to 89 percent of device-related endocarditis. Episodes arising within two weeks of implantation are more likely to be due to *S. aureus*.

Successful treatment of an infected biomaterial implant, regardless of the involved component, generally requires removal of the implant and administration of antibiotics targeting the causative bacteria. Importantly, medical therapy alone is associated with high mortality and risk of recurrence.

Prosthetic valve endocarditis (PVE) is a serious infection with potentially fatal consequences.

Bacteria can reach the valve prosthesis by direct contamination intraoperatively or via hematogenous spread during the initial days and weeks after surgery. The bacteria have direct access to the prosthesis-annulus interface and to perivalvular tissue along suture pathways because the valve sewing ring, cardiac annulus, and anchoring sutures are not endothelialized early after valve implantation. The valve's structures are coated with host proteins, such as fibronectin and fibrinogen, to which bacteria can adhere and initiate infection.

The most frequently encountered bacteria in early PVE (within two months of implantation) are *S. aureus* and coagulase-negative staphylococci.

The most frequently encountered bacteria in late PVE (two months after valve implantation) are streptococci and *S. aureus*, followed by coagulase-negative staphylococci and enterococci.

Coagulase-negative staphylococci causing PVE during the initial year after surgery are almost exclusively *Staphylococcus epidermidis*. Between 84 and 87 percent of said bacteria are methicillin resistant and thus resistant to all beta-lactam antibiotics.

Periprosthetic joint infection (PJI) is another pathogenesis that occurs in 1 to 2 percent of joint replacement surgeries and is a leading cause of arthroplasty failure.

Biofilms play an important role in the pathogenesis of PJIs. Bacteria within biofilm become resistant to therapy; as a result, antibacterial therapy is often unsuccessful unless the biofilm is physically disrupted or removed by surgical debridement.

Prosthetic joint infections have the following characteristics. Early-onset infections are usually acquired during implantation and are often due to virulent bacteria, such as *Staphylococcus aureus*, or mixed infections. Delayed-onset infections are also usually acquired during implantation. Consistent with the indolent presentation, delayed infections are usually caused by less virulent bacteria, such as coagulase-negative staphylococci or enterococci. Late-onset infections resulting from hematogenous seeding are typically acute and often due to *S. aureus*, or beta hemolytic streptococci.

The present invention allows to inhibit Periprosthetic joint infection (PJIs) without surgery. In particular embodiments, the implant is treated with the pyrimidine derivatives of the invention prior to implantation. Additionally or alternatively, the patient is administered the pyrimidine derivatives of the invention to prevent or treat the infection.

In further aspects the invention provides the use of pyrimidine derivatives of formula (I) or salts thereof as inhibitor of biofilm formation on a surface of a medical device susceptible to be used as a biomaterial implant or not.

In particular embodiments, the biofilm formation is caused by Gram-positive bacteria.

By medical device one particularly means any instrument, tool device like for example surgical device, needle, tube, gloves and the like relating to medicine or the practice of human or veterinary medicine, or intended for use to heal or treat or prevent a disease, such as for example an oxygenator, peristaltic pump chambers, kidney membranes and the like; medical product such as wound dressing, soft tissue fillers, root canal fillers, contact lens, blood bag; but also biomaterials that need to be sterile to be introduced in the mammal host, Preferably pyrimidine derivatives of formula (I) or an acceptable salt or prodrug thereof is bearing difluorophenylcyclopropyl group;
and are most preferably (N-((1R,2S)-2-(3,4-difluorophenyl)cyclopropyl)-9-methyl-2-(propylthio)-9H-purin-6-amine (1c);
9-allyl-N-((1R,2S)-2-(3,4-difluorophenyl)cyclopropyl)-2-(propylthio)-9H-purin-6-amine (15c);
N-((1R,2S)-2-(3,4-difluorophenyl)cyclopropyl)-9-(prop-2-yn-1-yl)-2-(propylthio)-9H-purin-6-amine (17c);
(1S,2R,3S,4R)-4-(6-(((1R,2S)-2-(3,4-difluorophenyl)cyclopropyl)amino)-2-(propylthio)-9H-purin-9-yl)cyclopentane-1,2,3-triol (19d);
N-((1R,2S)-2-(3,4-difluorophenyl)cyclopropyl)-9-methyl-2-(methylthio)-9H-purin-6-amine (22c);
N-((1R,2S)-2-(3,4-difluorophenyl)cyclopropyl)-9-ethyl-2-(methylthio)-9H-purin-6-amine (24c);
N-((1R,2S)-2-(3,4-difluorophenyl)cyclopropyl)-2-(ethylthio)-9-methyl-9H-purin-6-amine (20c);
N-((1R,2S)-2-(3,4-difluorophenyl)cyclopropyl)-9-ethyl-2-(ethylthio)-9H-purin-6-amine (21c);
2-(butylthio)-N-((1R,2S)-2-(3,4-difluorophenyl)cyclopropyl)-9-methyl-9H-purin-6-amine (25c);
N-((1R,2S)-2-(3,4-difluorophenyl)cyclopropyl)-1-methyl-6-(methylthio)-1H-pyrazolo[3,4-d]pyrimidin-4-amine (27k);
N-((1R,2S)-2-(3,4-difluorophenyl)cyclopropyl)-1-ethyl-6-(methylthio)-1H-pyrazolo[3,4-d]pyrimidin-4-amine (30k);
N-((1R,2S)-2-(3,4-difluorophenyl)cyclopropyl)-6-(ethylthio)-1-methyl-1H-pyrazolo[3,4-d]pyrimidin-4-amine hydrochloride (28x.HCl);
N-((1R,2S)-2-(3,4-difluorophenyl)cyclopropyl)-1-isopropyl-6-(methylthio)-1H-pyrazolo[3,4-d]pyrimidin-4-amine hydrochloride(33k.HCl);
N-((1R,2S)-2-(3,4-difluorophenyl)cyclopropyl)-7-ethyl-2-(methylthio)-7H-pyrrolo[2,3-d]pyrimidin-4-amine hydrochloride (35p.HCl);
or isomers, racemic mixtures thereof, pharmaceutically acceptable acid addition salts, pharmaceutically acceptable metal salts, or alkylated ammonium salts or prodrug thereof.

The most preferred inhibitor of biofilm on a surface is N-((1R,2S)-2-(3,4-difluorophenyl)cyclopropyl)-9-methyl-2-(propylthio)-9H-purin-6-amine (1c) as illustrated:

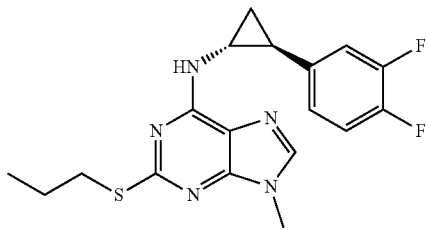

or isomers, racemic mixtures thereof, pharmaceutically acceptable acid addition salts, pharmaceutically acceptable metal salts, or alkylated ammonium salts or prodrug thereof.

Medical devices and biomaterial implants are susceptible to bacterial colonization and may respectively become infected by a bacterial biofilm formation, either when they are used outside of the human or animal body or inside of the human or animal body.

To avoid having to remove the infected biomaterial implant from the host or to avoid a further administration to the host of a high dose of antibiotics to inhibit bacterial infection, one has surprisingly found that applying pyrimidine derivative of formula (I) or acceptable salts thereof, directly on the surface of the medical device or of the biomaterial implant, prevents bacterial contamination.

Such application may be carried out, by various techniques well-known in the art, such as for example dipping the surface to be coated or spraying the surface with either pyrimidine derivatives of formula (I) or salts thereof or with a pharmaceutical composition comprising pyrimidine derivatives of formula (I) or isomers, racemic mixtures thereof, pharmaceutically acceptable acid addition salts, pharmaceutically acceptable metal salts, or alkylated ammonium salts thereof.

By surface one means any type of surface such as rubber or plastic surface as for example surface made of polyethylene, polypropylene, polyurethane, polyvinyl chloride, polyvinylpyrrolidone, polytetrafluoroethylene, silicone or the like, or copolymers but also and preferably metallic surface such as stainless steel, silver, gold, titanium, metallic alloys pyrolytic carbon, and the like. It can also be used on bioabsorbable or biomaterial surface such as biological prosthesis or devices which are made of biological material such as for example porcine heart valve or bovine pericardium.

By inhibition of biofilm on a surface one means inhibition of the bacterial biofilm formation at all stages of its formation starting from the prevention or inhibition of adherence of bacteria on the surface at step 1 but also and mainly an inhibition in bacteria growth, multiplication, and formation of microcolonies on the surface at step 2. By inhibition of biofilm one also means inhibition of the matrix at the maturation step 3 and inhibition of bacteria dispersion from the matrix in a colonisation step. By inhibition of biofilm, one also means killing bacteria at all steps of the biofilm formation.

A further aspect according to the invention, is a method for killing or preventing bacterial growth during biofilm formation on a surface.

The method comprises applying pyrimidine derivative of formula (I) or isomers, racemic mixtures thereof, pharmaceutically acceptable acid addition salts, pharmaceutically acceptable metal salts, or alkylated ammonium salts thereof; on a surface either at a prevention step, reducing bacteria adherence and survival on the substrate or at a stage where the biofilm is already present, or even at a maturation step with a matrix formation wherein a more complex architecture of biofilm is established protecting bacteria as a barrier to conventional antibacterial agent.

Factors that make bacteria especially adept at surviving on various biomaterials or medical devices include adherence and production of a biofilm.

An initial stage of biofilm formation is the attachment/adherence to surface, which is stronger in shear stress conditions. A protein mainly responsible for this adhesion is the polysaccharide intercellular adhesin (PIA), which allows bacteria to bind to each other, as well as to surfaces, creating the biofilm. The second stage of biofilm formation is the development of a community structure and ecosystem, which gives rise to a mature biofilm. The final stage is the detachment from the surface with consequent spreading into other locations. In all stages of biofilm formation a quorum sensing (QS) system, mediating cell-to-cell communication, is involved.

Bacteria in the biofilm produce extracellular polymeric substances (EPS) consisting mainly of polysaccharides, nucleic acids (extracellular DNA) and proteins, that protect them from external threats, including immune system components and antimicrobials. Moreover, bacteria in the biofilm have a decreased metabolism, making them less susceptible to antibiotics; this is due to the fact that most antimicrobials require a certain degree of cellular activity in order to be effective. Another factor reinforcing such resistance is the impaired diffusion of the antibiotics throughout the biofilm because of the presence of the EPS matrix barrier.

It was also well-known that in the biofilm there is higher rate of plasmid exchange increasing the chances of developing naturally occurring and antimicrobial-induced resistance.

Strategies that have been developed to eliminate biofilms target 3 different steps in the biofilm formation: inhibition of the initial stage, i.e. the adhesion of bacteria to surfaces; disrupting the biofilm architecture during the maturation process or step 2; inhibiting the QS system or step 3.

Because of a high resistance of these biofilms to antibiotics there is an increasing need of control and prevention of microbial growth and biofilm formation at stage 2 to avoid removal of the biomaterial implant from the host together with a long treatment with antibiotics.

The method of killing bacteria or prevention of bacterial growth on a surface is generally applied to biomaterial implant or any medical devices, implantable or not.

The biomaterial implants or medical devices are preferably implantable foreign material for clinical use in host mammals such as prosthetic devices, pacemakers, implantable cardioverter-defibrillators, intravascular catheters, coronary stent, heart valves, intraocular lens and the like but include other non-implantable medical devices that needs to be sterile such as for example wound dressings, soft tissue fillers containing local anaesthetics, root canal fillers with ancillary medicinal substances and the like.

The method of killing bacteria or prevention of bacterial growth could also be applied to the surface of an experimental or surgical device in need of such antibacterial treatment. Practically the method may be applied and is not limited to any device, tool, instrument, relating to medicine or the practice of human or veterinary medicine, or intended for use to heal or treat or prevent a disease.

In a still further aspect, the present invention provides new pyrimidine derivatives of formula (I) or salt thereof, optionally comprising a detectable marker, for use in diagnosing or prognosing bacterial infection in a host mammal.

The term "detectable marker" as used herein refers to any type of tag which is detectable and thus allows the determination of the presence of the pyrimidine derivative. In particular embodiments, the marker is an isotope which allows the use of the pyrimidine derivative as a radiotracer.

The present invention also provides a pharmaceutical composition comprising the new pyrimidine derivatives of formula (I) or salt thereof, optionally comprising a detectable marker, for use in diagnosing or prognosing bacterial infection in a host mammal.

We have surprisingly found that pyrimidine derivatives of formula (I) or a composition thereof, optionally comprising a detectable isotope atom may be used to detect a bacterial infection in a host mammal; such as for example for the diagnosing of endocarditis, a disease developed after a prosthetic valve surgery. Indeed the pyrimidine derivatives according to the invention or compositions thereof comprising a detectable label can identify a bacterial infection in the host and can be absorbed by a bacterial cell. Pyrimidine derivatives or compositions thereof may therefore for instance be used as radiotracer for in vivo-imaging.

Generally, the detection method used in the diagnosis will depend on the nature of the marker. For instance, for the purpose of in-vivo imaging the pyrimidine derivative will comprise a radiotracer, and the type of detection instrument will depend of the radiotracer. For example, the pyrimidin derivative comprising optionally at least one detectable isotope according to the invention, can be detected using beta, gamma, positron or x-ray imaging wherein, for example beta or gamma irradiation is provided by the relevant isotope and is detected at an appropriate wavelength.

The pyrimidine derivative comprising optionally a detectable isotope may be used for example with X-Ray imaging, magnetic resonance spectroscopy (MRS) or imaging (MRI), ultrasonography, positron emission tomography (PET) and single emission computed tomography (SPECT).

The detectable pyrimidine derivative may be detected through isotope $^{19}$F or $^{13}$C or a combination thereof for MRS/MRI by well know organic chemistry techniques.

Other detectable pyrimidine derivative may also comprise an isotope selected from 19F, 11C, $^{75}$Br, $^{76}$Br or $^{120}$I or a combination thereof for PET techniques.

Other detectable pyrimidine derivatives comprise an isotope selected from $^{18}$F or $^{11}$C or a combination thereof for PET in-vivo imaging as described in Bengt Langström in Acta Chemica Scandinavia, 53:651-669 (1999) or the journal of Nuclear Medicine 58(7): 1094-1099(2017) A. M. J. Paans in https://cds.cern.ch/record/1005065/files/p363.pdf Pyrimidine derivative may also comprise $^{123}$I and $^{131}$I for SPECT as described by Kulkarni, Int. J. Rad. Appl. & Inst (partB)18:647(1991).

Pyrimidine derivative may also be detectable with technetium-99m($^{99m}$Tc). Modification of Pyrimidin derivative to introduce a ligand that binds to such metal ions can be carried out by a man skilled in the art. Preparing detectable derivatives of $^{99m}$Tc is well known in the art (Zhuang in Nuclear Medicine & Biology 26(2):217-24 (1999).

A preferred pyrimidine derivative of formula (I) or isomers, racemic mixtures thereof, pharmaceutically acceptable acid addition salts, pharmaceutically acceptable metal salts, or alkylated ammonium salts thereof; for use as radiotracer, such as in diagnosing or prognosing bacterial infection, comprises a phenyl cyclopropyl group as illustrated in formula (IV)

(IV)

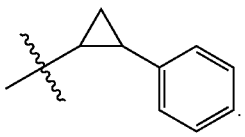

Most preferred pyrimidine derivatives of formula (I) or isomers, racemic mixtures thereof, pharmaceutically acceptable acid addition salts, pharmaceutically acceptable metal salts, or alkylated ammonium salts thereof, such as for use as radiotracer comprise a difluorophenylcyclopropyl group.

The most preferred pyrimidine derivatives of formula (I) or isomers, racemic mixtures thereof, pharmaceutically acceptable acid addition salts, pharmaceutically acceptable metal salts, or alkylated ammonium salts thereof; for use as a radiotracer comprise a 3,4 difluorophenylcyclopropyl group as illustrated in formula (II).

By radiotracer one means a pyrimidine derivative wherein one or more atoms are replaced by a radionuclide or isotope to be used as tracer to explore cells, tissues or fluids from a host mammal and identify the presence and importance of a bacterial infection in the host for example at the surface of a prosthetic valve.

By radionuclide or isotope, one means for example $^{3}H$, $^{18}F$, $^{19}F$, $^{11}C$, $^{13}C$, $^{14}C$, $^{75}Br$, $^{76}Br$, $^{120}I$, $^{123}I$, $^{125}I$, $^{131}I$, $^{15}O$, $^{13}N$.

By radiotracer, one also means pyrimidine derivative associated with a contrast agent such as for example a MRI contrast agent or MR tracers for Magnetic Resonance Imaging (MRI); or contrast agent used in contrast-enhanced ultrasound imaging.

The pyrimidine derivative or composition thereof used as radiotracer is administered locally or systemically by inhalation, ingestion or injection or via an implanted reservoir in the mammal host at a dose that is relevant to a selected imaging device. The administration may be orally, parenterally, topically, rectally, nasally, vaginally.

By parenterally, one means subcutaneously, intravenously, intraarterially, intraperitoneally, intrathecally, intraventricularly and the like.

Dose levels of administration to the host are depending upon his age, weight, general health, sex, time of administration, form of administration and the like and is well known by the one skilled in the art. They may vary between 0.001 μg/kg/day and 10,000 mg/kg/day according to the imaging technique selected.

A resulting in-vivo image of the bacterial infection of the host mammal is provided, for example at the prosthetic valve position.

Further applications of the pyrimidine derivatives of the present invention include monitoring bacterial contamination in samples such as in biological samples. Typical samples where this is of interest are water, blood, meat etc.

The invention is illustrated hereafter by the following non limiting examples.

1. Preparation of New Pyrimidine Derivatives:

Example 1

Synthesis of N-((1R,2S)-2-(3,4-difluorophenyl)cyclopropyl)-9-methyl-2-(propylthio)-9H-purin-6-amine (1c)

6-Chloro-$N^{4}$-methyl-2-(propylthio)pyrimidine-4,5-diamine (1a)

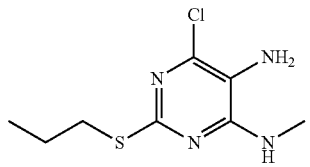

4,6-Dichloro-2-(propylthio)pyrimidin-5-amine (0.5 g, 2.1 mmol) was dissolved in methanol (2 mL) and supplemented with a solution of methylamine 33% w/w in methanol (0.76 mL, 6.3 mmol). The reaction mixture was introduced in a sealed vessel and heated at 100° C. for 1 h. After concentration of the reaction mixture to dryness under vacuum, the residue was purified by silica gel column chromatography.

Yield: 96%.

Melting point: 119-121° C.

$^{1}H$ NMR (DMSO-$d_{6}$) δ 0.95 (t, J=7.4 Hz, 3H, $SCH_{2}CH_{2}CH_{3}$), 1.64 (h, J=7.3 Hz, 2H, $SCH_{2}CH_{2}CH_{3}$), 2.87 (d, J=4.5 Hz, 3H, $NHCH_{3}$), 2.96 (t, J=7.2 Hz, 2H, $SCH_{2}CH_{2}CH_{3}$), 4.71 (s, 2H, $NH_{2}$), 7.01 (q, J=4.4 Hz, 1H, $NHCH_{3}$).

$^{13}C$ NMR (DMSO-$d_{6}$) δ 13.3 ($SCH_{2}CH_{2}CH_{3}$), 22.6 ($SCH_{2}CH_{2}CH_{3}$), 27.8 ($NHCH_{3}$), 32.1 ($SCH_{2}CH_{2}CH_{3}$), 120.0 (C-5), 137.1 (C-6), 153.2 (C-4), 155.4 (C-2).

6-Chloro-9-methyl-2-(propylthio)-9H-purine (1b)

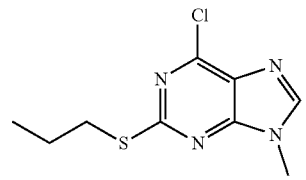

A solution of (1a) (233.0 mg, 1 mmol) in acetic acid (2.5 mL) and triethyl orthoformate (2.5 mL, 15 mmol) was heated at a temperature of 130° C. under reflux for 1 h. After distillation of the acetic acid and triethyl orthoformate under vacuum, the residue was purified by silica gel column chromatography.

Yield: 77%.

Melting point: 75-78° C.

$^{1}H$ NMR (DMSO-$d_{6}$) δ 1.01 (t, J=7.4 Hz, 3H, $SCH_{2}CH_{2}CH_{3}$), 1.74 (h, J=7.3 Hz, 2H, $SCH_{2}CH_{2}CH_{3}$), 3.18 (t, J=7.2 Hz, 2H, $SCH_{2}CH_{2}CH_{3}$), 3.79 (s, 3H, $NCH_{3}$), 8.48 (s, 1H, 8-H).

$^{13}$C NMR (DMSO-d$_6$) δ 13.2 (SCH$_2$CH$_2$CH$_3$), 22.0 (SCH$_2$CH$_2$CH$_3$), 29.9 (NCH$_3$), 32.6 (SCH$_2$CH$_2$CH$_3$), 127.9 (C-5), 147.0 (C-8), 148.7 (C-6), 153.2 (C-4), 163.9 (C-2).

N-((1R,2S)-2-(3,4-Difluorophenyl)cyclopropyl)-9-methyl-2-(propylthio)-9H-purin-6-amine (1c)

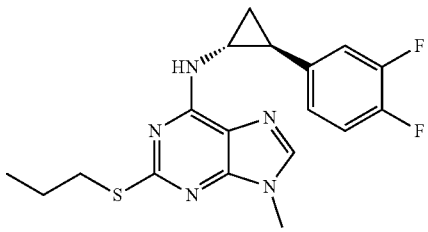 [SMILES: CCCSc1nc(N[C@@H]2C[C@H]2c2ccc(F)c(F)c2)c2ncn(C)c2n1]

A solution of (1b) (122.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.

Yield: 42%.
Melting point: 94-96° C.
$^1$H NMR (CDCl$_3$) δ 0.93 (t, J=7.4 Hz, 3H, SCH$_2$CH$_2$CH$_3$), 1.32 (m, 2H, NHCH(CH$_2$)CHPh), 1.65 (h, J=7.3 Hz, 2H, SCH$_2$CH$_2$CH$_3$), 2.09 (m, 1H, NHCH(CH$_2$)CHPh), 3.02 (m, 2H, SCH$_2$CH$_2$CH$_3$), 3.12 (bs, 1H, NHCH(CH$_2$)CHPh), 3.76 (s, 3H, NCH$_3$), 5.98 (bs, 1H, NH), 6.97 (m, 1H, 6'-H), 7.07 (m, 2H, 2'-H/5'-H), 7.59 (s, 1H, 8-H).
$^{13}$C NMR (CDCl$_3$) δ 13.4 (SCH$_2$CH$_2$CH$_3$), 16.2 (NHCH(CH$_2$)CHPh), 22.8 (SCH$_2$CH$_2$CH$_3$), 25.2 (NHCH(CH$_2$)CHPh), 29.7 (NCH$_3$), 33.2 (SCH$_2$CH$_2$CH$_3$), 33.4 (NHCH(CH$_2$)CHPh), 115.5 (d, J=17 Hz, C-2'), 116.9 (d, J=17 Hz, C-5'), 117.4 (C-5), 122.6 (C-6'), 137.9 (C-1'), 139.5 (C-8), 147.9-149.9 (dd, 246 Hz/13 Hz, C-4'), 149.2-151.2 (dd, 247 Hz/13 Hz, C-3'), 150.8 (C-4), 154.5 (C-6), 165.6 (C-2).

Example 2

Synthesis of 9-methyl-N-((1R,2S)-2-phenylcyclopropyl)-2-(propylthio)-9H-purin-6-amine (2c)

9-Methyl-N-((1R,2S)-2-phenylcyclopropyl)-2-(propylthio)-9H-purin-6-amine (2c)

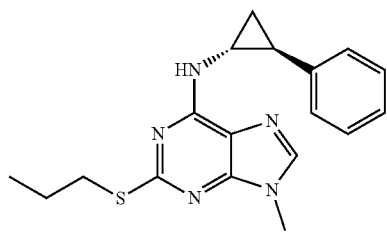 [SMILES: CCCSc1nc(N[C@@H]2C[C@H]2c2ccccc2)c2ncn(C)c2n1]

A solution of (1b) (122.0 mg, 0.5 mmol) in acetonitrile (2.5 mL) was supplemented with (1R,2S)-2-phenylcyclopropanamine (56.0 mg, 1.1 mmol) and triethylamine (0.13 mL) and then heated at 90° C. under reflux for 4 h. After distillation of the solvents under vacuum, the residue was purified by silica gel column chromatography.

Yield: 27%.
Melting point: 171-172.5° C.
$^1$H NMR (CDCl$_3$) δ 0.88 (t, J=7.4 Hz, 3H, SCH$_2$CH$_2$CH$_3$), 1.33 (m, 2H, NHCH(CH$_2$)CHPh), 1.60 (h, J=7.3 Hz, 2H, SCH$_2$CH$_2$CH$_3$), 2.13 (m, 1H, NHCH(CH$_2$)CHPh), 2.92 (m, 1H, SCH$_2$CH$_2$CH$_3$), 3.06 (m, 1H, SCH$_2$CH$_2$CH$_3$), 3.22 (bs, 1H, NHCH(CH$_2$)CHPh), 3.75 (s, 3H, NCH$_3$), 5.97 (bs, 1H, NH), 7.19 (m, 3H, 2'-H/4'-H/6'-H), 7.30 (m, 2H, 3'-H/5'-H), 7.58 (s, 1H, 8-H).
$^{13}$C NMR (CDCl$_3$) δ 13.3 (SCH$_2$CH$_2$CH$_3$), 16.8 (NHCH(CH$_2$)CHPh), 22.8 (SCH$_2$CH$_2$CH$_3$), 25.7 (NHCH(CH$_2$)CHPh), 29.7 (NCH$_3$), 33.3 (SCH$_2$CH$_2$CH$_3$), 33.5 (NHCH(CH$_2$)CHPh), 117.4 (C-5), 126.0 (C-4'), 126.2 (C-2'/C-6'), 128.3 (C-3'/C-5'), 139.5 (C-8), 140.9 (C-1'), 150.8 (C-4), 154.6 (C-6), 165.6 (C-2).

Example 3

Synthesis of N-((1R,2S)-2-(3,4-difluorophenyl)cyclopropyl)-9-ethyl-2-(propylthio)-9H-purin-6-amine (3c)

6-Chloro-N$^4$-ethyl-2-(propylthio)pyrimidine-4,5-diamine (3a)

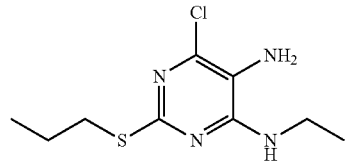

4,6-Dichloro-2-(propylthio)pyrimidin-5-amine (0.5 g, 2.1 mmol) was dissolved in a solution of ethylamine 2.0 M in methanol (3.2 mL, 6.4 mmol). The reaction mixture was introduced in a sealed vessel and heated at 100° C. for 1 h. After concentration of the reaction mixture to dryness under vacuum, the residue was purified by silica gel column chromatography.

Yield: 77%.
Melting point: 96-98° C.
$^1$H NMR (DMSO-d$_6$) δ 0.95 (t, J=7.4 Hz, 3H, SCH$_2$CH$_2$CH$_3$), 1.16 (t, J=7.2 Hz, 3H, NHCH$_2$CH$_3$), 1.63 (h, J=7.3 Hz, 2H, SCH$_2$CH$_2$CH$_3$), 2.94 (t, J=7.2 Hz, 2H, SCH$_2$CH$_2$CH$_3$), 3.37 (m, 2H, NHCH$_2$CH$_3$), 4.75 (s, 2H, NH$_2$), 6.95 (t, J=4.8 Hz, 1H, NHCH$_2$CH$_3$).
$^{13}$C NMR (DMSO-d$_6$) δ 13.3 (SCH$_2$CH$_2$CH$_3$), 14.3 (NHCH$_2$CH$_3$), 22.7 (SCH$_2$CH$_2$CH$_3$), 32.1 (SCH$_2$CH$_2$CH$_3$), 35.7 (NHCH$_2$CH$_3$), 119.8 (C-5), 137.3 (C-6), 152.5 (C-4), 155.3 (C-2).

6-Chloro-9-ethyl-2-(propylthio)-9H-purine (3b)

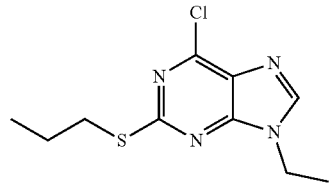 [SMILES: CCCSc1nc(Cl)c2ncn(CC)c2n1]

A solution of (3a) (247.0 mg, 1 mmol) in acetic acid (2.5 mL) and triethyl orthoformate (2.5 mL, 15 mmol) was heated at a temperature of 130° C. under reflux for 1 h. After distillation of the acetic acid and triethyl orthoformate under vacuum, the residue was purified by silica gel column chromatography.

Yield: 77%.

Melting point: 96-97.5° C.

$^1$H NMR (DMSO-$d_6$) δ 1.01 (t, J=7.4 Hz, 3H, SCH$_2$CH$_2$CH$_3$), 1.44 (t, J=7.3 Hz, 3H, NCH$_2$CH$_3$), 1.74 (h, J=7.3 Hz, 2H, SCH$_2$CH$_2$CH$_3$), 3.17 (t, J=7.2 Hz, 2H, SCH$_2$CH$_2$CH$_3$), 4.24 (q, J=7.3 Hz, 2H, NCH$_2$CH$_3$), 8.56 (s, 1H, 8-H).

$^{13}$C NMR (DMSO-$d_6$) δ 13.2 (SCH$_2$CH$_2$CH$_3$), 14.6 (NCH$_2$CH$_3$), 22.0 (SCH$_2$CH$_2$CH$_3$), 32.6 (SCH$_2$CH$_2$CH$_3$), 39.9 (NCH$_2$CH$_3$), 128.1 (C-5), 146.0 (C-8), 148.8 (C-6), 152.7 (C-4), 163.8 (C-2).

N-((1R,2S)-2-(3,4-Difluorophenyl)cyclopropyl)-9-ethyl-2-(propylthio)-9H-purin-6-amine (3c)

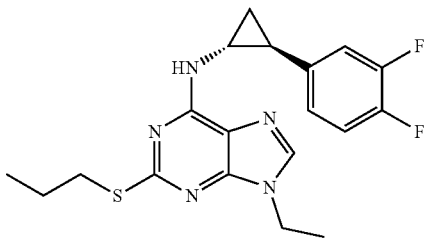 [SMILES: CCCSc1nc(N[C@@H]2C[C@H]2c2ccc(F)c(F)c2)c2ncn(CC)c2n1]

A solution of (3b) (129.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.

Yield: 43%.

Melting point: 109.5-111.5° C.

$^1$H NMR (CDCl$_3$) δ 0.94 (t, J=7.4 Hz, 3H, SCH$_2$CH$_2$CH$_3$), 1.32 (m, 2H, NHCH(CH$_2$)CHPh), 1.50 (t, J=7.3 Hz, 3H, NCH$_2$CH$_3$), 1.67 (h, J=7.3 Hz, 2H, SCH$_2$CH$_2$CH$_3$), 2.09 (m, 1H, NHCH(CH$_2$)CHPh), 3.03 (m, 2H, SCH$_2$CH$_2$CH$_3$), 3.12 (bs, 1H, NHCH(CH$_2$)CHPh), 4.18 (q, J=7.3 Hz, 2H, NCH$_2$CH$_3$), 5.90 (bs, 1H, NH), 6.99 (m, 1H, 6'-H), 7.08 (m, 2H, 2'-H/5'-H), 7.63 (s, 1H, 8-H).

$^{13}$C NMR (CDCl$_3$) δ 13.4 (SCH$_2$CH$_2$CH$_3$), 15.5 (NCH$_2$CH$_3$), 16.1 (NHCH(CH$_2$)CHPh), 22.9 (SCH$_2$CH$_2$CH$_3$), 25.2 (NHCH(CH$_2$)CHPh), 33.2 (SCH$_2$CH$_2$CH$_3$), 33.3 (NHCH(CH$_2$)CHPh), 38.7 (NCH$_2$CH$_3$), 115.6 (d, J=17 Hz, C-2'), 116.9 (d, J=17 Hz, C-5'), 117.6 (C-5), 122.7 (C-6'), 137.9 (C-1'), 138.5 (C-8), 147.9-149.9 (dd, 246 Hz/13 Hz, C-4'), 149.2-151.2 (dd, 247 Hz/13 Hz, C-3'), 150.3 (C-4), 154.5 (C-6), 165.4 (C-2).

Example 4

Synthesis of N-((1R,2S)-2-(3,4-difluorophenyl)cyclopropyl)-9-propyl-2-(propylthio)-9H-purin-6-amine (4c)

6-Chloro-N$^4$-propyl-2-(propylthio)pyrimidine-4,5-diamine (4a)

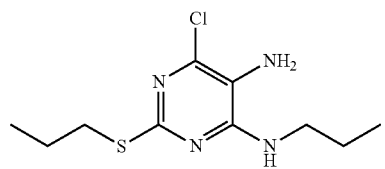

4,6-Dichloro-2-(propylthio)pyrimidin-5-amine (0.5 g, 2.1 mmol) was dissolved in methanol (2 mL) and supplemented with n-propylamine (370.0 mg, 6.3 mmol). The reaction mixture was introduced in a sealed vessel and heated at 100° C. for 30 min. After concentration of the reaction mixture to dryness under vacuum, the residue was purified by silica gel column chromatography.

Yield: 91%.

Melting point: 100-102° C.

$^1$H NMR (DMSO-$d_6$) δ 0.91 (t, J=7.4 Hz, 3H, NHCH$_2$CH$_2$CH$_3$), 0.95 (t, J=7.3 Hz, 3H, SCH$_2$CH$_2$CH$_3$), 1.56 (h, J=7.3 Hz, 2H, NHCH$_2$CH$_2$CH$_3$), 1.64 (h, J=7.3 Hz, 2H, SCH$_2$CH$_2$CH$_3$), 2.93 (t, J=7.2 Hz, 2H, SCH$_2$CH$_2$CH$_3$), 3.32 (m, 2H, NHCH$_2$CH$_2$CH$_3$), 4.76 (s, 2H, NH$_2$), 6.96 (t, J=4.8 Hz, 1H, NHCH$_2$CH$_2$CH$_3$).

$^{13}$C NMR (DMSO-$d_6$) δ 11.5 (NHCH$_2$CH$_2$CH$_3$), 13.3 (SCH$_2$CH$_2$CH$_3$), 21.9 (NHCH$_2$CH$_2$CH$_3$), 22.8 (SCH$_2$CH$_2$CH$_3$), 32.1 (SCH$_2$CH$_2$CH$_3$), 42.7 (NHCH$_2$CH$_2$CH$_3$), 119.8 (C-5), 137.3 (C-6), 152.6 (C-4), 155.2 (C-2).

6-Chloro-9-propyl-2-(propylthio)-9H-purine (4b)

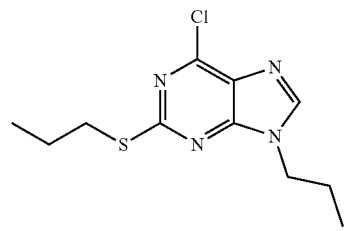 [SMILES: CCCSc1nc(Cl)c2ncn(CCC)c2n1]

A solution of (4a) (261.0 mg, 1 mmol) in acetic acid (2.5 mL) and triethyl orthoformate (2.5 mL, 15 mmol) was heated at a temperature of 130° C. under reflux for 1 h. After distillation of the acetic acid and triethyl orthoformate under vacuum, the residue was purified by silica gel column chromatography.

Yield: 94%.

Melting point: liquid.

$^1$H NMR (DMSO-$d_6$) δ 0.85 (t, J=7.4 Hz, 3H, NCH$_2$CH$_2$CH$_3$), 1.01 (t, J=7.4 Hz, 3H, SCH$_2$CH$_2$CH$_3$), 1.74 (h, J=7.3 Hz, 2H, SCH$_2$CH$_2$CH$_3$), 1.86 (h, J=7.3 Hz, 2H, NCH$_2$CH$_2$CH$_3$), 3.17 (t, J=7.2 Hz, 2H, SCH$_2$CH$_2$CH$_3$), 4.18 (t, J=7.0 Hz, 2H, NCH$_2$CH$_2$CH$_3$), 8.55 (s, 1H, 8-H).

$^{13}$C NMR (DMSO-d$_6$) δ 10.9 (NCH$_2$CH$_2$CH$_3$), 13.2 (SCH$_2$CH$_2$CH$_3$), 22.1 (SCH$_2$CH$_2$CH$_3$), 22.3 (NCH$_2$CH$_2$CH$_3$), 32.6 (SCH$_2$CH$_2$CH$_3$), 45.3 (NCH$_2$CH$_2$CH$_3$), 128.0 (C-5), 146.4 (C-8), 148.9 (C-6), 152.9 (C-4), 163.8 (C-2).

N-((1R,2S)-2-(3,4-Difluorophenyl)cyclopropyl)-9-propyl-2-(propylthio)-9H-purin-6-amine (4c)

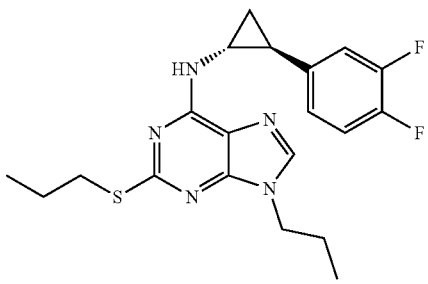 [SMILES: CCCSc1nc(N[C@@H]2C[C@H]2c2ccc(F)c(F)c2)c2ncn(CCC)c2n1]

A solution of (4b) (136.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.

Yield: 45%.

Melting point: 97-99° C.

$^1$H NMR (CDCl$_3$) δ 0.94 (t, J=7.4 Hz, 6H, NCH$_2$CH$_2$CH$_3$/SCH$_2$CH$_2$CH$_3$), 1.32 (m, 2H, NHCH(CH$_2$)CHPh), 1.67 (h, J=7.3 Hz, 2H, SCH$_2$CH$_2$CH$_3$), 1.90 (h, J=7.4 Hz, 2H, NCH$_2$CH$_2$CH$_3$), 2.09 (m, 1H, NHCH(CH$_2$)CHPh), 3.03 (m, 2H, SCH$_2$CH$_2$CH$_3$), 3.11 (bs, 1H, NHCH(CH$_2$)CHPh), 4.09 (t, J=7.1 Hz, 2H, NCH$_2$CH$_2$CH$_3$), 5.86 (bs, 1H, NH), 7.00 (m, 1H, 6'-H), 7.09 (m, 2H, 2'-H/5'-H), 7.61 (s, 1H, 8-H).

$^{13}$C NMR (CDCl$_3$) δ 11.2 (NCH$_2$CH$_2$CH$_3$), 13.4 (SCH$_2$CH$_2$CH$_3$), 15.7 (NHCH(CH$_2$)CHPh), 22.9 (SCH$_2$CH$_2$CH$_3$), 23.3 (NCH$_2$CH$_2$CH$_3$), 25.2 (NHCH(CH$_2$)CHPh), 33.2 (SCH$_2$CH$_2$CH$_3$), 33.3 (NHCH(CH$_2$)CHPh), 45.3 (NCH$_2$CH$_2$CH$_3$), 115.6 (d, J=17 Hz, C-2'), 116.9 (d, J=17 Hz, C-5'), 117.6 (C-5), 122.7 (C-6'), 137.9 (C-1'), 139.0 (C-8), 147.9-149.9 (dd, 246 Hz/13 Hz, C-4'), 149.2-151.2 (dd, 247 Hz/13 Hz, C-3'), 150.5 (C-4), 154.5 (C-6), 165.4 (C-2).

Example 5

Synthesis of N-((1R,2S)-2-(3,4-difluorophenyl)cyclopropyl)-9-isopropyl-2-(propylthio)-9H-purin-6-amine (5c)

6-Chloro-N$^4$-isopropyl-2-(propylthio)pyrimidine-4,5-diamine (5a)

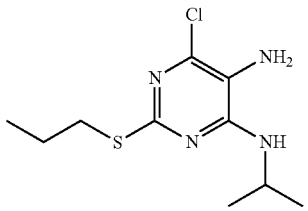 [SMILES: CCCSc1nc(Cl)c(N)c(NC(C)C)n1]

4,6-Dichloro-2-(propylthio)pyrimidin-5-amine (0.5 g, 2.1 mmol) was dissolved in methanol (2 mL) and supplemented with isopropylamine (370.0 mg, 6.3 mmol). The reaction mixture was introduced in a sealed vessel and heated at 100° C. for 90 min. After concentration of the reaction mixture to dryness under vacuum, the residue was purified by silica gel column chromatography.

Yield: 95%.

Melting point: 81-83° C.

$^1$H NMR (DMSO-d$_6$) δ 0.95 (t, J=7.3 Hz, 3H, SCH$_2$CH$_2$CH$_3$), 1.19 (d, J=6.5 Hz, 6H, NHCH(CH$_3$)$_2$), 1.63 (h, J=7.3 Hz, 2H, SCH$_2$CH$_2$CH$_3$), 2.93 (t, J=7.2 Hz, 2H, SCH$_2$CH$_2$CH$_3$), 4.16 (m, 1H, NHCH(CH$_3$)$_2$), 4.81 (s, 2H, NH$_2$), 6.69 (d, J=6.9 Hz, 1H, NHCH(CH$_3$)$_2$).

$^{13}$C NMR (DMSO-d$_6$) δ 13.3 (SCH$_2$CH$_2$CH$_3$), 22.2 (NHCH(CH$_3$)$_2$), 22.8 (SCH$_2$CH$_2$CH$_3$), 32.1 (SCH$_2$CH$_2$CH$_3$), 42.6 (NHCH(CH$_3$)$_2$), 119.7 (C-5), 137.3 (C-6), 151.7 (C-4), 155.1 (C-2).

6-Chloro-9-isopropyl-2-(propylthio)-9H-purine (5b)

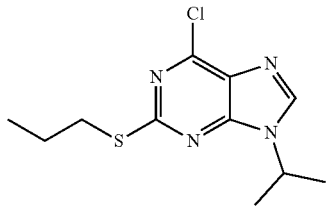 [SMILES: CCCSc1nc(Cl)c2ncn(C(C)C)c2n1]

A solution of (5a) (261.0 mg, 1 mmol) in acetic acid (2.5 mL) and triethyl orthoformate (2.5 mL, 15 mmol) was heated at a temperature of 130° C. under reflux for 1 h. After distillation of the acetic acid and triethyl orthoformate under vacuum, the residue was purified by silica gel column chromatography.

Yield: 37%.

Melting point: 121-122.5° C.

$^1$H NMR (DMSO-d$_6$) δ 1.01 (t, J=7.4 Hz, 3H, SCH$_2$CH$_2$CH$_3$), 1.56 (d, J=6.8 Hz, 6H, NCH(CH$_3$)$_2$), 1.74 (h, J=7.3 Hz, 2H, SCH$_2$CH$_2$CH$_3$), 3.16 (t, J=7.2 Hz, 2H, SCH$_2$CH$_2$CH$_3$), 4.80 (hept, J=6.8 Hz, 1H, NCH(CH$_3$)$_2$), 8.62 (s, 1H, 8-H).

$^{13}$C NMR (DMSO-d$_6$) δ 13.3 (SCH$_2$CH$_2$CH$_3$), 21.7 (NCH(CH$_3$)$_2$), 22.1 (SCH$_2$CH$_2$CH$_3$), 32.6 (SCH$_2$CH$_2$CH$_3$), 47.9 (NCH(CH$_3$)$_2$), 128.4 (C-5), 144.7 (C-8), 148.9 (C-6), 152.3 (C-4), 163.5 (C-2).

N-((1R,2S)-2-(3,4-Difluorophenyl)cyclopropyl)-9-isopropyl-2-(propylthio)-9H-purin-6-amine (5c)

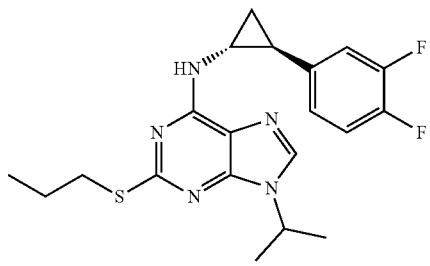 [SMILES: CCCSc1nc(N[C@@H]2C[C@H]2c2ccc(F)c(F)c2)c2ncn(C(C)C)c2n1]

A solution of (5b) (136.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.

Yield: 47%.
Melting point: 98.5-100.5° C.
$^1$H NMR (CDCl$_3$) δ 0.95 (t, J=7.4 Hz, 3H, SCH$_2$CH$_2$CH$_3$), 1.31 (m, 2H, NHCH(CH$_2$)CHPh), 1.58 (dd, J=6.8 Hz/1.6 Hz, 6H, NCH(CH$_3$)$_2$), 1.68 (h, J=7.3 Hz, 2H, SCH$_2$CH$_2$CH$_3$), 2.08 (m, 1H, NHCH(CH$_2$)CHPh), 3.04 (m, 2H, SCH$_2$CH$_2$CH$_3$), 3.10 (bs, 1H, NHCH(CH$_2$)CHPh), 4.77 (hept, J=6.8 Hz, 1H, NCH(CH$_3$)$_2$), 5.95 (bs, 1H, NH), 7.00 (m, 1H, 6'-H), 7.09 (m, 2H, 2'-H/5'-H), 7.68 (s, 1H, 8-H).
$^{13}$C NMR (CDCl$_3$) δ 13.5 (SCH$_2$CH$_2$CH$_3$), 16.0 (NHCH(CH$_2$)CHPh), 22.6 (NCH(CH$_3$)$_2$), 22.9 (SCH$_2$CH$_2$CH$_3$), 25.2 (NHCH(CH$_2$)CHPh), 33.2 (SCH$_2$CH$_2$CH$_3$), 33.3 (NHCH(CH$_2$)CHPh), 47.0 (NCH(CH$_3$)$_2$), 115.7 (d, J=17 Hz, C-2'), 116.9 (d, J=17 Hz, C-5'), 117.9 (C-5), 122.8 (C-6'), 136.7 (C-8), 137.9 (C-1'), 147.9-149.9 (dd, 246 Hz/13 Hz, C-4'), 149.2-151.2 (dd, 247 Hz/13 Hz, C-3'), 150.0 (C-4), 154.6 (C-6), 165.1 (C-2).

Example 6

Synthesis of 9-cyclopropyl-N-((1R,2S)-2-(3,4-difluorophenyl)cyclopropyl)-2-(propylthio)-9H-purin-6-amine (6c)

6-Chloro-N$^4$-cyclopropyl-2-(propylthio)pyrimidine-4,5-diamine (6a)

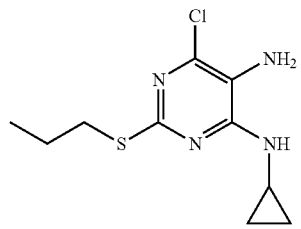 [SMILES: CCCSc1nc(Cl)c(N)c(NC2CC2)n1]

4,6-Dichloro-2-(propylthio)pyrimidin-5-amine (0.5 g, 2.1 mmol) was dissolved in methanol (2 mL) and supplemented with cyclopropylamine (360.0 mg, 6.3 mmol). The reaction mixture was introduced in a sealed vessel and heated at 100° C. for 30 min. After concentration of the reaction mixture to dryness under vacuum, the residue was purified by silica gel column chromatography.

Yield: 92%.
Melting point: 96-98° C.
$^1$H NMR (DMSO-d$_6$) δ 0.49 (s, 2H, NHCH(CH$_2$)$_2$), 0.73 (d, J=5.7 Hz, 2H, NHCH(CH$_2$)$_2$), 0.95 (t, J=7.1 Hz, 3H, SCH$_2$CH$_2$CH$_3$), 1.66 (h, J=7.0 Hz, 2H, SCH$_2$CH$_2$CH$_3$), 2.80 (m, 1H, NHCH(CH$_2$)$_2$), 2.97 (t, J=6.9 Hz, 2H, SCH$_2$CH$_2$CH$_3$), 4.74 (s, 2H, NH$_2$), 7.09 (s, 1H, NHCH(CH$_2$)$_2$).
$^{13}$C NMR (DMSO-d$_6$) δ 6.2 (NHCH(CH$_2$)$_2$), 13.3 (SCH$_2$CH$_2$CH$_3$), 22.8 (SCH$_2$CH$_2$CH$_3$), 24.1 (NHCH(CH$_2$)$_2$), 32.2 (SCH$_2$CH$_2$CH$_3$), 120.0 (C-5), 137.3 (C-6), 153.4 (C-4), 155.2 (C-2).

6-Chloro-9-cyclopropyl-2-(propylthio)-9H-purine (6b)

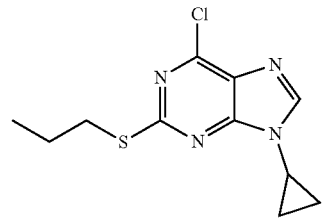 [SMILES: CCCSc1nc(Cl)c2ncn(C3CC3)c2n1]

A solution of (6a) (259.0 mg, 1 mmol) in acetic acid (2.5 mL) and triethyl orthoformate (2.5 mL, 15 mmol) was heated at a temperature of 130° C. under reflux for 1 h. After distillation of the acetic acid and triethyl orthoformate under vacuum, the residue was purified by silica gel column chromatography.

Yield: 58%.
Melting point: 128.5-130° C.
$^1$H NMR (DMSO-d$_6$) δ 1.02 (t, J=7.4 Hz, 3H, SCH$_2$CH$_2$CH$_3$), 1.09 (m, 2H, NCH(CH$_2$)$_2$), 1.16 (m, 2H, NCH(CH$_2$)$_2$), 1.75 (h, J=7.3 Hz, 2H, SCH$_2$CH$_2$CH$_3$), 3.17 (t, J=7.2 Hz, 2H, SCH$_2$CH$_2$CH$_3$), 3.55 (m, 1H, NCH(CH$_2$)$_2$), 8.52 (s, 1H, 8-H).
$^{13}$C NMR (DMSO-d$_6$) δ 5.4 (NCH(CH$_2$)$_2$), 13.3 (SCH$_2$CH$_2$CH$_3$), 22.1 (SCH$_2$CH$_2$CH$_3$), 25.6 (NCH(CH$_2$)$_2$), 32.7 (SCH$_2$CH$_2$CH$_3$), 128.2 (C-5), 146.7 (C-8), 148.8 (C-6), 153.9 (C-4), 163.9 (C-2).

9-Cyclopropyl-N-((1R,2S)-2-(3,4-difluorophenyl)cyclopropyl)-2-(propylthio)-9H-purin-6-amine (6c)

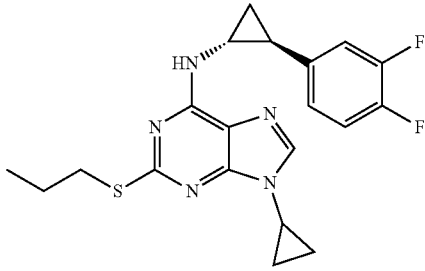 [SMILES: CCCSc1nc(N[C@@H]2C[C@H]2c2ccc(F)c(F)c2)c2ncn(C3CC3)c2n1]

A solution of (6b) (135.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.

Yield: 40%.

Melting point: 137-139° C.

$^1$H NMR (CDCl$_3$) δ 0.95 (t, J=7.4 Hz, 3H, SCH$_2$CH$_2$CH$_3$), 1.10 (m, 2H, NCH(CH$_2$)$_2$), 1.13 (m, 2H, NCH(CH$_2$)$_2$), 1.31 (m, 2H, NHCH(CH$_2$)CHPh), 1.68 (h, J=7.3 Hz, 2H, SCH$_2$CH$_2$CH$_3$), 2.08 (m, 1H, NHCH(CH$_2$)CHPh), 3.03 (m, 2H, SCH$_2$CH$_2$CH$_3$), 3.10 (bs, 1H, NHCH(CH$_2$)CHPh), 3.38 (tt, J=7.1 Hz/3.9 Hz, 1H, NCH(CH$_2$)$_2$), 5.88 (bs, 1H, NH), 6.99 (m, 1H, 6'-H), 7.08 (m, 2H, 2'-H/5'-H), 7.61 (s, 1H, 8-H).

$^{13}$C NMR (CDCl$_3$) δ 5.9 (NCH(CH$_2$)$_2$), 13.5 (SCH$_2$CH$_2$CH$_3$), 16.1 (NHCH(CH$_2$)CHPh), 22.9 (SCH$_2$CH$_2$CH$_3$), 25.2 (NHCH(CH$_2$)CHPh), 25.3 (NCH(CH$_2$)$_2$), 33.2 (SCH$_2$CH$_2$CH$_3$), 33.3 (NHCH(CH$_2$)CHPh), 115.6 (d, J=17 Hz, C-2'), 116.9 (d, J=17 Hz, C-5'), 117.4 (C-5), 122.7 (C-6'), 137.9 (C-1'), 139.4 (C-8), 147.9-149.9 (dd, 246 Hz/13 Hz, C-4'), 149.2-151.2 (dd, 247 Hz/13 Hz, C-3'), 151.6 (C-4), 154.4 (C-6), 165.6 (C-2).

Example 7

Synthesis of 9-butyl-N-((1R,2S)-2-(3,4-difluorophenyl)cyclopropyl)-2-(propylthio)-9H-purin-6-amine (7c)

N$^4$-Butyl-6-chloro-2-(propylthio)pyrimidine-4,5-diamine (7a)

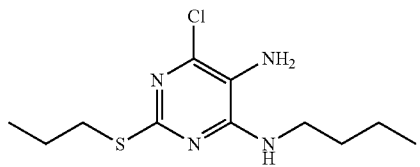 [SMILES: CCCCNc1nc(SCCC)nc(Cl)c1N]

4,6-Dichloro-2-(propylthio)pyrimidin-5-amine (0.5 g, 2.1 mmol) was dissolved in methanol (2 mL) and supplemented with n-butylamine (460.0 mg, 6.3 mmol). The reaction mixture was introduced in a sealed vessel and heated at 100° C. for 30 min. After concentration of the reaction mixture to dryness under vacuum, the residue was purified by silica gel column chromatography.

Yield: 95%.

Melting point: liquid.

$^1$H NMR (DMSO-d$_6$) δ 0.91 (t, J=7.4 Hz, 3H, NHCH$_2$CH$_2$CH$_2$CH$_3$), 0.95 (t, J=7.4 Hz, 3H, SCH$_2$CH$_2$CH$_3$), 1.35 (h, J=7.4 Hz, 2H, NHCH$_2$CH$_2$CH$_2$CH$_3$), 1.55 (p, J=7.5 Hz, 2H, NHCH$_2$CH$_2$CH$_2$CH$_3$), 1.64 (h, J=7.4 Hz, 2H, SCH$_2$CH$_2$CH$_3$), 2.95 (t, J=7.3 Hz, 2H, SCH$_2$CH$_2$CH$_3$), 3.37 (m, 2H, NHCH$_2$CH$_2$CH$_2$CH$_3$), 4.76 (s, 2H, NH$_2$), 6.94 (t, J=5.2 Hz, 1H, NHCH$_2$CH$_2$CH$_2$CH$_3$).

$^{13}$C NMR (DMSO-d$_6$) δ 13.3 (SCH$_2$CH$_2$CH$_3$), 13.7 (NHCH$_2$CH$_2$CH$_2$CH$_3$), 19.6 (NHCH$_2$CH$_2$CH$_2$CH$_3$), 22.8 (SCH$_2$CH$_2$CH$_3$), 30.8 (NHCH$_2$CH$_2$CH$_2$CH$_3$), 32.1 (SCH$_2$CH$_2$CH$_3$), 40.6 (NHCH$_2$CH$_2$CH$_2$CH$_3$), 119.8 (C-5), 137.3 (C-6), 152.6 (C-4), 155.2 (C-2).

9-Butyl-6-chloro-2-(propylthio)-9H-purine (7b)

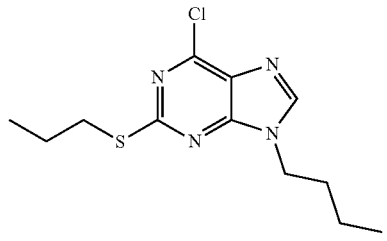 [SMILES: CCCCn1cnc2c(Cl)nc(SCCC)nc21]

A solution of (7a) (275.0 mg, 1 mmol) in acetic acid (2.5 mL) and triethyl orthoformate (2.5 mL, 15 mmol) was heated at a temperature of 130° C. under reflux for 1 h. After distillation of the acetic acid and triethyl orthoformate under vacuum, the residue was purified by silica gel column chromatography.

Yield: 72%.

Melting point: liquid.

$^1$H NMR (DMSO-d$_6$) δ 0.90 (t, J=7.4 Hz, 3H, NCH$_2$CH$_2$CH$_2$CH$_3$), 1.01 (t, J=7.4 Hz, 3H, SCH$_2$CH$_2$CH$_3$), 1.26 (h, J=7.4 Hz, 2H, NCH$_2$CH$_2$CH$_2$CH$_3$), 1.74 (h, J=7.3 Hz, 2H, SCH$_2$CH$_2$CH$_3$), 1.83 (p, J=7.2 Hz, 2H, NCH$_2$CH$_2$CH$_2$CH$_3$), 3.16 (t, J=7.2 Hz, 2H, SCH$_2$CH$_2$CH$_3$), 4.22 (t, J=7.1 Hz, 2H, NCH$_2$CH$_2$CH$_2$CH$_3$), 8.56 (s, 1H, 8-H).

$^{13}$C NMR (DMSO-d$_6$) δ 13.2 (SCH$_2$CH$_2$CH$_3$), 13.3 (NCH$_2$CH$_2$CH$_2$CH$_3$), 19.2 (NCH$_2$CH$_2$CH$_2$CH$_3$), 22.1 (SCH$_2$CH$_2$CH$_3$), 30.9 (NCH$_2$CH$_2$CH$_2$CH$_3$), 32.6 (SCH$_2$CH$_2$CH$_3$), 43.3 (NCH$_2$CH$_2$CH$_2$CH$_3$), 127.9 (C-5), 146.3 (C-8), 148.9 (C-6), 152.8 (C-4), 163.8 (C-2).

9-Butyl-N-((1R,2S)-2-(3,4-difluorophenyl)cyclopropyl)-2-(propylthio)-9H-purin-6-amine (7c)

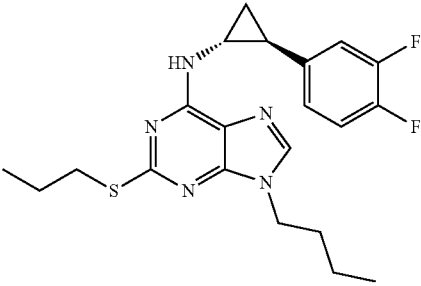 [SMILES: CCCCn1cnc2c(N[C@@H]3C[C@H]3c3ccc(F)c(F)c3)nc(SCCC)nc21]

A solution of (7b) (143.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.

Yield: 61%.

Melting point: 85-87° C.

$^1$H NMR (CDCl$_3$) δ 0.95 (m, 6H, NCH$_2$CH$_2$CH$_2$CH$_3$/SCH$_2$CH$_2$CH$_3$), 1.33 (m, 4H, NCH$_2$CH$_2$CH$_2$CH$_3$/NHCH (CH₂)CHPh), 1.68 (h, J=7.3 Hz, 2H, SCH₂CH₂CH₃), 1.86 (p, J=7.3 Hz, 2H, NCH₂CH₂CH₂CH₃), 2.10 (m, 1H, NHCH (CH₂)CHPh), 3.03 (m, 2H, SCH₂CH₂CH₃), 3.13 (bs, 1H, NHCH(CH₂)CHPh), 4.14 (t, J=7.1 Hz, 2H, NCH₂CH₂CH₂CH₃), 6.19 (bs, 1H, NH), 6.99 (m, 1H, 6'-H), 7.08 (m, 2H, 2'-H/5'-H), 7.64 (s, 1H, 8-H).

$^{13}$C NMR (CDCl₃) δ 13.5 (SCH₂CH₂CH₃/NCH₂CH₂CH₂CH₃), 16.0 (NHCH(CH₂)CHPh), 19.8 (NCH₂CH₂CH₂CH₃), 22.9 (SCH₂CH₂CH₃), 25.2 (NHCH (CH₂)CHPh), 31.9 (NCH₂CH₂CH₂CH₃), 33.2 (SCH₂CH₂CH₃), 33.4 (NHCH(CH₂)CHPh), 43.5 (NCH₂CH₂CH₂CH₃), 115.7 (d, J=17 Hz, C-2'), 116.9 (d, J=17 Hz, C-5'), 117.5 (C-5), 122.7 (C-6'), 136.5 (C-8), 137.9 (C-1'), 147.9-149.9 (dd, 246 Hz/13 Hz, C-4'), 149.2-151.2 (dd, 247 Hz/13 Hz, C-3'), 150.4 (C-4), 154.3 (C-6), 165.8 (C-2).

Example 8

Synthesis of 9-(sec-butyl)-N-(1R,2S)-2-(3,4-difluorophenyl)cyclopropyl)-2-(propylthio)-9H-purin-6-amine (8c)

N⁴-(sec-Butyl)-6-chloro-2-(propylthio)pyrimidine-4,5-diamine (8a)

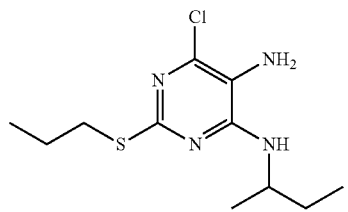 [SMILES: CCCSc1nc(Cl)c(N)c(NC(C)CC)n1]

4,6-Dichloro-2-(propylthio)pyrimidin-5-amine (0.5 g, 2.1 mmol) was dissolved in methanol (2 mL) and supplemented with sec-butylamine (460.0 mg, 6.3 mmol). The reaction mixture was introduced in a sealed vessel and heated at 100° C. for 90 min. After concentration of the reaction mixture to dryness under vacuum, the residue was purified by silica gel column chromatography.

Yield: 81%.

Melting point: liquid.

$^{1}$H NMR (DMSO-d₆) δ 0.87 (t, J=7.4 Hz, 3H, NHCH (CH₃)CH₂CH₃), 0.95 (t, J=7.3 Hz, 3H, SCH₂CH₂CH₃), 1.15 (d, J=6.6 Hz, 3H, NHCH(CH₃)CH₂CH₃), 1.53 (m, 2H, NHCH(CH₃)CH₂CH₃), 1.64 (h, J=7.3 Hz, 2H, SCH₂CH₂CH₃), 2.93 (t, J=7.2 Hz, 2H, SCH₂CH₂CH₃), 4.01 (hept, J=6.6 Hz, 1H, NHCH(CH₃)CH₂CH₃), 4.81 (s, 2H, NH₂), 6.64 (d, J=7.5 Hz, 1H, NHCH(CH₃)CH₂CH₃).

$^{13}$C NMR (DMSO-d₆) δ 10.5 (NHCH(CH₃)CH₂CH₃), 13.3 (SCH₂CH₂CH₃), 19.8 (NHCH(CH₃)CH₂CH₃), 22.8 (SCH₂CH₂CH₃), 28.6 (NHCH(CH₃)CH₂CH₃), 32.1 (SCH₂CH₂CH₃), 47.9 (NHCH(CH₃)CH₂CH₃), 119.7 (C-5), 137.3 (C-6), 152.0 (C-4), 155.0 (C-2).

9-(sec-Butyl)-6-chloro-2-(propylthio)-9H-purine (8b)

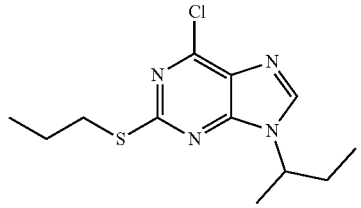 [SMILES: CCCSc1nc(Cl)c2ncn(C(C)CC)c2n1]

A solution of (8a) (275.0 mg, 1 mmol) in acetic acid (2.5 mL) and triethyl orthoformate (2.5 mL, 15 mmol) was heated at a temperature of 130° C. under reflux for 4 h. After distillation of the acetic acid and triethyl orthoformate under vacuum, the residue was purified by silica gel column chromatography.

Yield: 39%.

Melting point: 64-66° C.

$^{1}$H NMR (DMSO-d₆) δ 0.74 (t, J=7.4 Hz, 3H, NCH(CH₃)CH₂CH₃), 1.01 (t, J=7.4 Hz, 3H, SCH₂CH₂CH₃), 1.57 (d, J=6.9 Hz, 3H, NCH(CH₃)CH₂CH₃), 1.74 (h, J=7.3 Hz, 2H, SCH₂CH₂CH₃), 1.95 (m, 2H, NCH(CH₃)CH₂CH₃), 3.15 (m, 2H, SCH₂CH₂CH₃), 4.57 (m, 1H, NCH(CH₃)CH₂CH₃), 8.63 (s, 1H, 8-H).

$^{13}$C NMR (DMSO-d₆) δ 10.5 (NCH(CH₃)CH₂CH₃), 13.3 (SCH₂CH₂CH₃), 19.8 (NCH(CH₃)CH₂CH₃), 22.1 (SCH₂CH₂CH₃), 28.3 (NCH(CH₃)CH₂CH₃), 32.6 (SCH₂CH₂CH₃), 53.6 (NCH(CH₃)CH₂CH₃), 128.2 (C-5), 145.1 (C-8), 149.0 (C-6), 152.5 (C-4), 163.6 (C-2).

9-(sec-Butyl)-N-((1R,2S)-2-(3,4-difluorophenyl)cyclopropyl)-2-(propylthio)-9H-purin-6-amine (8c)

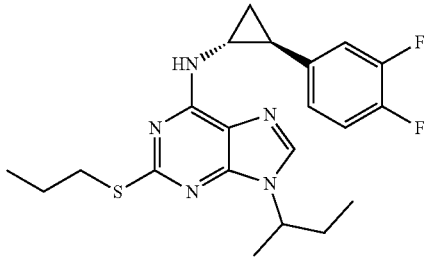 [SMILES: CCCSc1nc(N[C@@H]2C[C@H]2c2ccc(F)c(F)c2)c2ncn(C(C)CC)c2n1]

A solution of (8b) (143.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 4 h. After distillation of acetonitrile and triethylamine under vacuum, the residue was purified by silica gel column chromatography.

Yield: 66%.

Melting point: 68-71° C.

$^{1}$H NMR (CDCl₃) δ 0.85 (td, J=7.4 Hz/1.6 Hz, 3H, NCH(CH₃)CH₂CH₃), 0.96 (t, J=7.3 Hz, 3H, SCH₂CH₂CH₃), 1.33 (m, 2H, NHCH(CH₂)CHPh), 1.57 (d, J=6.9 Hz, 3H, NCH(CH₃)CH₂CH₃), 1.69 (h, J=7.3 Hz, 2H, SCH₂CH₂CH₃), 1.95 (m, 2H, NCH(CH₃)CH₂CH₃), 2.10 (m, 1H, NHCH(CH₂)CHPh), 3.03 (m, 2H, SCH₂CH₂CH₃), 3.11 (bs, 1H, NHCH(CH₂)CHPh), 4.52 (m, 1H, NCH(CH₃)

CH$_2$CH$_3$), 6.12 (bs, 1H, NH), 7.00 (m, 1H, 6'-H), 7.10 (m, 2H, 2'-H/5'-H), 7.67 (s, 1H, 8-H).

$^{13}$C NMR (CDCl$_3$) δ 10.7 (NCH(CH$_3$)CH$_2$CH$_3$), 13.5 (SCH$_2$CH$_2$CH$_3$), 15.9 (NHCH(CH$_2$)CHPh), 20.6 (NCH(CH$_3$)CH$_2$CH$_3$), 22.9 (SCH$_2$CH$_2$CH$_3$), 25.2 (NHCH(CH$_2$)CHPh), 29.5 (NCH(CH$_3$)CH$_2$CH$_3$), 33.2 (SCH$_2$CH$_2$CH$_3$), 33.3 (NHCH(CH$_2$)CHPh), 53.0 (NCH(CH$_3$)CH$_2$CH$_3$), 115.8 (d, J=17 Hz, C-2'), 116.9 (d, J=17 Hz, C-5'), 117.3 (C-5), 122.8 (C-6'), 137.0 (C-8), 137.9 (C-1'), 147.9-149.9 (dd, 246 Hz/13 Hz, C-4'), 149.2-151.2 (dd, 247 Hz/13 Hz, C-3'), 150.3 (C-4), 154.4 (C-6), 165.1 (C-2).

Example 9

Synthesis of 9-(tert-butyl)-N-((1R,2S)-2-(3,4-difluorophenyl)cyclopropyl)-2-(propylthio)-9H-purin-6-amine (9c)

N$^4$-(tert-Butyl)-6-chloro-2-(propylthio)pyrimidine-4,5-diamine (9a)

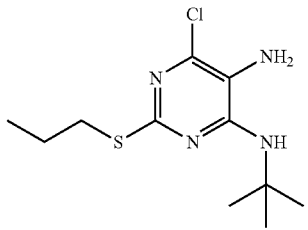 [SMILES: CCCSc1nc(Cl)c(N)c(NC(C)(C)C)n1]

4,6-Dichloro-2-(propylthio)pyrimidin-5-amine (0.5 g, 2.1 mmol) was dissolved in methanol (2 mL) and supplemented with tert-butylamine (460.0 mg, 6.3 mmol). The reaction mixture was introduced in a sealed vessel and heated at 100° C. for 24 h. After concentration of the reaction mixture to dryness under vacuum, the residue was purified by silica gel column chromatography.

Yield: 88%.

Melting point: 88-89° C.

$^1$H NMR (DMSO-d$_6$) δ 0.95 (t, J=7.3 Hz, 3H, SCH$_2$CH$_2$CH$_3$), 1.43 (s, 9H, NHC(CH$_3$)$_3$), 1.62 (h, J=7.3 Hz, 2H, SCH$_2$CH$_2$CH$_3$), 2.95 (t, J=7.3 Hz, 2H, SCH$_2$CH$_2$CH$_3$), 4.91 (bs, 2H, NH$_2$), 6.19 (s, 1H, NHC(CH$_3$)$_3$).

$^{13}$C NMR (DMSO-d$_6$) δ 13.3 (SCH$_2$CH$_2$CH$_3$), 22.9 (SCH$_2$CH$_2$CH$_3$), 28.5 (NHC(CH$_3$)$_3$), 31.9 (SCH$_2$CH$_2$CH$_3$), 51.9 (NHC(CH$_3$)$_3$), 120.3 (C-5), 137.6 (C-6), 152.1 (C-4), 154.5 (C-2).

9-(tert-Butyl)-6-chloro-2-(propylthio)-9H-purine (9b)

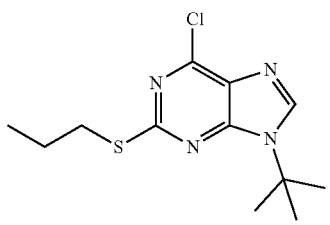 [SMILES: CCCSc1nc(Cl)c2ncn(C(C)(C)C)c2n1]

A solution of (9a) (275.0 mg, 1 mmol) in acetic acid (2.5 mL) and triethyl orthoformate (2.5 mL, 15 mmol) was heated at a temperature of 130° C. under reflux for 10 h. After distillation of the acetic acid and triethyl orthoformate under vacuum, the residue was purified by silica gel column chromatography.

Yield: 41%.

Melting point: 116-117° C.

$^1$H NMR (DMSO-d$_6$) δ 1.02 (t, J=7.4 Hz, 3H, SCH$_2$CH$_2$CH$_3$), 1.74 (m, 11H, SCH$_2$CH$_2$CH$_3$/NC(CH$_3$)$_3$), 3.14 (t, J=7.2 Hz, 2H, SCH$_2$CH$_2$CH$_3$), 8.54 (s, 1H, 8-H).

$^{13}$C NMR (DMSO-d$_6$) δ 13.3 (SCH$_2$CH$_2$CH$_3$), 22.1 (SCH$_2$CH$_2$CH$_3$), 28.3 (NC(CH$_3$)$_3$), 32.7 (SCH$_2$CH$_2$CH$_3$), 58.0 (NC(CH$_3$)$_3$), 129.0 (C-5), 144.2 (C-8), 149.3 (C-6), 152.6 (C-4), 162.9 (C-2).

9-(tert-Butyl)-N-((1R,2S)-2-(3,4-difluorophenyl)cyclopropyl)-2-(propylthio)-9H-purin-6-amine (9c)

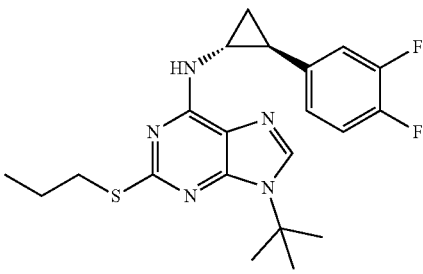 [SMILES: CCCSc1nc(N[C@@H]2C[C@H]2c2ccc(F)c(F)c2)c2ncn(C(C)(C)C)c2n1]

A solution of (9b) (143.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 2 h. After distillation of acetonitrile and triethylamine under vacuum, the residue was purified by silica gel column chromatography.

Yield: 56%.

Melting point: 125-128° C.

$^1$H NMR (CDCl$_3$) δ 1.01 (t, J=7.4 Hz, 3H, SCH$_2$CH$_2$CH$_3$), 1.29 (m, 2H, NHCH(CH$_2$)CHPh), 1.77 (m, 11H, SCH$_2$CH$_2$CH$_3$/NC(CH$_3$)$_3$), 2.08 (m, 1H, NHCH(CH$_2$)CHPh), 3.06 (m, 3H, SCH$_2$CH$_2$CH$_3$/NHCH(CH$_2$)CHPh), 5.95 (bs, 1H, NH), 7.08 (m, 2H, 5'-H/6'-H), 7.17 (m, 1H, 2'-H), 7.70 (s, 1H, 8-H).

$^{13}$C NMR (CDCl$_3$) δ 13.6 (SCH$_2$CH$_2$CH$_3$), 15.6 (NHCH(CH$_2$)CHPh), 23.1 (SCH$_2$CH$_2$CH$_3$), 25.2 (NHCH(CH$_2$)CHPh), 29.0 (NC(CH$_3$)$_3$), 33.0 (NHCH(CH$_2$)CHPh), 33.2 (SCH$_2$CH$_2$CH$_3$), 57.1 (NC(CH$_3$)$_3$), 116.2 (d, J=17 Hz, C-2'), 116.9 (d, J=17 Hz, C-5'), 118.9 (C-5), 123.1 (C-6'), 136.5 (C-8), 137.8 (C-1'), 147.9-149.9 (dd, 246 Hz/13 Hz, C-4'), 149.2-151.2 (dd, 247 Hz/13 Hz, C-3'), 150.7 (C-4), 154.9 (C-6), 164.3 (C-2).

Example 10

Synthesis of 9-cyclobutyl-N-((1R,2S)-2-(3,4-difluorophenyl)cyclopropyl)-2-(propylthio)-9H-purin-6-amine (10c)

6-Chloro-N⁴-cyclobutyl-2-(propylthio)pyrimidine-4,5-diamine (10a)

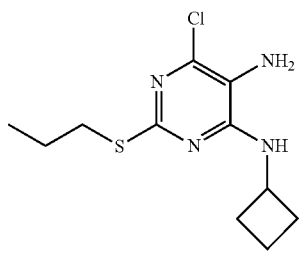 [SMILES: CCCSc1nc(Cl)c(N)c(NC2CCC2)n1]

4,6-Dichloro-2-(propylthio)pyrimidin-5-amine (0.5 g, 2.1 mmol) was dissolved in methanol (2 mL) and supplemented with cyclobutylamine (440.0 mg, 6.3 mmol). The reaction mixture was introduced in a sealed vessel and heated at 100° C. for 1 h. After concentration of the reaction mixture to dryness under vacuum, the residue was purified by silica gel column chromatography.

Yield: 96%.

Melting point: 73-75.5° C.

$^1$H NMR (DMSO-$d_6$) δ 0.96 (t, J=7.4 Hz, 3H, SCH$_2$CH$_2$CH$_3$), 1.63 (h, J=7.3 Hz, 2H, SCH$_2$CH$_2$CH$_3$), 1.72 (m, 2H, NHCH(CH$_2$)$_3$), 1.95 (m, 2H, NHCH(CH$_2$)$_3$), 2.29 (m, 2H, NHCH(CH$_2$)$_3$), 2.94 (t, J=7.2 Hz, 2H, SCH$_2$CH$_2$CH$_3$), 4.38 (h, J=8.0 Hz, 1H, NHCH(CH$_2$)$_3$), 4.80 (s, 2H, NH$_2$), 7.11 (d, J=6.3 Hz, 1H, NHCH(CH$_2$)$_3$).

$^{13}$C NMR (DMSO-$d_6$) δ 13.3 (SCH$_2$CH$_2$CH$_3$), 14.9 (NHCH(CH$_2$)$_3$), 22.7 (SCH$_2$CH$_2$CH$_3$), 30.2 (NHCH(CH$_2$)$_3$), 32.1 (SCH$_2$CH$_2$CH$_3$), 46.3 (NHCH(CH$_2$)$_3$), 119.7 (C-5), 137.4 (C-6), 151.5 (C-4), 155.1 (C-2).

6-Chloro-9-cyclobutyl-2-(propylthio)-9H-purine (10b)

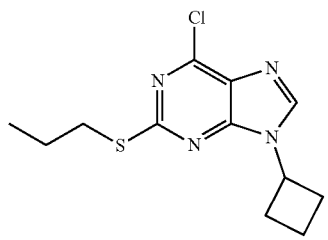 [SMILES: CCCSc1nc(Cl)c2ncn(C3CCC3)c2n1]

A solution of (10a) (273.0 mg, 1 mmol) in acetic acid (2.5 mL) and triethyl orthoformate (2.5 mL, 15 mmol) was heated at a temperature of 130° C. under reflux for 1 h. After distillation of the acetic acid and triethyl orthoformate under vacuum, the residue was purified by silica gel column chromatography.

Yield: 62%.

Melting point: 89-91.5° C.

$^1$H NMR (DMSO-$d_6$) δ 1.02 (t, J=7.3 Hz, 3H, SCH$_2$CH$_2$CH$_3$), 1.75 (h, J=7.3 Hz, 2H, SCH$_2$CH$_2$CH$_3$), 1.90 (m, 2H, NCH(CH$_2$)$_3$), 2.47 (m, 2H, NCH(CH$_2$)$_3$), 2.73 (m, 2H, NCH(CH$_2$)$_3$), 3.17 (t, J=7.2 Hz, 2H, SCH$_2$CH$_2$CH$_3$), 5.03 (p, J=8.6 Hz, 1H, NCH(CH$_2$)$_3$), 8.66 (s, 1H, 8-H).

$^{13}$C NMR (DMSO-$d_6$) δ 13.3 (SCH$_2$CH$_2$CH$_3$), 14.8 (NCH(CH$_2$)$_3$), 22.1 (SCH$_2$CH$_2$CH$_3$), 29.2 (NCH(CH$_2$)$_3$), 32.7 (SCH$_2$CH$_2$CH$_3$), 48.8 (NCH(CH$_2$)$_3$), 128.3 (C-5), 145.1 (C-8), 148.9 (C-6), 152.5 (C-4), 163.7 (C-2).

9-Cyclobutyl-N-((1R,2S)-2-(3,4-difluorophenyl)cyclopropyl)-2-(propylthio)-9H-purin-6-amine (10c)

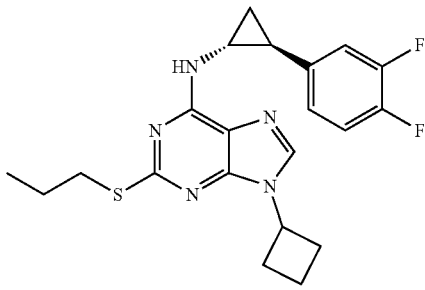 [SMILES: CCCSc1nc(N[C@@H]2C[C@H]2c2ccc(F)c(F)c2)c2ncn(C3CCC3)c2n1]

A solution of (10b) (142.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 2 h. After distillation of acetonitrile and triethylamine under vacuum, the residue was purified by silica gel column chromatography.

Yield: 76%.

Melting point: 143-145° C.

$^1$H NMR (CDCl$_3$) δ 0.96 (t, J=7.4 Hz, 3H, SCH$_2$CH$_2$CH$_3$), 1.32 (m, 2H, NHCH(CH$_2$)CHPh), 1.70 (h, J=7.3 Hz, 2H, SCH$_2$CH$_2$CH$_3$), 1.95 (m, 2H, NCH(CH$_2$)$_3$), 2.09 (m, 1H, NHCH(CH$_2$)CHPh), 2.56 (m, 2H, NCH(CH$_2$)$_3$), 2.64 (m, 2H, NCH(CH$_2$)$_3$), 3.04 (m, 2H, SCH$_2$CH$_2$CH$_3$), 3.10 (bs, 1H, NHCH(CH$_2$)CHPh), 4.95 (p, J=8.6 Hz, 1H, NCH(CH$_2$)$_3$), 6.06 (bs, 1H, NH), 7.00 (m, 1H, 6'-H), 7.09 (m, 2H, 2'-H/5'-H), 7.74 (s, 1H, 8-H).

$^{13}$C NMR (CDCl$_3$) δ 13.5 (SCH$_2$CH$_2$CH$_3$), 15.3 (NCH(CH$_2$)$_3$), 16.0 (NHCH(CH$_2$)CHPh), 22.9 (SCH$_2$CH$_2$CH$_3$), 25.2 (NHCH(CH$_2$)CHPh), 30.5 (NCH(CH$_2$)$_3$), 33.2 (SCH$_2$CH$_2$CH$_3$), 33.3 (NHCH(CH$_2$)CHPh), 48.8 (NCH(CH$_2$)$_3$), 115.8 (d, J=17 Hz, C-2'), 116.9 (d, J=17 Hz, C-5'), 117.5 (C-5), 122.8 (C-6'), 137.3 (C-8), 137.8 (C-1'), 147.9-149.9 (dd, 246 Hz/13 Hz, C-4'), 149.2-151.2 (dd, 247 Hz/13 Hz, C-3'), 150.4 (C-4), 154.5 (C-6), 165.2 (C-2).

Example 11

Synthesis of N-((1R,2S)-2-(3,4-difluorophenylcyclopropyl)-9-pentyl-2-(propylthio)-9H-purin-6-amine (11c)

6-Chloro-N$^4$-pentyl-2-(propylthio)pyrimidine-4,5-diamine (11a)

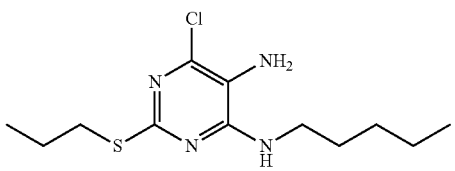 [SMILES: CCCCCNc1nc(SCCC)nc(Cl)c1N]

4,6-Dichloro-2-(propylthio)pyrimidin-5-amine (0.5 g, 2.1 mmol) was dissolved in methanol (2 mL) and supplemented with n-pentylamine (550.0 mg, 6.3 mmol). The reaction mixture was introduced in a sealed vessel and heated at 100° C. for 30 min. After concentration of the reaction mixture to dryness under vacuum, the residue was purified by silica gel column chromatography.

Yield: 96%.

Melting point: 68-69° C.

$^1$H NMR (DMSO-d$_6$) δ 0.87 (t, J=7.0 Hz, 3H, NHCH$_2$CH$_2$CH$_2$CH$_2$CH$_3$), 0.95 (t, J=7.4 Hz, 3H, SCH$_2$CH$_2$CH$_3$), 1.30 (m, 4H, NHCH$_2$CH$_2$CH$_2$CH$_2$CH$_3$), 1.55 (p, J=7.3 Hz, 2H, NHCH$_2$CH$_2$CH$_2$CH$_2$CH$_3$), 1.63 (h, J=7.3 Hz, 2H, SCH$_2$CH$_2$CH$_3$), 2.94 (t, J=7.2 Hz, 2H, SCH$_2$CH$_2$CH$_3$), 3.34 (m, 2H, NHCH$_2$CH$_2$CH$_2$CH$_2$CH$_3$), 4.75 (s, 2H, NH$_2$), 6.95 (t, J=5.2 Hz, 1H, NHCH$_2$CH$_2$CH$_2$CH$_2$CH$_3$).

$^{13}$C NMR (DMSO-d$_6$) δ 13.3 (SCH$_2$CH$_2$CH$_3$), 13.9 (NHCH$_2$CH$_2$CH$_2$CH$_2$CH$_3$), 21.9 (NHCH$_2$CH$_2$CH$_2$CH$_2$CH$_3$), 22.8 (SCH$_2$CH$_2$CH$_3$), 28.3 (NHCH$_2$CH$_2$CH$_2$CH$_2$CH$_3$), 28.7 (NHCH$_2$CH$_2$CH$_2$CH$_2$CH$_3$), 32.1 (SCH$_2$CH$_2$CH$_3$), 40.8 (NHCH$_2$CH$_2$CH$_2$CH$_2$CH$_3$), 119.8 (C-5), 137.3 (C-6), 152.6 (C-4), 155.2 (C-2).

6-Chloro-9-pentyl-2-(propylthio)-9H-purine (11b)

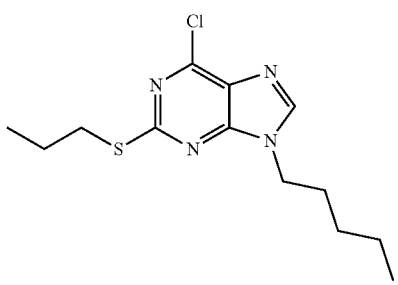 [SMILES: CCCCCn1cnc2c(Cl)nc(SCCC)nc21]

A solution of (11a) (289.0 mg, 1 mmol) in acetic acid (2.5 mL) and triethyl orthoformate (2.5 mL, 15 mmol) was heated at a temperature of 130° C. under reflux for 1 h. After distillation of the acetic acid and triethyl orthoformate under vacuum, the residue was purified by silica gel column chromatography.

Yield: 87%.

Melting point: liquid.

$^1$H NMR (DMSO-d$_6$) δ 0.85 (t, J=7.3 Hz, 3H, NCH$_2$CH$_2$CH$_2$CH$_2$CH$_3$), 1.02 (t, J=7.4 Hz, 3H, SCH$_2$CH$_2$CH$_3$), 1.23 (m, 2H, NCH$_2$CH$_2$CH$_2$CH$_2$CH$_3$), 1.31 (m, 2H, NCH$_2$CH$_2$CH$_2$CH$_2$CH$_3$), 1.75 (h, J=7.3 Hz, 2H, SCH$_2$CH$_2$CH$_3$), 1.86 (p, J=7.2 Hz, 2H, NCH$_2$CH$_2$CH$_2$CH$_2$CH$_3$), 3.17 (t, J=7.2 Hz, 2H, SCH$_2$CH$_2$CH$_3$), 4.22 (t, J=7.1 Hz, 2H, NCH$_2$CH$_2$CH$_2$CH$_2$CH$_3$), 8.56 (s, 1H, 8-H).

$^{13}$C NMR (DMSO-d$_6$) δ 13.3 (SCH$_2$CH$_2$CH$_3$), 13.7 (NCH$_2$CH$_2$CH$_2$CH$_2$CH$_3$), 21.5 (NCH$_2$CH$_2$CH$_2$CH$_2$CH$_3$), 22.1 (SCH$_2$CH$_2$CH$_3$), 28.1 (NCH$_2$CH$_2$CH$_2$CH$_2$CH$_3$), 28.5 (NCH$_2$CH$_2$CH$_2$CH$_2$CH$_3$), 32.6 (SCH$_2$CH$_2$CH$_3$), 43.6 (NCH$_2$CH$_2$CH$_2$CH$_2$CH$_3$), 127.9 (C-5), 146.3 (C-8), 148.9 (C-6), 152.8 (C-4), 163.8 (C-2).

N-((1R,2S)-2-(3,4-Difluorophenyl)cyclopropyl)-9-pentyl-2-(propylthio)-9H-purin-6-amine (11c)

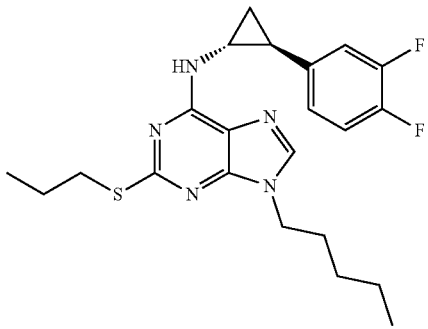 [SMILES: CCCCCn1cnc2c(N[C@@H]3C[C@H]3c3ccc(F)c(F)c3)nc(SCCC)nc21]

A solution of (11b) (150.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 3 h. After distillation of acetonitrile and triethylamine under vacuum, the residue was purified by silica gel column chromatography.

Yield: 83%.

Melting point: 98-100.5° C.

$^1$H NMR (CDCl$_3$) δ 0.89 (t, J=7.2 Hz, 3H, NCH$_2$CH$_2$CH$_2$CH$_2$CH$_3$), 0.95 (t, J=7.4 Hz, 3H, SCH$_2$CH$_2$CH$_3$), 1.32 (m, 6H, NCH$_2$CH$_2$CH$_2$CH$_2$CH$_3$/NHCH(CH$_2$)CHPh), 1.68 (h, J=7.3 Hz, 2H, SCH$_2$CH$_2$CH$_3$), 1.87 (p, J=7.3 Hz, 2H, NCH$_2$CH$_2$CH$_2$CH$_2$CH$_3$), 2.09 (m, 1H, NHCH(CH$_2$)CHPh), 3.04 (m, 2H, SCH$_2$CH$_2$CH$_3$), 3.10 (bs, 1H, NHCH(CH$_2$)CHPh), 4.12 (t, J=7.2 Hz, 2H, NCH$_2$CH$_2$CH$_2$CH$_2$CH$_3$), 5.97 (bs, 1H, NH), 7.00 (m, 1H, 6'-H), 7.09 (m, 2H, 2'-H/5'-H), 7.60 (s, 1H, 8-H).

$^{13}$C NMR (CDCl$_3$) δ 13.5 (SCH$_2$CH$_2$CH$_3$), 13.9 (NCH$_2$CH$_2$CH$_2$CH$_2$CH$_3$), 16.0 (NHCH(CH$_2$)CHPh), 22.2 (NCH$_2$CH$_2$CH$_2$CH$_2$CH$_3$), 22.9 (SCH$_2$CH$_2$CH$_3$), 25.2 (NHCH(CH$_2$)CHPh), 28.7 (NCH$_2$CH$_2$CH$_2$CH$_2$CH$_3$), 29.7 (NCH$_2$CH$_2$CH$_2$CH$_2$CH$_3$), 33.2 (SCH$_2$CH$_2$CH$_3$), 33.3 (NHCH(CH$_2$)CHPh), 43.7 (NCH$_2$CH$_2$CH$_2$CH$_2$CH$_3$), 115.7 (d, J=17 Hz, C-2'), 116.9 (d, J=17 Hz, C-5'), 117.5 (C-5), 122.7 (C-6'), 137.9 (C-11), 139.0 (C-8), 147.9-149.9 (dd, 246 Hz/13 Hz, C-4'), 149.2-151.2 (dd, 247 Hz/13 Hz, C-3'), 150.5 (C-4), 154.6 (C-6), 165.4 (C-2).

Example 12

Synthesis of 9-cyclopentyl-N-((1R,2S)-2-(3,4-difluorophenyl)cyclopropyl)-2-(propylthio)-9H-purin-6-amine (12c)

6-Chloro-N⁴-cyclopentyl-2-(propylthio)pyrimidine-4,5-diamine (12a)

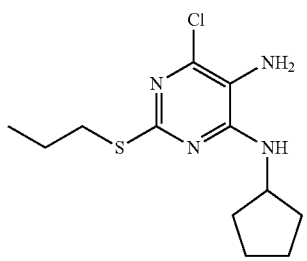 [SMILES: CCCSc1nc(Cl)c(N)c(NC2CCCC2)n1]

4,6-Dichloro-2-(propylthio)pyrimidin-5-amine (0.5 g, 2.1 mmol) was dissolved in methanol (2 mL) and supplemented with cyclopentylamine (536.0 mg, 6.3 mmol). The reaction mixture was introduced in a sealed vessel and heated at 100° C. for 2 h. After concentration of the reaction mixture to dryness under vacuum, the residue was purified by silica gel column chromatography.

Yield: 95%.

Melting point: 86-88° C.

$^1$H NMR (DMSO-d$_6$) δ 0.95 (t, J=7.4 Hz, 3H, SCH$_2$CH$_2$CH$_3$), 1.49 (m, 2H, NHCH(CH$_2$)$_4$), 1.55 (m, 2H, NHCH(CH$_2$)$_4$), 1.64 (m, 2H, SCH$_2$CH$_2$CH$_3$), 1.70 (m, 2H, NHCH(CH$_2$)$_4$), 1.96 (m, 2H, NHCH(CH$_2$)$_4$), 2.94 (t, J=7.2 Hz, 2H, SCH$_2$CH$_2$CH$_3$), 4.25 (h, J=6.7 Hz, 1H, NHCH(CH$_2$)$_4$), 4.83 (s, 2H, NH$_2$), 6.76 (d, J=6.3 Hz, 1H, NHCH(CH$_2$)$_4$).

$^{13}$C NMR (DMSO-d$_6$) δ 13.3 (SCH$_2$CH$_2$CH$_3$), 22.9 (SCH$_2$CH$_2$CH$_3$), 23.5 (NHCH(CH$_2$)$_4$), 32.1 (SCH$_2$CH$_2$CH$_3$), 32.2 (NHCH(CH$_2$)$_4$), 52.7 (NHCH(CH$_2$)$_4$), 119.9 (C-5), 137.2 (C-6), 152.0 (C-4), 155.0 (C-2).

6-Chloro-9-cyclopentyl-2-(propylthio)-9H-purine (12b)

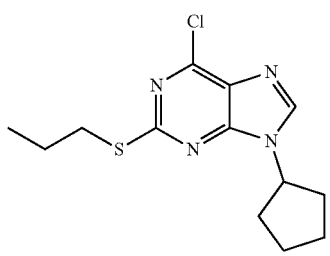 [SMILES: CCCSc1nc(Cl)c2ncn(C3CCCC3)c2n1]

A solution of (12a) (287.0 mg, 1 mmol) in acetic acid (2.5 mL) and triethyl orthoformate (2.5 mL, 15 mmol) was heated at a temperature of 130° C. under reflux for 1 h. After distillation of the acetic acid and triethyl orthoformate under vacuum, the residue was purified by silica gel column chromatography.

Yield: 37%.

Melting point: 81-83° C.

$^1$H NMR (DMSO-d$_6$) δ 1.01 (t, J=7.3 Hz, 3H, SCH$_2$CH$_2$CH$_3$), 1.74 (m, 4H, SCH$_2$CH$_2$CH$_3$/NCH(CH$_2$)$_4$), 1.90 (m, 2H, NCH(CH$_2$)$_4$), 2.06 (m, 2H, NCH(CH$_2$)$_4$), 2.19 (m, 2H, NCH(CH$_2$)$_4$), 3.16 (t, J=7.2 Hz, 2H, SCH$_2$CH$_2$CH$_3$), 4.90 (p, J=7.6 Hz, 1H, NCH(CH$_2$)$_4$), 8.59 (s, 1H, 8-H).

$^{13}$C NMR (DMSO-d$_6$) δ 13.2 (SCH$_2$CH$_2$CH$_3$), 22.1 (SCH$_2$CH$_2$CH$_3$), 23.8 (NCH(CH$_2$)$_4$), 31.5 (NCH(CH$_2$)$_4$), 32.6 (SCH$_2$CH$_2$CH$_3$), 56.4 (NCH(CH$_2$)$_4$), 128.5 (C-5), 145.2 (C-8), 148.9 (C-6), 152.5 (C-4), 163.5 (C-2).

9-Cyclopentyl-N-(1R,2S)-2-(3,4-difluorophenyl)cyclopropyl)-2-(propylthio)-9H-purin-6-amine (12c)

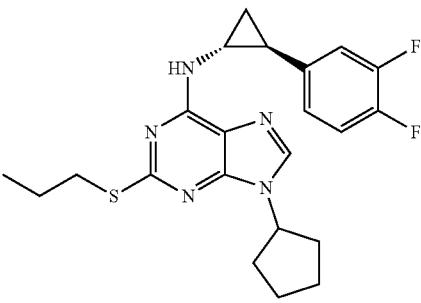 [SMILES: CCCSc1nc(N[C@@H]2C[C@H]2c2ccc(F)c(F)c2)c2ncn(C3CCCC3)c2n1]

A solution of (12b) (149.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 3 h. After distillation of acetonitrile and triethylamine under vacuum, the residue was purified by silica gel column chromatography.

Yield: 35%.

Melting point: 112-114° C.

$^1$H NMR (CDCl$_3$) δ 0.95 (t, J=7.4 Hz, 3H, SCH$_2$CH$_2$CH$_3$), 1.31 (m, 2H, NHCH(CH$_2$)CHPh), 1.68 (h, J=7.4 Hz, 2H, SCH$_2$CH$_2$CH$_3$), 1.79 (m, 2H, NCH(CH$_2$)$_4$), 1.94 (m, 2H, NCH(CH$_2$)$_4$), 1.99 (m, 2H, NCH(CH$_2$)$_4$), 2.09 (m, 1H, NHCH(CH$_2$)CHPh), 2.26 (m, 2H, NCH(CH$_2$)$_4$), 3.04 (m, 2H, SCH$_2$CH$_2$CH$_3$), 3.10 (bs, 1H, NHCH(CH$_2$)CHPh), 4.84 (p, J=7.4 Hz, 1H, NCH(CH$_2$)$_4$), 5.92 (bs, 1H, NH), 7.00 (m, 1H, 6'-H), 7.09 (m, 2H, 2'-H/5'-H), 7.65 (s, 1H, 8-H).

$^{13}$C NMR (CDCl$_3$) δ 13.5 (SCH$_2$CH$_2$CH$_3$), 16.0 (NHCH(CH$_2$)CHPh), 22.9 (SCH$_2$CH$_2$CH$_3$), 24.1 (NCH(CH$_2$)$_4$), 25.3 (NHCH(CH$_2$)CHPh), 32.6 (NCH(CH$_2$)$_4$), 33.2 (SCH$_2$CH$_2$CH$_3$), 33.3 (NHCH(CH$_2$)CHPh), 56.0 (NCH(CH$_2$)$_4$), 115.7 (d, J=17 Hz, C-2'), 116.9 (d, J=17 Hz, C-5'), 117.9 (C-5), 122.8 (C-6'), 137.4 (C-8), 137.9 (C-1'), 147.9-149.9 (dd, 246 Hz/13 Hz, C-4'), 149.2-151.2 (dd, 247 Hz/13 Hz, C-3'), 150.0 (C-4), 154.6 (C-6), 165.2 (C-2).

Example 13

Synthesis of N-((1R,2S)-2-(3,4-difluorophenyl)cyclopropyl-9-hexyl-2-(propylthio)-9H-purin-6-amine (13c)

6-Chloro-N⁴-hexyl-2-(propylthio)pyrimidine-4,5-diamine (13a)

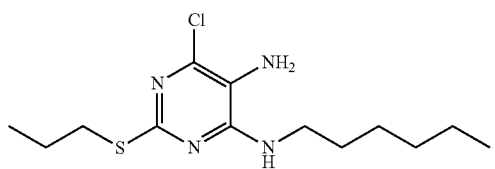 [SMILES: CCCCCCNc1nc(SCCC)nc(Cl)c1N]

4,6-Dichloro-2-(propylthio)pyrimidin-5-amine (0.5 g, 2.1 mmol) was dissolved in methanol (2 mL) and supplemented with n-hexylamine (638.0 mg, 6.3 mmol). The reaction mixture was introduced in a sealed vessel and heated at 100° C. for 1 h. After concentration of the reaction mixture to dryness under vacuum, the residue was purified by silica gel column chromatography.

Yield: 85%.

Melting point: 54-57° C.

$^1$H NMR (DMSO-$d_6$) δ 0.87 (t, J=6.4 Hz, 3H, NHCH$_2$CH$_2$CH$_2$CH$_2$CH$_2$CH$_3$), 0.95 (t, J=7.3 Hz, 3H, SCH$_2$CH$_2$CH$_3$), 1.29 (m, 6H, NHCH$_2$CH$_2$CH$_2$CH$_2$CH$_2$CH$_3$), 1.54 (p, J=6.9 Hz, 2H, NHCH$_2$CH$_2$CH$_2$CH$_2$CH$_2$CH$_3$), 1.63 (h, J=7.3 Hz, 2H, SCH$_2$CH$_2$CH$_3$), 2.94 (t, J=7.2 Hz, 2H, SCH$_2$CH$_2$CH$_3$), 3.34 (m, 2H, NHCH$_2$CH$_2$CH$_2$CH$_2$CH$_2$CH$_3$), 4.76 (s, 2H, NH$_2$), 6.95 (t, J=4.9 Hz, 1H, NHCH$_2$CH$_2$CH$_2$CH$_2$CH$_2$CH$_3$).

$^{13}$C NMR (DMSO-$d_6$) δ 13.3 (SCH$_2$CH$_2$CH$_3$), 13.9 (NHCH$_2$CH$_2$CH$_2$CH$_2$CH$_2$CH$_3$), 22.1 (NHCH$_2$CH$_2$CH$_2$CH$_2$CH$_2$CH$_3$), 22.8 (SCH$_2$CH$_2$CH$_3$), 26.1 (NHCH$_2$CH$_2$CH$_2$CH$_2$CH$_2$CH$_3$), 28.6 (NHCH$_2$CH$_2$CH$_2$CH$_2$CH$_2$CH$_3$), 31.0 (NHCH$_2$CH$_2$CH$_2$CH$_2$CH$_2$CH$_3$), 32.1 (SCH$_2$CH$_2$CH$_3$), 40.9 (NHCH$_2$CH$_2$CH$_2$CH$_2$CH$_2$CH$_3$), 119.8 (C-5), 137.3 (C-6), 152.6 (C-4), 155.2 (C-2).

6-Chloro-9-hexyl-2-(propylthio)-9H-purine (13b)

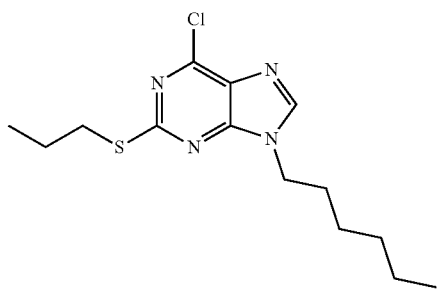 [SMILES: CCCCCCn1cnc2c(Cl)nc(SCCC)nc21]

A solution of (13a) (303.0 mg, 1 mmol) in acetic acid (2.5 mL) and triethyl orthoformate (2.5 mL, 15 mmol) was heated at a temperature of 130° C. under reflux for 1 h. After distillation of the acetic acid and triethyl orthoformate under vacuum, the residue was purified by silica gel column chromatography.

Yield: 90%.

Melting point: liquid.

$^1$H NMR (DMSO-$d_6$) δ 0.83 (t, J=6.8 Hz, 3H, NCH$_2$CH$_2$CH$_2$CH$_2$CH$_2$CH$_3$), 1.01 (t, J=7.4 Hz, 3H, SCH$_2$CH$_2$CH$_3$), 1.25 (m, 6H, NCH$_2$CH$_2$CH$_2$CH$_2$CH$_2$CH$_3$), 1.74 (h, J=7.3 Hz, 2H, SCH$_2$CH$_2$CH$_3$), 1.84 (p, J=7.2 Hz, 2H, NCH$_2$CH$_2$CH$_2$CH$_2$CH$_2$CH$_3$), 3.16 (t, J=7.2 Hz, 2H, SCH$_2$CH$_2$CH$_3$), 4.21 (t, J=7.1 Hz, 2H, NCH$_2$CH$_2$CH$_2$CH$_2$CH$_2$CH$_3$), 8.56 (s, 1H, 8-H).

$^{13}$C NMR (DMSO-$d_6$) δ 13.3 (SCH$_2$CH$_2$CH$_3$), 13.8 (NCH$_2$CH$_2$CH$_2$CH$_2$CH$_2$CH$_3$), 21.9 (NCH$_2$CH$_2$CH$_2$CH$_2$CH$_2$CH$_3$), 22.1 (SCH$_2$CH$_2$CH$_3$), 25.5 (NCH$_2$CH$_2$CH$_2$CH$_2$CH$_2$CH$_3$), 28.8 (NCH$_2$CH$_2$CH$_2$CH$_2$CH$_2$CH$_3$), 30.5 (NCH$_2$CH$_2$CH$_2$CH$_2$CH$_2$CH$_3$), 32.6 (SCH$_2$CH$_2$CH$_3$), 43.6 (NCH$_2$CH$_2$CH$_2$CH$_2$CH$_2$CH$_3$), 127.9 (C-5), 146.3 (C-8), 148.9 (C-6), 152.8 (C-4), 163.8 (C-2).

N-((1R,2S)-2-(3,4-Difluorophenyl)cyclopropyl)-9-hexyl-2-(propylthio)-9H-purin-6-amine (13c)

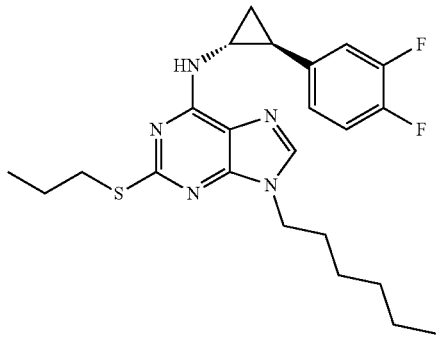 [SMILES: CCCCCCn1cnc2c(N[C@@H]3C[C@H]3c3ccc(F)c(F)c3)nc(SCCC)nc21]

A solution of (13b) (157.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.

Yield: 60%.

Melting point: 84-86° C.

$^1$H NMR (CDCl$_3$) δ 0.88 (m, 3H, NCH$_2$CH$_2$CH$_2$CH$_2$CH$_2$CH$_3$), 0.95 (t, J=7.4 Hz, 3H, SCH$_2$CH$_2$CH$_3$), 1.30 (m, 8H, NCH$_2$CH$_2$CH$_2$CH$_2$CH$_2$CH$_3$/NHCH(CH$_2$)CHPh), 1.68 (h, J=7.3 Hz, 2H, SCH$_2$CH$_2$CH$_3$), 1.86 (m, 2H, NCH$_2$CH$_2$CH$_2$CH$_2$CH$_2$CH$_3$), 2.09 (m, 1H, NHCH(CH$_2$)CHPh), 3.03 (m, 2H, SCH$_2$CH$_2$CH$_3$), 3.10 (bs, 1H, NHCH(CH$_2$)CHPh), 4.12 (t, J=7.2 Hz, 2H, NCH$_2$CH$_2$CH$_2$CH$_2$CH$_2$CH$_3$), 5.96 (bs, 1H, NH), 6.99 (m, 1H, 6'-H), 7.09 (m, 2H, 2'-H/5'-H), 7.60 (s, 1H, 8-H).

$^{13}$C NMR (CDCl$_3$) δ 13.5 (SCH$_2$CH$_2$CH$_3$), 14.0 (NCH$_2$CH$_2$CH$_2$CH$_2$CH$_2$CH$_3$), 16.0 (NHCH(CH$_2$)CHPh), 22.5 (NCH$_2$CH$_2$CH$_2$CH$_2$CH$_2$CH$_3$), 22.9 (SCH$_2$CH$_2$CH$_3$), 25.2 (NHCH(CH$_2$)CHPh), 26.3 (NCH$_2$CH$_2$CH$_2$CH$_2$CH$_2$CH$_3$), 29.9 (NCH$_2$CH$_2$CH$_2$CH$_2$CH$_2$CH$_3$), 31.2 (NCH$_2$CH$_2$CH$_2$CH$_2$CH$_2$CH$_3$), 33.2 (SCH$_2$CH$_2$CH$_3$), 33.3 (NHCH(CH$_2$)CHPh), 43.7 (NCH$_2$CH$_2$CH$_2$CH$_2$CH$_2$CH$_3$), 115.7 (d, J=17 Hz, C-2'), 116.9 (d, J=17 Hz, C-5'), 117.5 (C-5), 122.7 (C-6'), 137.9 (C-1'), 139.0 (C-8), 147.9-149.9

(dd, 246 Hz/13 Hz, C-4'), 149.2-151.2 (dd, 247 Hz/13 Hz, C-3'), 150.5 (C-4), 154.6 (C-6), 165.4 (C-2).

Example 14

Synthesis of 9-cyclohexyl-N-((1R,2S)-2-(3,4-difluorophenyl)cyclopropyl)-2-(propylthio)-9H-purin-6-amine (14c)

6-Chloro-N⁴-cyclohexyl-2-(propylthio)pyrimidine-4,5-diamine (14a)

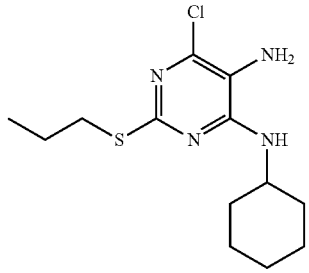 [SMILES: CCCSc1nc(Cl)c(N)c(NC2CCCCC2)n1]

4,6-Dichloro-2-(propylthio)pyrimidin-5-amine (0.5 g, 2.1 mmol) was dissolved in methanol (2 mL) and supplemented with cyclohexylamine (625.0 mg, 6.3 mmol). The reaction mixture was introduced in a sealed vessel and heated at 100° C. for 1 h. After concentration of the reaction mixture to dryness under vacuum, the residue was purified by silica gel column chromatography.

Yield: 91%.

Melting point: 90-93° C.

$^1$H NMR (DMSO-$d_6$) δ 0.96 (t, J=7.4 Hz, 3H, SCH$_2$CH$_2$CH$_3$), 1.22 (m, 5H, NHCH(CH$_2$)$_5$), 1.64 (m, 3H, SCH$_2$CH$_2$CH$_3$/NHCH(CH$_2$)$_5$), 1.75 (m, 2H, NHCH(CH$_2$)$_5$), 1.93 (m, 2H, NHCH(CH$_2$)$_5$), 2.92 (t, J=7.3 Hz, 2H, SCH$_2$CH$_2$CH$_3$), 3.84 (m, 1H, NHCH(CH$_2$)$_5$), 4.82 (s, 2H, NH$_2$), 6.68 (d, J=7.1 Hz, 1H, NHCH(CH$_2$)$_5$).

$^{13}$C NMR (DMSO-$d_6$) δ 13.4 (SCH$_2$CH$_2$CH$_3$), 23.0 (SCH$_2$CH$_2$CH$_3$), 24.8 (NHCH(CH$_2$)$_5$), 25.3 (NHCH(CH$_2$)$_5$), 32.1 (SCH$_2$CH$_2$CH$_3$), 32.3 (NHCH(CH$_2$)$_5$), 49.9 (NHCH(CH$_2$)$_5$), 119.7 (C-5), 137.4 (C-6), 151.6 (C-4), 155.0 (C-2).

6-Chloro-9-cyclohexyl-2-(propylthio)-9H-purine (14b)

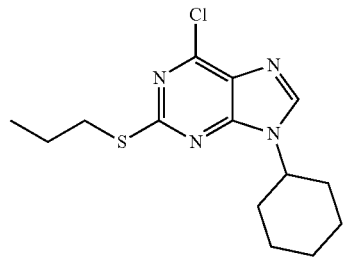 [SMILES: CCCSc1nc(Cl)c2ncn(C3CCCCC3)c2n1]

A solution of (14a) (301.0 mg, 1 mmol) in acetic acid (2.5 mL) and triethyl orthoformate (2.5 mL, 15 mmol) was heated at a temperature of 130° C. under reflux for 2 h. After distillation of the acetic acid and triethyl orthoformate under vacuum, the residue was purified by silica gel column chromatography.

Yield: 62%.

Melting point: 93-95° C.

$^1$H NMR (DMSO-$d_6$) δ 1.02 (t, J=7.3 Hz, 3H, SCH$_2$CH$_2$CH$_3$), 1.25 (m, 1H, NCH(CH$_2$)$_5$), 1.44 (m, 2H, NCH(CH$_2$)$_5$), 1.75 (m, 3H, SCH$_2$CH$_2$CH$_3$/NCH(CH$_2$)$_5$), 1.87 (m, 2H, NCH(CH$_2$)$_5$), 1.99 (m, 4H, NCH(CH$_2$)$_5$), 3.15 (t, J=7.2 Hz, 2H, SCH$_2$CH$_2$CH$_3$), 4.41 (m, 1H, NCH(CH$_2$)$_5$), 8.61 (s, 1H, 8-H).

$^{13}$C NMR (DMSO-$d_6$) δ 13.3 (SCH$_2$CH$_2$CH$_3$), 22.2 (SCH$_2$CH$_2$CH$_3$), 24.8 (NCH(CH$_2$)$_5$), 25.0 (NCH(CH$_2$)$_5$), 31.7 (NCH(CH$_2$)$_5$), 32.7 (SCH$_2$CH$_2$CH$_3$), 55.0 (NCH(CH$_2$)$_5$), 128.3 (C-5), 144.8 (C-8), 149.0 (C-6), 152.3 (C-4), 163.5 (C-2).

9-Cyclohexyl-N-((1R,2S)-2-(3,4-difluorophenyl)cyclopropyl)-2-(propylthio)-9H-purin-6-amine (14c)

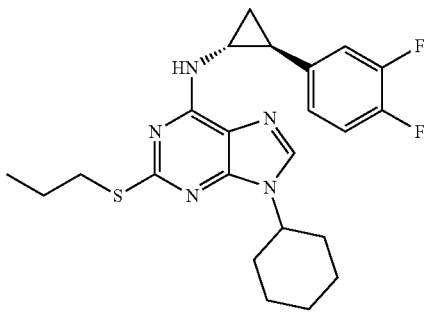 [SMILES: CCCSc1nc(N[C@@H]2C[C@H]2c2ccc(F)c(F)c2)c2ncn(C3CCCCC3)c2n1]

A solution of (14b) (156.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.

Yield: 84%.

Melting point: 85-88° C.

$^1$H NMR (CDCl$_3$) δ 0.94 (t, J=7.4 Hz, 3H, SCH$_2$CH$_2$CH$_3$), 1.30 (m, 3H, NHCH(CH$_2$)CHPh/NCH(CH$_2$)$_5$), 1.49 (m, 2H, NCH(CH$_2$)$_5$), 1.68 (h, J=7.3 Hz, 2H, SCH$_2$CH$_2$CH$_3$), 1.79 (m, 3H, NCH(CH$_2$)$_5$) 1.92 (m, 2H, NCH(CH$_2$)$_5$), 2.08 (m, 1H, NHCH(CH$_2$)CHPh), 2.14 (m, 2H, NCH(CH$_2$)$_5$), 3.03 (m, 2H, SCH$_2$CH$_2$CH$_3$), 3.11 (bs, 1H, NHCH(CH$_2$)CHPh), 4.36 (m, 1H, NCH(CH$_2$)$_5$), 5.98 (bs, 1H, NH), 6.99 (m, 1H, 6'-H), 7.08 (m, 2H, 2'-H/5'-H), 7.67 (s, 1H, 8-H).

$^{13}$C NMR (CDCl$_3$) δ 13.5 (SCH$_2$CH$_2$CH$_3$), 16.1 (NHCH(CH$_2$)CHPh), 23.0 (SCH$_2$CH$_2$CH$_3$), 25.2 (NHCH(CH$_2$)CHPh), 25.3 (NCH(CH$_2$)$_5$), 25.6 (NCH(CH$_2$)$_5$), 33.2 (SCH$_2$CH$_2$CH$_3$), 33.3 (NHCH(CH$_2$)CHPh), 54.2 (NCH(CH$_2$)$_5$), 115.6 (d, J=17 Hz, C-2'), 116.9 (d, J=17 Hz, C-5'), 117.7 (C-5), 122.7 (C-6'), 137.0 (C-8), 138.0 (C-1'), 147.9-149.9 (dd, 246 Hz/13 Hz, C-4'), 149.2-151.2 (dd, 247 Hz/13 Hz, C-3'), 150.5 (C-4), 154.6 (C-6), 165.0 (C-2).

Example 15

Synthesis of 9-allyl-N-((1R,2S)-2-(3,4-difluorophenyl)cyclopropyl)-2-(propylthio)-9H-purin-6-amine (15c)

N⁴-Allyl-6-chloro-2-(propylthio)pyrimidine-4,5-diamine (15a)

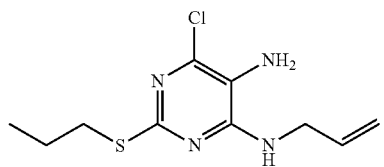 [SMILES: C=CCNc1nc(SCCC)nc(Cl)c1N]

4,6-Dichloro-2-(propylthio)pyrimidin-5-amine (0.5 g, 2.1 mmol) was dissolved in methanol (2 mL) and supplemented with allylamine (360.0 mg, 6.3 mmol). The reaction mixture was introduced in a sealed vessel and heated at 100° C. for 30 min. After concentration of the reaction mixture to dryness under vacuum, the residue was purified by silica gel column chromatography.

Yield: 92%.
Melting point: 55-57° C.

$^1$H NMR (DMSO-$d_6$) δ 0.94 (t, J=7.4 Hz, 3H, SCH$_2$CH$_2$CH$_3$), 1.62 (h, J=7.3 Hz, 2H, SCH$_2$CH$_2$CH$_3$), 2.93 (t, J=7.2 Hz, 2H, SCH$_2$CH$_2$CH$_3$), 4.02 (tt, J=5.4 Hz/1.5 Hz, 2H, NHCH$_2$CHCH$_2$), 4.80 (s, 2H, NH$_2$), 5.11 (dq, J=10.3 Hz/1.4 Hz, 1H, NHCH$_2$CHCH$_2$), 5.18 (dq, J=17.2 Hz/1.5 Hz, 1H, NHCH$_2$CHCH$_2$), 5.92 (ddt, J=17.1 Hz/10.4 Hz/5.3 Hz, 1H, NHCH$_2$CHCH$_2$), 7.15 (t, J=5.4 Hz, 1H, NHCH$_2$CHCH$_2$).

$^{13}$C NMR (DMSO-$d_6$) δ 13.3 (SCH$_2$CH$_2$CH$_3$), 22.7 (SCH$_2$CH$_2$CH$_3$), 32.1 (SCH$_2$CH$_2$CH$_3$), 43.1 (NHCH$_2$CHCH$_2$), 115.6 (NHCH$_2$CHCH$_2$), 120.0 (C-5), 135.0 (NHCH$_2$CHCH$_2$), 137.5 (C-6), 152.3 (C-4), 155.2 (C-2).

9-allyl-6-chloro-2-(propylthio)-9H-purine (15b)

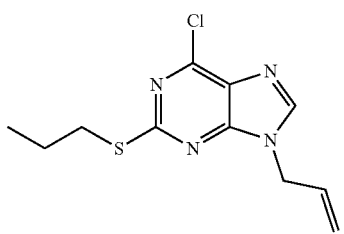 [SMILES: C=CCn1cnc2c(Cl)nc(SCCC)nc21]

A solution of (15a) (259.0 mg, 1 mmol) in acetic acid (2.5 mL) and triethyl orthoformate (2.5 mL, 15 mmol) was heated at a temperature of 130° C. under reflux for 2 h. After distillation of the acetic acid and triethyl orthoformate under vacuum, the residue was purified by silica gel column chromatography.

Yield: 89%.
Melting point: 47.5-49.5° C.

$^1$H NMR (DMSO-$d_6$) δ 1.00 (t, J=7.4 Hz, 3H, SCH$_2$CH$_2$CH$_3$), 1.73 (h, J=7.3 Hz, 2H, SCH$_2$CH$_2$CH$_3$), 3.15 (t, J=7.2 Hz, 2H, SCH$_2$CH$_2$CH$_3$), 4.87 (dt, J=5.5 Hz/1.3 Hz, 2H, NCH$_2$CHCH$_2$), 5.13 (dd, J=17.1 Hz/1.3 Hz, 1H, NCH$_2$CHCH$_2$), 5.24 (dd, J=10.3 Hz/1.3 Hz, 1H, NCH$_2$CHCH$_2$), 6.07 (m, 1H, NCH$_2$CHCH$_2$), 8.52 (s, 1H, 8-H).

$^{13}$C NMR (DMSO-$d_6$) δ 13.2 (SCH$_2$CH$_2$CH$_3$), 22.0 (SCH$_2$CH$_2$CH$_3$), 32.6 (SCH$_2$CH$_2$CH$_3$), 45.7 (NCH$_2$CHCH$_2$), 118.2 (NCH$_2$CHCH$_2$), 127.9 (C-5), 132.4 (NCH$_2$CHCH$_2$), 146.2 (C-8), 149.0 (C-6), 152.7 (C-4), 164.1 (C-2).

9-Allyl-N-((1R,2S)-2-(3,4-difluorophenyl)cyclopropyl)-2-(propylthio)-9H-purin-6-amine (15c)

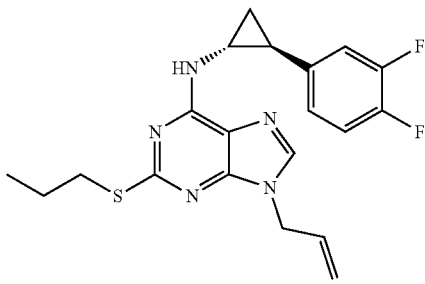 [SMILES: C=CCn1cnc2c(N[C@@H]3C[C@H]3c3ccc(F)c(F)c3)nc(SCCC)nc21]

A solution of (15b) (135.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.

Yield: 89%.
Melting point: liquid.

$^1$H NMR (CDCl$_3$) δ 0.94 (t, J=7.4 Hz, 3H, SCH$_2$CH$_2$CH$_3$), 1.32 (m, 2H, NHCH(CH$_2$)CHPh), 1.66 (h, J=7.2 Hz, 2H, SCH$_2$CH$_2$CH$_3$), 2.09 (m, 1H, NHCH(CH$_2$)CHPh), 3.04 (m, 2H, SCH$_2$CH$_2$CH$_3$), 3.12 (bs, 1H, NHCH(CH$_2$)CHPh), 4.74 (d, J=5.9 Hz, 2H, NCH$_2$CHCH$_2$), 5.23 (dd, J=17.1 Hz/1.0 Hz, 1H, NCH$_2$CHCH$_2$), 5.30 (dd, J=10.2 Hz/1.0 Hz, 1H, NCH$_2$CHCH$_2$), 6.01 (m, 2H, NCH$_2$CHCH$_2$/NH), 6.99 (m, 1H, 6'-H), 7.08 (m, 2H, 2'-H/5'-H), 7.62 (s, 1H, 8-H).

$^{13}$C NMR (CDCl$_3$) δ 13.4 (SCH$_2$CH$_2$CH$_3$), 16.1 (NHCH(CH$_2$)CHPh), 22.8 (SCH$_2$CH$_2$CH$_3$), 25.2 (NHCH(CH$_2$)CHPh), 33.2 (SCH$_2$CH$_2$CH$_3$), 33.3 (NHCH(CH$_2$)CHPh), 45.6 (NCH$_2$CHCH$_2$), 115.6 (d, J=17 Hz, C-2'), 116.9 (d, J=17 Hz, C-5'), 117.3 (C-5), 119.0 (NCH$_2$CHCH$_2$), 122.7 (C-6'), 132.0 (NCH$_2$CHCH$_2$), 137.9 (C-1'), 138.7 (C-8), 147.9-149.9 (dd, 246 Hz/13 Hz, C-4'), 149.2-151.2 (dd, 247 Hz/13 Hz, C-3'), 150.3 (C-4), 154.6 (C-6), 165.7 (C-2).

Example 16

Synthesis of 2-(6-(((1R,2S)-2-(3,4-difluorophenyl)cyclopropyl)amino)-2-(propylthio)-9H-purin-9-yl)ethanol (16c)

2-((5-Amino-6-chloro-2-(propylthio)pyrimidin-4-yl)amino)ethanol (16a)

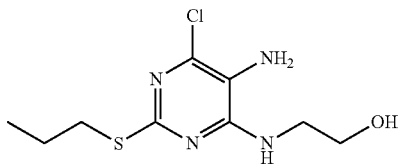 [SMILES: CCCSc1nc(Cl)c(N)c(NCCO)n1]

4,6-Dichloro-2-(propylthio)pyrimidin-5-amine (0.5 g, 2.1 mmol) was dissolved in methanol (2 mL) and supplemented with 2-aminoethanol (385.0 mg, 6.3 mmol). The reaction mixture was introduced in a sealed vessel and heated at 100° C. for 30 min. After concentration of the reaction mixture to dryness under vacuum, the residue was purified by silica gel column chromatography.

Yield: 79%.
Melting point: 99-102° C.
$^1$H NMR (DMSO-$d_6$) δ 0.95 (t, J=7.4 Hz, 3H, SCH$_2$CH$_2$CH$_3$), 1.63 (h, J=7.3 Hz, 2H, SCH$_2$CH$_2$CH$_3$), 2.93 (t, J=7.2 Hz, 2H, SCH$_2$CH$_2$CH$_3$), 3.43 (d, J=5.7 Hz, 2H, NHCH$_2$CH$_2$OH), 3.55 (d, J=5.7 Hz, 2H, NHCH$_2$CH$_2$OH), 4.78 (t, J=5.5 Hz, 1H, NHCH$_2$CH$_2$OH), 4.80 (s, 2H, NH$_2$), 7.03 (t, J=5.2 Hz, 1H, NHCH$_2$CH$_2$OH).
$^{13}$C NMR (DMSO-$d_6$) δ 13.3 (SCH$_2$CH$_2$CH$_3$), 22.7 (SCH$_2$CH$_2$CH$_3$), 32.1 (SCH$_2$CH$_2$CH$_3$), 43.7 (NHCH$_2$CH$_2$OH), 59.2 (NHCH$_2$CH$_2$OH), 120.0 (C-5), 137.4 (C-6), 152.7 (C-4), 155.1 (C-2).

2-(6-Chloro-2-(propylthio)-9H-purin-9-yl)ethanol (16b)

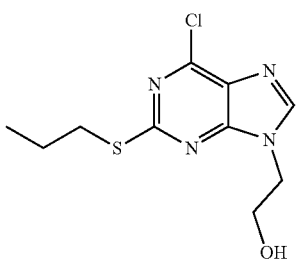 [SMILES: CCCSc1nc(Cl)c2ncn(CCO)c2n1]

A solution of (16a) (263.0 mg, 1 mmol) in acetic acid (2.5 mL) and triethyl orthoformate (2.5 mL, 15 mmol) was heated at a temperature of 130° C. under reflux for 4 h. After distillation of the acetic acid and triethyl orthoformate under vacuum, the residue was purified by silica gel column chromatography.

Yield: 57%.
Melting point: 81-83° C.
$^1$H NMR (DMSO-$d_6$) δ 1.01 (t, J=7.4 Hz, 3H, SCH$_2$CH$_2$CH$_3$), 1.73 (h, J=7.4 Hz, 2H, SCH$_2$CH$_2$CH$_3$), 3.17 (t, J=7.2 Hz, 2H, SCH$_2$CH$_2$CH$_3$), 3.78 (q, J=5.4 Hz, 2H, NCH$_2$CH$_2$OH), 4.26 (t, J=5.4 Hz, 2H, NCH$_2$CH$_2$OH), 4.99 (t, J=5.6 Hz, 1H, OH), 8.48 (s, 1H, 8-H).
$^{13}$C NMR (DMSO-$d_6$) δ 13.2 (SCH$_2$CH$_2$CH$_3$), 22.0 (SCH$_2$CH$_2$CH$_3$), 32.6 (SCH$_2$CH$_2$CH$_3$), 46.5 (NCH$_2$CH$_2$OH), 58.7 (NCH$_2$CH$_2$OH), 128.0 (C-5), 146.8 (C-8), 148.7 (C-6), 153.0 (C-4), 163.7 (C-2).

2-(6-(((1R,2S)-2-(3,4-Difluorophenyl)cyclopropyl)amino)-2-(propylthio)-9H-purin-9-yl)ethanol (16c)

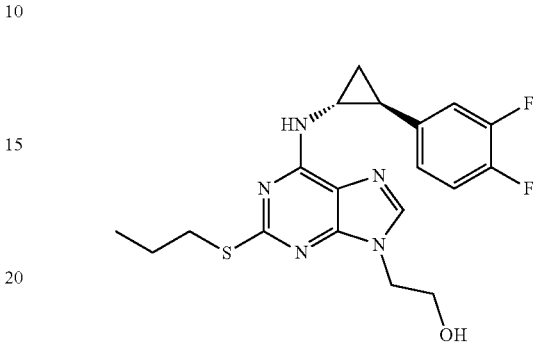

A solution of (16b) (137.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.

Yield: 42%.
Melting point: 81-83° C.
$^1$H NMR (CDCl$_3$) δ 0.95 (t, J=7.4 Hz, 3H, SCH$_2$CH$_2$CH$_3$), 1.32 (m, 2H, NHCH(CH$_2$)CHPh), 1.66 (bh, J=7.3 Hz, 3H, OH/SCH$_2$CH$_2$CH$_3$), 2.09 (m, 1H, NHCH(CH$_2$)CHPh), 3.01 (m, 2H, SCH$_2$CH$_2$CH$_3$), 3.11 (bs, 1H, NHCH(CH$_2$)CHPh), 4.02 (m, 2H, NCH$_2$CH$_2$OH), 4.29 (m, 2H, NCH$_2$CH$_2$OH), 6.05 (bs, 1H, NH), 7.00 (m, 1H, 6'-H), 7.09 (m, 2H, 2'-H/5'-H), 7.61 (s, 1H, 8-H).
$^{13}$C NMR (CDCl$_3$) δ 13.4 (SCH$_2$CH$_2$CH$_3$), 15.9 (NHCH(CH$_2$)CHPh), 22.6 (SCH$_2$CH$_2$CH$_3$), 25.2 (NHCH(CH$_2$)CHPh), 33.1 (SCH$_2$CH$_2$CH$_3$), 33.2 (NHCH(CH$_2$)CHPh), 48.2 (NCH$_2$CH$_2$OH), 61.6 (NCH$_2$CH$_2$OH), 115.7 (d, J=17 Hz, C-2'), 117.0 (d, J=17 Hz, C-5'), 117.7 (C-5), 122.7 (C-6'), 137.7 (C-1'), 139.7 (C-8), 147.9-149.9 (dd, 246 Hz/13 Hz, C-4'), 149.2-151.2 (dd, 247 Hz/13 Hz, C-3'), 150.1 (C-4), 154.6 (C-6), 165.8 (C-2).

Example 17

Synthesis of N-((1R,2S)-2-(3,4-difluorophenyl)cyclopropyl)-9-(prop-2-yn-1-yl)-2-(propylthio)-9H-purin-6-amine hydrochloride (17c.HCl)

6-Chloro-$N^4$-(prop-2-yn-1-yl)-2-(propylthio)pyrimidine-4,5-diamine (17a)

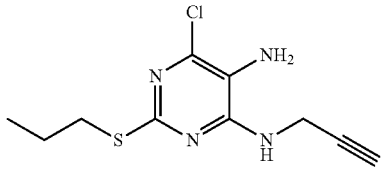 [SMILES: C#CCNc1nc(SCCC)nc(Cl)c1N]

4,6-Dichloro-2-(propylthio)pyrimidin-5-amine (0.5 g, 2.1 mmol) was dissolved in methanol (2 mL) and supplemented with propargylamine (347.0 mg, 6.3 mmol). The reaction mixture was introduced in a sealed vessel and heated at 100° C. for 3 h. After concentration of the reaction mixture to dryness under vacuum, the residue was purified by silica gel column chromatography.

Yield: 78%.

Melting point: 90-92° C.

$^1$H NMR (DMSO-d$_6$) δ 0.96 (t, J=7.4 Hz, 3H, SCH$_2$CH$_2$CH$_3$), 1.66 (h, J=7.3 Hz, 2H, SCH$_2$CH$_2$CH$_3$), 2.97 (t, J=7.2 Hz, 2H, SCH$_2$CH$_2$CH$_3$), 3.15 (t, J=2.4 Hz, 1H, NHCH$_2$CCH), 4.16 (dd, J=4.8 Hz/2.3 Hz, 2H, NHCH$_2$CCH), 4.83 (s, 2H, NH$_2$), 7.41 (t, J=4.7 Hz, 1H, NHCH$_2$CCH).

$^{13}$C NMR (DMSO-d$_6$) δ 13.3 (SCH$_2$CH$_2$CH$_3$), 22.7 (SCH$_2$CH$_2$CH$_3$), 30.1 (NHCH$_2$CCH), 32.2 (SCH$_2$CH$_2$CH$_3$), 73.1 (NHCH$_2$CCH), 81.1 (NHCH$_2$CCH), 120.3 (C-5), 137.9 (C-6), 151.8 (C-4), 155.1 (C-2).

6-Chloro-9-(prop-2-yn-1-yl)-2-(propylthio)-9H-purine (17b)

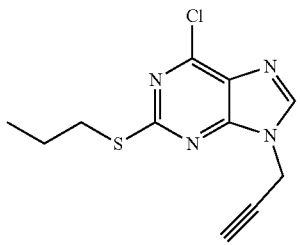 [SMILES: C#CCn1cnc2c(Cl)nc(SCCC)nc21]

A solution of (17a) (258.0 mg, 1 mmol) in acetic acid (2.5 mL) and triethyl orthoformate (2.5 mL, 15 mmol) was heated at a temperature of 130° C. under reflux for 2 h. After distillation of the acetic acid and triethyl orthoformate under vacuum, the residue was purified by silica gel column chromatography.

Yield: 62%.

Melting point: 68-70° C.

$^1$H NMR (DMSO-d$_6$) δ 1.01 (t, J=7.4 Hz, 3H, SCH$_2$CH$_2$CH$_3$), 1.75 (h, J=7.3 Hz, 2H, SCH$_2$CH$_2$CH$_3$), 3.19 (t, J=7.2 Hz, 2H, SCH$_2$CH$_2$CH$_3$), 3.57 (t, J=2.5 Hz, 1H, NCH$_2$CCH), 5.13 (d, J=2.5 Hz, 2H, NCH$_2$CCH), 8.58 (s, 1H, 8-H).

$^{13}$C NMR (DMSO-d$_6$) δ 13.2 (SCH$_2$CH$_2$CH$_3$), 22.0 (SCH$_2$CH$_2$CH$_3$), 32.7 (SCH$_2$CH$_2$CH$_3$), 33.1 (NCH$_2$CCH), 76.6 (NCH$_2$CCH), 77.2 (NCH$_2$CCH), 127.9 (C-5), 145.5 (C-8), 149.1 (C-6), 152.3 (C-4), 164.4 (C-2).

N-((1R,2S)-2-(3,4-Difluorophenyl)cyclopropyl)-9-(prop-2-yn-1-yl)-2-(propylthio)-9H-purin-6-amine (17c)

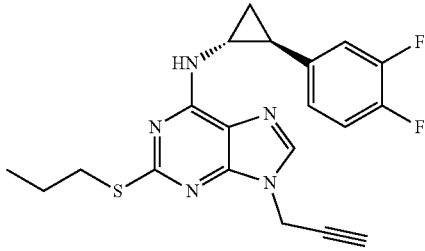 [SMILES: C#CCn1cnc2c(N[C@@H]3C[C@H]3c3ccc(F)c(F)c3)nc(SCCC)nc21]

A solution of (17b) (134.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 4 h. After distillation of acetonitrile and triethylamine under vacuum, the residue was purified by silica gel column chromatography.

Yield: 86%.

Melting point: 72-74° C.

$^1$H NMR (CDCl$_3$) δ 0.94 (t, J=7.4 Hz, 3H, SCH$_2$CH$_2$CH$_3$), 1.33 (m, 2H, NHCH(CH$_2$)CHPh), 1.65 (h, J=7.3 Hz, 2H, SCH$_2$CH$_2$CH$_3$), 2.09 (m, 1H, NHCH(CH$_2$)CHPh), 2.50 (t, J=2.6 Hz, 1H, NCH$_2$CCH), 3.03 (m, 2H, SCH$_2$CH$_2$CH$_3$), 3.12 (bs, 1H, NHCH(CH$_2$)CHPh), 4.90 (d, J=2.6 Hz, 2H, NCH$_2$CCH), 6.00 (bs, 1H, NH), 6.98 (m, 1H, 6'-H), 7.08 (m, 2H, 2'-H/5'-H), 7.84 (s, 1H, 8-H).

$^{13}$C NMR (CDCl$_3$) δ 13.4 (SCH$_2$CH$_2$CH$_3$), 16.1 (NHCH(CH$_2$)CHPh), 22.8 (SCH$_2$CH$_2$CH$_3$), 25.2 (NHCH(CH$_2$)CHPh), 32.8 (NCH$_2$CCH), 33.2 (SCH$_2$CH$_2$CH$_3$), 33.3 (NHCH(CH$_2$)CHPh), 74.9 (NCH$_2$CCH), 76.1 (NCH$_2$CCH), 115.6 (d, J=17 Hz, C-2'), 116.9 (d, J=17 Hz, C-5'), 117.3 (C-5), 122.6 (C-6'), 137.8 (C-1'), 138.1 (C-8), 147.9-149.9 (dd, 246 Hz/13 Hz, C-4'), 149.2-151.2 (dd, 247 Hz/13 Hz, C-3'), 149.9 (C-4), 154.6 (C-6), 166.0 (C-2).

N-((1R,2S)-2-(3,4-Difluorophenyl)cyclopropyl)-9-(prop-2-yn-1-yl)-2-(propylthio)-9H-purin-6-amine hydrochloride (17c.HCl)

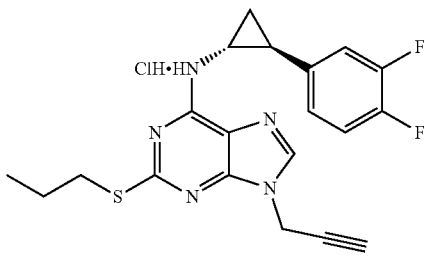

To a solution of (17c) (200.0 mg, 0.5 mmol) in diethyl ether (5 mL) was added dropwise a saturated solution of HCl in diethyl ether. The resulting precipitate of the title compound was collected by filtration, washed with diethyl ether and dried.

Yield: 99%.

Melting point: 178-180° C.

Example 18

Synthesis of N-((1R,2S)-2-(3,4-difluorophenyl)cyclopropyl)-2-(propylthio)-9-(2,2,2-trifluoroethyl)-9H-purin-6-amine (18c)

6-Chloro-2-(propylthio)-N$^4$-(2,2,2-trifluoroethyl)pyrimidine-4,5-diamine (18a)

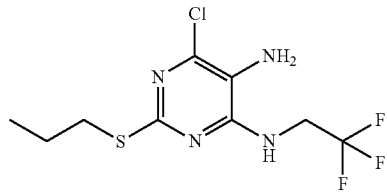 [SMILES: CCCSc1nc(Cl)c(N)c(NCC(F)(F)F)n1]

4,6-Dichloro-2-(propylthio)pyrimidin-5-amine (0.5 g, 2.1 mmol) was dissolved in methanol (2 mL) and supplemented with 2,2,2-trifluoroethanamine (625.0 mg, 6.3 mmol). The reaction mixture was introduced in a sealed vessel and heated at 100° C. for 24 h. After concentration of the reaction mixture to dryness under vacuum, the residue was purified by silica gel column chromatography.

Yield: 76%.

Melting point: 107-109° C.

$^1$H NMR (DMSO-d$_6$) δ 0.95 (t, J=7.4 Hz, 3H, SCH$_2$CH$_2$CH$_3$), 1.63 (h, J=7.3 Hz, 2H, SCH$_2$CH$_2$CH$_3$), 2.95 (t, J=7.2 Hz, 2H, SCH$_2$CH$_2$CH$_3$), 4.29 (m, 2H, NHCH$_2$CF$_3$), 4.95 (s, 2H, NH$_2$), 7.53 (s, 1H, NHCH$_2$CF$_3$).

$^{13}$C NMR (DMSO-d$_6$) δ 13.2 (SCH$_2$CH$_2$CH$_3$), 22.6 (SCH$_2$CH$_2$CH$_3$), 32.1 (SCH$_2$CH$_2$CH$_3$), 41.2 (q, J=33 Hz, NHCH$_2$CF$_3$), 120.5 (C-5), 122.7-126.0 (m, NHCH$_2$CF$_3$), 138.8 (C-6), 151.9 (C-4), 154.8 (C-2).

6-Chloro-2-(propylthio)-9-(2,2,2-trifluoroethyl)-9H-purine (18b)

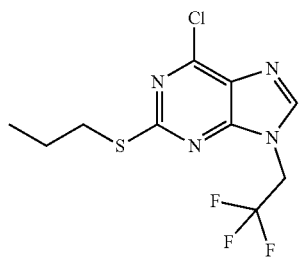 [SMILES: CCCSc1nc(Cl)c2ncn(CC(F)(F)F)c2n1]

A solution of (18a) (301.0 mg, 1 mmol) in acetic acid (2.5 mL) and triethyl orthoformate (2.5 mL, 15 mmol) was heated at a temperature of 130° C. under reflux for 2 h. After distillation of the acetic acid and triethyl orthoformate under vacuum, the residue was purified by silica gel column chromatography.

Yield: 48%.

Melting point: 140-143° C.

$^1$H NMR (DMSO-d$_6$) δ 1.00 (t, J=7.4 Hz, 3H, SCH$_2$CH$_2$CH$_3$), 1.73 (h, J=7.3 Hz, 2H, SCH$_2$CH$_2$CH$_3$), 3.19 (t, J=7.2 Hz, 2H, SCH$_2$CH$_2$CH$_3$), 5.27 (q, J=9.2 Hz, 2H, NCH$_2$CF$_3$), 8.60 (s, 1H, 8-H).

$^{13}$C NMR (DMSO-d$_6$) δ 13.1 (SCH$_2$CH$_2$CH$_3$), 22.0 (SCH$_2$CH$_2$CH$_3$), 32.6 (SCH$_2$CH$_2$CH$_3$), 43.9 (q, J=35 Hz, NCH$_2$CF$_3$), 123.4 (q, J=280 Hz, NCH$_2$CF$_3$), 127.6 (C-5), 146.2 (C-8), 149.6 (C-6), 152.9 (C-4), 165.2 (C-2).

N-((1R,2S)-2-(3,4-Difluorophenyl)cyclopropyl)-2-(propylthio)-9-(2,2,2-trifluoroethyl)-9H-purin-6-amine (18c)

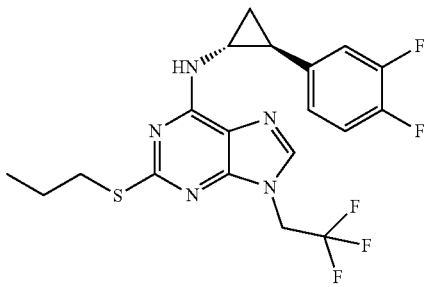 [SMILES: CCCSc1nc(N[C@@H]2C[C@H]2c2ccc(F)c(F)c2)c2ncn(CC(F)(F)F)c2n1]

A solution of (18b) (156.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.

Yield: 89%.

Melting point: 102-104° C.

$^1$H NMR (CDCl$_3$) δ 0.95 (t, J=7.4 Hz, 3H, SCH$_2$CH$_2$CH$_3$), 1.34 (m, 2H, NHCH(CH$_2$)CHPh), 1.67 (h, J=7.3 Hz, 2H, SCH$_2$CH$_2$CH$_3$), 2.11 (m, 1H, NHCH(CH$_2$)CHPh), 3.03 (m, 2H, SCH$_2$CH$_2$CH$_3$), 3.10 (bs, 1H, NHCH(CH$_2$)CHPh), 4.73 (qd, J=8.5 Hz/3.1 Hz, 2H, NCH$_2$CF$_3$), 6.06 (bs, 1H, NH), 6.99 (m, 1H, 6'-H), 7.09 (m, 2H, 2'-H/5'-H), 7.70 (s, 1H, 8-H).

$^{13}$C NMR (CDCl$_3$) δ 13.4 (SCH$_2$CH$_2$CH$_3$), 15.9 (NHCH(CH$_2$)CHPh), 22.7 (SCH$_2$CH$_2$CH$_3$), 25.2 (NHCH(CH$_2$)CHPh), 33.2 (SCH$_2$CH$_2$CH$_3$), 33.3 (NHCH(CH$_2$)CHPh), 44.0 (q, J=36 Hz, NCH$_2$CF$_3$), 115.7 (d, J=17 Hz, C-2'), 116.8 (C-5), 117.0 (d, J=17 Hz, C-5'), 122.7 (C-6'), 122.8 (q, J=279 Hz, CF$_3$), 137.7 (C-1'), 138.2 (C-8), 148.0-150.0 (dd, J=246 Hz/13 Hz, C-4'), 149.2-151.2 (dd, J=247 Hz/13 Hz, C-3'), 150.6 (C-4), 154.7 (C-6), 166.8 (C-2).

Example 19

Synthesis of (1S,2R,3S,4R)-4-(6-(((1R,2S)-2-(3,4-difluorophenyl)cyclopropyl)amino)-2-(propylthio)-9H-purin-9-yl)cyclopentane-1,2,3-triol (19d)

(3aR,4S,6R,6aS)-6-((5-Amino-6-chloro-2-(propylthio)pyrimidin-4-yl)amino)-2,2-dimethyltetrahydro-3aH-cyclopenta[d][1,3]dioxol-4-ol (19a)

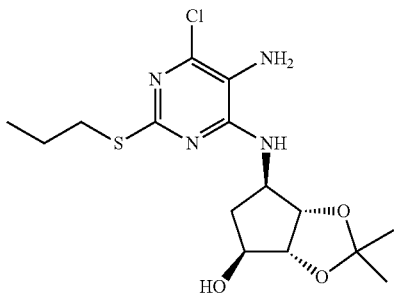 [SMILES: CCCSc1nc(Cl)c(N)c(N[C@@H]2C[C@H](O)[C@H]3OC(C)(C)O[C@H]32)n1]

4,6-Dichloro-2-(propylthio)pyrimidin-5-amine (0.5 g, 2.1 mmol) was dissolved in methanol (2 mL) and supplemented with (3aR,4S,6R,6aS)-6-amino-2,2-dimethyltetrahydro-3aH-cyclopenta[d][1,3]dioxol-4-ol (1.1 g, 6.3 mmol). The reaction mixture was introduced in a sealed vessel and heated at 100° C. for 12 h. After concentration of the reaction mixture to dryness under vacuum, the residue was purified by silica gel column chromatography.

Yield: 90%.
Melting point: ND.
$^1$H NMR (DMSO-$d_6$) δ 0.96 (t, J=7.4 Hz, 3H, SCH$_2$CH$_2$CH$_3$), 1.21 (s, 3H, C(CH$_3$)$_2$), 1.36 (s, 3H, C(CH$_3$)$_2$), 1.64 (h, J=7.4 Hz, 2H, SCH$_2$CH$_2$CH$_3$), 1.71 (m, 1H, 5'-H), 2.22 (m, 1H, 5'-H), 2.98 (t, J=7.2 Hz, 2H, SCH$_2$CH$_2$CH$_3$), 4.06 (bs, 1H, 4'-H), 4.26 (bs, 1H, 6'-H), 4.41 (d, J=5.9 Hz, 1H, 3a'-H), 4.51 (d, J=6.0 Hz, 1H, 6a'-H), 4.70 (s, 2H, NH$_2$), 5.27 (d, J=3.1 Hz, 1H, OH), 6.63 (d, J=7.1 Hz, 1H, NH).
$^{13}$C NMR (DMSO-$d_6$) δ 13.3 (SCH$_2$CH$_2$CH$_3$), 22.9 (SCH$_2$CH$_2$CH$_3$), 24.1 (C(CH$_3$)$_2$), 26.5 (C(CH$_3$)$_2$), 32.1 (SCH$_2$CH$_2$CH$_3$), 35.9 (C-5'), 57.2 (C-6'), 75.3 (C-4'), 84.5 (C-6a'), 85.7 (3a'), 109.7 (C(CH$_3$)$_2$), 119.7 (C-5), 136.6 (C-6), 152.4 (C-4), 155.9 (C-2).

(3aR,4S,6R,6aS)-6-(6-Chloro-2-(propylthio)-9H-purin-9-yl)-2,2-dimethyltetrahydro-3aH-cyclopenta[d][1,3]dioxol-4-ol (19b)

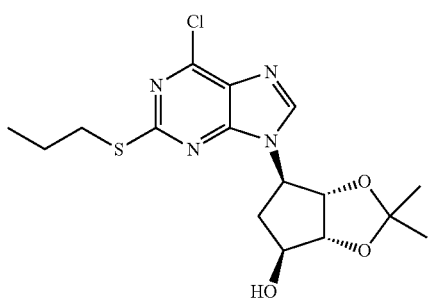 [SMILES: CCCSc1nc(Cl)c2ncn([C@@H]3C[C@H](O)[C@H]4OC(C)(C)O[C@H]43)c2n1]

A solution of (19a) (375.0 mg, 1 mmol) in acetic acid (2.5 mL) and triethyl orthoformate (2.5 mL, 15 mmol) was heated at a temperature of 130° C. under reflux for 10 h. After distillation of the acetic acid and triethyl orthoformate under vacuum, the residue was purified by silica gel column chromatography.

Yield: 23%.
Melting point: ND.
$^1$H NMR (DMSO-$d_6$) δ 1.02 (t, J=7.4 Hz, 3H, SCH$_2$CH$_2$CH$_3$), 1.25 (s, 3H, C(CH$_3$)$_2$), 1.45 (s, 3H, C(CH$_3$)$_2$), 1.75 (h, J=7.2 Hz, 2H, SCH$_2$CH$_2$CH$_3$), 2.25 (m, 1H, 5'-H), 2.51 (m, 1H, 5'-H), 3.16 (t, J=7.2 Hz, 2H, SCH$_2$CH$_2$CH$_3$), 4.18 (bs, 1H, 4'-H), 4.56 (d, J=6.2 Hz, 1H, 3a'-H), 4.86 (m, 1H, 6'-H), 5.04 (dd, J=6.1 Hz/1.9 Hz, 1H, 6a'-H), 5.47 (bs, 1H, OH), 8.59 (s, 1H, 8-H).
$^{13}$C NMR (DMSO-$d_6$) δ 13.3 (SCH$_2$CH$_2$CH$_3$), 22.2 (SCH$_2$CH$_2$CH$_3$), 24.3 (C(CH$_3$)$_2$), 26.6 (C(CH$_3$)$_2$), 32.7 (SCH$_2$CH$_2$CH$_3$), 36.4 (C-5'), 60.4 (C-6'), 74.6 (C-4'), 83.9 (C-6a'), 86.1 (C-3a'), 110.9 (C(CH$_3$)$_2$), 128.1 (C-5), 146.0 (C-8), 148.9 (C-6), 152.7 (C-4), 163.9 (C-2).

(3aR,4S,6R,6aS)-6-(6-(((1R,2S)-2-(3,4-Difluorophenyl)cyclopropyl)amino)-2-(propylthio)-9H-purin-9-yl)-2,2-dimethyltetrahydro-3aH-cyclopenta[d][1,3]dioxol-4-ol (19c)

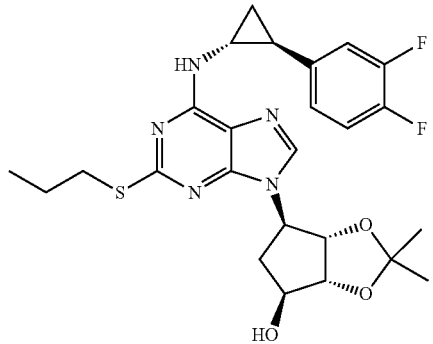 [SMILES: CCCSc1nc(N[C@@H]2C[C@H]2c2ccc(F)c(F)c2)c2ncn([C@@H]3C[C@H](O)[C@H]4OC(C)(C)O[C@H]43)c2n1]

A solution of (19b) (193.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.

Yield: 91%.
Melting point: ND.
$^1$H NMR (CDCl$_3$) δ 0.90 (t, J=7.4 Hz, 3H, SCH$_2$CH$_2$CH$_3$), 1.32 (s, 3H, C(CH$_3$)$_2$), 1.34 (m, 2H, NHCH(CH$_2$)CHPh), 1.51 (s, 3H, C(CH$_3$)$_2$), 1.61 (h, J=7.3 Hz, 2H, SCH$_2$CH$_2$CH$_3$), 2.09 (m, 1H, NHCH(CH$_2$)CHPh), 2.13 (m, 1H, 5"-H), 2.96 (m, 3H, 5"-H/SCH$_2$CH$_2$CH$_3$), 3.13 (bs, 1H, NHCH(CH$_2$)CHPh), 4.42 (m, 1H, 4"-H), 4.74 (m, 1H, 6"-H), 4.79 (d, J=5.3 Hz, 1H, 3a"-H), 4.98 (d, J=5.3 Hz, 1H, 6a"-H), 5.99 (bs, 1H, OH), 6.03 (bs, 1H, NH), 6.93 (m, 1H, 6'-H), 7.05 (m, 2H, 2'-H/5'-H), 7.67 (s, 1H, 8-H).
$^{13}$C NMR (CDCl$_3$) δ 13.3 (SCH$_2$CH$_2$CH$_3$), 16.2 (NHCH(CH$_2$)CHPh), 22.6 (SCH$_2$CH$_2$CH$_3$), 24.5 (C(CH$_3$)$_2$), 25.2 (NHCH(CH$_2$)CHPh), 27.1 (C(CH$_3$)$_2$), 33.2 (SCH$_2$CH$_2$CH$_3$), 33.3 (NHCH(CH$_2$)CHPh), 38.8 (C-5"), 64.0 (C-6"), 76.0 (C-4"), 86.2 (C-6a"), 88.0 (C-3a"), 111.4 (C(CH$_3$)$_2$), 115.3 (d, J=17 Hz, C-2'), 117.0 (d, J=17 Hz, C-5'), 118.3 (C-5), 122.4 (C-6'), 137.7 (C-1'), 139.8 (C-8), 148.0-150.0 (dd, 246 Hz/13 Hz, C-4'), 149.3-151.3 (dd, 247 Hz/13 Hz, C-3'), 150.5 (C-4), 154.7 (C-6), 165.7 (C-2).

(1S,2R,3S,4R)-4-(6-(((1R,2S)-2-(3,4-Difluorophenyl)cyclopropyl)amino)-2-(propylthio)-9H-purin-9-yl)cyclopentane-1,2,3-triol (19d)

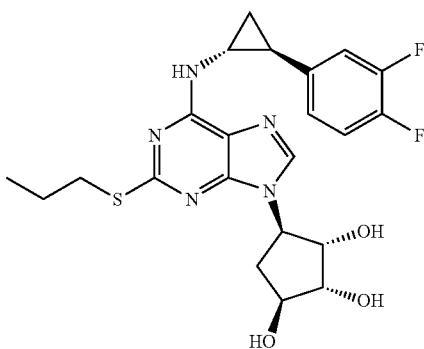 [SMILES: CCCSc1nc(N[C@@H]2C[C@H]2c2ccc(F)c(F)c2)c2ncn([C@@H]3C[C@H](O)[C@@H](O)[C@H]3O)c2n1]

A solution of (19c) (259.0 mg, 0.5 mmol) in methanol (2 mL) and 12N HCl (1 mL) was stirred at room temperature for 2 h. After distillation of the solvents under vacuum, the residue was purified by silica gel column chromatography.
Yield: 76%.
Melting point: 92-94° C.
$^1$H NMR (CDCl$_3$) δ 0.87 (t, J=7.3 Hz, 3H, SCH$_2$CH$_2$CH$_3$), 1.34 (m, 2H, NHCH(CH$_2$)CHPh), 1.59 (h, J=7.3 Hz, 2H, SCH$_2$CH$_2$CH$_3$), 2.10 (m, 1H, NHCH(CH$_2$)CHPh), 2.14 (m, 1H, 5''-H), 2.71 (bs, 1H, 3''-OH), 2.83 (m, 1H, SCH$_2$CH$_2$CH$_3$), 2.98 (m, 2H, 5''-H/SCH$_2$CH$_2$CH$_3$), 3.12 (bs, 1H, NHCH(CH$_2$)CHPh), 4.14 (m, 1H, 3''-H), 4.27 (m, 1H, 1''-H), 4.47 (bs, 1H, 2''-OH), 4.56 (m, 1H, 4''-H), 4.76 (m, 1H, 2''-H), 4.98 (bs, 1H, 1''-OH), 6.16 (bs, 1H, NH), 6.93 (m, 1H, 6'-H), 7.04 (m, 2H, 2'-H/5'-H), 7.59 (s, 1H, 8-H).
$^{13}$C NMR (CDCl$_3$) δ 13.2 (SCH$_2$CH$_2$CH$_3$), 16.2 (NHCH(CH$_2$)CHPh), 22.5 (SCH$_2$CH$_2$CH$_3$), 25.2 (NHCH(CH$_2$)CHPh), 33.1 (SCH$_2$CH$_2$CH$_3$), 33.3 (NHCH(CH$_2$)CHPh), 35.8 (C-5''), 61.5 (C-4''), 74.8 (C-1''), 76.9 (C-2''), 78.0 (C-3''), 115.3 (d, J=17 Hz, C-2'), 117.0 (d, J=17 Hz, C-5'), 118.3 (C-5), 122.3 (C-6'), 137.8 (C-1'), 139.0 (C-8), 148.0-150.0 (dd, 246 Hz/13 Hz, C-4'), 149.3-151.3 (dd, 247 Hz/13 Hz, C-3'), 149.3 (C-4), 154.6 (C-6), 165.8 (C-2).

Example 20

Synthesis of N-((1R,2S)-2-(3,4-difluorophenyl)cyclopropyl-2-(ethylthio)-9-methyl-9H-purin-6-amine (20c)

2-(Ethylthio)pyrimidine-4,6-diol (20e)

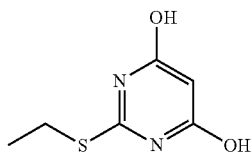

2-Thiobarbituric acid (2.5 g, 17.4 mmol) was dissolved in KOH 10% (25 mL) and supplemented with ethyl iodide (1.63 mL, 20.0 mmol). The reaction mixture was introduced in a sealed vessel and heated at 80° C. for 1 h. After cooling on an ice bath to 5° C., the mixture was acidified by addition of hydrochloric acid 6N and the resulting precipitate was filtered off and washed with diethyl ether.
Yield: 69%.
Melting point: >300° C.
$^1$H NMR (DMSO-d$_6$) δ 1.28 (t, J=7.3 Hz, 3H, CH$_3$), 3.08 (q, J=7.3 Hz, 2H, SCH$_2$), 5.12 (s, 1H, CH), 11.68 (bs, 2H, OH).
$^{13}$C NMR (DMSO-d$_6$) δ 14.6 (SCH$_3$), 24.0 (CH$_2$), 85.6 (CH), 158.1 (C-4/C-6), 162.8 (C-2)

2-(Ethylthio)-5-nitropyrimidine-4,6-diol (20f)

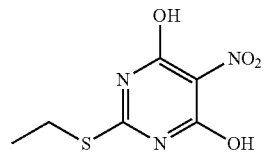

To 6 mL of acetic acid cooled at 5° C. on an ice bath were added fuming nitric acid (2.5 mL) and (20e) (1.8 g, 10.5 mmol). After 1 hour stirring at room temperature, the mixture was cooled at 5° C. on an ice bath, water (50 mL) was added and the resulting precipitate was filtered off.
Yield: 69%.
Melting point: 210-213° C. (decomposition).
$^1$H NMR (DMSO-d$_6$) δ 1.31 (t, J=7.3 Hz, 3H, CH$_3$), 3.17 (q, J=7.3 Hz, 2H, SCH$_2$).
$^{13}$C NMR (DMSO-d$_6$) δ 14.4 (CH$_3$), 24.7 (SCH$_2$), 117.4 (C-5), 158.9 (C-4/C-6), 164.0 (C-2).

4,6-Dichloro-2-(ethylthio)-5-nitropyrimidine (20g)

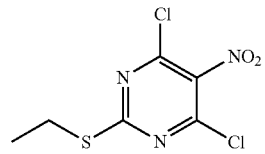

To a solution of (20f) (1.5 g, 6.9 mmol) in POCl$_3$ (10 mL) cooled at 5° C. on an ice bath was added dropwise 2,6-lutidine (2.5 mL). After 2 hours stirring at 80° C., the mixture was poured on crushed ice and extracted with ethyl acetate (3×50 mL). The organic layers were washed with water and with an aqueous saturated solution of sodium hydrogenocarbonate and ethyl acetate was evaporated to dryness under vacuum. The resulting oily residue was used without further purification in the next step (20h).
Yield: 85%.
Melting point: oil.
$^1$H NMR (DMSO-d$_6$) δ 1.35 (t, J=7.3 Hz, 3H, CH$_3$), 3.18 (q, J=7.3 Hz, 2H, SCH$_2$).
$^{13}$C NMR (DMSO-d$_6$) δ 14.0 (CH$_3$), 25.3 (SCH$_2$), 149.1 (C-4/C-6), 154.5 (C-5), 165.4 (C-2).

4,6-Dichloro-2-(ethylthio)pyrimidin-5-amine (20h)

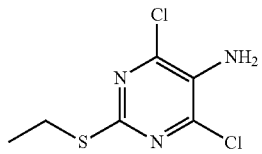

To a solution of (20g) (1.0 g, 3.9 mmol) in methanol (10 mL) and acetic acid (4 mL) was added iron powder (1.07 g, 19.5 mmol). After 1 hour stirring at room temperature, ethyl acetate (50 mL) was added and the suspension was filtered. The filtrate was washed with water and with an aqueous saturated solution of sodium hydrogenocarbonate and the organic layer was evaporated to dryness under vacuum. Water was added on the residue and the resulting precipitate was filtered off.

Yield: 86%.
Melting point: 48-50° C.
$^1$H NMR (DMSO-$d_6$) δ 1.28 (t, J=7.3 Hz, 3H, CH$_3$), 3.02 (q, J=7.3 Hz, 2H, SCH$_2$), 5.90 (s, 2H, NH$_2$).
$^{13}$C NMR (DMSO-$d_6$) δ14.3 (CH$_3$), 24.9 (SCH$_2$), 133.5 (C-5), 143.7 (C-4/C-6), 153.8 (C-2).

6-Chloro-2-(ethylthio)-N$^4$-methylpyrimidine-4,5-diamine (20a)

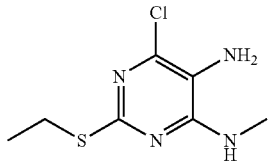

4,6-Dichloro-2-(ethylthio)pyrimidin-5-amine (20h) (0.5 g, 2.2 mmol) was dissolved in methanol (2 mL) and supplemented with a solution of methylamine 33% w/w in methanol (0.80 mL, 6.6 mmol). The reaction mixture was introduced in a sealed vessel and heated at 100° C. for 1 h. After concentration of the reaction mixture to dryness under vacuum, the residue was purified by silica gel column chromatography.

Yield: 87%.
Melting point: 112-114° C.
$^1$H NMR (DMSO-$d_6$) δ 1.27 (t, J=7.2 Hz, 3H, CH$_3$), 2.87 (d, J=3.8 Hz, 3H, NHCH$_3$), 2.97 (q, J=7.2 Hz, 2H, SCH$_2$), 4.70 (s, 2H, NH$_2$), 7.00 (s, 1H, NH).
$^{13}$C NMR (DMSO-$d_6$) δ 14.9 (CH$_3$), 24.5 (SCH$_2$), 27.8 (NHCH$_3$), 120.1 (C-5), 137.2 (C-6), 153.3 (C-4), 155.4 (C-2).

6-Chloro-2-(ethylthio)-9-methyl-9H-purine (20b)

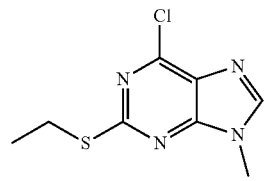

A solution of (20a) (219.0 mg, 1 mmol) in acetic acid (2.5 mL) and triethyl orthoformate (2.5 mL, 15 mmol) was heated at a temperature of 130° C. under reflux for 1 h. After distillation of the acetic acid and triethyl orthoformate under vacuum, the residue was purified by silica gel column chromatography.

Yield: 86%.
Melting point: 89-100° C.
$^1$H NMR (DMSO-$d_6$) δ 1.37 (t, J=7.3 Hz, 3H, CH$_3$), 3.20 (q, J=7.3 Hz, 2H, SCH$_2$), 3.79 (s, 3H, NCH$_3$), 8.48 (s, 1H, CH).
$^{13}$C NMR (DMSO-$d_6$) δ 14.3 (CH$_3$), 25.2 (SCH$_2$), 30.0 (NCH$_3$), 127.9 (C-5), 147.0 (C-8), 148.8 (C-6), 153.2 (C-4), 163.8 (C-2).

N-((1R,2S)-2-(3,4-Difluorophenyl)cyclopropyl)-2-(ethylthio)-9-methyl-9H-purin-6-amine (20c)

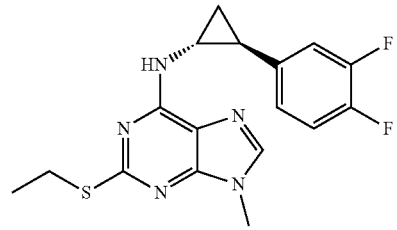 [SMILES: CCSc1nc(N[C@@H]2C[C@H]2c2ccc(F)c(F)c2)c2ncn(C)c2n1]

A solution of (20b) (114.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.

Yield: 89%.
Melting point: 116-118.5° C.
$^1$H NMR (CDCl$_3$) δ 1.25 (t, J=7.3 Hz, 3H, CH$_3$), 1.32 (m, 2H, NHCH(CH$_2$)CHPh), 2.09 (ddd, J=9.5 Hz/6.3 Hz/3.2 Hz, 1H, NHCH(CH$_2$)CHPh), 3.02 (m, 2H, SCH$_2$), 3.12 (bs, 1H, NHCH(CH$_2$)CHPh), 3.76 (s, 3H, NCH$_3$), 5.96 (bs, 1H, NH), 6.97 (m, 1H, 6'-H), 7.07 (m, 2H, 2'-H/5'-H), 7.60 (s, 1H, 8-H).
$^{13}$C NMR (CDCl$_3$) δ 14.9 (CH$_3$), 16.3 (NHCH(CH$_2$) CHPh), 25.4 (NHCH(CH$_2$)CHPh), 25.7 (SCH$_2$), 29.8 (NCH$_3$), 33.5 (NHCH(CH$_2$)CHPh), 115.6 (d, J=17 Hz, C-2'), 117.1 (d, J=17 Hz, C-5'), 117.6 (C-5), 122.7 (C-6'), 138.1 (C-1'), 139.7 (C-8), 148.0-150.0 (dd, J=246 Hz/13 Hz, C-4'), 149.3-151.3 (dd, J=247 Hz/13 Hz, C-3'), 150.9 (C-4), 154.7 (C-6), 165.6 (C-2).

Example 21

Synthesis of N-((1R,2S)-2-(3,4-difluorophenylcyclopropyl)-9-ethyl-2-(ethylthio)-9H-purin-6-amine (21c)

6-Chloro-N⁴-ethyl-2-(ethylthio)pyrimidine-4,5-diamine (21a)

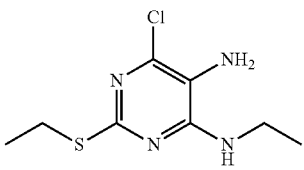

4,6-Dichloro-2-(ethylthio)pyrimidin-5-amine (20h) (0.5 g, 2.2 mmol) was dissolved in a solution of ethylamine 2.0 M in methanol (3.3 mL, 6.6 mmol). The reaction mixture was introduced in a sealed vessel and heated at 100° C. for 1 h. After concentration of the reaction mixture to dryness under vacuum, the residue was purified by silica gel column chromatography.

Yield: 91%.

Melting point: 93-95° C.

$^1$H NMR (DMSO-$d_6$) δ 1.16 (t, J=7.2 Hz, 3H, NHCH$_2$CH$_3$), 1.27 (t, J=7.2 Hz, 3H, SCH$_2$CH$_3$), 2.96 (q, J=7.2 Hz, 2H, SCH$_2$CH$_3$), 3.38 (p, J=6.1 Hz, 2H, NHCH$_2$CH$_3$), 4.74 (s, 2H, NH$_2$), 6.93 (s, 1H, NH).

$^{13}$C NMR (DMSO-$d_6$) δ 14.4 (NHCH$_2$CH$_3$), 15.0 (SCH$_2$CH$_3$), 24.5 (SCH$_2$CH$_3$), 35.8 (NHCH$_2$CH$_3$), 119.9 (C-5), 137.3 (C-6), 152.6 (C-4), 155.2 (C-2).

6-Chloro-9-ethyl-2-(ethylthio)-9H-purine (21b)

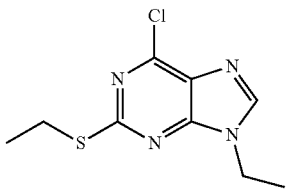

A solution of (21a) (233.0 mg, 1 mmol) in acetic acid (2.5 mL) and triethyl orthoformate (2.5 mL, 15 mmol) was heated at a temperature of 130° C. under reflux for 1 h. After distillation of the acetic acid and triethyl orthoformate under vacuum, the residue was purified by silica gel column chromatography.

Yield: 91%.

Melting point: 64-66° C.

$^1$H NMR (DMSO-$d_6$) δ 1.37 (t, J=7.3 Hz, 3H, SCH$_2$CH$_3$), 1.45 (t, J=7.3 Hz, 3H, NCH$_2$CH$_3$), 3.19 (q, J=7.3 Hz, 2H, SCH$_2$), 4.25 (q, J=7.3 Hz, 2H, NCH$_2$), 8.56 (s, 1H, CH).

$^{13}$C NMR (DMSO-$d_6$) δ 14.3 (SCH$_2$CH$_3$), 14.7 (NCH$_2$CH$_3$), 25.2 (SCH$_2$), 39.0 (NCH$_2$), 128.1 (C-5), 146.1 (C-8), 148.9 (C-6), 152.7 (C-4), 163.7 (C-2).

N-((1R,2S)-2-(3,4-Difluorophenyl)cyclopropyl)-9-ethyl-2-(ethylthio)-9H-purin-6-amine (21c)

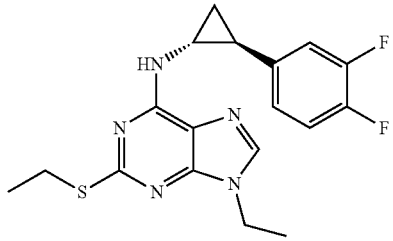 [SMILES: CCSc1nc(N[C@@H]2C[C@H]2c2ccc(F)c(F)c2)c2ncn(CC)c2n1]

A solution of (21b) (121.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.

Yield: 96%.

Melting point: 107.5-109.5° C.

$^1$H NMR (CDCl$_3$) δ 1.26 (t, J=7.3 Hz, 3H, SCH$_2$CH$_3$), 1.32 (m, 2H, NHCH(CH$_2$)CHPh), 1.50 (t, J=7.3 Hz, 3H, NCH$_2$CH$_3$), 2.08 (ddd, J=9.5 Hz/6.4 Hz/3.3 Hz, 1H, NHCH(CH$_2$)CHPh), 3.03 (m, 2H, SCH$_2$CH$_3$), 3.11 (bs, 1H, NHCH(CH$_2$)CHPh), 4.19 (q, J=7.3 Hz, 2H, NCH$_2$CH$_3$), 5.94 (bs, 1H, NH), 6.98 (m, 1H, 6'-H), 7.08 (m, 2H, 2'-H/5'-H), 7.63 (s, 1H, 8-H).

$^{13}$C NMR (CDCl$_3$) δ 14.9 (SCH$_2$CH$_3$), 15.7 (NCH$_2$CH$_3$), 16.3 (NHCH(CH$_2$)CHPh), 25.4 (NHCH(CH$_2$)CHPh), 25.7 (SCH$_2$CH$_3$), 33.5 (NHCH(CH$_2$)CHPh), 38.8 (NCH$_2$CH$_3$), 115.7 (d, J=17 Hz, C-2'), 117.0 (d, J=17 Hz, C-5'), 117.8 (C-5), 122.8 (C-6'), 138.1 (C-1'), 138.6 (C-8), 148.0-150.0 (dd, J=246 Hz/13 Hz, C-4'), 149.3-151.3 (dd, J=247 Hz/13 Hz, C-3'), 150.4 (C-4), 154.7 (C-6), 165.3 (C-2).

Example 22

Synthesis of N-((1R,2S)-2-(3,4-difluorophenyl)cyclopropyl)-9-methyl-2-(methylthio)-9H-purin-6-amine (22c)

2-(Methylthio)pyrimidine-4,6-diol (22e)

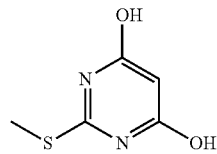

2-Thiobarbituric acid (2.5 g, 17.4 mmol) was dissolved in KOH 10% (25 mL) and supplemented with methyl iodide (1.25 mL, 20.0 mmol). The reaction mixture was introduced in a sealed vessel and heated at 80° C. for 1 h. After cooling on an ice bath to 5° C., the mixture was acidified by addition of hydrochloric acid 6N and the resulting precipitate was filtered off and washed with diethyl ether.

Yield: 77%.

Melting point: >300° C.

$^1$H NMR (DMSO-d$_6$) δ 2.46 (s, 3H, SCH$_3$), 5.13 (s, 1H, CH), 11.71 (bs, 2H, OH).
$^{13}$C NMR (DMSO-d$_6$) δ 12.7 (SCH$_3$), 85.5 (CH), 158.9 (C-4/C-6), 163.5 (C-2).

2-(Methylthio)-5-nitropyrimidine-4,6-diol (22f)

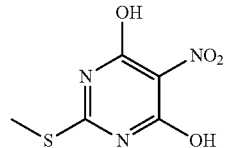

To 6 mL of acetic acid cooled at 5° C. on an ice bath were added fuming nitric acid (2.5 mL) and (22e) (2.0 g, 12.6 mmol). After 1 hour stirring at room temperature, the mixture was cooled at 5° C. on an ice bath, water (50 mL) was added and the resulting precipitate was filtered off.
Yield: 67%.
Melting point: 220-221° C. (decomposition).
$^1$H NMR (DMSO-d$_6$) δ 2.56 (s, 3H, SCH$_3$).
$^{13}$C NMR (DMSO-d$_6$) δ 13.2 (SCH$_3$), 117.4 (C-5), 158.7 (C-4/C-6), 164.6 (C-2).

4,6-Dichloro-2-(methylthio)-5-nitropyrimidine (22g)

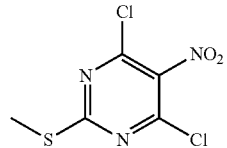

To a solution of (22f) (1.5 g, 7.4 mmol) in POCl$_3$ (10 mL) cooled at 5° C. on an ice bath was added dropwise 2,6-lutidine (2.5 mL). After 2 hours stirring at 80° C., the mixture was poured on crushed ice and the resulting precipitate was filtered off.
Yield: 92%.
Melting point: 63-64° C.
$^1$H NMR (DMSO-d$_6$) δ 2.56 (s, 3H, SCH$_3$).
$^{13}$C NMR (DMSO-d$_6$) δ 13.5 (SCH$_3$), 149.0 (C-4/C-6), 154.5 (C-5), 166.1 (C-2).

4,6-Dichloro-2-(methylthio)pyrimidin-5-amine (22h)

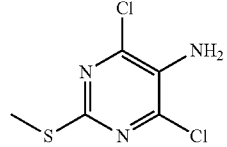

To a solution of (22g) (1.0 g, 4.2 mmol) in methanol (10 mL) and acetic acid (4 mL) was added iron powder (1.07 g, 19.5 mmol). After 1 hour stirring at room temperature, ethyl acetate (50 mL) was added and the suspension was filtered. The filtrate was washed with water and with an aqueous saturated solution of sodium hydrogenocarbonate and the organic layer was evaporated to dryness under vacuum. Water was added on the residue and the resulting precipitate was filtered off.
Yield: 95%.
Melting point: 105-108° C.
$^1$H NMR (DMSO-d$_6$) δ 2.45 (s, 3H, SCH$_3$), 5.90 (s, 2H, NH$_2$).
$^{13}$C NMR (DMSO-d$_6$) δ 13.8 (SCH$_3$), 133.4 (C-5), 143.7 (C-4/C-6), 154.4 (C-2).

6-Chloro-N$^4$-methyl-2-(methylthio)pyrimidine-4,5-diamine (22a)

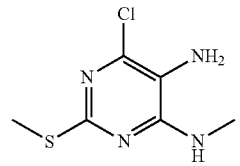

4,6-Dichloro-2-(methylthio)pyrimidin-5-amine (22h) (0.5 g, 2.4 mmol) was dissolved in methanol (2 mL) and supplemented with a solution of methylamine 33% w/w in methanol (0.87 mL, 7.2 mmol). The reaction mixture was introduced in a sealed vessel and heated at 100° C. for 1 h. After concentration of the reaction mixture to dryness under vacuum, the residue was purified by silica gel column chromatography.
Yield: 82%.
Melting point: 141-143° C.
$^1$H NMR (DMSO-d$_6$) δ 2.38 (s, 3H, SCH$_3$), 2.88 (d, J=3.0 Hz, 3H, NHCH$_3$), 4.70 (s, 2H, NH$_2$), 7.01 (s, 1H, NH).
$^{13}$C NMR (DMSO-d$_6$) δ 13.5 (SCH$_3$), 27.8 (NHCH$_3$), 120.1 (C-5), 137.2 (C-6), 153.3 (C-4), 155.9 (C-2).

6-Chloro-9-methyl-2-(methylthio)-9H-purine (22b)

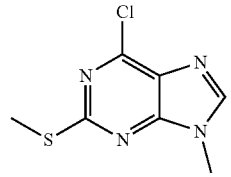

A solution of (22a) (205.0 mg, 1 mmol) in acetic acid (2.5 mL) and triethyl orthoformate (2.5 mL, 15 mmol) was heated at a temperature of 130° C. under reflux for 1 h. After distillation of the acetic acid and triethyl orthoformate under vacuum, the residue was purified by silica gel column chromatography.
Yield: 92%.
Melting point: 140-142° C.
$^1$H NMR (DMSO-d$_6$) δ 2.61 (s, 3H, SCH$_3$), 3.80 (s, 3H, NCH$_3$), 8.49 (s, 1H, CH).
$^{13}$C NMR (DMSO-d$_6$) δ 14.1 (SCH$_3$), 30.0 (NCH$_3$), 127.9 (C-5), 147.0 (C-8), 148.8 (C-6), 153.2 (C-4), 164.4 (C-2).

N-((1R,2S)-2-(3,4-Difluorophenyl)cyclopropyl)-9-methyl-2-(methylthio)-9H-purin-6-amine (22c)

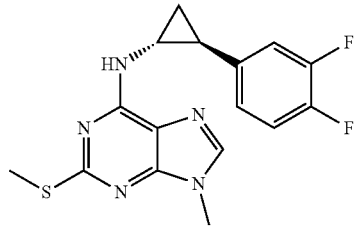 [SMILES: CSc1nc(N[C@@H]2C[C@H]2c2ccc(F)c(F)c2)c2ncn(C)c2n1]

A solution of (22b) (107.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.

Yield: 80%.

Melting point: 156-159° C.

$^1$H NMR (CDCl$_3$) δ 1.33 (m, 2H, NHCH(CH$_2$)CHPh), 2.09 (m, 1H, NHCH(CH$_2$)CHPh), 2.45 (s, 3H, SCH$_3$), 3.12 (bs, 1H, NHCH(CH$_2$)CHPh), 3.77 (s, 3H, NCH$_3$), 5.95 (bs, 1H, NH), 7.00 (m, 1H, 6'-H), 7.09 (m, 2H, 2'-H/5'-H), 7.60 (s, 1H, 8-H).

$^{13}$C NMR (CDCl$_3$) δ 14.5 (SCH$_3$), 16.1 (NHCH(CH$_2$)CHPh), 25.4 (NHCH(CH$_2$)CHPh), 29.8 (NCH$_3$), 33.4 (NHCH(CH$_2$)CHPh), 115.9 (d, J=17 Hz, C-2'), 117.0 (d, J=17 Hz, C-5'), 117.5 (C-5), 122.9 (C-6'), 137.9 (C-1'), 139.7 (C-8), 148.0-150.0 (dd, J=246 Hz/13 Hz, C-4'), 149.3-151.3 (dd, J=247 Hz/13 Hz, C-3'), 151.0 (C-4), 154.7 (C-6), 166.0 (C-2).

Example 23

Synthesis of N-((1R,2S)-2-(3,4-difluorophenyl)cyclopropyl)-9-methyl-2-propoxy-9H-purin-6-amine hydrochloride (23t.HCl)

N-((1R,2S)-2-(3,4-Difluorophenyl)cyclopropyl)-9-methyl-2-(methylsulfonyl)-9H-purin-6-amine (23q)

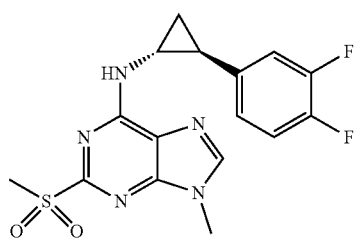 [SMILES: Cn1cnc2c(N[C@@H]3C[C@H]3c3ccc(F)c(F)c3)nc(S(C)(=O)=O)nc21]

A solution of (22c) (125.0 mg, 0.36 mmol) in methylene chloride (10 mL) was cooled to 5° C. on an ice bath and supplemented with 3-chloroperbenzoic acid (140.0 mg, 0.80 mmol). After stirring at room temperature for 4 hours, the mixture was washed with a solution of NaOH 0.1 M (2×10 mL). The organic layer was dried, filtered and methylene chloride was evaporated to dryness under vacuum. The residue was suspended in ethyl acetate and filtered off.

Yield: 88%.

Melting point: 206-208.5° C.

$^1$H NMR (CDCl$_3$) δ 1.38 (m, 2H, NHCH(CH$_2$)CHPh), 2.17 (td, J=8.0 Hz/3.3 Hz, 1H, NHCH(CH$_2$)CHPh), 3.08 (bs, 1H, NHCH(CH$_2$)CHPh), 3.19 (s, 3H, SO$_2$CH$_3$), 3.91 (s, 3H, NCH$_3$), 6.49 (bs, 1H, NH), 7.11 (m, 3H, 2'-H/5'-H/6'-H), 7.88 (s, 1H, 8-H).

$^{13}$C NMR (CDCl$_3$) δ 15.7 (NHCH(CH$_2$)CHPh), 25.4 (NHCH(CH$_2$)CHPh), 30.5 (NCH$_3$), 33.1 (NHCH(CH$_2$)CHPh), 39.4 (SO$_2$CH$_3$), 115.8 (d, J=16 Hz, C-2'), 117.3 (d, J=17 Hz, C-5'), 120.9 (C-5), 123.3 (C-6'), 137.3 (C-1'), 143.0 (C-8), 148.5-149.9 (dd, J=247 Hz/12 Hz, C-4'), 149.7-151.1 (dd, J=248 Hz/13 Hz, C-3'), 149.2 (C-4), 155.7 (C-6).

N-((1R,2S)-2-(3,4-Difluorophenyl)cyclopropyl)-9-methyl-2-propoxy-9H-purin-6-amine (23t)

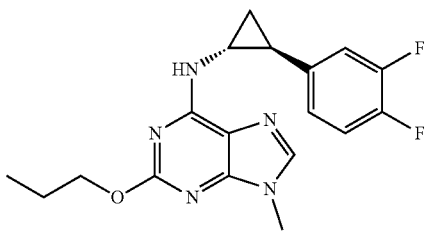

Sodium was dissolved in propan-1-ol (3 mL) on an iced bath and (23q) (150.0 mg, 0.40 mmol) was added. After stirring at room temperature for 3 hours, the mixture was partitioned between water (50 mL) and dichloromethane (2×50 mL). The combined organic layers were dried and evaporated to dryness under vacuum. The residue was purified by silica gel column chromatography and the resulting oil was engaged in the next step (23t.HCl) without further purification.

Yield: 73%.

$^1$H NMR (CDCl$_3$) δ 0.94 (t, J=7.5 Hz, 3H, OCH$_2$CH$_2$CH$_3$), 1.30 (dt, J=7.5 Hz/6.2 Hz, 1H, NHCH(CH$_2$)CHPh), 1.39 (ddd, J=9.7 Hz/5.9 Hz/4.7 Hz, 1H, NHCH(CH$_2$)CHPh), 1.75 (h, J=7.3 Hz, 2H, OCH$_2$CH$_2$CH$_3$), 2.10 (m, 1H, NHCH(CH$_2$)CHPh), 3.16 (bs, 1H, NHCH(CH$_2$)CHPh), 3.74 (s, 3H, NCH$_3$), 4.18 (m, 2H, OCH$_2$CH$_2$CH$_3$), 6.86 (bs, 1H, NH), 6.94 (m, 1H, 6'-H), 7.07 (m, 2H, 2'-H/5'-H), 7.57 (s, 1H, 8-H).

$^{13}$C NMR (CDCl$_3$) δ 10.5 (OCH$_2$CH$_2$CH$_3$), 16.2 (NHCH(CH$_2$)CHPh), 22.4 (OCH$_2$CH$_2$CH$_3$), 25.1 (NHCH(CH$_2$)CHPh), 29.8 (NCH$_3$), 33.6 (NHCH(CH$_2$)CHPh), 69.3 (OCH$_2$CH$_2$CH$_3$), 115.4 (C-5), 115.7 (C-2'), 117.0 (C-5'), 122.6 (C-6'), 138.3 (C-1'), 139.1 (C-8), 148.0-149.9 (C-4'), 149.4-151.3 (C-3'), 151.7 (C-4), 156.1 (C-6), 162.6 (C-2).

73

N-((1R,2S)-2-(3,4-Difluorophenyl)cyclopropyl)-9-methyl-2-propoxy-9H-purin-6-amine hydrochloride (23t.HCl)

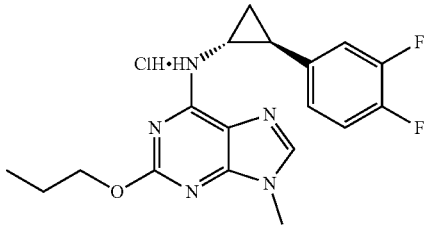

To a solution of (23t) (90.0 mg, 0.25 mmol) in diethyl ether (5 mL) was added dropwise a saturated solution of HCl in diethyl ether. The resulting precipitate of the title compound was collected by filtration, washed with diethyl ether and dried.

Yield: 95%.

Melting point: 199-202° C.

Example 24

Synthesis of N-((1R,2S)-2-(3,4-difluorophenyl)cyclopropyl)-9-ethyl-2-(methylthio)-9H-purin-6-amine (24c)

6-Chloro-$N^4$-ethyl-2-(methylthio)pyrimidine-4,5-diamine (24a)

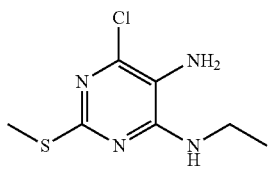

4,6-Dichloro-2-(methylthio)pyrimidin-5-amine (22h) (0.5 g, 2.4 mmol) was dissolved in a solution of ethylamine 2.0 M in methanol (3.6 mL, 7.2 mmol). The reaction mixture was introduced in a sealed vessel and heated at 100° C. for 1 h. After concentration of the reaction mixture to dryness under vacuum, the residue was purified by silica gel column chromatography.

Yield: 86%.

Melting point: 120-122° C.

$^1$H NMR (DMSO-d$_6$) δ 1.16 (t, J=7.2 Hz, 3H, CH$_3$), 2.37 (s, 3H, SCH$_3$), 3.38 (qd, J=7.2 Hz/5.3 Hz, 2H, NCH$_2$), 4.76 (s, 2H, NH$_2$), 6.94 (t, J=4.8 Hz, 1H, NH).

$^{13}$C NMR (DMSO-d$_6$) δ 13.5 (SCH$_3$), 14.3 (CH$_3$), 35.7 (NCH$_2$), 119.8 (C-5), 137.2 (C-6), 152.4 (C-4), 155.7 (C-2).

74

6-Chloro-9-ethyl-2-(methylthio)-9H-purine (24b)

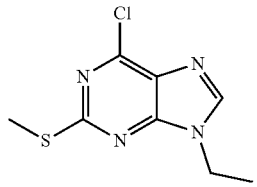

A solution of (24a) (219.0 mg, 1 mmol) in acetic acid (2.5 mL) and triethyl orthoformate (2.5 mL, 15 mmol) was heated at a temperature of 130° C. under reflux for 1 h. After distillation of the acetic acid and triethyl orthoformate under vacuum, the residue was purified by silica gel column chromatography.

Yield: 77%.

Melting point: 99.5-101.5° C.

$^1$H NMR (DMSO-d$_6$) δ 1.45(t, J=7.3 Hz, 3H, CH$_3$), 2.60 (s, 3H, SCH$_3$), 4.25 (q, J=7.3 Hz, 2H, NCH$_2$), 8.57 (s, 1H, CH).

$^{13}$C NMR (DMSO-d$_6$) δ 14.1 (SCH$_3$), 14.7 (CH$_3$), 39.0 (NCH$_2$), 128.0 (C-5), 146.0 (C-8), 148.8 (C-6), 152.7 (C-4), 164.3 (C-2).

N-((1R,2S)-2-(3,4-Difluorophenyl)cyclopropyl)-9-ethyl-2-(methylthio)-9H-purin-6-amine (24c)

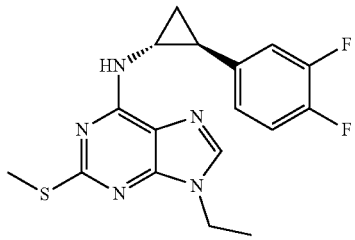 [SMILES: CCn1cnc2c(N[C@@H]3C[C@H]3c3ccc(F)c(F)c3)nc(SC)nc21]

A solution of (24b) (114.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.

Yield: 38%.

Melting point: 126-127.5° C.

$^1$H NMR (CDCl$_3$) δ 1.31 (td, J=8.0 Hz/6.9 Hz/4.0 Hz, 2H, NHCH(CH$_2$)CHPh), 1.51 (t, J=7.3 Hz, 3H, CH$_3$), 2.08 (td, J=8.1 Hz/6.7 Hz/3.2 Hz, 1H, NHCH(CH$_2$)CHPh), 2.45 (s, 3H, SCH$_3$), 3.11 (bs, 1H, NHCH(CH$_2$)CHPh), 4.20 (q, J=7.3 Hz, 2H, NCH$_2$), 5.97 (bs, 1H, NH), 7.01 (m, 1H, 6'-H), 7.10 (m, 2H, 2'-H/5'-H), 7.64 (s, 1H, 8-H).

$^{13}$C NMR (CDCl$_3$) δ 14.6 (SCH$_3$), 15.6 (CH$_3$), 16.1 (NHCH(CH$_2$)CHPh), 25.4 (NHCH(CH$_2$)CHPh), 33.4 (NHCH(CH$_2$)CHPh), 38.8 (NCH$_2$), 115.9 (d, J=17 Hz, C-2'), 117.0 (d, J=17 Hz, C-5'), 117.7 (C-5), 123.0 (C-6'), 138.0 (C-1'), 138.6 (C-8), 148.0-150.0 (dd, J=246 Hz/13 Hz, C-4'), 149.3-151.3 (dd, J=247 Hz/13 Hz, C-3'), 150.4 (C-4), 154.7 (C-6), 165.8 (C-2).

Example 25

Synthesis of 2-(butylthio)-N-((1R,2S)-2-(3,4-difluorophenyl)cyclopropyl)-9-methyl-9H-purin-6-amine (25c)

2-(Butylthio)pyrimidine-4,6-diol (25e)

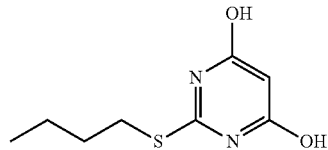

2-Thiobarbituric acid (2.5 g, 17.4 mmol) was dissolved in KOH 10% (25 mL) and supplemented with butyl iodide (2.27 mL, 20.0 mmol). The reaction mixture was introduced in a sealed vessel and heated at 80° C. for 1 h. After cooling on an ice bath to 5° C., the mixture was acidified by addition of hydrochloric acid 6N and the resulting precipitate was filtered off and washed with diethyl ether.

Yield: 72%.

Melting point: >300° C.

$^1$H NMR (DMSO-d$_6$) δ 0.90 (t, J=7.4 Hz, 3H, SCH$_2$CH$_2$CH$_2$CH$_3$), 1.38 (h, J=7.4 Hz, 2H, SCH$_2$CH$_2$CH$_2$CH$_3$), 1.60 (p, J=7.4 Hz, 2H, SCH$_2$CH$_2$CH$_2$CH$_3$), 3.09 (t, J=7.3 Hz, 2H, SCH$_2$CH$_2$CH$_2$CH$_3$), 5.12 (s, 1H, CH), 11.64 (bs, 2H, OH).

$^{13}$C NMR (DMSO-d$_6$) δ 13.5 (SCH$_2$CH$_2$CH$_2$CH$_3$), 21.3 (SCH$_2$CH$_2$CH$_2$CH$_3$), 29.2 (SCH$_2$CH$_2$CH$_2$CH$_3$), 30.8 (SCH$_2$CH$_2$CH$_2$CH$_3$), 85.6 (CH), 158.1 (C-4/C-6), 162.9 (C-2).

2-(Butylthio)-5-nitropyrimidine-4,6-diol (25f)

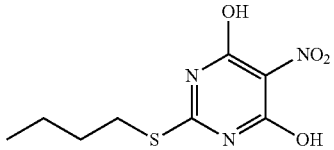 [SMILES: CCCCSc1nc(O)c([N+](=O)[O-])c(O)n1]

To 6 mL of acetic acid cooled at 5° C. on an ice bath were added fuming nitric acid (2.5 mL) and (25e) (2.0 g, 10.0 mmol). After 1 hour stirring at room temperature, the mixture was cooled at 5° C. on an ice bath, water (50 mL) was added and the resulting precipitate was filtered off.

Yield: 68%.

Melting point: 178-179.5° C. (decomposition).

$^1$H NMR (DMSO-d$_6$) δ 0.90 (t, J=7.4 Hz, 3H, SCH$_2$CH$_2$CH$_2$CH$_3$), 1.39 (h, J=7.4 Hz, 2H, SCH$_2$CH$_2$CH$_2$CH$_3$), 1.63 (p, J=7.4 Hz, 2H, SCH$_2$CH$_2$CH$_2$CH$_3$), 3.18 (t, J=7.3 Hz, 2H, SCH$_2$CH$_2$CH$_2$CH$_3$).

$^{13}$C NMR (DMSO-d$_6$) δ 13.5 (SCH$_2$CH$_2$CH$_2$CH$_3$), 21.2 (SCH$_2$CH$_2$CH$_2$CH$_3$), 29.9 (SCH$_2$CH$_2$CH$_2$CH$_3$), 30.5 (SCH$_2$CH$_2$CH$_2$CH$_3$), 117.5 (C-5), 158.9 (C-4/C-6), 164.2 (C-2).

2-(Butylthio)-4,6-dichloro-5-nitropyrimidine (25g)

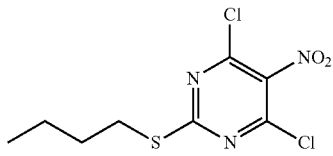 [SMILES: CCCCSc1nc(Cl)c([N+](=O)[O-])c(Cl)n1]

To a solution of (25f) (1.5 g, 6.1 mmol) in POCl$_3$ (10 mL) cooled at 5° C. on an ice bath was added dropwise 2,6-lutidine (2.5 mL). After 2 hours stirring at 80° C., the mixture was poured on crushed ice and extracted with ethyl acetate (3×50 mL). The organic layers were washed with water and with an aqueous saturated solution of sodium hydrogenocarbonate and ethyl acetate was evaporated to dryness under vacuum. The resulting oily residue was used without further purification in the next step (25h).

Yield: 92%.

Melting point: oil.

$^1$H NMR (DMSO-d$_6$) δ 0.90 (t, J=7.3 Hz, 3H, SCH$_2$CH$_2$CH$_2$CH$_3$), 1.39 (h, J=7.4 Hz, 2H, SCH$_2$CH$_2$CH$_2$CH$_3$), 1.65 (p, J=7.4 Hz, 2H, SCH$_2$CH$_2$CH$_2$CH$_3$), 3.17 (t, J=7.2 Hz, 2H, SCH$_2$CH$_2$CH$_2$CH$_3$).

$^{13}$C NMR (DMSO-d$_6$) δ 13.4 (SCH$_2$CH$_2$CH$_2$CH$_3$), 21.2 (SCH$_2$CH$_2$CH$_2$CH$_3$), 30.2 (SCH$_2$CH$_2$CH$_2$CH$_3$), 30.3 (SCH$_2$CH$_2$CH$_2$CH$_3$), 149.0 (C-4/C-6), 154.7 (C-5), 165.6 (C-2).

2-(Butylthio)-4,6-dichloropyrimidin-5-amine (25h)

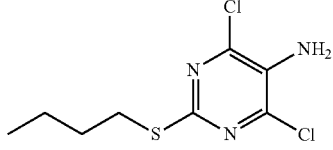

To a solution of (25g) (1 g, 3.5 mmol) in methanol (10 mL) and acetic acid (4 mL) was added iron powder (0.78 g, 14.0 mmol). After 1 hour stirring at room temperature, ethyl acetate (50 mL) was added and the suspension was filtered. The filtrate was washed with water and with an aqueous saturated solution of sodium hydrogenocarbonate and the organic layer was evaporated to dryness under vacuum. The resulting oily residue was used without further purification in the next step (25a).

Yield: 97%.

Melting point: oil.

$^1$H NMR (DMSO-d$_6$) δ 0.90 (t, J=7.4 Hz, 3H, SCH$_2$CH$_2$CH$_2$CH$_3$), 1.39 (h, J=7.4 Hz, 2H, SCH$_2$CH$_2$CH$_2$CH$_3$), 1.61 (p, J=7.4 Hz, 2H, SCH$_2$CH$_2$CH$_2$CH$_3$), 3.03 (t, J=7.2 Hz, 2H, SCH$_2$CH$_2$CH$_2$CH$_3$), 5.88 (s, 2H, NH$_2$).

$^{13}$C NMR (DMSO-d$_6$) δ 13.5 (SCH$_2$CH$_2$CH$_2$CH$_3$), 21.3 (SCH$_2$CH$_2$CH$_2$CH$_3$), 30.2 (SCH$_2$CH$_2$CH$_2$CH$_3$), 30.7 (SCH$_2$CH$_2$CH$_2$CH$_3$), 133.5 (C-5), 143.7 (C-4/C-6), 154.0 (C-2).

2-(Butylhio)-6-chloro-2-N⁴-methylpyrimidine-4,5-diamine (25a)

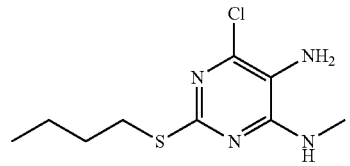

2-(Butylthio)-4,6-dichloropyrimidin-5-amine (25h) (0.5 g, 2.0 mmol) was dissolved in methanol (2 mL) and supplemented with a solution of methylamine 33% w/w in methanol (0.73 mL, 6.0 mmol). The reaction mixture was introduced in a sealed vessel and heated at 100° C. for 1 h. After concentration of the reaction mixture to dryness under vacuum, the residue was purified by silica gel column chromatography.

Yield: 87%.

Melting point: oil.

$^1$H NMR (DMSO-$d_6$) δ 0.89 (t, J=7.4 Hz, 3H, SCH$_2$CH$_2$CH$_2$CH$_3$), 1.38 (h, J=7.4 Hz, 2H, SCH$_2$CH$_2$CH$_2$CH$_3$), 1.61 (p, J=7.4 Hz, 2H, SCH$_2$CH$_2$CH$_2$CH$_3$), 2.87 (d, J=4.5 Hz, 3H, NHCH$_3$), 2.98 (t, J=7.3 Hz, 2H, SCH$_2$CH$_2$CH$_2$CH$_3$), 4.69 (s, 2H, NH$_2$), 6.99 (q, J=4.4 Hz, 1H, NHCH$_3$).

$^{13}$C NMR (DMSO-$d_6$) δ 13.6 (SCH$_2$CH$_2$CH$_2$CH$_3$), 21.5 (SCH$_2$CH$_2$CH$_2$CH$_3$), 27.8 (NHCH$_3$), 29.8 (SCH$_2$CH$_2$CH$_2$CH$_3$), 31.4 (SCH$_2$CH$_2$CH$_2$CH$_3$), 120.0 (C-5), 137.2 (C-6), 153.3 (C-4), 155.5 (C-2).

2-(Butylthio)-6-chloro-9-methyl-9H-purine (25b)

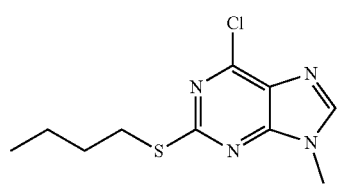 [SMILES: CCCCSc1nc(Cl)c2ncn(C)c2n1]

A solution of (25a) (247.0 mg, 1 mmol) in acetic acid (2.5 mL) and triethyl orthoformate (2.5 mL, 15 mmol) was heated at a temperature of 130° C. under reflux for 1 h. After distillation of the acetic acid and triethyl orthoformate under vacuum, the residue was purified by silica gel column chromatography.

Yield: 76%.

Melting point: 56-58° C.

$^1$H NMR (DMSO-$d_6$) δ 0.93 (t, J=7.4 Hz, 3H, SCH$_2$CH$_2$CH$_2$CH$_3$), 1.44 (h, J=7.4 Hz, 2H, SCH$_2$CH$_2$CH$_2$CH$_3$), 1.70 (p, J=7.4 Hz, 2H, SCH$_2$CH$_2$CH$_2$CH$_3$), 3.20 (t, J=7.3 Hz, 2H, SCH$_2$CH$_2$CH$_2$CH$_3$), 3.79 (s, 3H, NCH$_3$), 8.48 (s, 1H, CH).

$^{13}$C NMR (DMSO-$d_6$) δ 13.5 (SCH$_2$CH$_2$CH$_2$CH$_3$), 21.4 (SCH$_2$CH$_2$CH$_2$CH$_3$), 30.0 (NCH$_3$), 30.3 (SCH$_2$CH$_2$CH$_2$CH$_3$), 30.8 (SCH$_2$CH$_2$CH$_2$CH$_3$), 127.9 (C-5), 147.0 (C-8), 148.8 (C-6), 153.2 (C-4), 163.9 (C-2).

2-(Butylthio)-N-((1R,2S)-2-(3,4-difluorophenyl)cyclopropyl)-9-methyl-9H-purin-6-amine (25c)

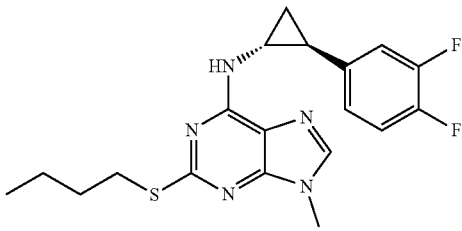 [SMILES: CCCCSc1nc(N[C@@H]2C[C@H]2c2ccc(F)c(F)c2)c2ncn(C)c2n1]

A solution of (25b) (128.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.

Yield: 66%.

Melting point: 98-100° C.

$^1$H NMR (CDCl$_3$) δ 0.89 (t, J=7.4 Hz, 3H, SCH$_2$CH$_2$CH$_2$CH$_3$), 1.33 (m, 4H, NHCH(CH$_2$)CHPh/SCH$_2$CH$_2$CH$_2$CH$_3$), 1.62 (p, J=7.3 Hz, 2H, SCH$_2$CH$_2$CH$_2$CH$_3$), 2.09 (ddd, J=9.5 Hz/6.4 Hz/3.2 Hz, 1H, NHCH(CH$_2$)CHPh), 3.02 (m, 1H, SCH$_2$CH$_2$CH$_2$CH$_3$), 3.11 (m, 2H, NHCH(CH$_2$)CHPh/SCH$_2$CH$_2$CH$_2$CH$_3$), 3.76 (s, 3H, NCH$_3$), 5.92 (bs, 1H, NH), 6.98 (m, 1H, 6'-H), 7.07 (m, 2H, 2'-H/5'-H), 7.59 (s, 1H, 8-H).

$^{13}$C NMR (CDCl$_3$) δ 13.9 (SCH$_2$CH$_2$CH$_2$CH$_3$), 16.3 (NHCH(CH$_2$)CHPh), 22.1 (SCH$_2$CH$_2$CH$_2$CH$_3$), 25.3 (NHCH(CH$_2$)CHPh), 29.8 (NCH$_3$), 31.1 (SCH$_2$CH$_2$CH$_2$CH$_3$), 31.8 (SCH$_2$CH$_2$CH$_2$CH$_3$), 33.5 (NHCH(CH$_2$)CHPh), 115.7 (d, J=17 Hz, C-2'), 117.1 (d, J=17 Hz, C-5'), 117.6 (C-5), 122.8 (C-6'), 138.0 (C-1'), 139.7 (C-8), 148.0-150.0 (dd, J=246 Hz/13 Hz, C-4'), 149.4-151.4 (dd, J=247 Hz/13 Hz, C-3'), 150.8 (C-4), 154.7 (C-6), 165.6 (C-2).

Example 26

Synthesis of 2-(butylthio)-N-((1R,2S)-2-(3,4-difluorophenyl)cyclopropyl)-9-ethyl-9H-purin-6-amine (26c)

2-(Butylthio)-6-chloro-N⁴-ethylpyrimidine-4,5-diamine (26a)

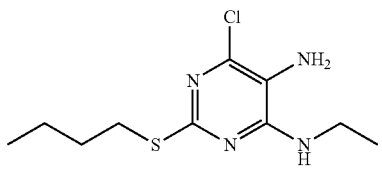 [SMILES: CCCCSc1nc(Cl)c(N)c(NCC)n1]

4,6-Dichloro-2-(ethylthio)pyrimidin-5-amine (25h) (0.5 g, 2.0 mmol) was dissolved in a solution of ethylamine 2.0 M in methanol (3.0 mL, 6.0 mmol). The reaction mixture was introduced in a sealed vessel and heated at 100° C. for 1 h. After concentration of the reaction mixture to dryness under vacuum, the residue was purified by silica gel column chromatography.

Yield: 91%.

Melting point: 80-82° C.

$^1$H NMR (DMSO-$d_6$) δ 0.89 (t, J=7.3 Hz, 3H, SCH$_2$CH$_2$CH$_2$CH$_3$), 1.16 (t, J=7.1 Hz, 3H, NHCH$_2$CH$_3$), 1.38 (h, J=7.3 Hz, 2H, SCH$_2$CH$_2$CH$_2$CH$_3$), 1.60 (p, J=7.3 Hz, 2H, SCH$_2$CH$_2$CH$_2$CH$_3$), 2.96 (t, J=7.3 Hz, 2H, SCH$_2$CH$_2$CH$_2$CH$_3$), 3.38 (p, J=7.0 Hz, 2H, NHCH$_2$CH$_3$), 4.74 (s, 2H, NH$_2$), 6.95 (t, J=4.7 Hz, 1H, NHCH$_2$CH$_3$).

$^{13}$C NMR (DMSO-$d_6$) δ 13.5 (SCH$_2$CH$_2$CH$_2$CH$_3$), 14.4 (NHCH$_2$CH$_3$), 21.5 (SCH$_2$CH$_2$CH$_2$CH$_3$), 29.8 (SCH$_2$CH$_2$CH$_2$CH$_3$), 31.5 (SCH$_2$CH$_2$CH$_2$CH$_3$), 35.7 (NHCH$_2$CH$_3$), 119.8 (C-5), 137.3 (C-6), 152.5 (C-4), 155.4 (C-2).

2-(Butylthio)-6-chloro-9-ethyl-9H-purine (26b)

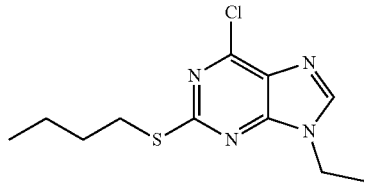 [SMILES: CCCCSc1nc(Cl)c2ncn(CC)c2n1]

A solution of (26a) (261.0 mg, 1 mmol) in acetic acid (2.5 mL) and triethyl orthoformate (2.5 mL, 15 mmol) was heated at a temperature of 130° C. under reflux for 1 h. After distillation of the acetic acid and triethyl orthoformate under vacuum, the residue was purified by silica gel column chromatography.

Yield: 70%.

Melting point: 69-71° C.

$^1$H NMR (DMSO-$d_6$) δ 0.93 (t, J=7.4 Hz, 3H, SCH$_2$CH$_2$CH$_2$CH$_3$), 1.45 (m, 5H, SCH$_2$CH$_2$CH$_2$CH$_3$/NCH$_2$CH$_3$), 1.70 (p, J=7.4 Hz, 2H, SCH$_2$CH$_2$CH$_2$CH$_3$), 3.19 (t, J=7.3 Hz, 2H, SCH$_2$CH$_2$CH$_2$CH$_3$), 4.25 (q, J=7.3 Hz, 2H, NCH$_2$CH$_3$), 8.56 (s, 1H, CH).

$^{13}$C NMR (DMSO-$d_6$) δ 13.5 (SCH$_2$CH$_2$CH$_2$CH$_3$), 14.7 (NCH$_2$CH$_3$), 21.4 (SCH$_2$CH$_2$CH$_2$CH$_3$), 30.3 (SCH$_2$CH$_2$CH$_2$CH$_3$), 30.8 (SCH$_2$CH$_2$CH$_2$CH$_3$), 39.0 (NCH$_2$CH$_3$), 128.1 (C-5), 146.0 (C-8), 148.9 (C-6), 152.7 (C-4), 163.8 (C-2).

2-(Butylthio)-N-((1R,2S)-2-(3,4-difluorophenyl)cyclopropyl)-9-ethyl-9H-purin-6-amine (26c)

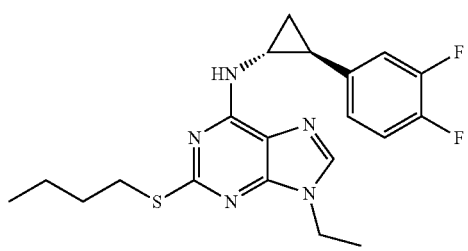 [SMILES: CCCCSc1nc(N[C@@H]2C[C@H]2c2ccc(F)c(F)c2)c2ncn(CC)c2n1]

A solution of (26b) (135.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.

Yield: 56%.

Melting point: 92-94° C.

$^1$H NMR (CDCl$_3$) δ 0.89 (t, J=7.4 Hz, 3H, SCH$_2$CH$_2$CH$_2$CH$_3$), 1.31 (m, 2H, NHCH(CH$_2$)CHPh), 1.36 (m, 2H, SCH$_2$CH$_2$CH$_2$CH$_3$), 1.50 (t, J=7.3 Hz, 3H, NCH$_2$CH$_3$), 1.63 (p, J=7.3 Hz, 2H, SCH$_2$CH$_2$CH$_2$CH$_3$), 2.09 (ddd, J=9.5 Hz/6.6 Hz/3.2 Hz, 1H, NHCH(CH$_2$)CHPh), 3.02 (m, 1H, SCH$_2$CH$_2$CH$_2$CH$_3$), 3.10 (m, 2H, NHCH(CH$_2$)CHPh/SCH$_2$CH$_2$CH$_2$CH$_3$), 4.18 (q, J=7.3 Hz, 2H, NCH$_2$CH$_3$), 5.93 (bs, 1H, NH), 6.99 (m, 1H, 6'-H), 7.08 (m, 2H, 2'-H/5'-H), 7.63 (s, 1H, 8-H).

$^{13}$C NMR (CDCl$_3$) δ 13.9 (SCH$_2$CH$_2$CH$_2$CH$_3$), 15.6 (NCH$_2$CH$_3$), 16.2 (NHCH(CH$_2$)CHPh), 22.1 (SCH$_2$CH$_2$CH$_2$CH$_3$), 25.4 (NHCH(CH$_2$)CHPh), 31.1 (SCH$_2$CH$_2$CH$_2$CH$_3$), 31.8 (SCH$_2$CH$_2$CH$_2$CH$_3$), 33.5 (NHCH(CH$_2$)CHPh), 38.8 (NCH$_2$CH$_3$), 115.8 (d, J=17 Hz, C-2'), 117.1 (d, J=17 Hz, C-5'), 117.8 (C-5), 122.9 (C-6'), 138.1 (C-1'), 138.6 (C-8), 148.2-150.1 (dd, J=246 Hz/12 Hz, C-4'), 149.4-151.4 (dd, J=235 Hz/10 Hz, C-3'), 150.3 (C-4), 154.7 (C-6), 165.6 (C-2).

Example 27

Synthesis of N-((1R,2S)-2-(3,4-difluorophenyl)cyclopropyl)-1-methyl-6-(methylthio)-1H-pyrazolo[3,4-d]pyrimidin-4-amine (27k)

4,6-Dichloro-2-(methylthio)pyrimidine-5-carbaldehyde (27i)

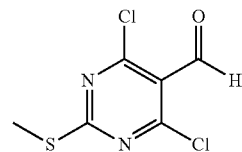

POCl$_3$ (3.2 mL) was cooled at 5° C. on an ice bath and supplemented dropwise by dimethylformamide (20 mL, 215 mmol). 2-(Methylthio)pyrimidine-4,6-diol (22e) (5 g, 31.6 mmol) was then added portion-wise and the mixture was stirred at 100° C. for 20 h. The mixture was poured on crushed ice and extracted with CH$_2$Cl$_2$ (3×50 mL). The combined organic layers were dried and evaporated to dryness under vacuum.

Yield: 52%.

Melting point: 87-89° C.

$^1$H NMR (DMSO-$d_6$) δ 2.57 (s, 3H, SCH$_3$), 10.07 (s, 1H, COH).

$^{13}$C NMR (DMSO-$d_6$) δ 13.3 (SCH$_3$), 112.9 (C-5), 159.3 (C-4/C-6), 168.2 (C-2), 186.6 (COH).

4-chloro-6-(methylthio)-1H-pyrazolo[3,4-d]pyrimidine (27i')

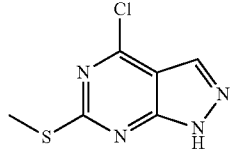

To a suspension of (27i) (2.5 g, 11.2 mmol) in THF (25 mL) cooled at 5° C. on an ice bath, were added dropwise hydrazine monohydrate (0.65 mL, 13 mmol) and triethylamine (1.8 mL, 13 mmol). After 1 hour stirring at 5° C., the mixture was evaporated to dryness under vacuum and the residue was purified by silica gel column chromatography.

Yield: 95%.

Melting point: >300° C.

$^1$H NMR (DMSO-$d_6$) δ 2.59 (s, 3H, SCH$_3$), 8.32 (s, 1H, CH), 14.25 (bs, 1H, NH).

$^{13}$C NMR (DMSO-$d_6$) δ 13.9 (SCH$_3$), 109.6 (C-3a), 133.1 (C-3), 152.9-155.4 (C-4/C-7a), 168.7 (C-6).

4-chloro-1-methyl-6-(methylthio)-1H-pyrazolo[3,4-d]pyrimidine (27j)

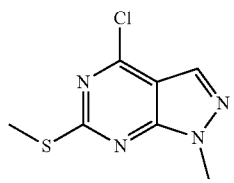

To a solution of (27i') (1.0 g, 5.0 mmol) in acetonitrile (10 mL) cooled at 5° C. on an ice bath, were added NaH (144 mg, 6.0 mmol) and iodomethane (0.47 mL, 7.5 mmol). After 3 hours stirring at 50° C., acetonitrile was evaporated to dryness under vacuum and the residue was partitioned between water (50 mL) and dichloromethane (2×50 mL). The combined organic layers were dried and evaporated to dryness under vacuum. The residue was purified by silica gel column chromatography.

Yield: 82%.

Melting point: 85-87° C.

$^1$H NMR (DMSO-$d_6$) δ 2.63 (s, 3H, SCH$_3$), 4.00 (s, 3H, NCH$_3$), 8.34 (s, 1H, CH).

$^{13}$C NMR (DMSO-$d_6$) δ 13.9 (SCH$_3$), 34.0 (NCH$_3$), 110.0 (C-3a), 132.3 (C-3), 152.9 (C-4), 153.5 (C-7a), 168.8 (C-6).

N-((1R,2S)-2-(3,4-difluorophenyl)cyclopropyl)-1-methyl-6-(methylthio)-1H-pyrazolo[3,4-d]pyrimidin-4-amine (27k)

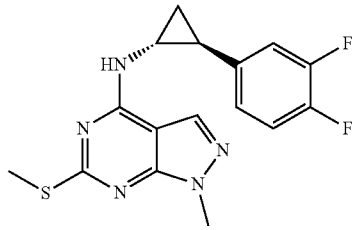 [SMILES: CSc1nc(N[C@@H]2C[C@H]2c2ccc(F)c(F)c2)c2cnn(C)c2n1]

A solution of (27j) (107.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography.

Yield: 84%.

Melting point: 128.5-130° C.

$^1$H NMR (CDCl$_3$) δ 1.40 (m, 2H, NHCH(CH$_2$)CHPh), 2.17 (s, 1H, NHCH(CH$_2$)CHPh), 2.55 (s, 3H, SCH$_3$), 3.10 (s, 1H, NHCH(CH$_2$)CHPh), 3.95 (s, 3H, NCH$_3$), 5.87 (bs, 1H, NH), 6.87 (m, 2H, 2'-H/6'-H), 7.12 (q, J=8.7 Hz, 1H, 5'-H), 7.59 (s, 1H, 3-H).

$^{13}$C NMR (CDCl$_3$) δ 14.2 (SCH$_3$), 18.3 (NHCH(CH$_2$)CHPh), 25.6 (NHCH(CH$_2$)CHPh), 33.8 (NCH$_3$), 34.9 (NHCH(CH$_2$)CHPh), 97.8 (C-3a), 114.6 (C-2'), 117.4 (C-5'), 121.7 (C-6'), 132.0 (C-3), 136.8 (C-1'), 149.7-150.8 (C-3'/C-4'), 154.8 (C-7a), 169.2 (C-6).

Example 28

Synthesis of N-((1R,2S)-2-(3,4-difluorophenyl)cyclopropyl)-6-(ethylthio)-1-methyl-1H-pyrazolo[3,4-d]pyrimidin-4-amine hydrochloride (28x.HCl)

N-((1R,2S)-2-(3,4-difluorophenyl)cyclopropyl)-1-methyl-6-(methylsulfonyl)-1H-pyrazolo[3,4-d]pyrimidin-4-amine (28r)

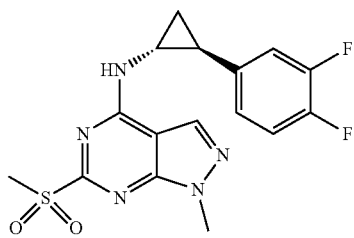 [SMILES: Cn1ncc2c(N[C@@H]3C[C@H]3c3ccc(F)c(F)c3)nc(S(C)(=O)=O)nc21]

A solution of (27j) (125.0 mg, 0.36 mmol) in methylene chloride (10 mL) was cooled to 5° C. on an ice bath and supplemented with 3-chloroperbenzoic acid (140.0 mg, 0.80 mmol). After stirring at room temperature for 4 hours, the mixture was washed with a solution of NaOH 0.1 M (2×10 mL). The organic layer was dried, filtered and methylene chloride was evaporated to dryness under vacuum. The resulting oily residue was used without further purification in the next step (28x).

Yield: 58%.

Melting point: oil.

$^1$H NMR (CDCl$_3$) δ 1.50 (m, 2H, NHCH(CH$_2$)CHPh), 2.23 (s, 1H, NHCH(CH$_2$)CHPh), 3.18 (s, 1H, NHCH(CH$_2$)CHPh), 3.34 (s, 3H, SO$_2$CH$_3$), 4.07 (s, 3H, NCH$_3$), 6.48 (s, 1H, NH), 6.86 (m, 2H, 2'-H/6'-H), 7.15 (s, 1H, 5'-H), 7.75 (s, 1H, 3-H).

$^{13}$C NMR (CDCl$_3$) δ 18.3 (NHCH(CH$_2$)CHPh), 26.1 (NHCH(CH$_2$)CHPh), 34.4 (NCH$_3$), 35.1 (NHCH(CH$_2$)CHPh), 39.1 (SO$_2$CH$_3$), 100.5 (C-3a), 114.5 (C-2'), 117.9 (C-5'), 121.8 (C-6'), 133.0 (C-3), 136.0 (C-1'), 150.1 (C-3'/C-4'), 153.4 (C-7a), 159.5 (C-4), 162.4 (C-6).

N-((1R,2S)-2-(3,4-difluorophenyl)cyclopropyl)-6-(ethylthio)-1-methyl-1H-pyrazolo[3,4-d]pyrimidin-4-amine hydrochloride (28x.HCl)

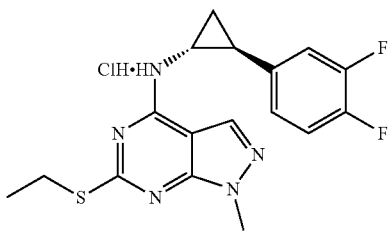

A solution of (28r) (150.0 mg, 0.40 mmol) in THF (6 mL) was supplemented with ethanethiol (0.06 mL, 0.80 mmol) and K$_2$CO$_3$ (110.0 mg, 0.80 mmol). After stirring at room temperature for 24 hours, THF was evaporated to dryness under vacuum and the residue was purified by silica gel column chromatography. The resulting oil was dissolved in diethyl ether (10 mL) and supplemented dropwise with a saturated solution of HCl in diethyl ether. The precipitate of the title compound was collected by filtration, washed with diethyl ether and dried.

Yield: 67%.

Melting point: 164-168° C.

$^1$H NMR (CDCl$_3$) δ 1.46 (t, J=7.3 Hz, 3H, SCH$_2$CH$_3$), 1.52 (d, J=6.0 Hz, 1H, NHCH(CH$_2$)CHPh), 1.69 (m, 1H, NHCH(CH$_2$)CHPh), 2.37 (s, 1H, NHCH(CH$_2$)CHPh), 3.09 (s, 1H, NHCH(CH$_2$)CHPh), 3.33 (q, J=7.2 Hz, 2H, SCH$_2$CH$_3$), 4.00 (s, 3H, NCH$_3$), 6.84 (d, J=7.0 Hz, 1H, 6'-H), 6.89 (t, J=8.5 Hz, 1H, 2'-H), 7.15 (q, J=8.4 Hz, 1H, 5'-H), 7.73 (s, 1H, 3-H), 10.48 (bs, 1H, NH).

$^{13}$C NMR (CDCl$_3$) δ 14.1 (SCH$_2$CH$_3$), 17.6 (NHCH(CH$_2$)CHPh), 25.5 (NHCH(CH$_2$)CHPh), 25.9 (SCH$_2$CH$_3$), 34.5 (NCH$_3$), 35.3 (NHCH(CH$_2$)CHPh), 96.3 (C-3a), 114.8 (C-2'), 118.1 (C-5'), 122.1 (C-6'), 135.5 (C-3), 135.3 (C-1'), 148.9-150.1 (C-4'), 150.3-151.4 (C-3'), 151.7 (C-4), 154.2 (C-7a), 160.8 (C-6).

Example 29

Synthesis of N-((1R,2S)-2-(3,4-difluorophenyl)cyclopropyl)-6-(propylthio)-1-methyl-1H-pyrazolo[3,4-d]pyrimidin-4-amine hydrochloride (29x. HCl)

N-((1R,2S)-2-(3,4-difluorophenyl)cyclopropyl)-1-methyl-6-(propylthio)-1H-pyrazolo[3,4-d]pyrimidin-4-amine hydrochloride (29x.HCl)

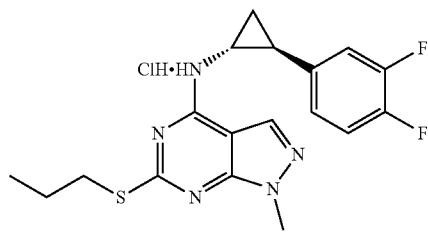

A solution of (28r) (150.0 mg, 0.40 mmol) in THF (6 mL) was supplemented with propanethiol (0.07 mL, 0.80 mmol) and K$_2$CO$_3$ (110.0 mg, 0.80 mmol). After stirring at room temperature for 24 hours, THF was evaporated to dryness under vacuum and the residue was purified by silica gel column chromatography. The resulting oil was dissolved in diethyl ether (10 mL) and supplemented dropwise with a saturated solution of HCl in diethyl ether. The precipitate of the title compound was collected by filtration, washed with diethyl ether and dried.

Yield: 66%.

Melting point: 110-115° C.

$^1$H NMR (CDCl$_3$) δ 1.08 (t, J=7.3 Hz, 3H, SCH$_2$CH$_2$CH$_3$), 1.51 (m, 1H, NHCH(CH$_2$)CHPh), 1.68 (m, 1H, NHCH(CH$_2$)CHPh), 1.82 (h, J=7.0 Hz, 2H, SCH$_2$CH$_2$CH$_3$), 2.36 (s, 1H, NHCH(CH$_2$)CHPh), 3.09 (m, 1H, NHCH(CH$_2$)CHPh/SCH$_2$CH$_2$CH$_3$), 3.29 (t, J=6.8 Hz, 1H, SCH$_2$CH$_2$CH$_3$), 4.00 (s, 3H, NCH$_3$), 6.84 (d, J=5.9 Hz, 1H, 6'-H), 6.89 (t, J=8.5 Hz, 1H, 2'-H), 7.15 (q, J=8.5 Hz, 1H, 5'-H), 7.73 (s, 1H, 3-H), 10.37 (bs, 1H, NH).

$^{13}$C NMR (CDCl$_3$) δ 13.5 (SCH$_2$CH$_2$CH$_3$), 17.6 (NHCH(CH$_2$)CHPh), 22.3 (SCH$_2$CH$_2$CH$_3$), 25.5 (NHCH(CH$_2$)CHPh), 33.3 (SCH$_2$CH$_2$CH$_3$), 34.4 (NCH$_3$), 35.3 (NHCH(CH$_2$)CHPh), 96.3 (C-3a), 114.8 (C-2'), 118.1 (C-5'), 122.1 (C-6'), 135.1 (C-3), 135.6 (C-1'), 148.9-150.1 (C-4'), 150.4-151.4 (C-3'), 151.8 (C-4), 154.3 (C-7a), 160.9 (C-6).

Example 30

Synthesis of N-((1R,2S)-2-(3,4-difluorophenyl)cyclopropyl)-1-ethyl-6-(methylthio)-1H-pyrazolo[3,4-d]pyrimidin-4-amine hydrochloride (30k.HCl)

4-chloro-1-ethyl-6-(methylthio)-1H-pyrazolo[3,4-d]pyrimidine (30j)

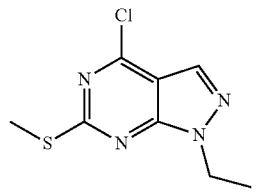

To a solution of (27i') (1.0 g, 5.0 mmol) in acetonitrile (10 mL) cooled at 5° C. on an ice bath, were added NaH (144 mg, 6.0 mmol) and iodoethane (0.60 mL, 7.5 mmol). After 3 hours stirring at 50° C., acetonitrile was evaporated to dryness under vacuum and the residue was partitioned between water (50 mL) and dichloromethane (2×50 mL). The combined organic layers were dried and evaporated to dryness under vacuum. The residue was purified by silica gel column chromatography.

Yield: 77%.

Melting point: 92-93.5° C.

$^1$H NMR (DMSO-$d_6$) δ 1.43 (t, J=7.2 Hz, 3H, NCH$_2$CH$_3$), 2.62 (s, 3H, SCH$_3$), 4.42 (q, J=7.2 Hz, 2H, NCH$_2$CH$_3$), 8.34 (s, 1H, CH).

$^{13}$C NMR (DMSO-$d_6$) δ 13.9 (SCH$_3$), 14.4 (NCH$_2$CH$_3$), 42.2 (NCH$_2$CH$_3$), 110.1 (C-3a), 132.3 (C-3), 153.0 (C-4/C-7a), 168.7 (C-6).

N-((1R,2S)-2-(3,4-difluorophenyl)cyclopropyl)-1-ethyl-6-(methylthio)-1H-pyrazolo[3,4-d]pyrimidin-4-amine hydrochloride (30k.HCl)

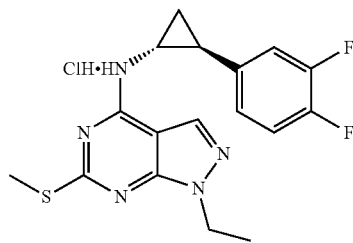

A solution of (30j) (114.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography. The resulting oil was dissolved in diethyl ether (10 mL) and supplemented dropwise with a saturated solution of HCl in diethyl ether. The precipitate of the title compound was collected by filtration, washed with diethyl ether and dried.

Yield: 54%.

Melting point: 176-180° C.

$^1$H NMR (CDCl$_3$) δ 1.51 (t, J=7.3 Hz, 4H, NHCH(CH$_2$)CHPh/NCH$_2$CH$_3$), 1.69 (s, 1H, NHCH(CH$_2$)CHPh), 2.37 (s, 1H, NHCH(CH$_2$)CHPh), 2.71 (s, 3H, SCH$_3$), 3.09 (s, 1H, NHCH(CH$_2$)CHPh), 4.41 (m, 2H, NCH$_2$CH$_3$), 6.85 (d, J=6.8 Hz, 1H, 6'-H), 6.89 (t, J=8.6 Hz, 1H, 2'-H), 7.16 (q, J=8.4 Hz, 1H, 5'-H), 7.75 (s, 1H, 3-H), 10.55 (s, 1H, NH).

$^{13}$C NMR (CDCl$_3$) δ 14.0 (SCH$_3$), 14.7 (NCH$_2$CH$_3$), 17.7 (NHCH(CH$_2$)CHPh), 25.4 (NHCH(CH$_2$)CHPh), 35.3 (NHCH(CH$_2$)CHPh), 43.0 (NCH$_2$CH$_3$), 96.3 (C-3a), 114.8 (C-2'), 118.1 (C-5'), 122.1 (C-6'), 135.2 (C-3), 135.5 (C-1'), 148.9-150.1 (C-4'), 150.3-151.5 (C-3'), 151.0 (C-7a), 154.2 (C-4), 160.8 (C-6).

Example 31

Synthesis of N-((1R,2S)-2-(3,4-difluorophenyl)cyclopropyl)-1-ethyl-6-(ethylthio)-1H-pyrazolo[3,4-d]pyrimidin-4-amine hydrochloride (31x.HCl)

N-((1R,2S)-2-(3,4-difluorophenyl)cyclopropyl)-1-ethyl-6-(methylsulfonyl)-1H-pyrazolo[3,4-d]pyrimidin-4-amine (31r)

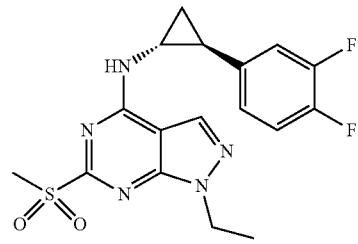 [SMILES: CCn1ncc2c(N[C@@H]3C[C@H]3c3ccc(F)c(F)c3)nc(S(C)(=O)=O)nc21]

A solution of (30k) (125.0 mg, 0.35 mmol) in methylene chloride (10 mL) was cooled to 5° C. on an ice bath and supplemented with 3-chloroperbenzoic acid (140.0 mg, 0.80 mmol). After stirring at room temperature for 4 hours, the mixture was washed with a solution of NaOH 0.1 M (2×10 mL). The organic layer was dried and filtered, methylene chloride was evaporated to dryness under vacuum and the residue was purified by silica gel column chromatography.

Yield: 87%.

Melting point: 95-100° C. (decomposition).

$^1$H NMR (CDCl$_3$) δ 1.51 (m, 5H, NHCH(CH$_2$)CHPh/NCH$_2$CH$_3$), 2.24 (s, 1H, NHCH(CH$_2$)CHPh), 3.20 (s, 1H, NHCH(CH$_2$)CHPh), 3.33 (s, 3H, SO$_2$CH$_3$), 4.53 (m, 2H, NCH$_2$CH$_3$), 6.58 (bs, 1H, NH), 6.90 (m, 2H, 2'-H/6'-H), 7.15 (m, 1H, 5'-H), 7.75 (s, 1H, 3-H).

$^{13}$C NMR (CDCl$_3$) δ 14.9 (NCH$_2$CH$_3$), 17.9 (NHCH(CH$_2$)CHPh), 25.7 (NHCH(CH$_2$)CHPh), 34.5 (NHCH(CH$_2$)CHPh), 39.2 (SO$_2$CH$_3$), 42.8 (NCH$_2$CH$_3$), 99.5 (C-3a), 114.8 (C-2'), 118.2 (C-5'), 122.1 (C-6'), 131.7 (C-3), 135.7 (C-1'), 148.9-150.1 (C-4'), 150.3-151.5 (C-3'), 152.8 (C-7a), 159.3 (C-4), 162.3 (C-6).

N-((1R,2S)-2-(3,4-difluorophenyl)cyclopropyl)-1-ethyl-6-(ethylthio)-1H-pyrazolo[3,4-d]pyrimidin-4-amine hydrochloride (31x.HCl)

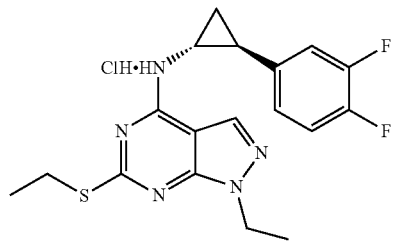

A solution of (31r) (150.0 mg, 0.38 mmol) in THF (6 mL) was supplemented with ethanethiol (0.06 mL, 0.80 mmol) and K$_2$CO$_3$ (110.0 mg, 0.80 mmol). After stirring at room temperature for 24 hours, THF was evaporated to dryness under vacuum and the residue was purified by silica gel column chromatography. The resulting oil was dissolved in diethyl ether (10 mL) and supplemented dropwise with a saturated solution of HCl in diethyl ether. The precipitate of the title compound was collected by filtration, washed with diethyl ether and dried.

Yield: 64%.

Melting point: 168-172° C.

$^1$H NMR (CDCl$_3$) δ 1.45 (t, J=7.3 Hz, 3H, SCH$_2$CH$_3$), 1.51 (t, J=7.2 Hz, 4H, NCH$_2$CH$_3$/NHCH(CH$_2$)CHPh), 1.69 (s, 1H, NHCH(CH$_2$)CHPh), 2.37 (s, 1H, NHCH(CH$_2$)CHPh), 3.09 (s, 1H, NHCH(CH$_2$)CHPh), 3.32 (q, J=7.1 Hz, 2H, SCH$_2$CH$_3$), 4.40 (hept, J=6.9 Hz, 2H, NCH$_2$CH$_3$), 6.85 (d, J=6.2 Hz, 1H, 6'-H), 6.89 (t, J=8.8 Hz, 1H, 2'-H), 7.15 (q, J=8.5 Hz, 1H, 5'-H), 7.74 (s, 1H, 3-H), 10.49 (bs, 1H, NH).

$^{13}$C NMR (CDCl$_3$) δ 14.1 (SCH$_2$CH$_3$), 14.7 (NCH$_2$CH$_3$), 17.6 (NHCH(CH$_2$)CHPh), 25.4 (NHCH(CH$_2$)CHPh), 25.9 (SCH$_2$CH$_3$), 35.3 (NHCH(CH$_2$)CHPh), 43.0 (NCH$_2$CH$_3$), 100.1 (C-3a), 114.8 (C-2'), 118.1 (C-5'), 122.1 (C-6'), 135.2 (C-3), 135.6 (C-1'), 148.9-150.1 (C-4'), 150.3-151.4 (C-3'), 151.1 (C-4), 154.2 (C-7a), 160.4 (C-6).

Example 32

Synthesis of N-((1R,2S)-2-(3,4-difluorophenyl)cyclopropyl)-1-ethyl-6-(propylthio)-1H-pyrazolo[3,4-d]pyrimidin-4-amine hydrochloride (32x.HCl)

N-((1R,2S)-2-(3,4-difluorophenyl)cyclopropyl)-1-ethyl-6-(propylthio)-1H-pyrazolo[3,4-d]pyrimidin-4-amine hydrochloride (32x.HCl)

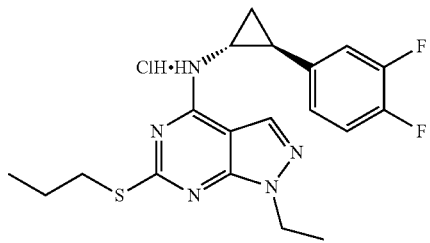

A solution of (31r) (150.0 mg, 0.38 mmol) in THF (6 mL) was supplemented with propanethiol (0.07 mL, 0.80 mmol) and K$_2$CO$_3$ (110.0 mg, 0.80 mmol). After stirring at room temperature for 24 hours, THF was evaporated to dryness under vacuum and the residue was purified by silica gel column chromatography. The resulting oil was dissolved in diethyl ether (10 mL) and supplemented dropwise with a saturated solution of HCl in diethyl ether. The precipitate of the title compound was collected by filtration, washed with diethyl ether and dried.

Yield: 62%.

Melting point: 150-154° C.

$^1$H NMR (CDCl$_3$) δ 1.08 (t, J=7.3 Hz, 3H, SCH$_2$CH$_2$CH$_3$), 1.51 (t, J=7.3 Hz, 4H, NCH$_2$CH$_3$/NHCH(CH$_2$)CHPh), 1.69 (s, 1H, NHCH(CH$_2$)CHPh), 1.82 (h, J=7.3 Hz, 2H, SCH$_2$CH$_2$CH$_3$), 2.37 (s, 1H, NHCH(CH$_2$)CHPh), 3.08 (s, 1H, NHCH(CH$_2$)CHPh), 3.28 (t, J=7.1 Hz, 2H, SCH$_2$CH$_2$CH$_3$), 4.39 (hept, J=6.9 Hz, 2H, NCH$_2$CH$_3$), 6.85 (d, J=7.0 Hz, 1H, 6'-H), 6.89 (t, J=8.8 Hz, 1H, 2'-H), 7.15 (q, J=8.4 Hz, 1H, 5'-H), 7.73 (s, 1H, 3-H), 10.50 (bs, 1H, NH).

$^{13}$C NMR (CDCl$_3$) δ 13.5 (SCH$_2$CH$_2$CH$_3$), 14.7 (NCH$_2$CH$_3$), 17.6 (NHCH(CH$_2$)CHPh), 22.3 (SCH$_2$CH$_2$CH$_3$), 25.4 (NHCH(CH$_2$)CHPh), 33.3 (SCH$_2$CH$_2$CH$_3$), 35.3 (NHCH(CH$_2$)CHPh), 43.0 (NCH$_2$CH$_3$), 96.3 (C-3a), 114.8 (C-2'), 118.1 (C-5'), 122.1 (C-6'), 135.2 (C-3), 141.3 (C-1'), 149.2-150.4 (C-4'), 150.3-151.4 (C-3'), 151.1 (C-4), 154.2 (C-7a), 160.6 (C-6).

Example 33

Synthesis of N-((1R,2S)-2-(3,4-difluorophenyl)cyclopropyl)-1-isopropyl-6-(methylthio)-1H-pyrazolo[3,4-d]pyrimidin-4-amine hydrochloride (33k.HCl)

4-chloro-1-isopropyl-6-(methylthio)-1H-pyrazolo[3,4-d]pyrimidine (33j)

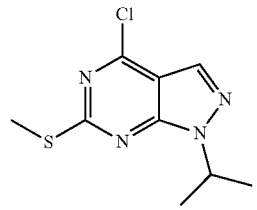

To a solution of (27i') (1.0 g, 5.0 mmol) in acetonitrile (10 mL) cooled at 5° C. on an ice bath, were added NaH (144 mg, 6.0 mmol) and 2-iodopropane (0.75 mL, 7.5 mmol). After 3 hours stirring at 50° C., acetonitrile was evaporated to dryness under vacuum and the residue was partitioned between water (50 mL) and dichloromethane (2×50 mL). The combined organic layers were dried and evaporated to dryness under vacuum. The residue was purified by silica gel column chromatography.

Yield: 73%.

Melting point: 114-115.5° C.

$^1$H NMR (DMSO-d$_6$) δ 1.50 (d, J=6.5 Hz, 6H, CH(CH$_3$)$_2$), 2.62 (s, 3H, SCH$_3$), 5.07 (hept, J=6.6 Hz, 1H, CH(CH$_3$)$_2$), 8.33 (s, 1H, CH).

$^{13}$C NMR (DMSO-d$_6$) δ 14.4 (SCH$_3$), 22.1 (CH(CH$_3$)$_2$), 49.9 (CH(CH$_3$)$_2$), 110.7 (C-3a), 132.6 (C-3), 153.0-153.4 (C-4/C-7a), 169.0 (C-6).

N-((1R,2S)-2-(3,4-difluorophenyl)cyclopropyl)-1-isopropyl-6-(methylthio)-1H-pyrazolo[3,4-d]pyrimidin-4-amine hydrochloride (33k.HCl)

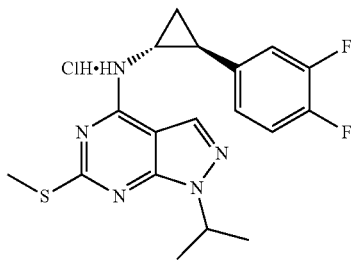

A solution of (33j) (121.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography. The resulting oil was dissolved in diethyl ether (10 mL) and supplemented dropwise with a saturated solution of HCl in diethyl ether. The precipitate of the title compound was collected by filtration, washed with diethyl ether and dried.

Yield: 87%.

Melting point: 159-163° C.

$^1$H NMR (CDCl$_3$) δ 1.50 (q, J=6.7 Hz, 1H, NHCH(CH$_2$)CHPh), 1.54 (d, J=6.7 Hz, 3H, NCH(CH$_3$)$_2$), 1.55 (d, J=6.7 Hz, 3H, NCH(CH$_3$)$_2$), 1.70 (ddd, J=10.4 Hz/6.6 Hz/4.5 Hz, 1H, NHCH(CH$_2$)CHPh), 2.37 (ddd, J=9.7 Hz/6.4 Hz/3.1 Hz, 1H, NHCH(CH$_2$)CHPh), 2.71 (s, 3H, SCH$_3$), 3.09 (dq, J=7.3 Hz/3.2 Hz, 1H, NHCH(CH$_2$)CHPh), 5.08 (hept, J=6.7 Hz, 1H, NCH(CH$_3$)$_2$), 6.84 (d, J=8.4 Hz, 1H, 6'-H), 6.89 (m, 1H, 2'-H), 7.16 (dt, J=9.6 Hz/8.4 Hz, 1H, 5'-H), 7.75 (s, 1H, 3-H), 10.57 (s, 1H, NH).

$^{13}$C NMR (CDCl$_3$) δ 14.0 (SCH$_3$), 17.7 (NHCH(CH$_2$)CHPh), 21.9 (CH(CH$_3$)$_2$), 25.4 (NHCH(CH$_2$)CHPh), 35.2 (NHCH(CH$_2$)CHPh), 50.1 (CH(CH$_3$)$_2$), 96.3 (C-3a), 114.7 (C-2'), 118.1 (C-5'), 122.0 (C-6'), 135.0 (C-3), 135.6 (C-1'), 148.9-150.1 (C-4'), 150.3-151.5 (C-3'), 150.4 (C-7a), 154.1 (C-4), 160.4 (C-6).

Example 34

Synthesis of N-((1R,2S)-2-(3,4-difluorophenyl)cyclopropyl)-6-(methylthio)-1-propyl-1H-pyrazolo[3,4-d]pyrimidin-4-amine hydrochloride (34k.HCl)

4-Chloro-1-propyl-6-(methylthio)-1-propyl-1H-pyrazolo[3,4-d]pyrimidine (34j)

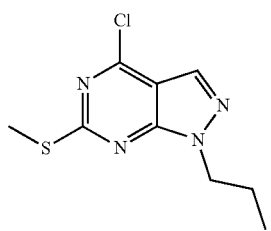

To a solution of (27i') (1.0 g, 5.0 mmol) in acetonitrile (10 mL) cooled at 5° C. on an ice bath, were added NaH (144 mg, 6.0 mmol) and 1-iodopropane (0.73 mL, 7.5 mmol). After 3 hours stirring at 50° C., acetonitrile was evaporated to dryness under vacuum and the residue was partitioned between water (50 mL) and dichloromethane (2×50 mL). The combined organic layers were dried and evaporated to dryness under vacuum. The residue was purified by silica gel column chromatography.

Yield: 78%.

Melting point: 41-43° C.

$^1$H NMR (DMSO-d$_6$) δ 0.83 (t, J=6.0 Hz, 3H, NCH$_2$CH$_2$CH$_3$), 1.88 (h, J=6.1 Hz, 2H, NCH$_2$CH$_2$CH$_3$), 2.62 (s, 3H, SCH$_3$), 4.35 (t, J=6.2 Hz, 2H, NCH$_2$CH$_2$CH$_3$), 8.35 (s, 1H, CH).

$^{13}$C NMR (DMSO-d$_6$) δ 11.0 (NCH$_2$CH$_2$CH$_3$), 13.9 (SCH$_3$), 22.2 (NCH$_2$CH$_2$CH$_3$), 48.6 (NCH$_2$CH$_2$CH$_3$), 110.0 (C-3a), 132.4 (C-3), 153.0 (C-4), 153.5 (C-7a), 168.7 (C-6).

N-((1R,2S)-2-(3,4-difluorophenyl)cyclopropyl)-6-(methylthio)-1-propyl-1H-pyrazolo[3,4-d]pyrimidin-4-amine hydrochloride (34k.HCl)

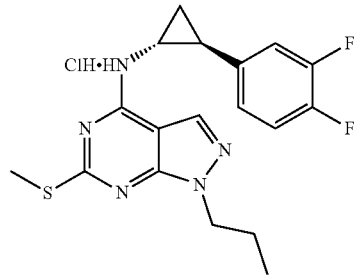

A solution of (34j) (121.0 mg, 0.5 mmol) in acetonitrile (2.5 mL) was supplemented with (1R,2S)-2-(3,4-difluorophenyl)cyclopropanamine (93.0 mg, 0.55 mmol) and triethylamine (0.13 mL) and then heated at 90° C. under reflux for 1 h. After distillation of acetonitrile and triethylamine under vacuum, the residue was purified by silica gel column chromatography. The resulting oil was dissolved in diethyl ether (10 mL) and supplemented dropwise with a saturated solution of HCl in diethyl ether. The precipitate of the title compound was collected by filtration, washed with diethyl ether and dried.

Yield: 76%.

Melting point: 155-159° C.

$^1$H NMR (CDCl$_3$) δ 0.93 (t, J=7.4 Hz, 3H, NCH$_2$CH$_2$CH$_3$), 1.51 (q, J=6.7 Hz, 1H, NHCH(CH$_2$)CHPh), 1.69 (m, 1H, NHCH(CH$_2$)CHPh), 1.94 (h, J=7.3 Hz, 2H, NCH$_2$CH$_2$CH$_3$), 2.38 (ddd, J=9.6 Hz/6.4 Hz/3.0 Hz, 1H, NHCH(CH$_2$)CHPh), 2.71 (s, 3H, SCH$_3$), 3.09 (dd, J=6.7 Hz/3.5 Hz, 1H, NHCH(CH$_2$)CHPh), 4.32 (m, 2H, NCH$_2$CH$_2$CH$_3$), 6.85 (d, J=8.3 Hz, 1H, 6'-H), 6.89 (m, 1H, 2'-H), 7.16 (m, 1H, 5'-H), 7.75 (s, 1H, 3-H), 10.57 (s, 1H, NH).

$^{13}$C NMR (CDCl$_3$) δ 11.3 (NCH$_2$CH$_2$CH$_3$), 14.0 (SCH$_3$), 17.6 (NHCH(CH$_2$)CHPh), 22.8 (NCH$_2$CH$_2$CH$_3$), 25.4 (NHCH(CH$_2$)CHPh), 35.3 (NHCH(CH$_2$)CHPh), 49.5 (NCH$_2$CH$_2$CH$_3$), 96.1 (C-3a), 114.8 (C-2'), 118.1 (C-5'), 122.0 (C-6'), 135.2 (C-3), 135.5 (C-1), 148.9-150.1 (C-4'), 150.3-151.5 (C-3'), 151.5 (C-7a), 154.2 (C-4), 160.8 (C-6).

Example 35

Synthesis of N-((1R,2S)-2-(3,4-difluorophenyl)cyclopropyl)-7-ethyl-2-(methylthio)-7H-pyrrolo[2,3-d]pyrimidin-4-amine hydrochloride (35p.HCl)

6-Amino-2-(methylthio)pyrimidin-4-ol (35l)

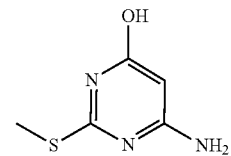

6-Amino-2-mercaptopyrimidin-4-ol (2.5 g, 17.5 mmol) was dissolved in KOH 10% (25 mL) and supplemented with methyl iodide (1.25 mL, 20.0 mmol). The reaction mixture was introduced in a sealed vessel and heated at 80° C. for 1 h. After cooling on an ice bath to 5° C., the mixture was acidified by addition of hydrochloric acid 6N and the resulting precipitate was filtered off and dried.

Yield: 95%.

Melting point: 261-264° C.

$^1$H NMR (DMSO-$d_6$) δ 2.42 (s, 3H, SCH$_3$), 4.90 (s, 1H, CH), 6.44 (s, 2H, NH$_2$), 11.47 (s, 1H, OH).

$^{13}$C NMR (DMSO-$d_6$) δ 12.6 (SCH$_3$), 81.2 (C-5), 163.6 (C-2), 164.3 (C-6).

2-(Methylthio)-7H-pyrrolo[2,3-d]pyrimidin-4-ol (35m)

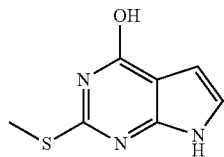

To a suspension of 35l (1.57 g, 10.0 mmol) in water (40 mL) were added sodium acetate (2.0 g, 24.5 mmol) and a 50% chloracetaldehyde aqueous solution (2 mL, 14.2 mmol). After 1 hour at 80° C., the reaction mixture was cooled on an ice bath to 5° C. and the resulting precipitate was filtered off and purified by silica gel column chromatography.

Yield: 45%.

Melting point: >300° C.

$^1$H NMR (DMSO-$d_6$) δ 2.52 (s, 3H, SCH$_3$), 6.36 (m, 1H, 5-H), 6.91 (m, 1H, 6-H), 11.75 (s, 1H, NH), 12.03 (s, 1H, OH).

$^{13}$C NMR (DMSO-$d_6$) δ 12.8 (SCH$_3$), 102.0 (C-5), 104.2 (C-4a), 119.3 (C-6), 148.3 (C-7a), 154.2 (C-2), 158.8 (C-4).

4-Chloro-2-(methylthio)-7H-pyrrolo[2,3-d]pyrimidine (35n)

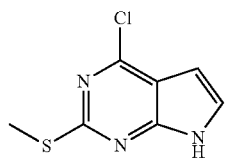

To a solution of (35m) (1.0 g, 5.5 mmol) in POCl$_3$ (10 mL) cooled at 5° C. on an ice bath was added dropwise diethylaniline (1.0 mL, 6.2 mmol). After 2 hours stirring at 80° C., the mixture was poured on crushed ice and the resulting precipitate was filtered off and purified by silica gel column chromatography.

Yield: 33%.

Melting point: 206-208° C.

$^1$H NMR (DMSO-$d_6$) δ 2.56 (s, 3H, SCH$_3$), 6.52 (s, 1H, 5-H), 7.52 (s, 1H, 6-H), 12.39 (s, 1H, NH).

$^{13}$C NMR (DMSO-$d_6$) δ 13.8 (SCH$_3$), 99.0 (C-5), 113.2 (C-4a), 126.9 (C-6), 150.4-152.7 (C-4/C-7a), 162.7 (C-2).

N-((1R,2S)-2-(3,4-difluorophenyl)cyclopropyl)-2-(methylthio)-7H-pyrrolo[2,3-d]pyrimidin-4-amine (35o')

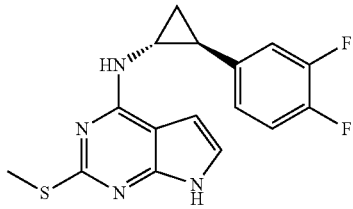 [SMILES: CSc1nc(N[C@@H]2C[C@H]2c2ccc(F)c(F)c2)c2cc[nH]c2n1]

A solution of (35n) (200.0 mg, 1.0 mmol) in acetonitrile (5 mL) was supplemented with (1R,2S)-2-(3,4-difluorophenyl)cyclopropanamine (340.0 mg, 2.0 mmol) and triethylamine (0.30 mL) and then heated at 90° C. under reflux for 1 h. After distillation of acetonitrile and triethylamine under vacuum, the residue was purified by silica gel column chromatography.

Yield: 15%.

Melting point: 208-211° C.

$^1$H NMR (DMSO-$d_6$) δ 1.34 (m, 2H, NHCH(CH$_2$)CHPh), 2.03 (s, 1H, NHCH(CH$_2$)CHPh), 2.30 (s, 3H, SCH$_3$), 3.03 (s, 1H, NHCH(CH$_2$)CHPh), 6.40 (s, 1H, 5-H), 6.93 (s, 1H, 2'-H), 7.08 (s, 1H, 6'-H), 7.33 (m, 2H, 6-H/5'-H), 7.84 (s, 1H, NHCH(CH$_2$)CHPh), 11.40 (s, 1H, NH).

$^{13}$C NMR (CDCl$_3$) δ 13.3 (SCH$_3$), 99.5 (C-5), 112.1 (C-4a), 117.0 (C-5'), 119.9 (C-2'), 122.9 (C-6'), 139.6 (C-1'), 147.0-148.3 (C-4'), 148.6-150.0 (C-3'), 162.3 (C-2).

N-((1R,2S)-2-(3,4-difluorophenyl)cyclopropyl)-7-ethyl-2-(methylthio)-7H-pyrrolo[2,3-d]pyrimidin-4-amine hydrochloride (35p.HCl)

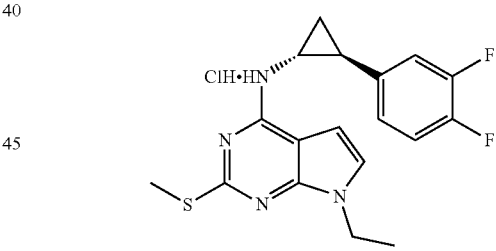

To a solution of (35o') (166.0 mg, 0.5 mmol) in acetonitrile (10 mL) cooled at 5° C. on an ice bath, were added NaH (15 mg, 0.6 mmol) and iodoethane (0.060 mL, 0.75 mmol). After 1 hour stirring at 50° C., acetonitrile was evaporated to dryness under vacuum and the residue was partitioned between water (50 mL) and dichloromethane (2×50 mL). The combined organic layers were dried and evaporated to dryness under vacuum. The residue was purified by silica gel column chromatography. The resulting oil was dissolved in diethyl ether (10 mL) and supplemented dropwise with a saturated solution of HCl in diethyl ether. The precipitate of the title compound was collected by filtration, washed with diethyl ether and dried.

Yield: 74%.

Melting point: 189-194° C. $^1$H NMR (CDCl$_3$) δ 1.46 (t, J=7.3 Hz, 4H, NHCH(CH$_2$)CHPh/NCH$_2$CH$_3$), 1.66 (m, 1H, NHCH(CH$_2$)CHPh), 2.30 (m, 1H, NHCH(CH$_2$)CHPh), 2.70

(s, 3H, SCH$_3$), 3.09 (m, 1H, NHCH(CH$_2$)CHPh), 4.22 (q, J=7.3 Hz, 2H, NCH$_2$CH$_3$), 6.35 (d, J=3.4 Hz, 1H, 5-H), 6.81 (d, J=8.3 Hz, 1H, 6'-H), 6.87 (m, 1H, 2'-H), 6.90 (d, J=3.6 Hz, 1H, 6-H), 7.13 (q, J=8.5 Hz, 1H, 5'-H), 9.99 (s, 1H, NH).

$^{13}$C NMR (CDCl$_3$) δ 14.0 (SCH$_3$), 15.5 (NCH$_2$CH$_3$), 17.9 (NHCH(CH$_2$)CHPh), 25.7 (NHCH(CH$_2$)CHPh), 35.2 (NHCH(CH$_2$)CHPh), 40.3 (NCH$_2$CH$_3$), 98.1 (C-4a), 103.4 (C-5), 114.8 (C-2'), 117.8 (C-5'), 122.0 (C-6'), 125.4 (C-6), 136.4 (C-1'), 148.3 (7a), 149.1-151.1 (C-3'/C-4'), 153.4 (C-4), 155.9 (C-2).

2. Examples of Pyrimidines Derivatives for Use in Prevention and Treatment of Bacterial Infection

Example 1

Antibacterial Effects of Molecules 2329, 2348, 2412, 2452, and 2461 on *S. epidermidis*: Determination of Minimal Inhibitory Concentration (MIC)

Molecules 2329, 2348, 2412, 2452, and 2461 correspond respectively to the following formulations:

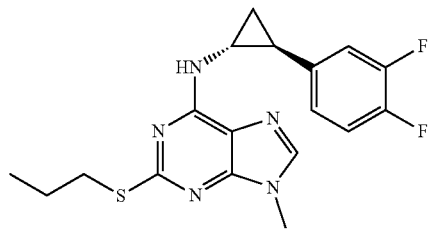

2329 (1c)

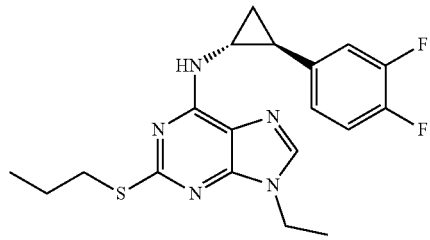

2348 (3c)

2329 is N-((1R,2S)-2-(3,4-difluorophenyl)cyclopropyl)-9-methyl-2-(propylthio)-9H-purin-6-amine (also called 1c above)

2348 is N-((1R,2S)-2-(3,4-difluorophenyl)cyclopropyl)-9-ethyl-2-(propylthio)-9H-purin-6-amine (also called 3c above)

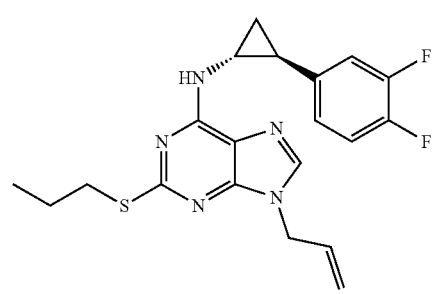

2412 (15c)

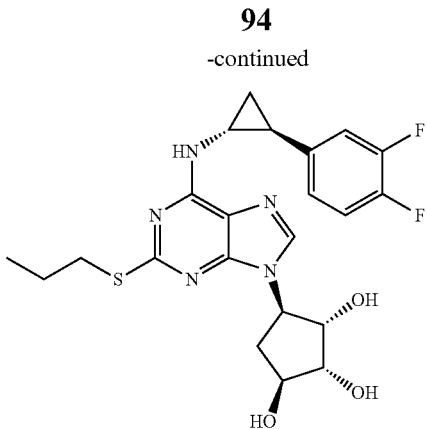

2461 (19d)

2412 is 9-allyl-N-((1R,2S)-2-(3,4-difluorophenyl)cyclopropyl)-2-(propylthio)-9H-purin-6-amine (also called 15c)

2461 is (1S,2R,3S,4R)-4-(6-(((1R,2S)-2-(3,4-difluorophenyl)cyclopropyl)amino)-2-(propylthio)-9H-purin-9-yl)cyclopentane-1,2,3-triol (also called 19d).

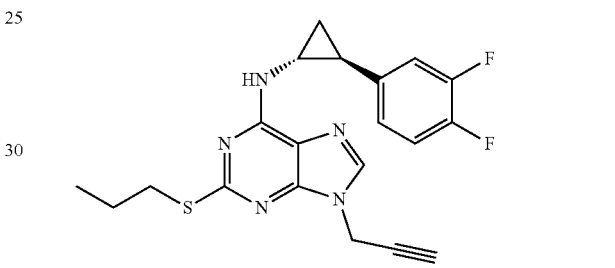

2452 (17c)

2452 is N-((1R,2S)-2-(3,4-difluorophenyl)cyclopropyl)-9-(prop-2-yn-1-yl)-2-(propylthio)-9H-purin-6-amine (also called 17c).

The Minimal Inhibitory Concentration (MIC) of molecules 2329, 2348, 2412, 2452 and 2461 was determined on *Staphylococcus epidermidis* (ATCC 35984, also known as RP62A) according to EUCAST (European Committee on Antimicrobial Susceptibility Testing) recommendations.

Briefly, a single colony grown on a Tryptic Soy Agar (TSA) plate was resuspended and cultured in Tryptic Soy Broth (TSB) overnight (O/N) in aerobic conditions (37° C. with 220 rpm shaking), next day a 1:50 inoculum in Mueller-Hinton broth (MHB) was incubated in aerobic conditions for 3 hr and an inoculum of 1:100 dilution, corresponding to 3×10$^5$ CFU/ml, was incubated in presence or absence of different concentrations of the molecules in 1% DMSO (vehicle). After O/N growth the OD of each culture was measured at 600 nm in a spectrophotometer (OD$_{600}$). The MIC represents the concentration at which there is no visible growth of bacteria, i.e. ΔOD at 600 nm equal to zero (blank is the medium alone).

The MIC for molecules 2329, 2348 and 2461 against *S. epidermidis* (ATCC 35984) is equal to 20 μM, while it is above 50 μM for molecules 2412 and 2452.

Example 2

Antibacterial Effects of Molecules 2329, 2348, 2412, 2452, and 2461 on *S. aureus*: Determination of Minimal Inhibitory Concentration (MIC)

Further experiments are conducted using different strains of *S. aureus*, as clinically relevant Gram-positive bacterial strains: S. aureus ATCC 25904, methicillin-resistant S. aureus (MRSA) ATCC BAA-1556, Glycopeptide intermediate-resistant (GISA) S. aureus Mu-50 (ATCC 700695) in order to determine the Minimal Inhibitory Concentration (MIC) which is the minimal concentration required to prevent bacterial growth. The bioluminescent strain S. aureus Xen29 (ATCC 12600) was also used. This strain is derived from the parental strain S. aureus ATCC 12600, a pleural fluid isolate, which is also designated as NCTC8532. S. aureus Xen29 possesses a stable copy of the modified Photorhabdus luminescens luxABCDE operon at a single integration site on the bacterial chromosome.

A single colony selected from the different strains of S. aureus is resuspended and cultured in brain heart infusion (BHI) broth overnight (O/N) in aerobic conditions (37° C. with 220 rpm shaking), next day a 1:100 inoculum in Mueller-Hinton broth (MHB) is incubated in aerobic conditions for 3 hr (=OD0.08-0.1) and an inoculum of 1:300 dilution, corresponding to $3 \times 10^5$ CFU/ml, is incubated in presence or absence of different concentrations of the tested molecules in 1% DMSO. After O/N growth the OD of each culture was measured at 600 nm ($OD_{600}$) in a spectrophotometer (Victor 3-Perkin Elmer). The MIC represents the concentration at which there is no visible growth of bacteria, i.e. ΔOD at 600 nm equal to zero (blank is the medium alone). MIC for 2329, 2348, 2412, 2452, and 2461 against S. aureus ATCC 25904 and Xen29 (ATCC 12600) are equal to 20-25 μM. Molecule 2329 is the most potent against methicillin-resistant S. aureus (MRSA) ATCC BAA-1556, with a MIC equal to 20 μM, while molecules 2348 and 2461 had a MIC of 25 μM, and the MIC for molecules 2412 and 2452 is comprised between 2-25 and 50 μM. The MIC of molecule 2329 against Glycopeptide intermediate-resistant (GISA) S. aureus Mu-50 (ATCC 700695) is in between 25 and 30 μM, while it is above 50 μM for molecules 2348, 2412, and 2452.

Example 3

Antibacterial Effects of Molecules 2329, 2348, 2412, 2452, And 2461 on E. faecalis: Determination of Minimal Inhibitory Concentration (MIC)

Further experiments were conducted using the clinically relevant Gram-positive bacterial strain of vancomycin-resistant (VRE) E. faecalis ATCC BAA-2365, in order to determine the Minimal Inhibitory Concentration (MIC) which is the minimal concentration required to prevent bacterial growth.

A single colony selected from E. faecalis VRE is resuspended and cultured in the brain heart infusion (BHI) broth overnight (O/N) in aerobic conditions (37° C. with 220 rpm shaking), next day a 1:100 inoculum in Mueller-Hinton broth (MHB) is incubated in aerobic conditions for 3 hr (OD=0.08-0.1) and an inoculum of 1:300 dilution, corresponding to $3 \times 10^5$ CFU/ml, is incubated in presence or absence of different concentrations of the tested molecules in 1% DMSO. After O/N growth the OD of each culture is measured at 600 nm ($OD_{600}$) in a spectrophotometer (Victor 3-Perkin Elmer). The MIC represents the concentration at which there is no visible growth of bacteria, i.e. ΔOD at 600 nm equal to zero (blank is the medium alone). MIC for molecules 2329 and 2461 against E. faecalis vancomycin-resistant (VRE) ATCC BAA-2365 was equal to 25 μM, while it is above 50 μM for molecules 2348, 2412 and 2452.

The results of all experiments are illustrated in Table 1.

TABLE 1

MIC: minimal inhibitory concentration of pyrimidine derivatives determined in Mueller-Hinton broth (MHB) against MRSA: methicillin-resistant S. aureus; GISA: Glycopeptide intermediate-resistant S. aureus; VRE: vancomycin-resistant E. faecalis; MIC is expressed in μM. nd: not determined.

| | Strains | | | | | |
|---|---|---|---|---|---|---|
| Mole- | S. aureus | | | | S. epidermidis | E. faecalis |
| cules | ATCC25904 | Xen29 | MRSA | GISA | RP62 | VRE |
| 2329 (1c) | 20-25 μM | 20-25 μM | 20 μM | 25-30 μM | 20 μM | 25 μM |
| 2348 (3c) | 20-25 μM | 20-25 μM | 25 μM | >50 μM | 20 μM | >50 μM |
| 2412 (15c) | 20-25 μM | 20-25 μM | 25-50 μM | >50 μM | >50 μM | >50 μM |
| 2452 (17c) | 20-25 μM | 20-25 μM | 25-50 μM | >50 μM | >50 μM | >50 μM |
| 2461 (19d) | 20-25 μM | 20-25 μM | 25 μM | nd | 20 μM | 25 μM |

Example 4

Use of Molecules 2329, 2348 as Inhibitors of S. aureus Biofilm Formation

Bioluminescent S. aureus (Xen29, Perkin Elmer-(ATCC 12600)) is grown overnight in TSB medium, before being diluted 100 fold in fresh TSB, and incubated aerobically at 37° C. until bacteria culture reached an $OD_{600}$ of 0.6 (corresponding to approximately $1-3 \times 10^8$ CFU/ml). Bacteria cultures are then diluted to $1 \times 10^4$ CFU/ml in fresh TSB. 600 μl aliquots of diluted bacteria suspensions are distributed in each well of a 48-well plate. Bacteria are allowed to adhere for 3 hours under static conditions at 37° C. After removing media, wells are rinsed 2 times with PBS to eliminate planktonic bacteria and re-filled with TSB supplemented with 0.5% glucose Molecules 2329 or 2348 are then added at 10 μM final concentration. Biofilm formation is imaged every 60 min, for 13 hours, using a IVIS camera system (Xenogen Corp.) Total photon emission from each well is then quantified using the Living Image software package (Xenogen Corp.).

In FIG. 1, biofilm formation is represented as the intensity of photon signal per surface unit. Molecules 2329 and 2348 fully prevented biofilm formation when used at a dose of 10 μM.

Example 5

Use of Molecules 2412 and 2452 to Delay S. aureus Biofilm Formation

Bioluminescent S. aureus (Xen29, Perkin Elmer-(ATCC 12600)) is grown overnight in TSB medium, before being diluted 100 fold in fresh TSB, and incubated aerobically at 37° C. until bacteria culture reached an $OD_{600}$ of 0.6 (corresponding to approximately $1-3 \times 10^8$ CFU/ml). Bacteria cultures are then diluted to $1 \times 10^4$ CFU/ml in fresh TSB.

600 μl aliquots of diluted bacteria suspensions were distributed in each well of a 48-well plate. Bacteria are allowed to adhere for 3 hours under static conditions at 37° C. After removing media, wells are rinsed 2 times with PBS to eliminate planktonic bacteria and re-filled with TSB supplemented with 0.5% glucose Molecules 2412 or 2452 are then added at 10 μM final concentration. Biofilm formation is imaged every 60 min, for 13 hours, using a IVIS camera system (Xenogen Corp.) Total photon emission from each well is then quantified using the Living Image software package (Xenogen Corp.).

In FIG. 1, biofilm formation is represented as the intensity of photon signal per surface unit. Molecules 2412 and 2452 are able to delay biofilm formation when used at a dose of 10 μM as compared to vehicle control (DMSO 1%).

Example 6

Effect of Molecule 2329 on *S. epidermidis* (ATCC 35984)24h-Mature Biofilm

In another experiment we let adhere $0.5 \times 10^8$ CFU/ml *S. epidermidis* cells for 4 hr and let the biofilm form for additional 24 hr in presence of 0.25% glucose, at this point we treated the biofilm with different concentrations of molecule 2329 for 24 h in TSB with 0.25% glucose and determined the biofilm biomass using the crystal violet staining.

For biofilm analysis, we first washed the biofilm 3 times with NaCl 0.9% to eliminate all planktonic bacteria, before incubation with a staining Crystal Violet 1% solution in distilled $H_2O$ ($dH_2O$).

Figure 2:
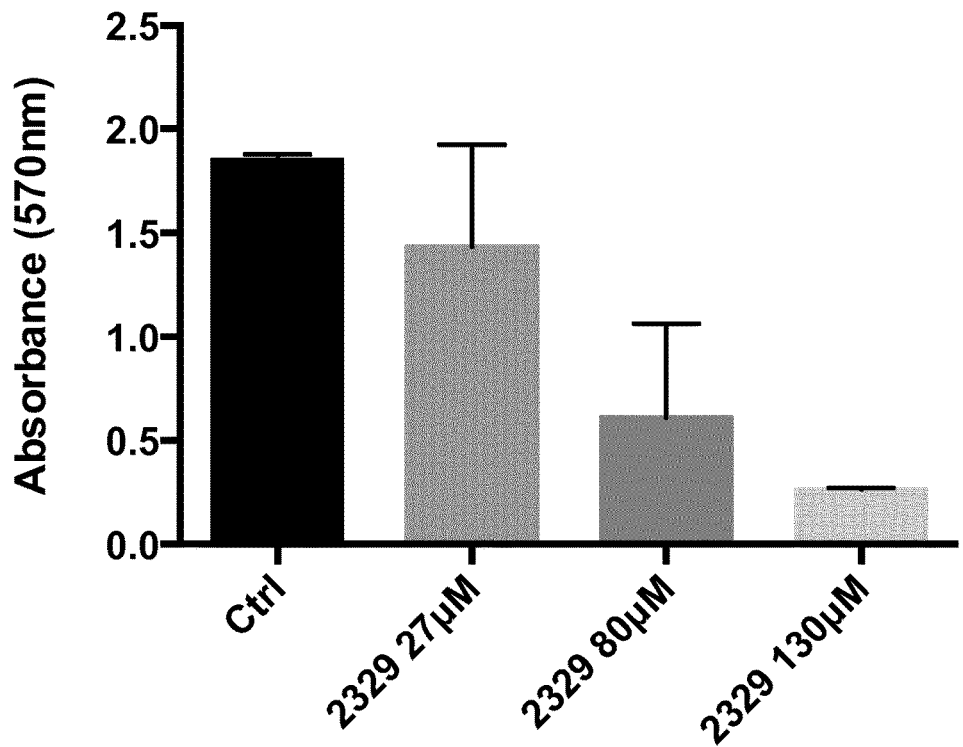
FIG. 2 illustrates the effect of a 24 h treatment with different concentrations of the molecule 2329 (1c) on a mature biofilm (step 3: 24-hour biofilm) of *S. epidermidis*. *S. epidermidis* biofilm biomass, stained with crystal violet is proportional to absorbance of the dye at 570 nm.

Wells are washed 3 times with $dH_2O$ to eliminate unbound crystal violet. 400 μl Acetic Acid 10% is then added and incubated at RT for 10 min. Absorbance is measured in triplicate at 570 nm, reflecting total biomass of the biofilm. FIG. 2 shows that 2329 80 μM could reduce the *S. epidermidis* 24-hour mature biofilm.

Example 7

Antibacterial Effects of Pyrazolopyrimidine Molecules 2539, 2544, 2666 2676, 2693, 2783, 2784 and 2782 and of Purine Molecules 2498, 2511, 2525, 2527, 2833 and 2840 on *Staphylococcus epidermidis* (*S. epidermidis*—(ATCC 35984)) Also Called MRSE: Determination of Minimal Inhibitory Concentration (MIC)

Pyrazolopyrimidine molecules 2539, 2544, 2666, 2676, 2693, 2783, 2784 and 2782 correspond to the following formulations:

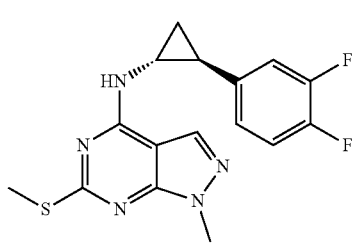
2539 (27k)

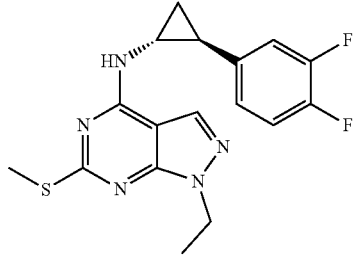
2544 (30k)

2539 is N-((1R,2S)-2-(3,4-difluorophenyl)cyclopropyl)-1-methyl-6-(methylthio)-1H-pyrazolo[3,4-d]pyrimidin-4-amine (also called 27k above);

2544 is N-((1R,2S)-2-(3,4-difluorophenyl)cyclopropyl)-1-ethyl-6-(methylthio)-1H-pyrazolo[3,4-d]pyrimidin-4-amine (also called 30k above).

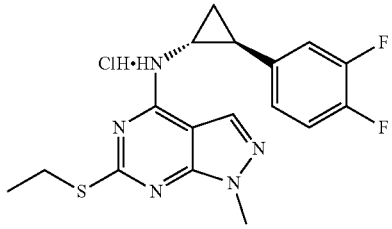
2666 (28x.HCl)

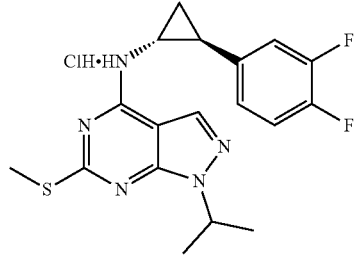
2676 (33k.HCl)

2666 is N-((1R,2S)-2-(3,4-difluorophenyl)cyclopropyl)-6-(ethylthio)-1-methyl-1H-pyrazolo[3,4-d]pyrimidin-4-amine hydrochloride (also called 28x.HCl above);

2676 is N-((1R,2S)-2-(3,4-difluorophenyl)cyclopropyl)-1-isopropyl-6-(methylthio)-1H-pyrazolo[3,4-d]pyrimidin-4-amine hydrochloride (also called 33k.HCl above).

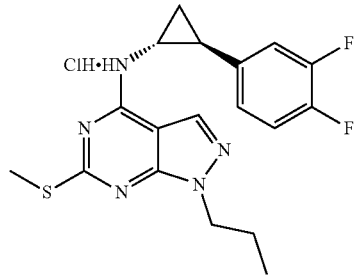
2693 (34k.HCl)

2693 is N-((1R,2S)-2-(3,4-difluorophenyl)cyclopropyl)-6-(methylthio)-1-propyl-1H-pyrazolo[3,4-d]pyrimidin-4-amine hydrochloride (also called 34k.HCl above).

2783 (31x.HCl)

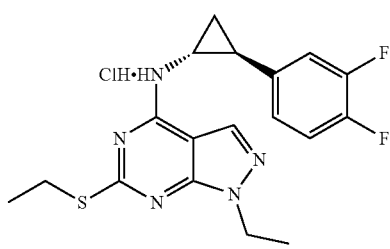

2782 (29x.HCl)

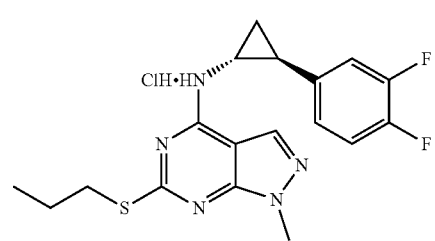

2783 is N-((1R,2S)-2-(3,4-difluorophenyl)cyclopropyl)-6-(ethylthio)-1-ethyl-1H-pyrazolo[3,4-d]pyrimidin-4-amine hydrochloride (also called 31x.HCl above);

2782 is N-((1R,2S)-2-(3,4-difluorophenyl)cyclopropyl)-6-(propylthio)-1-methyl-1H-pyrazolo[3,4-d]pyrimidin-4-amine hydrochloride (also called 29x.HCl above).

2784 (32x.HCl)

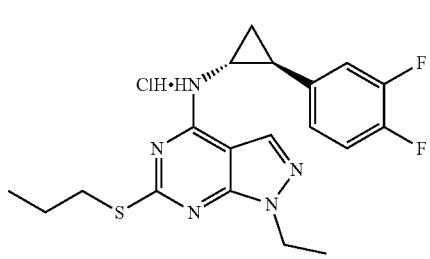

2784 is N-((1R,2S)-2-(3,4-difluorophenyl)cyclopropyl)-6-(propylthio)-1-ethyl-1H-pyrazolo[3,4-d]pyrimidin-4-amine hydrochloride (also called 32x.HCl above).

Purine molecules 2498, 2511, 2525, 2527, 2833 and 2840 correspond to the following formulations:

2498 (22c)

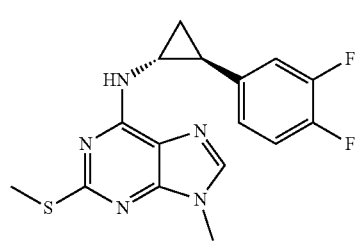

2511 (24c)

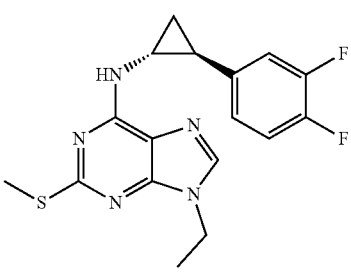

2498 is N-((1R,2S)-2-(3,4-difluorophenyl)cyclopropyl)-9-methyl-2-(methylthio)-9H-purin-6-amine (also called 22c above);

2511 is N-((1R,2S)-2-(3,4-difluorophenyl)cyclopropyl)-9-ethyl-2-(methylthio)-9H-purin-6-amine (also called 24c above).

2525 (20c)

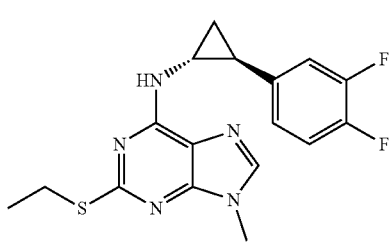

2527 (21c)

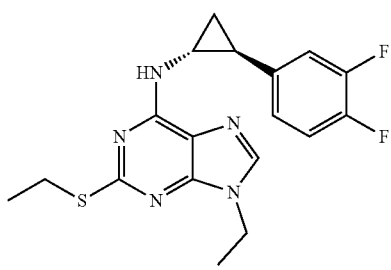

2525 is N-((1R,2S)-2-(3,4-difluorophenyl)cyclopropyl)-2-(ethylthio)-9-methyl-9H-purin-6-amine (also called 20c above);

2527 is N-((1R,2S)-2-(3,4-difluorophenyl)cyclopropyl)-9-ethyl-2-(ethylthio)-9H-purin-6-amine (also called 21c above).

2833 (25c)

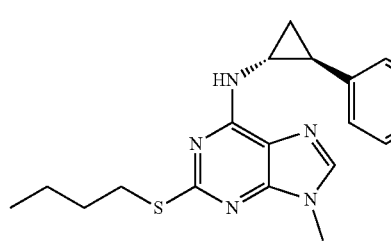

2840 (26c)

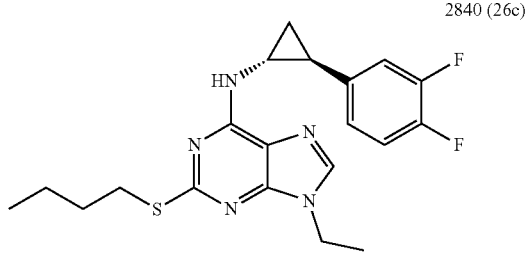

2833 is 2-(butylthio)-N-((1R,2S)-2-(3,4-difluorophenyl)cyclopropyl)-9-methyl-9H-purin-6-amine (also called 25c above);

2840 is 2-(butylthio)-N-((1R,2S)-2-(3,4-difluorophenyl)cyclopropyl)-9-ethyl-9H-purin-6-amine (also called 26c above).

The Minimal Inhibitory Concentration (MIC) of pyrazolopyrimidine molecules 2539, 2544, 2666, 2676, 2693, 2783, 2784 and 2782 and of purine molecules 2498, 2511, 2525, 2527, 2833, and 2840 was determined on *S. epidermidis* (ATCC 35984, also known as RP62A or MRSE) according to EUCAST (European Committee on Antimicrobial Susceptibility Testing) recommendations.

Briefly, a single colony grown on an agar plate was resuspended and cultured in Triptic Soy Broth (TSB) medium overnight (O/N) in aerobic conditions (37° C. with 220 rpm shaking), next day a 1:50 inoculum in Mueller-Hinton broth (MHB) was incubated in aerobic conditions for 3 hr (OD=0.08-0.1) and an inoculum of 1:300 dilution, corresponding to $3 \times 10^5$ CFU/ml, was incubated in presence or absence of different concentrations of each of the molecules in 1% DMSO (vehicle). After O/N growth the OD of each culture was measured at 600 nm (600) in a spectrophotometer (Victor 3-Perkin Elmer). The MIC represents the concentration at which there is no visible growth of bacteria, i.e. ΔOD at 600 nm equal to zero (where ΔOD is the difference between the OD with the molecule and the OD of the blank, the medium alone).

The pyrazolopyrimidine molecules 2539, 2544, 2666 and 2676 and purine molecules 2498, 2511, 2525, 2527 and 2833 were able to inhibit MRSE growth in MHB medium. MIC values are reported in Table 2. The pyrazolopyrimidine molecules 2693, 2782, 2783 and 2784, and the purine molecules 2511 and 2840 were inactive against *S. epidermidis* up to 100 μM.

Example 8

Antibacterial Effects of Pyrazolopyrimidine Molecules 2539, 2544, 2666 2676, 2693, 2783, 2784 and 2782 and of Purine Molecules 2498, 2511, 2525, 2527, 2833 and 2840 on *Staphylococcus aureus* (*S. aureus*): Determination of Minimal Inhibitory Concentration (MIC)

Further experiments are conducted using different strains of *S. aureus*, as clinically relevant Gram-positive bacterial strains: methicillin-resistant *S. aureus* (MRSA) ATCC BAA-1556 and *S. aureus* Xen29 (Perkin Elmer ATCC 12600).

To determine the MIC of the above mentioned molecules in MRSA or in Xen29, a single colony of MRSA or Xen29 is resuspended and cultured in brain heart infusion (BHI) broth overnight (O/N) in aerobic conditions (37° C. with 220 rpm shaking), next day a 1:100 inoculum in Mueller-Hinton broth (MHB) is incubated in aerobic conditions for 3 hr (OD=0.08-0.1) and an inoculum of 1:300 dilution, corresponding to $3 \times 10^5$ CFU/ml, is incubated in presence or absence of different concentrations of the tested molecules in 1% DMSO. After O/N growth the OD of each culture was measured at 600 nm ($OD_{600}$) in a spectrophotometer (Victor 3-Perkin Elmer). The MIC represents the concentration at which there is no visible growth of bacteria, i.e. ΔOD at 600 nm equal to zero (blank is the medium alone).

The pyrazolopyrimidine molecules 2539, 2544, 2666, 2676, 2693, 2783, 2782, 2784 and the purine molecules 2498, 2511, 2525, 2527, 2833 and 2840 were active against MRSA (ATCC BAA-1556), while molecules 2539, 2544, 2666, 2498, 2511, 2525, and 2527 were able to inhibit Xen29 (ATCC 12600) growth. MIC values of these molecules against these *S. aureus* strains are reported in Table 2.

TABLE 2

MIC values of pyrimidine derivatives, expressed in μM as determined in MHB medium against MRSE, MRSA and Xen29 Gram-positive strains. (nd: not determined). All molecules were tested up to a concentration of 100 μM.

| Molecule | $X^1$ | $X^2$ | Y | $R^1$ | $R^2$ | MRSE | MRSA | Xen29 |
|---|---|---|---|---|---|---|---|---|
| 2539 | N | C | S | $CH_3$ | $CH_3$ | 50 | 25 | 30 |
| 2544 | N | C | S | $CH_3$ | $CH_2CH_3$ | 80 | 50 | 50 |
| 2693 | N | C | S | $CH_3$ | $CH_2CH_2CH_3$ | >100 | 20 | >100 |
| 2676 | N | C | S | $CH_3$ | $CH(CH_3)_2$ | 50 | 20 | >100 |
| 2666 | N | C | S | $CH_2CH_3$ | $CH_3$ | 50 | 20 | 20 |
| 2783 | N | C | S | $CH_2CH_3$ | $CH_2CH_3$ | >100 | 25 | nd |
| 2782 | N | C | S | $CH_2CH_2CH_3$ | $CH_3$ | >100 | 25 | nd |
| 2784 | N | C | S | $CH_2CH_2CH_3$ | $CH_2CH_3$ | >100 | 50 | nd |
| 2498 | C | N | S | $CH_3$ | $CH_3$ | 60 | 30 | 30 |
| 2511 | C | N | S | $CH_3$ | $CH_2CH_3$ | >100 | 30 | 30 |
| 2525 | C | N | S | $CH_2CH_3$ | $CH_3$ | 40 | 25 | 30 |
| 2527 | C | N | S | $CH_2CH_3$ | $CH_2CH_3$ | 25 | 25 | 30 |
| 2833 | C | N | S | $CH_2CH_2CH_2CH_3$ | $CH_3$ | 30 | 50 | nd |
| 2840 | C | N | S | $CH_2CH_2CH_2CH_3$ | $CH_2CH_3$ | >100 | 50 | nd |

Example 9

Use of the Pyrazolopyrimidine Molecule 2666 and the Purine Molecule 2511 as Inhibitors of *Staphylococcus aureus* (Xen29-ATCC 12600) Biofilm Formation Bioluminescent *S. aureus* was grown O/N in TSB medium, before being diluted 100 fold in fresh TSB, and incubated aerobically at 37° C. until bacteria culture reached an OD600 of 0.6 (corresponding to approximately 1-3×10$^8$ CFU/ml). Bacteria cultures were then diluted to 1×10$^4$ CFU/ml in fresh TSB and aliquots of 600 µl were distributed in each well of a 48-well plate. Bacteria were allowed to adhere for 3 hours under static conditions at 37° C. After removing media, wells were rinsed 2 times with PBS to eliminate planktonic bacteria and re-filled with TSB supplemented with 0.5% glucose. Molecules 2666 and 2511 were then added at 20 µM final concentration. Biofilm formation is imaged every 60 min, for 13 hours, using a IVIS camera system (Xenogen Corp.) Total photon emission from each well (photon/second:p/s) is then quantified using the Living Image software package (Xenogen Corp.).

Figure 3:
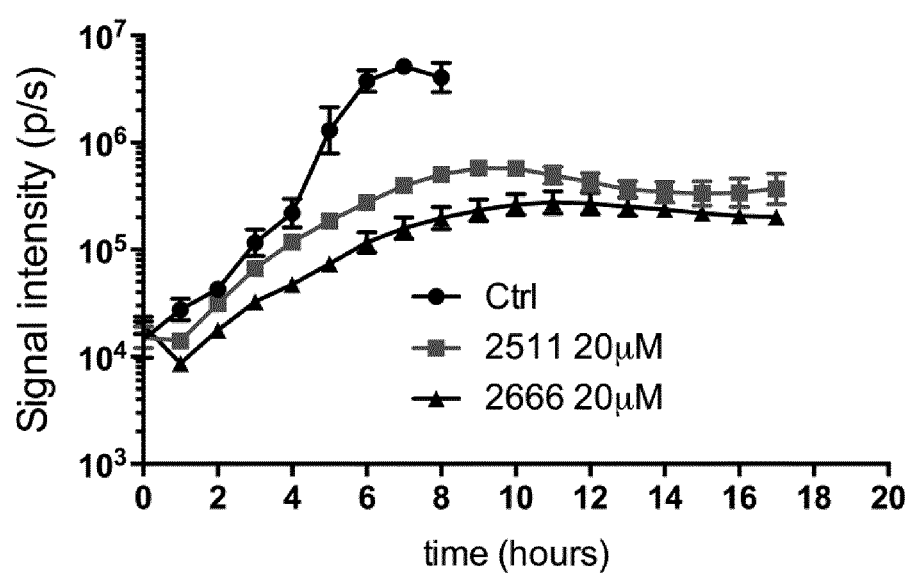
FIG. 3 illustrates kinetics of Inhibition of *Staphylococcus aureus* (Xen29-ATCC 12600) biofilm formation (step 2) in medium containing the pyrazolo molecule 2666 (28x.HCl) and the purine molecule 2511 (24c) at a concentration of 20 µM compared to medium containing the vehicle alone as control (Ctrl).

FIG. 3 shows the kinetics of inhibition of *Staphylococcus aureus* (Xen29-ATCC 12600) biofilm formation (step 2) by the pyrazolopyrimidine molecule 2666 and the purine molecule 2511 at 20 µM compared to the biofilm formation in the presence of the vehicle control (Ctrl).

The biofilm formation is proportional to the intensity of photon signal per second (radiance) irradiated from each well. Molecules 2666 and 2511 inhibited biofilm growth when used at 20 µM.

Example 10

Use of the Pyrazolopyrimidine Molecule 2666 as Bactericidal Agent Against MRSA and the Purine Molecules 2329 and 2833 as Bactericidal Agents Respectively Against MRSA and MRSE We have determined the Minimal Bactericidal Concentration (MBC) of the pyrazolopyrimidine molecule 2666 for the MRSA strain and the MBC of the purine molecules 2329 and 2833 for MRSA and the MRSE strain respectively.

To determine the MBC, bacteria were grown as per MIC determination in presence of the pyrazolopyrimidine molecule 2666 for MRSA or in presence of the purine molecule 2833 for MRSE or 2329 for MRSA. At 24 hours bacteria were plated on TSB agar plates by the broth microdilution method, and colonies formed on the plates were counted next day.

The MBC represents the lowest concentration at which 99.9% bacteria of the initial inoculum are killed over 24 hours.

The MBC of molecule 2666 and 2329 for MRSA was 40 µM, while the MBC of 2833 for MRSE was 50 µM, which corresponds to only around 2 times their MIC.

3. Comparison of Pyrimidine Derivatives According to the Present Invention with Purines Disclosed in WO2009/034386.

We have synthesized 2 molecules (25, 81) from WO2009/034386 examples. In this patent application, the ability of these 2 molecules to inhibit the MurI enzyme from *E. faecalis*, *E. faecium* and *S. aureus* is described. The 2 molecules were able to inhibit the enzymatic activity of MurI isozymes from *E. faecalis* and *E. faecium* with half maximal inhibitory concentrations (IC$_{50}$) equal to 2 and 5 µM, respectively (Table 9 of WO2009/034386). In contrast, IC$_{50}$>400 µM is reported against *S. aureus* MurI isozyme for the 2 molecules, indicating a failure to inhibit the MurI enzyme from this bacterial strain. WO2009/034386 does not report any other testing demonstrating the antibacterial efficacy of these purine molecules.

We found no antibacterial activity of these molecules against the two *S. aureus* strains tested, methicillin resistant strains (MRSA, ATCC BAA-1556) and Xen29 (Perkin Elmer-ATCC 12600) nor against *S. epidermidis* (MRSE ATCC 35984).

The molecules were synthesized according to a similar chemical pathway as described in the present invention, with the exception that the nucleophilic substitution of the chlorine atom on Xb is carried out by another amine.

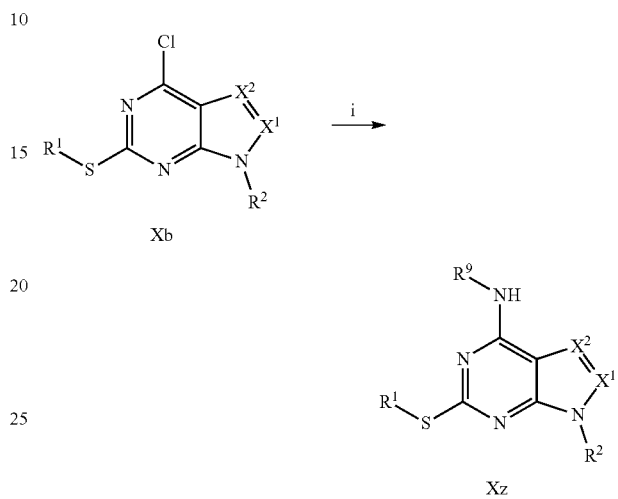

When R$^1$=CH$_3$, the corresponding alkoxy-substituted compounds Xz" wherein Y=O was provided starting from Xz according to scheme 6 below:

Scheme 6

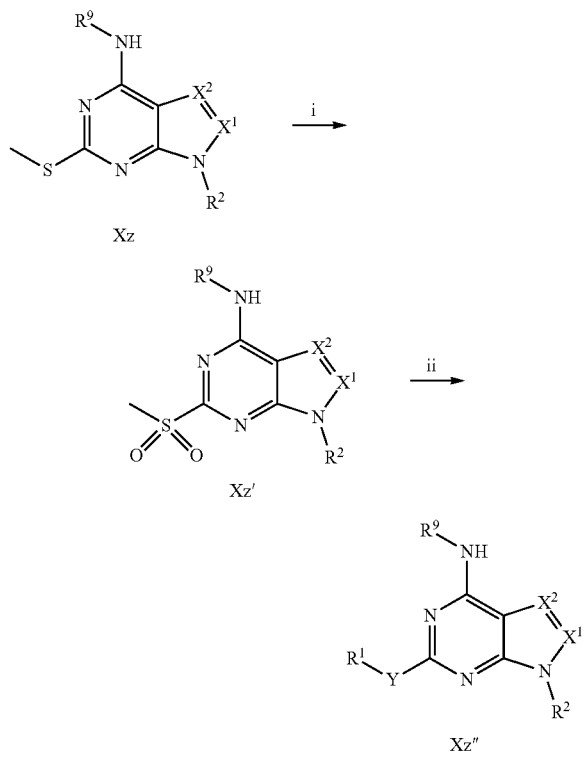

Example 1

2-(butylthio)-9-(3-chloro-2,6-difluorobenzyl)-9H-purin-6-amine (36z)

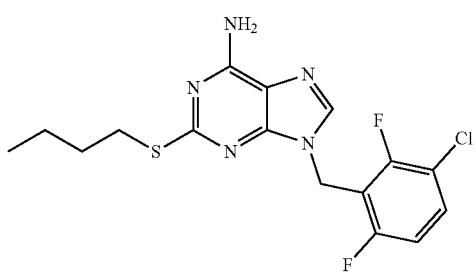 [SMILES: CCCCSc1nc(N)c2ncn(Cc3c(F)ccc(Cl)c3F)c2n1]

36z (molecule 25 in WO2009/034386) was synthesized according to a similar chemical pathway as described in the present invention, with the exception that the nucleophilic substitution of the chlorine atom on Xb is carried out with another amine $R^9$—$NH_2$, ammonia in the present example.

2-(Butylthio)-6-chloro-$N^4$-(3-chloro-2,6-difluorobenzyl)pyrimidine-4,5-diamine (36a)

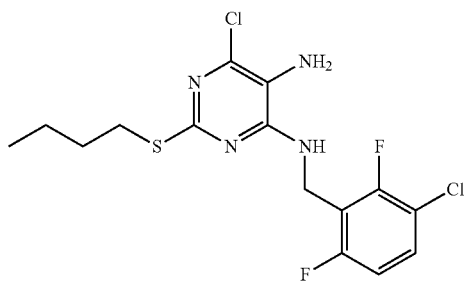 [SMILES: CCCCSc1nc(Cl)c(N)c(NCc2c(F)ccc(Cl)c2F)n1]

2-(Butylthio)-4,6-dichloropyrimidin-5-amine (25h) (0.5 g, 2.0 mmol) was dissolved in methanol (10 mL) and supplemented with 3-chloro-2,6-difluorobenzylamine (0.78 mL, 6.0 mmol). The reaction mixture was introduced in a sealed vessel and heated at 130° C. for 2 h. After concentration of the reaction mixture to dryness under vacuum, the residue was purified by silica gel column chromatography.

Yield: 77%.

Melting point: 148-150° C.

$^1$H NMR (DMSO-$d_6$) δ 0.88 (t, J=7.3 Hz, 3H, SCH$_2$CH$_2$CH$_2$CH$_3$), 1.37 (h, J=7.3 Hz, 2H, SCH$_2$CH$_2$CH$_2$CH$_3$), 1.58 (p, J=7.3 Hz, 2H, SCH$_2$CH$_2$CH$_2$CH$_3$), 2.97 (t, J=7.2 Hz, 2H, SCH$_2$CH$_2$CH$_2$CH$_3$), 4.65 (d, J=4.5 Hz, 2H, NHCH$_2$), 4.83 (s, 2H, NH$_2$), 7.20 (t, J=8.9 Hz, 1H, 5'-H), 7.34 (s, 1H, NH), 7.62 (q, J=8.6 Hz, 1H, 4'-H).

$^{13}$C NMR (DMSO-$d_6$) δ 13.5 (SCH$_2$CH$_2$CH$_2$CH$_3$), 21.4 (SCH$_2$CH$_2$CH$_2$CH$_3$), 29.7 (SCH$_2$CH$_2$CH$_2$CH$_3$), 31.2 (SCH$_2$CH$_2$CH$_2$CH$_3$), 33.4 (NCH$_2$), 112.6 (C-5'), 115.4 (C-3'), 116.0 (C-1'), 120.2 (C-5), 130.0 (C-4'), 137.7 (C-6), 151.8 (C-4), 155.1 (C-2), 155.2-157.2 (C-6'), 158.7-160.6 (C-2').

2-(Butylthio)-6-chloro-9-(3-chloro-2,6-difluorobenzyl)-9H-purine (36b)

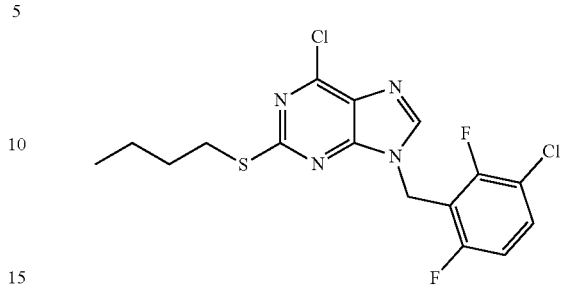

A solution of (36a) (393.0 mg, 1 mmol) in acetic acid (3.0 mL) and triethyl orthoformate (3.0 mL, 18 mmol) was heated at a temperature of 130° C. under reflux for 4 h. After distillation of the acetic acid and triethyl orthoformate under vacuum, the residue was purified by silica gel column chromatography.

Yield: 59%.

Melting point: 109-111° C.

$^1$H NMR (DMSO-$d_6$) δ 0.90 (t, J=7.4 Hz, 3H, SCH$_2$CH$_2$CH$_2$CH$_3$), 1.40 (h, J=7.4 Hz, 2H, SCH$_2$CH$_2$CH$_2$CH$_3$), 1.62 (p, J=7.3 Hz, 2H, SCH$_2$CH$_2$CH$_2$CH$_3$), 3.11 (t, J=7.2 Hz, 2H, SCH$_2$CH$_2$CH$_2$CH$_3$), 5.57 (s, 2H, NCH$_2$), 7.22 (td, J=9.1 Hz/1.5 Hz, 1H, 5'-H), 7.69 (td, J=8.8 Hz/5.8 Hz, 1H, 4'-H), 8.66 (s, 1H, 8-H).

$^{13}$C NMR (DMSO-$d_6$) δ 13.5 (SCH$_2$CH$_2$CH$_2$CH$_3$), 21.3 (SCH$_2$CH$_2$CH$_2$CH$_3$), 30.2 (SCH$_2$CH$_2$CH$_2$CH$_3$), 30.6 (SCH$_2$CH$_2$CH$_2$CH$_3$), 36.1 (NCH$_2$), 112.9 (C-5'), 113.1 (C-1'), 115.7 (C-3'), 127.7 (C-5), 131.3 (C-4'), 149.1 (C-4), 152.5 (C-6), 155.3-156.7 (C-6'), 158.8-160.2 (C-2'), 164.4 (C-2).

2-(Butylthio)-9-(3-chloro-2,6-difluorobenzyl)-9H-purin-6-amine (36z)

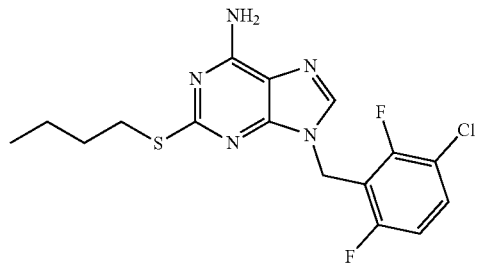 [SMILES: CCCCSc1nc(N)c2ncn(Cc3c(F)ccc(Cl)c3F)c2n1]

Ammonia was bubbled for 5 minutes in a solution of (36b) (200.0 mg, 0.5 mmol) in acetonitrile (2.5 mL) placed in a sealed vessel. The mixture was heated at 110° C. for 3 hours. After distillation of acetonitrile and ammonia under vacuum, the residue was purified by silica gel column chromatography.

Yield: 29%.

Melting point: 133.5-135.5° C.

The conformity and the purity of 36z was attested by NMR spectroscopy and elemental analysis and is reported hereafter:

¹H NMR (DMSO-d$_6$) δ 0.88 (t, J=7.4 Hz, 3H, SCH$_2$CH$_2$CH$_2$CH$_3$), 1.38 (h, J=7.4 Hz, 2H, SCH$_2$CH$_2$CH$_2$CH$_3$), 1.57 (p, J=7.3 Hz, 2H, SCH$_2$CH$_2$CH$_2$CH$_3$), 3.00 (t, J=7.2 Hz, 2H, SCH$_2$CH$_2$CH$_2$CH$_3$), 5.42 (s, 2H, NCH$_2$), 7.20 (t, J=8.8 Hz, 1H, 5'-H), 7.28 (s, 2H, NH$_2$), 7.66 (m, 1H, 4'-H), 8.11 (s, 1H, 8-H).

¹³C NMR (DMSO-d$_6$) δ 13.6 (SCH$_2$CH$_2$CH$_2$CH$_3$), 21.3 (SCH$_2$CH$_2$CH$_2$CH$_3$), 29.5 (SCH$_2$CH$_2$CH$_2$CH$_3$), 31.1 (SCH$_2$CH$_2$CH$_2$CH$_3$), 35.4 (NCH$_2$), 112.8 (C-5'), 113.9 (C-1'), 115.6 (C-3'), 116.2 (C-5), 130.9 (C-4'), 149.9 (C-4), 155.2-156.7 (C-6'), 155.4 (C-6), 158.8-160.2 (C-2'), 163.8 (C-2).

Anal. (C$_{16}$H$_{16}$ClF$_2$N$_5$S) theoretical: C, 50.06; H, 4.20; N, 18.25; S, 8.35. Found: C, 49.84; H, 4.25; N, 18.09; S, 7.93.

Molecule 36z has been tested for its potential antibacterial activity by determining its minimal inhibitory concentration (MIC) according to protocols recommended by EUCAST to assess the efficacy of antibiotics against bacterial strains. In brief MIC in MRSA (ATCC BAA-1556) or in Xen29 (Perkin Elmer-ATCC 12600) for 36z (molecule 25 in WO2009/034386) was determined by culturing a single colony of MRSA or Xen29 in brain heart infusion (BHI) broth overnight (O/N) in aerobic conditions (37° C. with 220 rpm shaking), while MIC for MRSE (ATCC 35984) was determined by culturing MRSE in TSB O/N. Next day a 1:100 inoculum in Mueller-Hinton broth (MHB) is incubated in aerobic conditions for 3 hr (OD=0.08-0.1) and an inoculum of 1:300 dilution, corresponding to 3×10⁵ CFU/ml, is incubated in presence or absence of different concentrations of the tested molecules in 1% DMSO. After O/N growth the OD of each culture was measured at 600 nm (OD$_{600}$) in a spectrophotometer (Victor 3-Perkin Elmer). The MIC represents the concentration at which there is no visible growth of bacteria, i.e. ΔOD at 600 nm equal to zero (blank is the medium alone). No antibacterial activity was found against MRSA (ATCC BAA-1556), Xen29 (Perkin Elmer-ATCC 12600 or MRSE (ATCC 35984) strains when the molecule was used at concentrations up to 200 μM.

Example 2

2-butoxy-9-(3-chloro-2,6-difluorobenzyp-N-(pyridin-3-ylmethyl)-9H-purin-6-amine (37z")

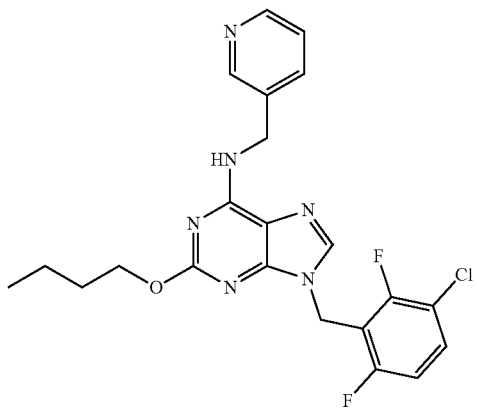 [SMILES: CCCCOc1nc(NCc2cccnc2)c2ncn(Cc3c(F)ccc(Cl)c3F)c2n1]

37 z" (molecule 81 in WO2009/034386) was synthesized according to a similar chemical pathway as described in the present invention, with the exception that the nucleophilic substitution of the chlorine atom on Xb is carried out with another amine R⁹—NH$_2$ (3-(aminomethyl)pyridine in the present example).

6-Chloro-N⁴-(3-chloro-2,6-difluorobenzyl)-2-(methylthio)pyrimidine-4,5-diamine (37a)

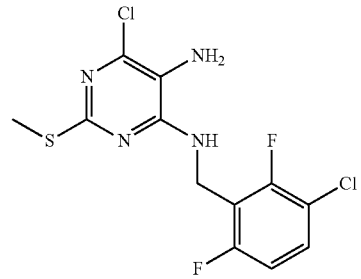 [SMILES: CSc1nc(Cl)c(N)c(NCc2c(F)ccc(Cl)c2F)n1]

4,6-Dichloro-2-(methylthio)pyrimidin-5-amine (22h) (0.5 g, 2.4 mmol) was dissolved in methanol (10 mL) and supplemented with 3-chloro-2,6-difluorobenzylamine (0.78 mL, 6.0 mmol). The reaction mixture was introduced in a sealed vessel and heated at 130° C. for 2 h. After concentration of the reaction mixture to dryness under vacuum, the residue was purified by silica gel column chromatography.

Yield: 96%.

Melting point: 207-212° C.

¹H NMR (DMSO-d$_6$) δ 2.36 (s, 3H, SCH$_3$), 4.65 (d, J=5.0 Hz, 2H, NHCH$_2$), 4.85 (s, 2H, NH$_2$), 7.19 (td, J=9.0 Hz/1.1 Hz, 1H, 5'-H), 7.38 (t, J=5.1 Hz, 1H, NH), 7.62 (td, J=8.7 Hz/5.7 Hz, 1H, 4'-H).

¹³C NMR (DMSO-d$_6$) δ 13.4 (SCH$_3$), 33.4 (NHCH$_2$), 112.6 (C-5'), 115.4 (C-3'), 116.1 (C-1'), 120.2 (C-5), 129.9 (C-4'), 137.7 (C-6), 151.8 (C-4), 155.5 (C-2), 155.5-156.9 (C-6'), 159.0-160.4 (C-2').

6-Chloro-9-(3-chloro-2,6-difluorobenzyl)-2-(methylthio)-9H-purine (37b)

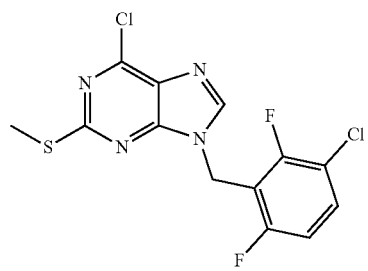 [SMILES: CSc1nc(Cl)c2ncn(Cc3c(F)ccc(Cl)c3F)c2n1]

A solution of (37a) (351.0 mg, 1 mmol) in acetic acid (3.0 mL) and triethyl orthoformate (3.0 mL, 18 mmol) was heated at a temperature of 130° C. under reflux for 4 hours. After distillation of the acetic acid and triethyl orthoformate under vacuum, the residue was purified by silica gel column chromatography.

Yield: 68%.

Melting point: 167-169.5° C.

¹H NMR (DMSO-d$_6$) δ 2.51 (s, 3H, SCH$_3$), 5.57 (s, 2H, NCH$_2$), 7.23 (td, J=9.0 Hz/1.1 Hz, 1H, 5'-H), 7.69 (td, J=8.8 Hz/5.8 Hz, 1H, 4'-H), 8.67 (s, 1H, 8-H).

$^{13}$C NMR (DMSO-d$_6$) δ 13.8 (SCH$_3$), 36.1 (NCH$_2$), 112.9 (C-5'), 113.0 (C-1'), 115.6 (C-3'), 127.6 (C-5), 131.3 (C-4'), 149.1 (C-4), 152.5 (C-6), 155.4-156.8 (C-6'), 158.8-160.2 (C-2'), 164.8 (C-2).

9-(3-Chloro-2,6-difluorobenzyl)-2-(methylthio)-N-(pyridin-3-ylmethyl)-9H-purin-6-amine (37z)

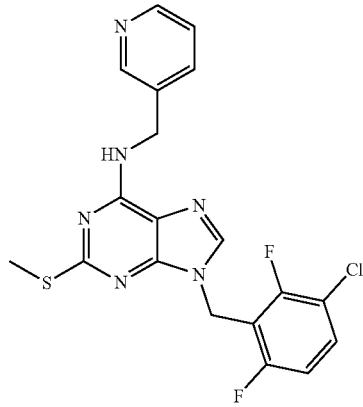 [SMILES: CSc1nc(NCc2cccnc2)c2ncn(Cc3c(F)ccc(Cl)c3F)c2n1]

A solution of (37b) (180.0 mg, 0.5 mmol) in acetonitrile (3 mL) was supplemented with 3-(aminomethyl)pyridine (0.10 mL, 1.0 mmol) and triethylamine (0.10 mL) and then heated at 90° C. under reflux for 5 hours. After distillation of acetonitrile and triethylamine under vacuum, the residue was purified by silica gel column chromatography.

Yield: 92%.

Melting point: 149-151° C.

$^1$H NMR (CDCl$_3$) δ 2.54 (s, 3H, SCH$_3$), 4.84 (bs, 2H, NHCH$_2$), 5.39 (s, 2H, NCH$_2$), 6.17 (bs, 1H, NHCH$_2$), 6.91 (t, J=8.8 Hz, 1H, 5"-H), 7.23 (dd, J=7.7 Hz/4.8 Hz, 1H, 5'-H), 7.39 (td, J=8.6 Hz/5.8 Hz, 1H, 4"-H), 7.70 (m, 2H, 8-H/6'-H), 8.51 (dd, J=4.7 Hz/1.3 Hz, 1H, 4'-H), 8.62 (d, J=1.6 Hz, 1H, 2'-H).

$^{13}$C NMR (CDCl$_3$) δ 14.5 (SCH$_3$), 35.3 (NCH$_2$), 42.1 (NHCH$_2$), 112.4 (C-5"), 113.3 (C-1"), 117.3 (C-3"/C-5), 123.6 (C-5'), 131.3 (C-4"), 134.4 (C-1'), 135.7 (C-6/C-6'), 138.8 (C-8), 149.0 (C-4'), 149.5 (C-2'), 153.9 (C-4), 156.2-157.7 (C-6"), 159.1-160.6 (C-2"), 166.4 (C-2).

9-(3-Chloro-2,6-difluorobenzyl)-2-(methylsulfonyl)-N-(pyridin-3-ylmethyl)-9H-purin-6-amine (37z')

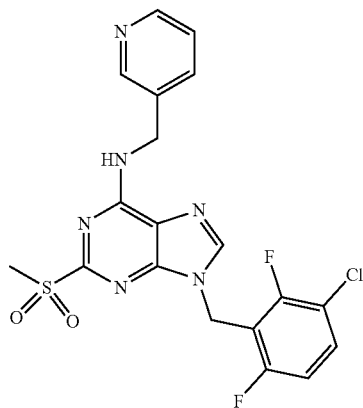 [SMILES: CS(=O)(=O)c1nc(NCc2cccnc2)c2ncn(Cc3c(F)ccc(Cl)c3F)c2n1]

A solution of (37z) (250.0 mg, 0.58 mmol) in methylene chloride (10 mL) was cooled to 5° C. on an ice bath and supplemented with 3-chloroperbenzoic acid (225.0 mg, 1.30 mmol). After stirring at room temperature for 2 hours, the mixture was washed with a solution of NaOH 0.1 M (2×10 mL). The organic layer was dried, filtered and methylene chloride was evaporated to dryness under vacuum. The residue was engaged in the next step (37z") without further purification.

Yield: 72%.

2-Butoxy-9-(3-chloro-2,6-difluorobenzyl)-N-(pyridin-3-ylmethyl)-9H-purin-6-amine (37z")

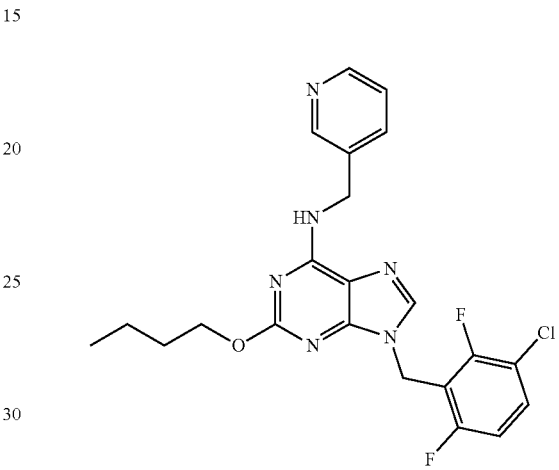

Sodium metal (46.0 mg, 2 mmol) was dissolved in butan-1-ol (3 mL) on an iced bath and (37z') (150.0 mg, 0.32 mmol) was added. After stirring at room temperature for 3 hours, the mixture was partitioned between water (50 mL) and dichloromethane (2×50 mL). The combined organic layers were dried and evaporated to dryness under vacuum. The residue was purified by silica gel column chromatography.

Yield: 78%.

Melting point: 143-145° C.

The conformity and the purity of compound 37z" was attested by NMR spectroscopy and elemental analysis and is reported hereafter:

$^1$H NMR (CDCl$_3$) δ 0.97 (t, J=7.4 Hz, 3H, OCH$_2$CH$_2$CH$_2$CH$_3$), 1.49 (h, J=7.4 Hz, 2H, OCH$_2$CH$_2$CH$_2$CH$_3$), 1.78 (p, J=7.3 Hz, 2H, OCH$_2$CH$_2$CH$_2$CH$_3$), 4.34 (t, J=6.8 Hz, 2H, OCH$_2$CH$_2$CH$_2$CH$_3$), 4.85 (bs, 2H, NHCH$_2$), 5.36 (s, 2H, NCH$_2$), 5.75 (bs, 1H, NHCH$_2$), 6.92 (td, J=8.9 Hz/1.5 Hz, 1H, 5"-H), 7.24 (dd, J=7.8 Hz/4.8 Hz, 1H, 5'-H), 7.39 (td, J=8.6 Hz/5.7 Hz, 1H, 4"-H), 7.63 (s, 1H, 8-H), 7.69 (d, J=7.9 Hz, 1H, 6'-H), 8.52 (dd, J=4.8 Hz/1.4 Hz, 1H, 4'-H), 8.62 (d, J=1.8 Hz, 1H, 2'-H).

$^{13}$C NMR (CDCl$_3$) δ 14.1 (OCH$_2$CH$_2$CH$_2$CH$_3$), 19.4 (OCH$_2$CH$_2$CH$_2$CH$_3$), 31.2 (OCH$_2$CH$_2$CH$_2$CH$_3$), 35.1 (NCH$_2$), 42.1 (NHCH$_2$), 67.5 (OCH$_2$CH$_2$CH$_2$CH$_3$), 112.4 (C-5"), 113.4 (C-1"), 117.3 (C-3"/C-5), 123.6 (C-5'), 131.3 (C-4"), 134.3 (C-1'), 135.6 (C-6/C-6'), 138.4 (C-8), 149.1 (C-4'), 149.5 (C-2'), 151.5 (C-4), 155.5 (C-6), 156.2-157.7 (C-6"), 159.2-160.6 (C-2"), 162.5 (C-2).

Anal. (C$_{22}$H$_{21}$ClF$_2$N$_6$O) theoretical: C, 57.58; H, 4.61; N, 18.31. Found: C, 57.19; H, 4.68; N, 18.07.

Molecule 37z" has been tested for its potential antibacterial activity by determining an eventual minimal inhibitory concentration according to protocols recommended by EUCAST to assess the efficacy of antibiotics against bacterial strains. In brief MIC in MRSA (ATCC BAA-1556) or in Xen29 (Perkin Elmer-ATCC 12600) for 37z" (molecule 81 in WO2009/034386) was determined by culturing a single colony of MRSA or Xen29 in brain heart infusion (BHI) broth overnight (O/N) in aerobic conditions (37° C. with 220 rpm shaking), while MIC for MRSE (ATCC 35984) was determined by culturing MRSE in TSB O/N. Next day a 1:100 inoculum in Mueller-Hinton broth (MHB) is incubated in aerobic conditions for 3 hr (OD=0.08-0.1) and an inoculum of 1:300 dilution, corresponding to $3\times10^5$ CFU/ml, is incubated in presence or absence of different concentrations of the tested molecules in 1% DMSO. After O/N growth the OD of each culture was measured at 600 nm ($OD_{600}$) in a spectrophotometer (Victor 3-Perkin Elmer). The MIC represents the concentration at which there is no visible growth of bacteria, i.e. ΔOD at 600 nm equal to zero (blank is the medium alone). NO antibacterial activity was found against MRSA (ATCC BAA-1556), Xen29 (Perkin Elmer-ATCC 12600) or MRSE (ATCC 35984) strains when the molecule was used at concentrations up to 200 μM.

Example 3

2-butoxy-N-cyclopropyl-9-(2,6-difluoro-3-methylbenzyl)-9H-purin-6-amine (38z")

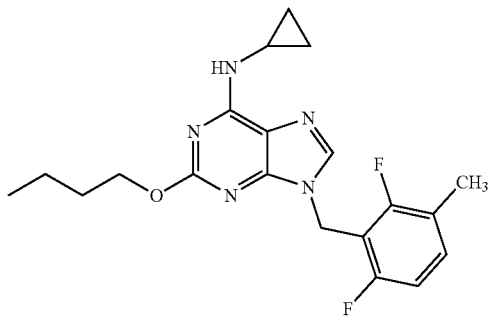 [SMILES: CCCCOc1nc(NC2CC2)c2ncn(Cc3c(F)ccc(C)c3F)c2n1]

We have synthesized 38z" (molecule 129 in WO2009/034386) that is bearing a cyclopropyl ring attached to the nitrogen atom linked at position-6 of the heterocycle ring. The chemical structure of this compound is the most tightly related to that of the compounds described in the present application.

6-Chloro-$N^4$-(2,6-difluoro-3-methylbenzyl)-2-(methylthio)pyrimidine-4,5-diamine (38a)

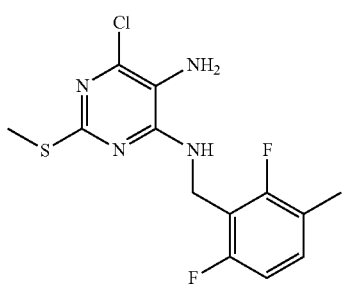

4,6-Dichloro-2-(methylthio)pyrimidin-5-amine (22h) (0.5 g, 2.4 mmol) was dissolved in methanol (10 mL) and supplemented with 2,6-difluoro-3-methylbenzylamine (0.80 mL, 6.0 mmol). The reaction mixture was introduced in a sealed vessel and heated at 130° C. for 2 h. After concentration of the reaction mixture to dryness under vacuum, the residue was purified by silica gel column chromatography.
Yield: 95%.
Melting point: 190-192° C.
$^1$H NMR (DMSO-$d_6$) δ 2.21 (s, 3H, $CH_3$), 2.38 (s, 3H, $SCH_3$), 4.61 (d, J=4.8 Hz, 2H, $NHCH_2$), 4.85 (s, 2H, $NH_2$), 7.01 (t, J=8.8 Hz, 1H, 5'-H), 7.27 (m, 2H, $NHCH_2$/4'-H).
$^{13}$C NMR (DMSO-$d_6$) δ 13.4 ($SCH_3$), 13.8 ($CH_3$), 33.1 ($NHCH_2$), 110.8 (C-5'), 113.4 (C-1'), 120.1 (C-5), 120.2 (C-3'), 130.8 (C-4'), 137.5 (C-6), 151.8 (C-4), 155.5 (C-2), 158.5-159.9 (C-2'/C-6').

6-Chloro-9-(2,6-difluoro-3-methylbenzyl)-2-(methylthio)-9H-purine (38b)

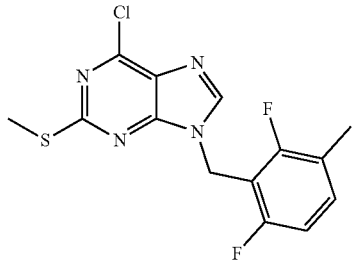

A solution of (38a) (331.0 mg, 1 mmol) in acetic acid (3.0 mL) and triethyl orthoformate (3.0 mL, 18 mmol) was heated at a temperature of 130° C. under reflux for 3 hours. After distillation of acetic acid and triethyl orthoformate under vacuum, the residue was purified by silica gel column chromatography.
Yield: 66%.
Melting point: 124-126° C.
$^1$H NMR (DMSO-$d_6$) Δ 2.19 (s, 3H, $CH_3$), 2.52 (s, 3H, $SCH_3$), 5.52 (s, 2H, $NCH_2$), 7.05 (t, J=8.9 Hz, 1H, 5'-H), 7.34 (q, J=8.4 Hz, 1H, 4'-H), 8.63 (s, 1H, 8-H).
$^{13}$C NMR (DMSO-$d_6$) δ 13.6 ($CH_3$), 13.8 ($SCH_3$), 35.9 ($NCH_2$), 110.6 (C-1'), 111.1 (m, C-5'), 120.6 (C-3'), 127.6 (C-5), 132.2 (C-4'), 149.0 (C-4), 152.5 (C-6), 158.3-159.7 (C-2'/C-6'), 164.7 (C-2).

N-Cyclopropyl-9-(2,6-difluoro-3-methylbenzyl)-2-(methylthio)-9H-purin-6-amine (38z)

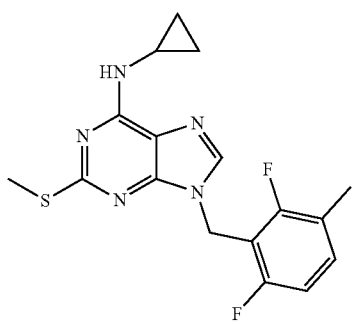

A solution of (38b) (170.0 mg, 0.5 mmol) in acetonitrile (3 mL) was supplemented with cyclopropylamine (0.07 mL, 1.0 mmol) and triethylamine (0.10 mL) and then heated at 90° C. under reflux for 5 hours. After distillation of acetonitrile and triethylamine under vacuum, the residue was purified by silica gel column chromatography.

Yield: 86%.

Melting point: 150-152° C.

$^1$H NMR (CDCl$_3$) δ 0.60 (m, 2H, CH(CH$_2$)$_2$), 0.86 (m, 2H, CH(CH$_2$)$_2$), 2.23 (s, 3H, CH$_3$), 2.60 (s, 3H, SCH$_3$), 3.06 (bs, 1H, CH(CH$_2$)$_2$), 5.36 (s, 2H, NCH$_2$), 5.77 (bs, 1H, NH), 6.83 (t, J=8.3 Hz, 1H, 5'-H), 7.14 (q, J=8.3 Hz, 1H, 4'-H), 7.66 (s, 1H, 8-H).

$^{13}$C NMR (CDCl$_3$) δ 7.6 (CH(CH$_2$)$_2$), 14.3 (CH$_3$), 14.6 (SCH$_3$), 24.4 (CH(CH$_2$)$_2$), 35.1 (NCH$_2$), 111.1 (C-5'), 111.2 (C-1'), 117.1 (C-5), 121.1 (C-3'), 132.0 (C-4'), 138.8 (C-8), 155.2 (C-4), 159.0-160.4 (C-2'/C-6'), 166.0 (C-2).

N-Cyclopropyl-9-(2,6-difluoro-3-methylbenzyl)-2-(methylsulfonyl)-9H-purin-6-amine (38z')

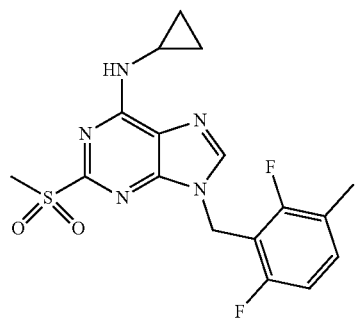

A solution of (38z) (195.0 mg, 0.54 mmol) in methylene chloride (10 mL) was cooled to 5° C. on an ice bath and supplemented with 3-chloroperbenzoic acid (208.0 mg, 1.20 mmol). After stirring at room temperature for 2 hours, the mixture was washed with a solution of NaOH 0.1 M (2×10 mL). The organic layer was dried, filtered and methylene chloride was evaporated to dryness under vacuum. The residue was engaged in the next step (38z") without further purification.

Yield: 69%.

2-Butoxy-N-cyclopropyl-9-(2,6-difluoro-3-methyl-benzyl)-9H-purin-6-amine (38z")

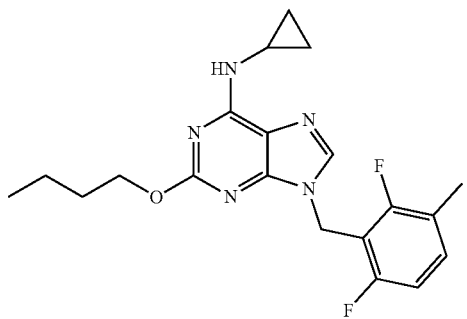 [SMILES: CCCCOc1nc(NC2CC2)c2ncn(Cc3c(F)ccc(C)c3F)c2n1]

Sodium metal (46.0 mg, 2 mmol) was dissolved in butan-1-ol (3 mL) on an iced bath and (37z') (150.0 mg, 0.38 mmol) was added. After stirring at room temperature for 3 hours, the mixture was partitioned between water (50 mL) and dichloromethane (2×50 mL). The combined organic layers were dried and evaporated to dryness under vacuum. The residue was purified by silica gel column chromatography.

Yield: 75%.

Melting point: 123-125° C.

The conformity and the purity of compound 38z" was attested by NMR spectroscopy and elemental analysis and is reported hereafter:

$^1$H NMR (CDCl$_3$) δ 0.60 (m, 2H, CH(CH$_2$)$_2$), 0.86 (m, 2H, CH(CH$_2$)$_2$), 0.98 (t, J=7.4 Hz, 3H, OCH$_2$CH$_2$CH$_2$CH$_3$), 1.50 (h, J=7.4 Hz, 2H, OCH$_2$CH$_2$CH$_2$CH$_3$), 1.81 (p, J=7.0 Hz, 2H, OCH$_2$CH$_2$CH$_2$CH$_3$), 2.23 (s, 3H, CH$_3$), 3.06 (bs, 1H, CH(CH$_2$)$_2$), 4.38 (t, J=6.9 Hz, 2H, OCH$_2$CH$_2$CH$_2$CH$_3$), 5.32 (s, 2H, NCH$_2$), 5.75 (bs, 1H, NH), 6.83 (td, J=8.7 Hz/1.1 Hz, 1H, 5'-H), 7.14 (q, J=8.3 Hz, 1H, 4'-H), 7.59 (s, 1H, 8-H).

$^{13}$C NMR (CDCl$_3$) δ 7.6 (CH(CH$_2$)$_2$), 14.1 (OCH$_2$CH$_2$CH$_2$CH$_3$), 14.3 (CH$_3$), 19.4 (OCH$_2$CH$_2$CH$_2$CH$_3$), 24.2 (CH(CH$_2$)$_2$), 31.2 (OCH$_2$CH$_2$CH$_2$CH$_3$), 34.8 (NCH$_2$), 67.2 (OCH$_2$CH$_2$CH$_2$CH$_3$), 111.0 (C-5'), 111.3 (C-1'), 115.8 (C-5), 121.2 (C-3'), 132.0 (C-4'), 138.4 (C-8), 156.8 (C-4), 158.7-160.6 (C-2'/C-6'), 160.7 (C-2).

Anal. (C$_{20}$H$_{23}$F$_2$N$_5$O) theoretical: C, 62.00; H, 5.98; N, 18.08. Found: C, 61.97; H, 6.07; N, 18.03.

The molecule 38z" (molecule 129 in WO2009/034386) was tested for its potential antibacterial activity by determining an eventual minimal inhibitory concentration according to protocols recommended by EUCAST to assess the efficacy of antibiotics against bacterial strains. In brief MIC in MRSA (ATCC BAA-1556) or in Xen29 (Perkin Elmer-ATCC 12600) for 38z" (molecule 129 in WO2009/034386) was determined by culturing a single colony of MRSA or Xen29 in brain heart infusion (BHI) broth overnight (O/N) in aerobic conditions (37° C. with 220 rpm shaking), while MIC for MRSE (ATCC 35984) was determined by culturing MRSE in TSB O/N. Next day a 1:100 inoculum in Mueller-Hinton broth (MHB) is incubated in aerobic conditions for 3 hr (OD=0.08-0.1) and an inoculum of 1:300 dilution, corresponding to 3×10$^5$ CFU/ml, is incubated in presence or absence of different concentrations of the tested molecules in 1% DMSO. After O/N growth the OD of each culture was measured at 600 nm (OD$_{600}$) in a spectrophotometer (Victor 3-Perkin Elmer). The MIC represents the concentration at which there is no visible growth of bacteria, i.e. ΔOD at 600 nm equal to zero (blank is the medium alone). NO antibacterial activity was found against MRSA, Xen29 and MRSE strains when the molecule was used at concentrations up to 200 μM.

The invention claimed is:
1. A pyrimidine derivative represented by formula (I)

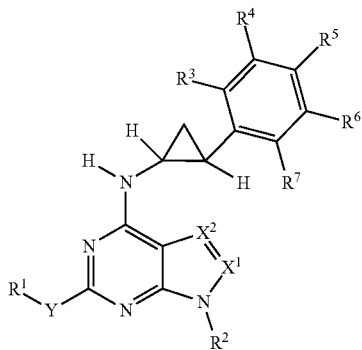

or optical isomers, racemic mixtures thereof, pharmaceutically acceptable acid addition salts, pharmaceutically acceptable metal salts, or alkylated ammonium salts thereof;
wherein:
$X^1$ and $X^2$ are independently N, CH, $CR^8$ wherein $R^8$ is $C_{1-6}$ alkyl, $C_{2-6}$ alkenyl or $C_{2-6}$ alkynyl; with the exception that if one of $X^1$ or $X^2$ is equal to N, then the remaining of $X^1$ or $X^2$ are selected from CH, $CR^8$;
—Y— is —O— or —S—;
$R^1$ and $R^2$ are independently $C_{1-6}$-alkyl, $C_{2-6}$-alkenyl, $C_{2-6}$-alkynyl, $C_{3-6}$-cycloalkyl, aryl, aryl-$C_{1-6}$-alkyl wherein the alkyl or cycloalkyl moiety is optionally mono or polysubstituted with OH or an halogen and the aryl moiety is optionally mono or polysubstituted with an halogen, —$C_{1-6}$ alkyl, —$C_{1-6}$ alkoxy, —OH, —$NO_2$, —CN, —$NH_2$, —$NHR^8$, —$N(R^8)_2$ —COOH, —$COOR^8$, —$CONH_2$, —$CONHR^8$, —$CON(R^8)_2$, —$SO_2NH_2$, —$SO_2NHR^8$, or —$SO_2N(R^8)_2$;
$R^3$, $R^4$, $R^5$, $R^6$ and $R^7$ are independently H, an halogen, a $C_{1-6}$ alkyl, $C_{1-6}$ alkoxy, —OH, —$NO_2$, —CN, —$NH_2$, —$NHR^8$, —$N(R^8)_2$ —COOH, —$COOR^8$, —$CONH_2$, —$CONHR^8$, —$CON(R^8)_2$, —$SO_2NH_2$, —$SO_2NHR^8$, or —$SO_2N(R^8)_2$.

2. The pyrimidine derivative according to claim 1 comprising at least one detectable isotope.

3. The pyrimidine derivative according to claim 2 wherein the detectable isotope is selected from 3H, $^{18}$F, $^{19}$F, $^{11}$C, $^{13}$C, $^{14}$C, $^{75}$Br, $^{76}$Br, $^{120}$I, $^{123}$I, $^{125}$I, $^{131}$I, $^{15}$O, and $^{13}$N.

4. The pyrimidine derivative according to anyone of claim 1 wherein $R^3$ and $R^7$ are hydrogen and $R^4$ and $R^5$ are independently an halogen.

5. The pyrimidine derivative according to claim 1, wherein $X^1$ is CH or $CR^8$ and $X^2$ is N.

6. The pyrimidine derivative according to claim 5 selected from the group consisting of:
N-((1R,2S)-2-(3,4-difluorophenyl)cyclopropyl)-9-methyl-2-(propylthio)-9H-purin-6-amine (1c);
9-methyl-N-((1R,2S)-2-phenylcyclopropyl)-2-(propylthio)-9H-purin-6-amine (2c);
N-((1R,2S)-2-(3,4-difluorophenyl)cyclopropyl)-9-ethyl-2-(propylthio)-9H-purin-6-amine (3c);
N-((1R,2S)-2-(3,4-difluorophenyl)cyclopropyl)-9-propyl-2-(propylthio)-9H-purin-6-amine (4c);
N-((1R,2S)-2-(3,4-difluorophenyl)cyclopropyl)-9-isopropyl-2-(propylthio)-9H-purin-6-amine (5c);
9-cyclopropyl-N-((1R,2S)-2-(3,4-difluorophenyl)cyclopropyl)-2-(propylthio)-9H-purin-6-amine (6c);
9-butyl-N-((1R,2S)-2-(3,4-difluorophenyl)cyclopropyl)-2-(propylthio)-9H-purin-6-amine (7c);
9-(sec-butyl)-N-((1R,2S)-2-(3,4-difluorophenyl)cyclopropyl)-2-(propylthio)-9H-purin-6-amine (8c);
9-(tert-butyl)-N-((1R,2S)-2-(3,4-difluorophenyl)cyclopropyl)-2-(propylthio)-9H-purin-6-amine (9c);
9-cyclobutyl-N-((1R,2S)-2-(3,4-difluorophenyl)cyclopropyl)-2-(propylthio)-9H-purin-6-amine (10c);
N-((1R,2S)-2-(3,4-difluorophenyl)cyclopropyl)-9-pentyl-2-(propylthio)-9H-purin-6-amine (11c);
9-cyclopentyl-N-((1R,2S)-2-(3,4-difluorophenyl)cyclopropyl)-2-(propylthio)-9H-purin-6-amine (12c);
N-((1R,2S)-2-(3,4-difluorophenyl)cyclopropyl)-9-hexyl-2-(propylthio)-9H-purin-6-amine (13c);
9-cyclohexyl-N-((1R,2S)-2-(3,4-difluorophenyl)cyclopropyl)-2-(propylthio)-9H-purin-6-amine (14c);
9-allyl-N-((1R,2S)-2-(3,4-difluorophenyl)cyclopropyl)-2-(propylthio)-9H-purin-6-amine (15c);
2-(6-(((1R,2S)-2-(3,4-difluorophenyl)cyclopropyl) amino)-2-(propylthio)-9H-purin-9-yl)ethanol (16c);
N-((1R,2S)-2-(3,4-difluorophenyl)cyclopropyl)-9-(prop-2-yn-1-yl)-2-(propylthio)-9H-purin-6-amine (17c);
N-((1R,2S)-2-(3,4-difluorophenyl)cyclopropyl)-2-(propylthio)-9-(2,2,2-trifluoroethyl)-9H-purin-6-amine (18c);
(1S,2R,3S,4R)-4-(6-(((1R,2S)-2-(3,4-difluorophenyl)cyclopropyl)amino)-2-(propylthio)-9H-purin-9-yl)cyclopentane-1,2,3-triol (19d);
N-((1R,2S)-2-(3,4-difluorophenyl)cyclopropyl)-2-(ethylthio)-9-methyl-9H-purin-6-amine (20c);
N-(1R,2S)-2-(3,4-difluorophenyl)cyclopropyl)-9-ethyl-2-(ethylthio)-9H-purin-6-amine (21c);
N-((1R,2S)-2-(3,4-difluorophenyl)cyclopropyl)-9-methyl-2-(methylthio)-9H-purin-6-amine (22c);
N-(1R,2S)-2-(3,4-difluorophenyl)cyclopropyl)-9-methyl-2-propoxy-9H-purin-6-amine hydrochloride (23t.HCl);
N-((1R,2S)-2-(3,4-difluorophenyl)cyclopropyl)-9-ethyl-2-(methylthio)-9H-purin-6-amine (24c);
2-(butylthio)-N-((1R,2S)-2-(3,4-difluorophenyl)cyclopropyl)-9-methyl-9H-purin-6-amine (25c); and
2-(butylthio)-N-((1R,2S)-2-(3,4-difluorophenyl)cyclopropyl)-9-ethyl-9H-purin-6-amine (26c);
or optical isomers, racemic mixtures thereof, pharmaceutically acceptable acid addition salts, pharmaceutically acceptable metal salts, or alkylated ammonium salts thereof.

7. The pyrimidine derivative according to claim 5 which is N-((1R,2S)-2-(3,4-difluorophenyl)cyclopropyl)-9-methyl-2-(propylthio)-9H-purin-6-amine (1c).

8. The pyrimidine derivative according to claim 1 wherein $X^1$ is N and $X^2$ is CH or $CR^8$.

9. The pyrimidine derivative according to claim 8 selected from the group consisting of:
N-((1R,2S)-2-(3,4-difluorophenyl)cyclopropyl)-1-methyl-6-(methylthio)-1H-pyrazolo[3,4-d]pyrimidin-4-amine (27k);
N-((1R,2S)-2-(3,4-difluorophenyl)cyclopropyl)-6-(ethylthio)-1-methyl-1H-pyrazolo[3,4-d]pyrimidin-4-amine hydrochloride (28x.HCl);
N-((1R,2S)-2-(3,4-difluorophenyl)cyclopropyl)-6-(propylthio)-1-methyl-1H-pyrazolo[3,4-d]pyrimidin-4-amine hydrochloride (29x.HCl);

N-((1R,2S)-2-(3,4-difluorophenyl)cyclopropyl)-1-ethyl-6-(methylthio)-1H-pyrazolo[3,4-d]pyrimidin-4-amine (30k);

N-((1R,2S)-2-(3,4-difluorophenyl)cyclopropyl)-1-ethyl-6-(ethylthio)-1H-pyrazolo[3,4-d]pyrimidin-4-amine hydrochloride (31x.HCl);

N-((1R,2S)-2-(3,4-difluorophenyl)cyclopropyl)-1-ethyl-6-(propylthio)-1H-pyrazolo[3,4-d]pyrimidin-4-amine hydrochloride (32x.HCl);

N-((1R,2S)-2-(3,4-difluorophenyl)cyclopropyl)-1-isopropyl-6-(methylthio)-1H-pyrazolo[3,4-d]pyrimidin-4-amine hydrochloride (33k.HCl); and N-((1R,2S)-2-(3,4-difluorophenyl)cyclopropyl)-6-(methylthio)-1-propyl-1H-pyrazolo[3,4-d]pyrimidin-4-amine hydrochloride (34k.HCl);

or optical isomers, racemic mixtures thereof, pharmaceutically acceptable acid addition salts, pharmaceutically acceptable metal salts, or alkylated ammonium salts thereof.

10. The pyrimidine derivative according to claim 1 wherein $X^1$ and $X^2$ are CH or $CR^8$.

11. The pyrimidine derivative according to claim 10 which is:

N-((1R,2S)-2-(3,4-difluorophenyl)cyclopropyl)-7-ethyl-2-(methylthio)-7H-pyrrolo [2,3-d]pyrimidin-4-amine hydrochloride (35p.HCl);

or optical isomers, racemic mixtures thereof, pharmaceutically acceptable acid addition salts, pharmaceutically acceptable metal salts, or alkylated ammonium salts thereof.

12. The pyrimidine derivative according to claim 1 wherein $R^3$ and $R^7$ are H and $R^4$, $R^5$ is a fluorine.

13. A method of treating a bacterial infection in mammal in need of such treatment comprising administering to the mammal the pyrimidine derivative according to claim 1.

14. A pharmaceutical composition comprising a pyrimidine derivative according to claim 1 in combination with pharmaceutically acceptable diluent, adjuvant and/or carrier.

15. A method of reducing bacterial infection in a host mammal, wherein said method comprises applying said pyrimidine derivative according to claim 1 on the surface of a biomaterial implant prior to implantation of said implant in said host mammal.

16. A method for reducing bacterial growth in biofilm formation comprising applying on a surface of a medical device, an effective amount of a pyrimidine derivative according to anyone of claim 1.

17. The method according to claim 16 wherein the medical device is a cardiovascular device.

18. A method of preparation of pyrimidine derivatives of formula (I) according to claim 5, wherein $X^1$ is CH or $CR^8$, $X^2$ is N; said method comprising the following steps:

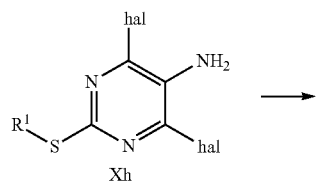

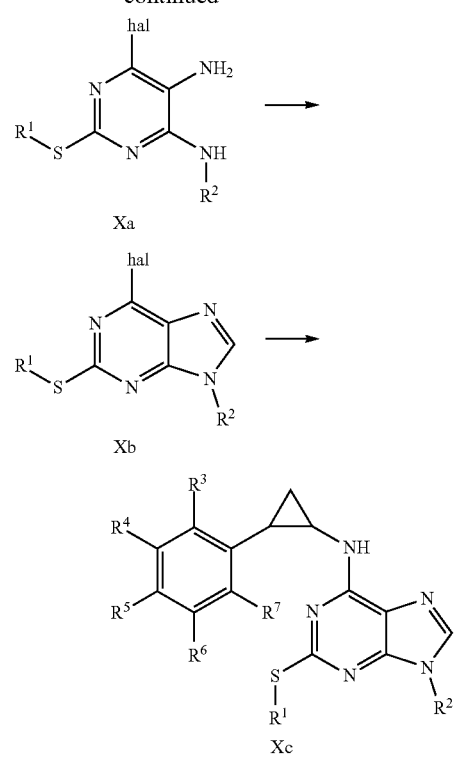

1) preparing a 2-substituted 4,6-dihalogenoropyrimidin-5-amine (Xh) as starting product;

2) reacting the 2-substituted 4,6-halogenopyrimidin-5-amine (Xh) with $R^2NH_2$ to obtain an intermediate (Xa) wherein $R^2$ is as defined in formula (I);

3) reacting the intermediate (Xa) with trialkyl orthoformate under heating in presence of an acid to obtain intermediate 2,9-disubstituted 6-halogeno-9H-purine (Xb);

4) substituting the halogen atom of intermediate (Xb) by a ($R^3$-$R^7$)-substituted phenylcyclopropylamine under heating to obtain a pyrimidine derivative of formula (I) wherein Y is S (Xc);

and optionally forming a pharmaceutically acceptable salt or prodrug thereof.

19. The method according to claim 18 wherein the starting product (Xh) is obtained by:

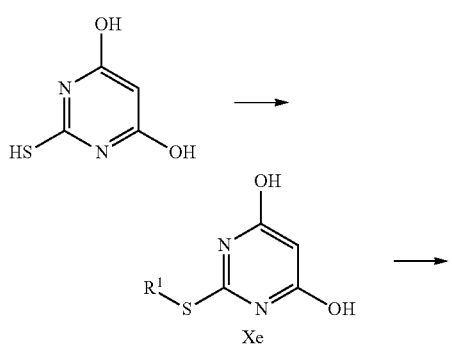

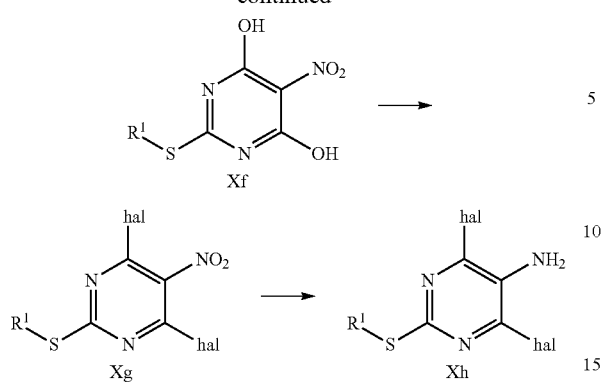

1) reacting thiobarbituric acid with R¹-halide under heating to obtain a 2-substituted pyrimidine-4,6-diol (Xe);
2) reacting 2-substituted pyrimidine-4,6-diol (Xe) under cooling with nitric acid to obtain intermediate (Xf), followed by nucleophilic substitution in the presence of an organic base to provide a 2-substituted 4,6-dihalogeno-5-nitropyrimidine (Xg);
3) reducing the 2-substituted 4,6-dihalogeno-5-nitropyrimidine (Xg) to a corresponding 2-substituted 4,6-dihalogenopyrimidin-5-amine (Xh).

20. The method according to claim 18 further comprising a reaction of conversion of a thioether group of Xc wherein Y is S; into a corresponding ether function (Y=O) to obtain a pyrimidine derivative of formula (I) wherein Y is O(Xt);

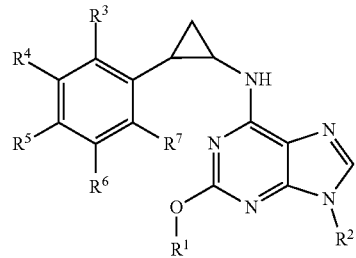

and optionally forming a pharmaceutically acceptable salt or thereof.

21. The method according to claim 18 further comprising a conversion reaction comprising:

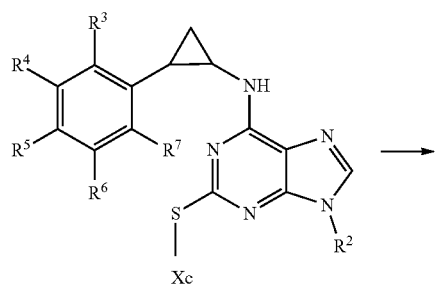

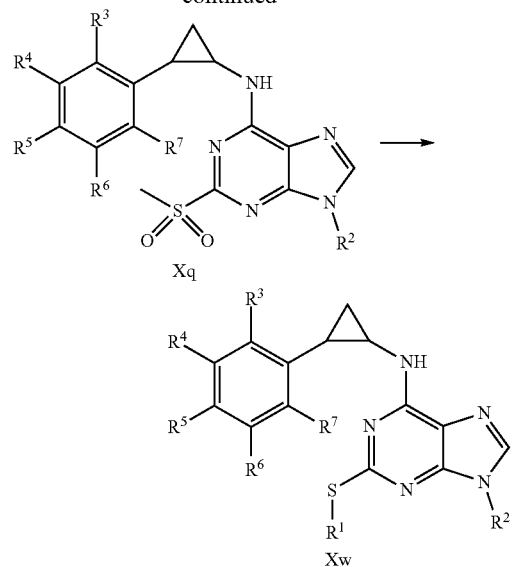

1) a first reaction of oxidation of the thioether function of (Xc) by a peracid to provide a methylsulfonyl group in an intermediate (Xq) and
2) a further reaction of nucleophilic substitution of the intermediate (Xq) with an alkyl thiol to provide pyrimidine derivatives of formula (I) wherein Y is S and R¹ is not methyl (Xw).

22. A method of preparation of a pyrimidine derivative of formula (I) wherein X¹ is N and X² is CH or CR⁸ according to claim 8; said method comprising the following steps:

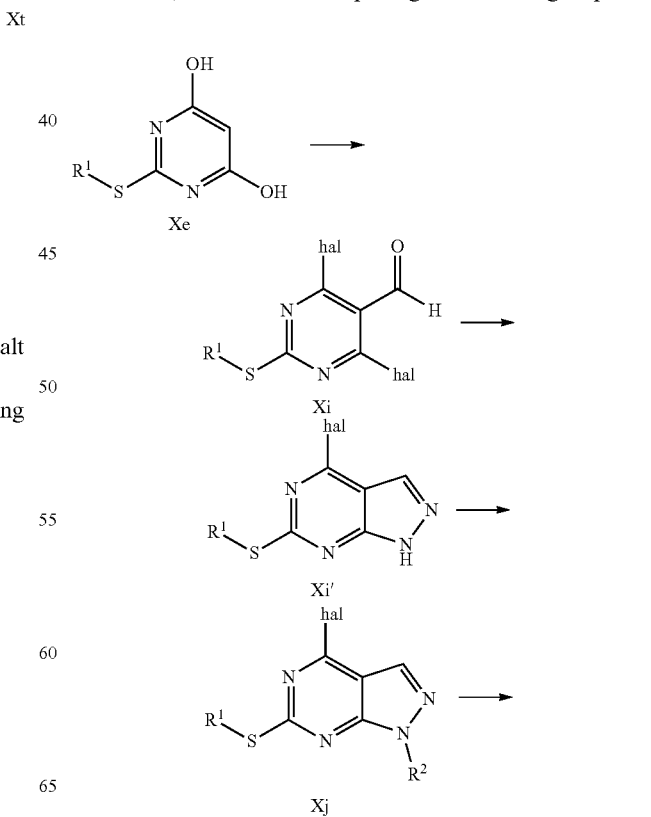

-continued

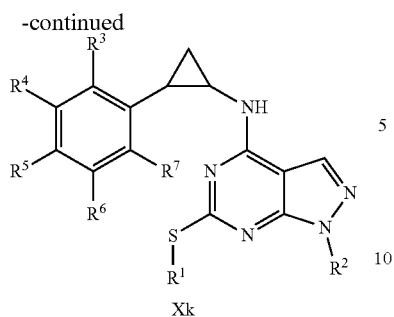

Xk 1) reacting thiobarbituric acid with a R¹-halide under heating to obtain a 2-substituted pyrimidine-4,6-diol (Xe);
2) reacting the 2-substituted pyrimidine 4,6-diol (Xe) with phosphoryl halide in presence of DMF to obtain the corresponding 2-substituted 4,6-dihalogenopyrimidin-5-carbaldehyde (Xi);
3) reacting under cooling, the 2-substituted 4,6-dihalogenopyrimidin-5-carbaldehyde (Xi) with a non-substituted hydrazine to provide a non alkylated 1H-pyrazolo[3,4-d]pyrimidine (Xi'), followed by an alkylation with a R²-halide to provide intermediate (Xj), and a nucleophilic substitution with a R³-R⁷-substituted phenylcyclopropylamine to provide (Xk);
and optionally forming a pharmaceutically acceptable salt thereof.

23. The method according to claim 22 further comprising a reaction of conversion of
a thioether group of Xk (Y=S) into a corresponding ether function (Y=O) to obtain pyrimidine derivatives of formula (I) wherein Y is O (Xu);

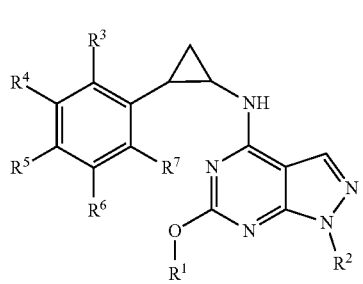

Xu and optionally forming a pharmaceutically acceptable salt thereof.

24. The method of preparation according to claim 22 further comprising a reaction of conversion comprising:

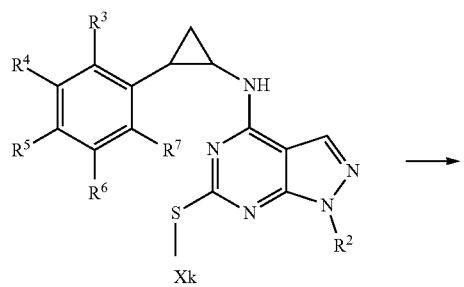

Xk

-continued

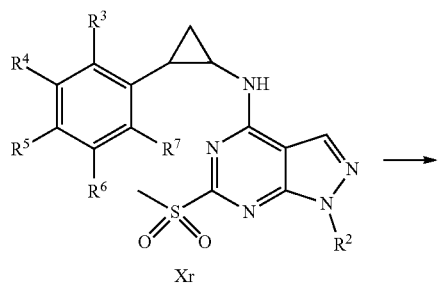

Xr

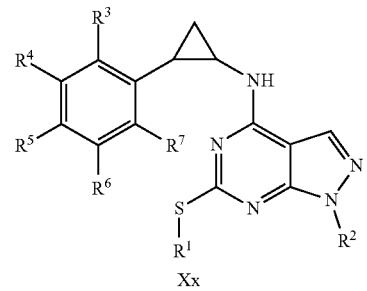

Xx a first reaction of oxidation of the thioether function of (Xk) by a peracid to provide a methylsulfonyl group in an intermediate (Xr) and a further reaction of nucleophilic substitution with an alkyl thiol to provide pyrimidines derivatives of formula (I) wherein Y is S and R¹ is not methyl (Xx);

and optionally forming a pharmaceutically acceptable salt thereof.

25. A method of preparation of pyrimidine derivatives of formula (I) wherein X¹ and X² are CH or CR⁸ according to claim 10; said method comprising the following steps:

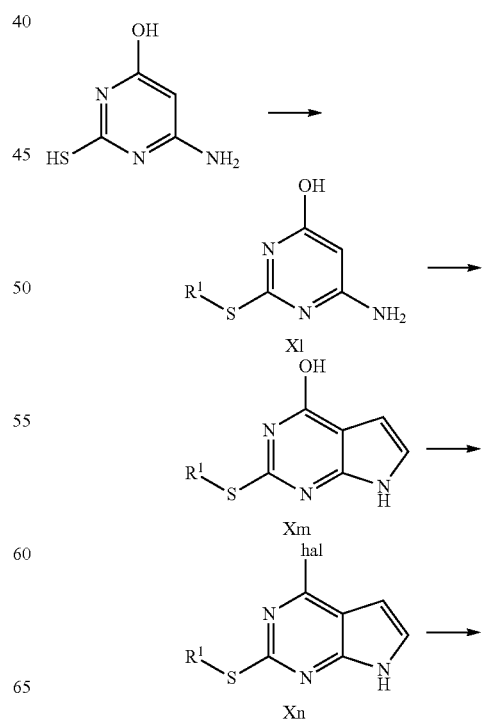

Xl

Xm hal

Xn

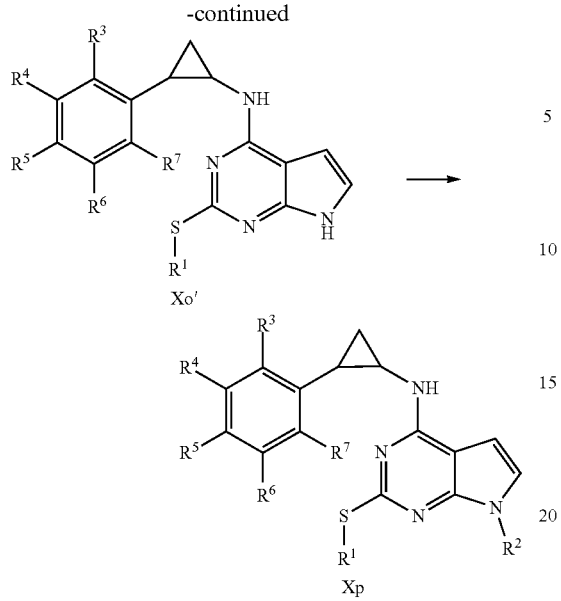

1) reacting under heating a 6-amino-4-hydroxypyrimidine-2-thiol with a R¹-halide in alkaline medium to provide a 2-substituted 6-aminopyrimidine-4-ol (X1);
2) converting the 2-substituted 6-aminopyrimidine-4-ol (X1) with halogenoacetaldehyde under heating to provide a 2-substituted 7H-pyrrolo[2,3-d]pyrimidine-4-ol (Xm);
3) reacting (Xm) with phosphoryl halide under heating to provide 2-substituted 4-halogeno-7H-pyrrolo [2,3-d] pyrimidine (Xn) 4) substituting an halogen atom of (Xn) with a (R³-R⁷)-substituted phenylcyclopropyl amine to provide Xo', followed by an alkylation with a R²-halide in alkaline medium to provide (Xp);
and optionally forming a pharmaceutically acceptable salt thereof.

26. The method according to claim 25 further comprising a reaction of conversion of
a thioether group of (Xp) wherein Y is S into a corresponding ether function (Y=O) to obtain pyrimidine derivatives of formula (I) wherein Y is O (Xv);

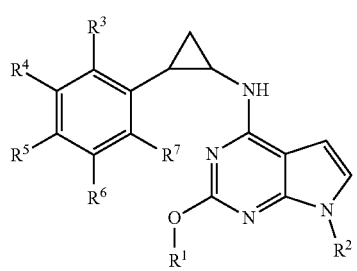

and optionally forming a pharmaceutically acceptable salt thereof.

27. The method according to claim 25 further comprising a reaction of conversion comprising:

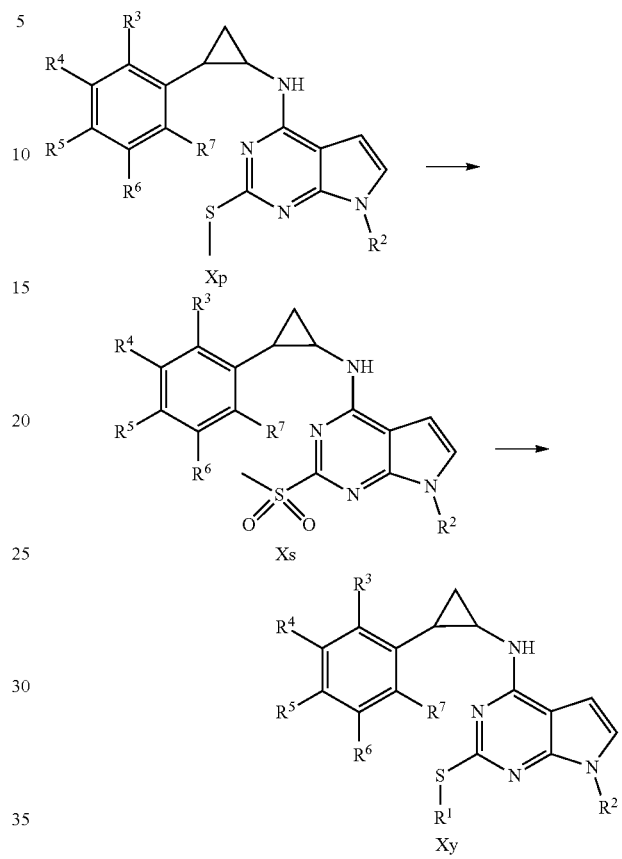

a first reaction of oxidation of the thioether function of (Xp) by a peracid to provide a methylsulfonyl group in an intermediate (Xs) and a further reaction of nucleophilic substitution with an alkyl thiol to provide pyrimidine derivatives of formula (I) wherein Y is S and R¹ is not methyl (Xy);
and optionally forming a pharmaceutically acceptable salt thereof.

28. A method of diagnosing or prognosing a bacterial infection comprising using the pyrimidine derivative according to claim 1 comprising a marker for use in diagnosing or prognosing bacterial infection.

29. The method according to claim 13, wherein the bacterial infection is caused by Gram-positive bacteria.

30. The method according to claim 13, wherein the bacterial infection is caused by one or more of methicillin-resistant *S. Aureus* (MRSA) methicillin-resistant *S. epidermidis* (MRSE), glycopeptide intermediate *S. aureus* (GISA), Coagulase-negative staphylococci (CoNS), Vancomycin-resistant enterococci (VRE), beta-hemolytic *Streptococcus agalactiae* (Group B *Streptococcus*, GBS).

* * * * *

UNITED STATES PATENT AND TRADEMARK OFFICE
CERTIFICATE OF CORRECTION

PATENT NO. : 11,434,241 B2  Page 1 of 3
APPLICATION NO. : 16/958023
DATED : September 6, 2022
INVENTOR(S) : Patrizio Lancellotti et al.

It is certified that error appears in the above-identified patent and that said Letters Patent is hereby corrected as shown below:

In the Specification

At Column 7, Line 23 (approx.), delete "formula(I)" and insert -- formula (I) --.

At Column 15-16, Line 10-15 (approx.), delete " 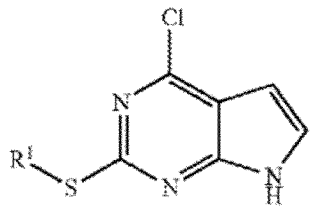 " and insert

-- 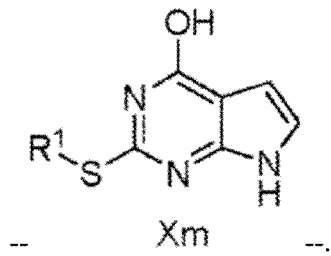 --.

At Column 15-16, Line 55-65 (approx.), delete " 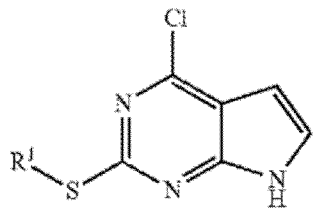 " and insert

Signed and Sealed this
Twenty-fourth Day of January, 2023

Katherine Kelly Vidal
*Director of the United States Patent and Trademark Office*

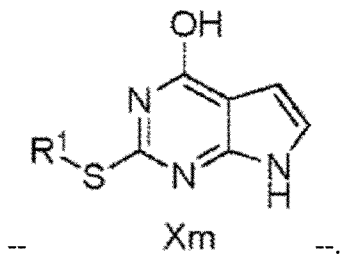

At Column 17, Line 21, delete "formula(I)" and insert -- formula (I) --.

At Column 23, Line 21, delete "host," and insert -- host. --.

At Column 26, Line 49, delete "Scandinavia," and insert -- Scandinavica, --.

At Column 26, Line 51, delete ".pdf" and insert -- .pdf. --.

At Column 39, Line 23 (approx.), delete "(1R," and insert -- ((1R, --.

At Column 45, Line 3-4, delete "difluorophenylcyclopropyl)" and insert -- difluorophenyl)cyclopropyl) --.

At Column 46, Line 65, delete "11," and insert -- 1'), --.

At Column 48, Line 14, delete "(1R,2S)" and insert -- ((1R,2S) --.

At Column 49, Line 3-4 (approx.), delete "cyclopropyl" and insert -- cyclopropyl) --.

At Column 63, Line 52-53 (approx.), delete "cyclopropyl" and insert -- cyclopropyl) --.

At Column 64, Line 15 (approx.), delete "(C-2)" and insert -- (C-2). --.

At Column 65, Line 24, delete "δ14.3" and insert -- δ 14.3 --.

At Column 67, Line 4-5, delete "difluorophenylcyclopropyl)" and insert -- difluorophenyl)cyclopropyl) --.

At Column 77, Line 1, delete "(Butylhio)" and insert -- (Butylthio) --.

At Column 91, Line 28, delete "chloracetaldehyde" and insert -- chloroacetaldehyde --.

At Column 93, Line 5 (approx.), delete "(CDCl₃)" and insert -- (CDCl₃) --.

At Column 95, Line 20 (approx.), delete "(=OD0.08-0.1)" and insert -- (OD=0.08-0.1) --.

At Column 96, Line 46, delete "glucose" and insert -- glucose. --.

CERTIFICATE OF CORRECTION (continued)
U.S. Pat. No. 11,434,241 B2

At Column 97, Line 6, delete "glucose" and insert -- glucose. --.

At Column 101, Line 28, delete "Triptic" and insert -- Tryptic --.

At Column 101, Line 36, delete "(600)" and insert -- (OD600) --.

At Column 107, Line 44 (approx.), delete "difluorobenzyp" and insert -- difluorobenzyl) --.

At Column 112, Line 41 (approx.), delete "Δ" and insert -- δ --.

In the Claims

At Column 115, Line 51, in Claim 3, delete "3H," and insert -- $^3$H, --.

At Column 115, Line 53, in Claim 4, after "to" delete "anyone of".

At Column 116, Line 36, in Claim 6, delete "N-(1" and insert -- N-((1 --.

At Column 116, Line 40, in Claim 6, delete "N-(1" and insert -- N-((1 --.

At Column 118, Line 33 (approx.), in Claim 18, delete "dihalogenoropyrimidin-" and insert -- dihalogenopyrimidin- --.

At Column 118, Line 48, in Claim 18, before "thereof." delete "or prodrug".

At Column 119, Line 50 (approx.), in Claim 20, before "thereof." delete "or".

At Column 123, Line 27, in Claim 25, delete "(X1);" and insert -- (Xl); --.

At Column 123, Line 29, in Claim 25, delete "(X1)" and insert -- (Xl) --.

At Column 124, Line 55, in Claim 30, delete "Aureus (MRSA)" and insert -- aureus (MRSA), --.